United States Patent
Ketcham et al.

(10) Patent No.: US 12,421,228 B2
(45) Date of Patent: Sep. 23, 2025

(54) NAPHTHYRIDINE DERIVATIVES AS PRC2 INHIBITORS

(71) Applicant: Mirati Therapeutics, Inc., Princeton, NJ (US)

(72) Inventors: John Michael Ketcham, San Diego, CA (US); Aaron Craig Burns, San Diego, CA (US); Matthew Arnold Marx, San Diego, CA (US)

(73) Assignee: MIRATI THERAPEUTICS, INC., Princeton, NJ (US)

( * ) Notice: Subject to any disclaimer, the term of this patent is extended or adjusted under 35 U.S.C. 154(b) by 913 days.

(21) Appl. No.: 17/605,094

(22) PCT Filed: Apr. 21, 2020

(86) PCT No.: PCT/US2020/029118
§ 371 (c)(1),
(2) Date: Oct. 20, 2021

(87) PCT Pub. No.: WO2020/219448
PCT Pub. Date: Oct. 29, 2020

(65) Prior Publication Data
US 2022/0213097 A1 Jul. 7, 2022

Related U.S. Application Data

(60) Provisional application No. 62/836,840, filed on Apr. 22, 2019.

(51) Int. Cl.
C07D 471/04 (2006.01)
A61P 35/00 (2006.01)

(52) U.S. Cl.
CPC ............ *C07D 471/04* (2013.01); *A61P 35/00* (2018.01)

(58) Field of Classification Search
CPC .................. C07D 471/04; A61P 35/00
See application file for complete search history.

(56) References Cited

U.S. PATENT DOCUMENTS

| | | |
|---|---|---|
| 8,410,088 B2 | 4/2013 | Kuntz et al. |
| 8,536,179 B2 | 9/2013 | Miller et al. |
| 8,962,620 B2 | 2/2015 | Kuntz et al. |
| 8,975,291 B2 | 3/2015 | Brackley, III et al. |
| 9,006,242 B2 | 4/2015 | Kuntz et al. |
| 9,040,515 B2 | 5/2015 | Edwards et al. |
| 9,045,477 B2 | 6/2015 | Campbell et al. |
| 9,382,234 B2 | 7/2016 | Knight et al. |
| 9,409,865 B2 | 8/2016 | Albrecht et al. |
| 9,469,646 B2 | 10/2016 | Albrecht et al. |
| 9,481,666 B2 | 11/2016 | Kania et al. |
| 9,505,745 B2 | 11/2016 | Blackledge, Jr. et al. |

(Continued)

FOREIGN PATENT DOCUMENTS

| | | |
|---|---|---|
| CN | 110563722 A | 12/2019 |
| JP | 2005518358 A | 6/2005 |

(Continued)

OTHER PUBLICATIONS https://pubchem.ncbi.nlm.nih.gov/substance/215463614/version/1, available Oct. 20, 2014.*

(Continued)

*Primary Examiner* — Andrew D Kosar
*Assistant Examiner* — Jonathan D Mahlum
(74) *Attorney, Agent, or Firm* — WILSON SONSINI GOODRICH & ROSATI

(57) ABSTRACT

Disclosed are compounds of formula (I) or (II) that inhibit Polycomb Repressive Complex 2 (PRC2) activity. In particular, the present invention relates to compounds, pharmaceutical compositions and methods of use, such as methods of treating cancer using the compounds and pharmaceutical compositions of the present invention.

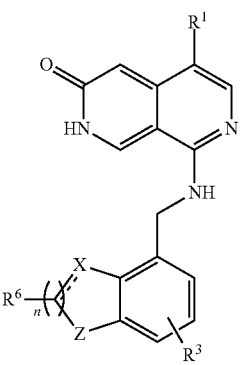

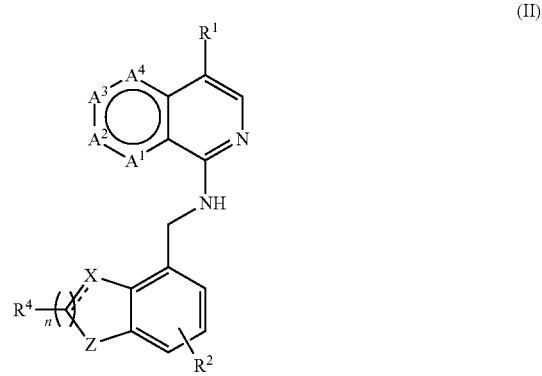

29 Claims, No Drawings

(56) References Cited

U.S. PATENT DOCUMENTS

| | | |
|---|---|---|
| 9,527,837 B2 | 12/2016 | Yu et al. |
| 9,549,931 B2 | 1/2017 | Kuntz et al. |
| 9,556,157 B2 | 1/2017 | Burgess et al. |
| 9,562,041 B2 | 2/2017 | Burgess et al. |
| 9,580,437 B2 | 2/2017 | Chan et al. |
| 9,624,205 B2 | 4/2017 | Campbell |
| 9,637,472 B2 | 5/2017 | Kuntz et al. |
| 9,701,666 B2 | 7/2017 | Kuntz et al. |
| 9,718,838 B2 | 8/2017 | Guo et al. |
| 9,745,305 B2 | 8/2017 | Albrecht et al. |
| 9,776,996 B2 | 10/2017 | Campbell et al. |
| 9,822,103 B2 | 11/2017 | Seitz et al. |
| 10,266,542 B2 | 4/2019 | Marx et al. |
| 11,091,495 B2 | 8/2021 | Marx et al. |
| 2013/0310379 A1 | 11/2013 | Albrecht et al. |
| 2014/0142083 A1 | 5/2014 | Kuntz et al. |
| 2014/0275081 A1 | 9/2014 | Kuntz et al. |
| 2014/0288123 A1 | 9/2014 | Albrecht et al. |
| 2014/0296283 A1 | 10/2014 | Campbell et al. |
| 2014/0303106 A1 | 10/2014 | Zheng et al. |
| 2014/0315945 A1 | 10/2014 | Campbell et al. |
| 2014/0315949 A1 | 10/2014 | Albrecht et al. |
| 2015/0011546 A1 | 1/2015 | Albrecht et al. |
| 2015/0239842 A1 | 8/2015 | Edwards et al. |
| 2015/0284370 A1 | 10/2015 | Kuntz et al. |
| 2015/0303106 A1 | 10/2015 | Wang et al. |
| 2015/0344427 A1 | 12/2015 | Kuntz et al. |
| 2015/0344459 A1 | 12/2015 | Kuntz et al. |
| 2015/0368229 A1 | 12/2015 | Albrecht et al. |
| 2016/0024081 A1 | 1/2016 | Campbell et al. |
| 2016/0031907 A1 | 2/2016 | Campbell et al. |
| 2016/0130261 A1 | 5/2016 | Burgess et al. |
| 2016/0159782 A1 | 6/2016 | Yu et al. |
| 2016/0176882 A1 | 6/2016 | Chan et al. |
| 2016/0185757 A1 | 6/2016 | Albrecht et al. |
| 2016/0297805 A1 | 10/2016 | Seitz et al. |
| 2016/0297806 A1 | 10/2016 | Kim et al. |
| 2016/0361309 A1 | 12/2016 | McCabe et al. |
| 2017/0015666 A1 | 1/2017 | Miller et al. |
| 2017/0066780 A1 | 3/2017 | Dominguez et al. |
| 2017/0073335 A1 | 3/2017 | Kanno et al. |
| 2017/0152239 A1 | 6/2017 | Edwards et al. |
| 2017/0320880 A1 | 11/2017 | Michaelides et al. |
| 2017/0348306 A1 | 12/2017 | Creasy et al. |
| 2018/0265517 A1 | 9/2018 | Marx et al. |
| 2019/0142837 A1 | 5/2019 | Chan et al. |
| 2019/0202828 A1 | 7/2019 | Chan et al. |
| 2021/0032252 A1 | 2/2021 | Marx et al. |
| 2021/0230168 A1 | 7/2021 | Marx et al. |
| 2022/0274990 A1 | 9/2022 | Marx et al. |
| 2023/0137025 A1 | 5/2023 | Marx et al. |

FOREIGN PATENT DOCUMENTS

| | | | |
|---|---|---|---|
| JP | 2018500342 A | 1/2018 | |
| WO | WO0123375 * | 4/2001 | |
| WO | WO-0123375 A2 * | 4/2001 | ........... C07D 401/06 |
| WO | WO-03044021 A2 | 5/2003 | |
| WO | WO-2010021381 A1 | 2/2010 | |
| WO | WO-2011140324 A1 | 11/2011 | |
| WO | WO-2011140325 A1 | 11/2011 | |
| WO | WO-2012082436 A2 | 6/2012 | |
| WO | WO-2012118812 A2 | 9/2012 | |
| WO | WO-2012142504 A1 | 10/2012 | |
| WO | WO-2012154760 A1 | 11/2012 | |
| WO | WO-2013155464 A1 | 10/2013 | |
| WO | WO-2013173441 A2 | 11/2013 | |
| WO | WO-2014049488 A1 | 4/2014 | |
| WO | WO-2014062720 A2 | 4/2014 | |
| WO | WO-2014097041 A1 | 6/2014 | |
| WO | WO-2014124418 A1 | 8/2014 | |
| WO | WO-2014151142 A1 | 9/2014 | |
| WO | WO-2014177982 A1 | 11/2014 | |
| WO | WO-2014195919 A1 | 12/2014 | |
| WO | WO-2015004618 A1 | 1/2015 | |
| WO | WO-2015010049 A1 | 1/2015 | |
| WO | WO-2015010078 A2 | 1/2015 | |
| WO | WO-2015023915 A1 | 2/2015 | |
| WO | WO-2015077193 A1 | 5/2015 | |
| WO | WO-2015077194 A1 | 5/2015 | |
| WO | WO-2015193765 A1 | 12/2015 | |
| WO | WO-2015193768 A1 | 12/2015 | |
| WO | WO-2016066697 A1 | 5/2016 | |
| WO | WO-2016073903 A1 | 5/2016 | |
| WO | WO-2016073956 A1 | 5/2016 | |
| WO | WO-2016102493 A1 | 6/2016 | |
| WO | WO-2016103155 A1 | 6/2016 | |
| WO | WO-2016103255 A1 | 6/2016 | |
| WO | WO-2016123387 A1 | 8/2016 | |
| WO | WO-2016130396 A1 | 8/2016 | |
| WO | WO-2017084494 A1 | 5/2017 | |
| WO | WO-2017100362 A2 | 6/2017 | |
| WO | WO-2017174023 A1 | 10/2017 | |
| WO | WO-2017184999 A1 | 10/2017 | |
| WO | WO-2017191545 A1 | 11/2017 | |
| WO | WO-2017210395 A1 | 12/2017 | |
| WO | WO-2017218953 A1 | 12/2017 | |
| WO | WO-2017219948 A1 | 12/2017 | |
| WO | WO-2017221092 A1 | 12/2017 | |
| WO | WO-2017221100 A1 | 12/2017 | |
| WO | WO-2019062435 A1 | 4/2019 | |
| WO | WO-2019120276 A1 | 6/2019 | |
| WO | WO-2019152419 A1 | 8/2019 | |
| WO | WO-2019158025 A1 | 8/2019 | |
| WO | WO-2020219448 A1 | 10/2020 | |
| WO | WO-2020247475 A1 | 12/2020 | |

OTHER PUBLICATIONS

Patani et al., Chem Rev, 1996, 96:3147-3176 (Year: 1996).*

Ansari et al. Novel 3-methylindoline inhibitors of EZH2: Design, synthesis and SAR. Bioog Med Chem Lett 27(2):217-222 (2016).

Antonysamy et al. Structural context of disease-associated mutations and putative mechanism of autoinhibition revealed by X-ray crystallographic analysis of the EZH2-SET domain. PLoS One 8(12):e84147 (2013).

Bradley et al. EZH2 inhibitor efficacy in non-Hodgkin's lymphoma does not require suppression of H3K27 monomethylation. Chem Biol 21(11):1463-75 (2014).

Brooun et al. Polycomb repressive complex 2 structure with inhibitor reveals a mechanism of activation and drug resistance. Nat Commun 7:11384 (2016) (w/Supp Material).

Campbell et al. EPZ011989, A Potent, Orally-Available EZH2 Inhibitor with Robust in Vivo Activity. ACS Med Chem Lett 6(5):491-495 (2015).

Cao et al. Role of histone H3 lysine 27 methylation in Polycomb-group silencing. Science 298:1039-1043 (2002).

Copeland. Epigenetic Medicinal Chemistry. ACS Med Chem Lett 7(2):124-7 (2015).

Denisenko et al. Point mutations in the WD40 domain of Eed block its interaction with Ezh2. Mol. Cell Biol. 18:5634-5642 (1998).

Garapaty-Rao et al. Identification of EZH2 and EZH1 Small Molecule Inhibitors with Selective Impact on Diffuse Large B Cell Lymphoma Cell Growth. Chem Biol 20(11):1329-39 (2013).

Hackam, et al. Translation of research evidence from animals to humans. JAMA. Oct. 11, 2006;296(14):1731-2.

He et al. Erratum: The EED protein-protein interaction inhibitor A-395 inactivates the PRC2 complex. Nat Chem Biol. 13(8):922 (2017).

Helin et al. Chromatin proteins and modifications as drug targets. Nature 502:480-488 (2013).

Horiuchi et al. Assay development for histone methyltransferases. Assay Drug Dev Technol. 4:227-236 (2013).

Huang et al. Discovery of First-in-Class, Potent and Orally Bioavailable EED inhibitor with Robust Anti-cancer Efficacy. J Med Chem 60(6):2215-2226 (2017).

Jordan. Tamoxifen: A most unlikely pioneering medicine. Nature Reviews: Drug Discovery 2:205-213 (2003).

(56) References Cited

OTHER PUBLICATIONS

Kleer et al. EZH2 is a marker of aggressive breast cancer and promotes neoplastic transformation of breast epithelial cells. PNAS USA 100(20):11606-11611 (2003).
Knutson et al. Selective Inhibition of EZH2 by EPZ-6438 Leads to Potent Antitumor Activity in EZH2-Mutant Non-Hodgkin Lymphoma. Mol Cancer Ther 13(4):842-54 (2014) (w/Supp Material).
Kung et al. Design and Synthesis of Pyridone-Containing 3,4-Dihydroisoquinoline-1(2H)-ones as a Novel Class of Enhancer of Zeste Homolog 2 (EZH2) Inhibitors. J Med Chem 59(18):8306-25 (2016).
Kung et al. Optimization of Orally Bioavailable Enhancer of Zeste Homolog 2 (EZH2) Inhibitors Using Ligand and Property-Based Design Strategies: Identification of Development Candidate (R)-5,8-Dichloro-7-(methoxy(oxetan-3-yl)methyl)-2-((4-methoxy-6-methyl-2-oxo-1,2-dihydropyridin-3-yl)methyl)-3,4-dihydroisoquinolin-1(2H)-one (PF-06821497). J Med Chem 61(3):650-665 (2018).
Kuntz et al. The Importance of Being Me: Magic Methyls, Methyltransferase Inhibitors, and the Discovery of Tazemetostat. J Med Chem 59(4):1556-64 (2016) (w/Supp Material).
Li et al. Discovery and Molecular Basis of a Diverse Set of Polycomb Repressive Complex 2 Inhibitors Recognition by EED. PLoS One 12(1):e0169855 (2017).
Lingel et al. Structure-Guided Design of EED Binders Allosterically Inhibiting the Epigenetic Polycomb Repressive Complex 2 (PRC2) Methyltransferase. 60(1):415-427 (2017).
McCabe et al. EZH2 inhibition as a therapeutic strategy for lymphoma with EZH2-activating mutations. Nature 492:108-112 (2012).
Nasveschuk et al. Discovery and Optimization of Tetramethylpiperidinyl Benzamides as Inhibitors of EZH2. ACS Med Chem Lett 5(4):378-83 (2014).
Pasqualucci et al. Analysis of the coding genome of diffuse large B-cell lymphoma. Nature Genet. 43(9):830-837 (2011).
PCT/US2019/015677 International Search Report and Written Opinion dated May 24, 2019.
PCT/US2020/029118 International Search Report and Written Opinion dated Jul. 9, 2020.
PCT/US2020/035891 International Search Report and Written Opinion dated Aug. 28, 2020.
Qi et al. an allosteric prC2 inhibitor targeting the H3K27me3 binding pocket of EED. Nat Chem Biol 13(4):381-388 (2017).
Santiago et al. Druggability of methyl-lysine biding sites. J Comput Aided Mol Des 25:1171-1178 (2011).
Souroullas et al. An oncogenic Ezh2 mutation induces tumors through global redistribution of histone 3 lysine 27 trimethylation. Nat Med 22(6):632-40 (2016).
Stazi et al. EZH2 inhibitors: a patent review (2014-2016). Expert Opin Ther Pat 27(7):797-813 (2017).
U.S. Appl. No. 17/116,270 Office Action dated Feb. 5, 2021.
U.S. Appl. No. 17/116,270 Office Action dated Jun. 10, 2021.
U.S. Appl. No. 17/219,379 Office Action dated Jun. 10, 2021.
Varambally, S. et al., Genomic Loss of microRNA-101 Leads to Overexpression of Histone Methyltransferase EZH2 in Cancer, Science, 322:1695-1699 (2008).
Vaswani et al. Identification of (R)-N-((4-Methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide (CPI-1205), a Potent and Selective Inhibitor of Histone Methyltransferase EZH2, Suitable for Phase I Clinical Trials for B-Cell Lymphomas. J Med Chem 59(21):9928-9941 (2016).
Wu et al. Identification of novel EZH2 inhibitors through pharmacophore-based virtual screening and biological assays. Bioog Med Chem Lett 26(15):3813-3817 (2016).
Yang et al. Allosteric Inactivation of Polycomb Repressive Complex 2 (PRC2) by Inhibiting Its Adapter Protein: Embryonic Ectodomain Development (EED). J Med Chem 60(6):2212-2214 (2017).
U.S. Appl. No. 17/822,667 Office Action dated Mar. 27, 2024.
Co-pending U.S. Appl. No. 19/045,764, inventors Marx; Matthew Arnold et al., filed Feb. 5, 2025.
U.S. Appl. No. 17/822,667 Office Action dated Oct. 4, 2024.

* cited by examiner

NAPHTHYRIDINE DERIVATIVES AS PRC2 INHIBITORS

CROSS-REFERENCE TO RELATED APPLICATIONS

This application is a § 371 U.S. National Stage Entry of International Application No. PCT/US2020/029118, filed Apr. 21, 2020, which claims the benefit of priority of U.S. Application No. 62/836,840, filed Apr. 22, 2019, the disclosures of which are hereby incorporated by reference in their entirety.

FIELD OF THE INVENTION

The present invention relates to compounds that inhibit the Polycomb Repressive Complex 2 (PRC2). In particular, the present invention relates to compounds, pharmaceutical compositions comprising the compounds and methods for use therefor.

BACKGROUND OF THE INVENTION

The Polycomb Repressive Complex 2 (PRC2) is a multiprotein complex that contributes to the epigenetic silencing of target genes to regulate development and homeostasis. The PRC2 complex is comprised of three core subunits: enhancer of zeste homolog 2 (EZH2), embryonic ectoderm development protein (EED), and suppressor of zeste 12 (SUZ12). Two additional non-essential subunits, AEBP2, and RbAp48, function to promote the enzymatic activity of the PRC2 complex (e.g., see Cao et al., (2002) Science 298: 1039-1043).

EZH2, the catalytic subunit of the PRC2 complex, is a histone methyltransferase that functions to silence target genes by tri-methylating lysine 27 of histone H3 (H3K27me3). EED is partially responsible for the recognition of trimethylated histone H3 lysine 27 and serves as scaffold protein for the assembly of the PRC2 complex. The interaction between EZH2 and EED subunits is essential for PRC2 complex histone methyltransferase activity and function (e.g., see Denisenko et al., (1998) Mol. Cell Biol. 18:5634-5642).

Aberrant PRC2 expression has been reported in several cancers. EZH2 is overexpressed in aggressive solid tumors, including the prostate, breast, skin, bladder, liver, pancreas, and head and neck cancers. For instance, EZH2 transcript and protein were shown to be consistently elevated in invasive breast carcinoma compared with normal breast epithelia and were strongly associated with breast cancer aggressiveness. Overexpression of EZH2 in immortalized human mammary epithelial cell lines promotes anchorage-independent growth and cell invasion. EZH2-mediated cell invasion required an intact SET domain and histone deacetylase activity (Kleer et al., (2003) Proc. Natl Acad. Sci USA 100(20):11606-11611). There also is a greater risk of recurrence after prostatectomy in tumors expressing high levels of EZH2 (Varambally et al, (2008) Science 322:1695-1699).

In addition to overexpression, somatic activating and inactivating mutations of the EZH2 subunit have been reported. Somatic activating mutations in EZH2 have been identified in follicular lymphoma and diffuse large B-cell lymphomas that result in increased levels of H3K27me3 (for a review, see Helin and Dhanak (2013) Nature 502:480-488; Pasqualucci et al., (2011) Nature Genet. 43(9):830-837). These mutations taken together with overexpression of EZH2 in various solid tumors suggests that mis-regulation of EZH2 can lead to silencing of genes by the PRC2 complex that are important to tumor growth and survival. Interestingly, however, inhibitors of the PRC2 complex that target non-catalytic subunits, e.g., EED, retain potent activity against cell lines harboring EZH2 activating mutations (e.g., He et al., (2017) Nat Chem Biol.: 13(8):922. doi: 10.1038/nchembio0817-922b).

SUMMARY OF THE INVENTION

We recognize that enhanced PRC2 activity contributes to undesired cellular proliferation and invasiveness of tumor cells, in part, through trimethylation of H3K27. Since increased H3K27me3 levels appear to contribute to cancer aggressiveness in many tumor types, the inhibition of PRC2 activity may provide therapeutic benefit for a wide range of cancers. The compounds of the present invention offer potential therapeutic benefit as inhibitors that bind to the EED subunit that may be useful for negatively modulating the activity of PRC2 in a cell or for treating various forms of cancer.

There is a need to develop new PRC2 inhibitors that retain potency against EZH2 activating mutations and that demonstrate improved cellular potency, efficacy, stability and safety compared to inhibitors targeting the SET domain of EZH2. The compounds and compositions of the present invention advantageously overcome one or more of these shortcomings by providing potent, selective and orally active compounds that bind to EED and inhibit PRC2 activity irrespective of EZH2 mutation status or expression levels.

In one aspect of the invention, compounds are provided represented by Formula (I):

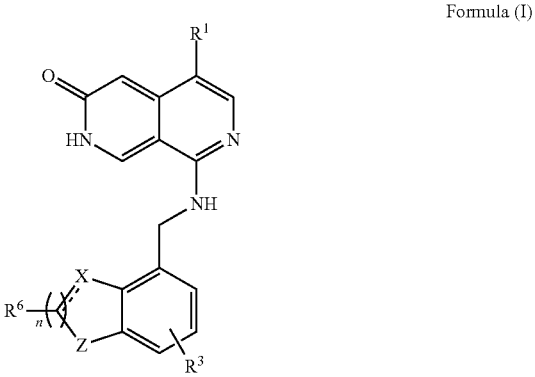

Formula (I)

and pharmaceutically acceptable salts thereof:
wherein;

═══ represents a single or a double bond;
Z is O or S;
X is O, $CR^5$, $CR^5OH$, or $C(R^5)_2$, wherein:
when X is O, ═══ is a single bond;
when X is $C(R^5)_2$, ═══ is a single bond;
when X is $CR^5OH$, ═══ is a single bond; or
when X is $CR^5$, ═══ is a double bond;
$R^1$ is aryl, heteroaryl, -L-cycloalkyl, —N($R^5$)heterocyclyl, or -L-heterocyclyl, wherein the aryl, the heteroaryl and the cyclyl portion of the -L-cycloalkyl, —N($R^5$) heterocyclyl, and -L-heterocyclyl are optionally substituted with one or more $R^2$;

each $R^2$ is independently oxo, cyano, halogen, —PO$_3$(C1-C3 alkyl)$_2$, alkoxy, hydroxyalkyl, heteroalkyl, aralkyl, haloalkyl, —COOR$^5$, —Y$^2$-haloalkyl, —Y$^1$—C1-C6 alkyl, —Y$^2$—C1-C6 alkyl, -L-cycloalkyl, -L-heteroaryl, -L-heterocyclyl, —Y$^1$-heterocyclyl, —Y$^2$—heterocyclyl, -L-N(R$^5$)$_2$, —O-L-N(R$^5$)$_2$, —C(CF$_3$)N(R$^5$)$_2$, —Y$^1$—N(R$^5$)$_2$, or —Y$^2$—N(R$^5$)$_2$ wherein the ring portion of the aralkyl, -L-cycloalkyl, -L-heteroaryl, -L-heterocyclyl and —Y$^1$-heterocyclyl is optionally substituted with one or more R$^4$;

R$^3$ is independently C1-C3 alkyl or halogen;

each R$^4$ is independently oxo, cyano, hydroxyl, alkoxy, halogen, haloalkyl, hydroxyalkyl, heteroalkyl, cycloalkyl, -L-N(R$^5$)$_2$, C1-C6 alkyl or —Y$^1$-heterocyclyl, wherein —Y$^1$-heterocyclyl is optionally substituted with one or more R$^7$;

L is a bond or C1-C4 alkylene;

Y$^1$ is a bond, —C(O)—, or —NHC(O)—;

Y$^2$ is a bond, —S—, —SO—, —SO$_2$—, or —NR$^5$SO$_2$—;

each R$^5$ is independently hydrogen or C1-C3 alkyl;

R$^6$ is independently hydrogen, C1-C3 alkyl, halogen, haloalkyl, hydroxyalkyl, or heteroalkyl;

each R$^7$ is independently oxo, cyano, hydroxyl, alkoxy, halogen, haloalkyl, hydroxyalkyl, heteroalkyl, cycloalkyl, -L-N(R$^5$)$_2$, or C1-C6 alkyl; and n is 1 or 2.

In one aspect of the invention, compounds are provided represented by Formula (II):

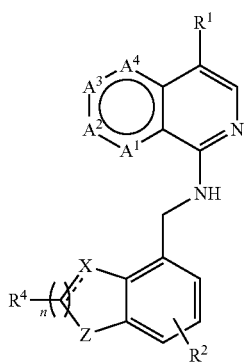

Formula (II)

and pharmaceutically acceptable salts thereof:
wherein;

------ represents a single or a double bond;

A$^1$, A$^2$, A$^3$ and A$^4$ are each independently N or CR$^4$, wherein no more than two of A$^1$, A$^2$, A$^3$ and A$^4$ are N;

Z is O or S;

X is O, CR$^5$, CR$^5$OH, or C(R$^5$)$_2$, wherein:
when X is O, ------ is a single bond;
when X is C(R$^5$)$_2$, ------ is a single bond;
when X is CR$^5$OH, ------ is a single bond; or
when X is CR$^{5'}$ ------ is a double bond;

R$^1$ is aryl, heteroaryl, -L-cycloalkyl, —N(R$^5$)heterocyclyl, or -L-heterocyclyl, wherein the aryl, the heteroaryl and the cyclyl portion of the -L-cycloalkyl, —N(R$^5$)heterocyclyl, and -L-heterocyclyl are optionally substituted with one or more R$^3$;

R$^2$ is independently C1-C3 alkyl or halogen;

each R$^3$ is independently oxo, cyano, halogen, —PO$_3$(C1-C3 alkyl)$_2$, alkoxy, hydroxyalkyl, heteroalkyl, aralkyl, haloalkyl, —COOR$^5$, —Y$^2$-haloalkyl, —Y$^1$—C1-C6 alkyl, —Y$^2$—C1-C6 alkyl, -L-cycloalkyl, -L-heteroaryl, -L-heterocyclyl, —Y$^1$-heterocyclyl, —Y$^2$-heterocyclyl, -L-N(R$^5$)$_2$, —O-L-N(R$^5$)$_2$, —C(CF$_3$)N(R$^5$)$_2$, —Y$^1$—N(R$^5$)$_2$, or —Y$^2$—N(R$^5$)$_2$ wherein the ring portion of the aralkyl, -L-cycloalkyl, -L-heteroaryl, -L-heterocyclyl and —Y$^1$-heterocyclyl is optionally substituted with one or more independently selected R$^6$;

R$^4$ is hydrogen, C1-C3 alkyl, halogen, haloalkyl, hydroxyalkyl, or heteroalkyl;

L is a bond or C1-C4 alkylene;

Y$^1$ is a bond, —C(O)—, or —NHC(O)—;

Y$^2$ is a bond, —S—, —SO—, —SO$_2$—, or —NR$^5$SO$_2$—, each R$^5$ is independently hydrogen or C1-C3 alkyl;

each R$^6$ is oxo, cyano, hydroxyl, alkoxy, halogen, haloalkyl, hydroxyalkyl, heteroalkyl, cycloalkyl, -L-N(R$^5$)$_2$, C1-C6 alkyl or —Y$^1$-heterocyclyl, wherein —Y$^1$-heterocyclyl is substituted with one or more R$^7$;

each R$^7$ is independently hydrogen, C1-C3 alkyl, halogen, haloalkyl, hydroxyalkyl, or heteroalkyl;

each R$^A$ is independently hydrogen, alkoxy, heteroalkyl, —N(R$^5$)$_2$, heteroalkylN(R$^5$)$_2$, C1-C3 alkyl, —S—C1-C3 alkyl or aryl; and n is 1 or 2.

In another aspect of the invention, pharmaceutical compositions are provided comprising a therapeutically effective amount of a compound of the present invention or a pharmaceutically acceptable salt thereof and a pharmaceutically acceptable excipient.

In yet another aspect of the invention, methods are provided for inhibiting PRC2 activity in a in a cell, comprising contacting the cell with a compound of Formula (I) or Formula (II). In one embodiment, the contacting is in vitro. In one embodiment, the contacting is in vivo.

Also provided herein are methods of inhibiting cell proliferation, in vitro or in vivo, the methods comprising contacting a cell with an effective amount of a compound of Formula (I) or Formula (II), or a pharmaceutically acceptable salt thereof, or a pharmaceutical composition thereof as defined herein.

Also provided are methods for treating cancer in a patient comprising administering a therapeutically effective amount of a compound or pharmaceutical composition of the present invention or a pharmaceutically acceptable salt thereof to a patient in need thereof.

Also provided herein are methods for treating cancer in a patient in need thereof, the methods comprising (a) determining that the cancer is associated with PRC2 mutation (e.g., a PRC2-associated cancer); and (b) administering to the patient a therapeutically effective amount of a compound of Formula (I) or Formula (II), or a pharmaceutically acceptable salt thereof, or a pharmaceutical composition thereof.

Also provided herein is a use of a compound of Formula (I) or Formula (II), or a pharmaceutically acceptable salt or solvate thereof, as defined herein in the manufacture of a medicament for the inhibition of activity of PRC2.

Also provided herein is the use of a compound of Formula (I) or Formula (II), or a pharmaceutically acceptable salt or solvate thereof, as defined herein, in the manufacture of a medicament for the treatment of a PRC2-associated disease or disorder.

In another aspect of the invention, intermediates are provided that are useful for the preparation of compounds of Formula (I) and Formula (II).

DETAILED DESCRIPTION OF THE INVENTION

The present invention relates to PRC2 inhibitors. In particular, the present invention relates to compounds that bind to EED to inhibit PRC2 activity, pharmaceutical compositions comprising a therapeutically effective amount of the compounds, and methods of use therefor.

Definitions

Unless defined otherwise, all terms and ranges used herein have the same meaning as is commonly understood by one of skill in the art to which this invention belongs, unless expressly defined otherwise. All patents, patent applications, and publications referred to herein are incorporated by reference to the extent they are consistent with the present disclosure.

For simplicity, chemical moieties are defined and referred to throughout primarily as univalent chemical moieties (e.g., alkyl, aryl, etc.). Nevertheless, such terms may also be used to convey corresponding multivalent moieties under the appropriate structural circumstances clear to those skilled in the art. For example, while an "alkyl" moiety generally refers to a monovalent radical (e.g. $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S).

As used herein, "Polycomb Repressive Complex 2" or "PRC2 complex" refers to a mammalian multiprotein complex comprising three core subunits: enhancer of zeste homolog 2 (EZH2), embryonic ectoderm development protein (EED), and suppressor of zeste 12 (SUZ12) and two additional non-essential subunits, AEBP2, and RbAp48.

As used herein, "EED" refers to the embryonic ectoderm development protein subunit of the PRC2 complex.

As used herein, "EZH2" or "EZH2 enzyme" refers to a mammalian histone methyltransferase, which is the catalytic subunit of the Polycomb Repressive Complex 2 (PRC2), and functions to silence target genes by tri-methylating lysine 27 of histone H3 (H3K27me3).

As used herein, an "PRC2 inhibitor" refers to compounds of the present invention that are represented by formula (I) as described herein. These compounds are capable of negatively modulating or inhibiting all or a portion of the enzymatic activity of the PRC2 complex. While not wanting to be bound by any theory, we theorize that the inhibitors of the present invention may inhibit PRC2 enzymatic activity by binding to EED to prevent assembly of the PRC2 complex on histone H3 tails thereby inhibiting its activity.

An "PRC2-associated disease or disorder" as used herein refers to diseases or disorders associated with or mediated by or having an activating EZH2 mutation and/or aberrant expression of PRC2. A non-limiting example of an PRC2-associated disease or disorder is a PRC2-associated cancer.

The term "amino" refers to —$NH_2$.

The term "acetyl" refers to "—$C(O)CH_3$.

As herein employed, the term "acyl" refers to an alkylcarbonyl or arylcarbonyl substituent wherein the alkyl and aryl portions are as defined herein.

The term "alkyl" as employed herein refers to straight and branched chain aliphatic groups having from 1 to 12 carbon atoms. As such, "alkyl" encompasses $C_1$, $C_2$, $C_3$, $C_4$, $C_5$, $C_6$, $C_7$, $C_8$, $C_9$, $C_{10}$, $C_{11}$ and $C_{12}$ groups. Examples of alkyl groups include, without limitation, methyl, ethyl, propyl, isopropyl, butyl, isobutyl, sec-butyl, tert-butyl, pentyl, and hexyl.

The term "alkenyl" as used herein means an unsaturated straight or branched chain aliphatic group with one or more carbon-carbon double bonds, having from 2 to 12 carbon atoms. As such, "alkenyl" encompasses $C_2$, $C_3$, $C_4$, $C_5$, $C_6$, $C_7$, $C_8$, $C_9$, $C_{10}$, $C_{11}$ and $C_{12}$ groups. Examples of alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms. As such, "alkynyl" encompasses $C_2$, $C_3$, $C_4$, $C_5$, $C_6$, $C_7$, $C_8$, $C_9$, $C_{10}$, $C_{11}$ and $C_{12}$ groups. Examples of alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Examples of alkylene groups include, without limitation, methylene, ethylene, propylene, and butylene. Exemplary alkenylene groups include, without limitation, ethenylene, propenylene, and butenylene. Exemplary alkynylene groups include, without limitation, ethynylene, propynylene, and butynylene.

The term "alkoxy" refers to —OC1-C6 alkyl.

The term "cycloalkyl" as employed herein is a saturated and partially unsaturated cyclic hydrocarbon group having 3 to 12 carbons. As such, "cycloalkyl" includes $C_3$, $C_4$, $C_5$, $C_6$, $C_7$, $C_8$, $C_9$, $C_{10}$, $C_{11}$ and $C_{12}$ cyclic hydrocarbon groups. Examples of cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are independently replaced O, S, or $NR^x$, wherein $R^x$ is hydrogen or C1-C3 alkyl. Examples of heteroalkyl groups include methoxymethyl, methoxyethyl and methoxypropyl.

An "aryl" group is a $C_6$-$C_{14}$ aromatic moiety comprising one to three aromatic rings. As such, "aryl" includes $C_6$, $C_{10}$, $C_{13}$, and $C_{14}$ cyclic hydrocarbon groups. An exemplary aryl group is a $C_6$-$C_{10}$ aryl group. Particular aryl groups include, without limitation, phenyl, naphthyl, anthracenyl, and fluorenyl.

An "aralkyl" or "arylalkyl" group comprises an aryl group covalently linked to an alkylene group wherein the moiety is linked to another group via the alkyl moiety. An exemplary aralkyl group is —(C1-C6)alkyl(C6-C10)aryl, including, without limitation, benzyl, phenethyl, and naphthylmethyl.

A "heterocyclyl" or "heterocyclic" group is a mono- or bicyclic (fused or spiro) ring structure having from 3 to 12 atoms, (3, 4, 5, 6, 7, 8, 9, 10, 11 or 12 atoms), for example 4 to 8 atoms, wherein one or more ring atoms are independently —C(O)—, N, $NR^5$, O, or S, and the remainder of the ring atoms are quaternary or carbonyl carbons. Examples of heterocyclic groups include, without limitation, epoxy, oxiranyl, oxetanyl, azetidinyl, aziridinyl, tetrahydrofuranyl, tetrahydropyranyl, tetrahydrothiophenyl, pyrrolidinyl, piperidinyl, piperazinyl, imidazolidinyl, thiazolidinyl, thiatanyl, dithianyl, trithianyl, azathianyl, oxathianyl, dioxolanyl, oxazolidinyl, oxazolidinonyl, decahydroquinolinyl, piperidonyl, 4-piperidonyl, thiomorpholinyl, dimethyl-morpholinyl, and morpholinyl. Specifically excluded from the scope of this term are compounds having adjacent ring O and/or S atoms.

As used herein, "L-heterocyclyl" refers to a heterocyclyl group covalently linked to another group via an alkylene linker L, where L is C1-C4 alkylene.

As used herein, the term "heteroaryl" refers to a group having 5 to 14 ring atoms, preferably 5, 6, 10, 13 or 14 ring atoms; having 6, 10, or 14 π electrons shared in a cyclic array; and having, in addition to carbon atoms, from one to three heteroatoms that are each independently N, O, or S. "Heteroaryl" also includes fused multicyclic (e.g., bicyclic) ring systems in which one or more of the fused rings is non-aromatic, provided that at least one ring is aromatic and at least one ring contains an N, O, or S ring atom.

Examples of heteroaryl groups include acridinyl, azocinyl, benzimidazolyl, benzofuranyl, benzo[d]oxazol-2(3H)-one, 2H-benzo[b][1,4]oxazin-3(4H)-one, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A "L-heteroaryl", "heteroaralkyl" or "heteroarylalkyl" group comprises a heteroaryl group covalently linked to another group via an alkylene linker. Examples of heteroalkyl groups comprise a $C_1$-$C_6$ alkyl group and a heteroaryl group having 5, 6, 9, or 10 ring atoms. Examples of heteroaralkyl groups include pyridylmethyl, pyridylethyl, pyrrolylmethyl, pyrrolylethyl, imidazolylmethyl, imidazolylethyl, thiazolylmethyl, thiazolylethyl, benzimidazolylmethyl, benzimidazolylethyl quinazolinylmethyl, quinolinylmethyl, quinolinylethyl, benzofuranylmethyl, indolinylethyl isoquinolinylmethyl, isoinodylmethyl, cinnolinylmethyl, and benzothiophenylethyl. Specifically excluded from the scope of this term are compounds having adjacent ring O and/or S atoms.

An "arylene," "heteroarylene," or "heterocyclylene" group is an bivalent aryl, heteroaryl, or heterocyclyl group, respectively, as defined hereinabove, that is positioned between and serves to connect two other chemical groups.

As employed herein, when a moiety (e.g., cycloalkyl, aryl, heteroaryl, heterocyclyl, urea, etc.) is described as "optionally substituted" without expressly stating the substituents it is meant that the group optionally has from one to four, preferably from one to three, more preferably one or two, non-hydrogen substituents.

The term "halogen" or "halo" as employed herein refers to chlorine, bromine, fluorine, or iodine.

The term "haloalkyl" refers to an alkyl chain in which one or more hydrogens have been replaced by a halogen. Exemplary haloalkyls are trifluoromethyl, difluoromethyl, flurochloromethyl, chloromethyl, and fluoromethyl.

The term "hydroxyalkyl" refers to an alkyl chain, as defined herein, wherein at least on hydrogen of the alkyl chain has been replaced by hydroxyl.

As used herein, "an effective amount" of a compound is an amount that is sufficient to negatively modulate or inhibit the activity of PRC2 complex.

As used herein, a "therapeutically effective amount" of a compound is an amount that is sufficient to ameliorate or in some manner reduce a symptom or stop or reverse progression of a condition, or negatively modulate or inhibit the activity of PRC2 complex. Such amount may be administered as a single dosage or may be administered according to a regimen, whereby it is effective.

As used herein, "treatment" means any manner in which the symptoms or pathology of a condition, disorder or disease in a patient are ameliorated or otherwise beneficially altered.

As used herein, "amelioration of the symptoms of a particular disorder by administration of a particular compound or pharmaceutical composition" refers to any lessening, whether permanent or temporary, lasting or transient, that can be attributed to or associated with administration of the composition.

Compounds

In one aspect of the invention, compounds are provided represented by Formula (I):

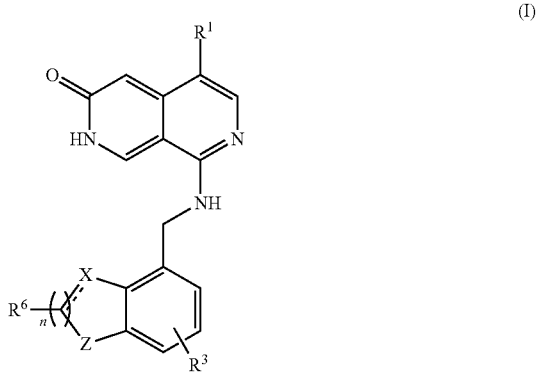

and pharmaceutically acceptable salts thereof:
wherein:

======= represents a single or a double bond;

Z is O or S;

X is O, $CR^5$, $CR^5OH$, $C(R^5)_2$, wherein:

when X is O, ======= is a single bond;

when X is $C(R^5)_2$, ======= is a single bond;

when X is $CR^5OH$, ======= is a single bond; or when X is $CR^{5'}$ ======= is a double bond;

$R^1$ is aryl, heteroaryl, -L-cycloalkyl, —N($R^5$)heterocyclyl, or -L-heterocyclyl, wherein the aryl, the heteroaryl and the cyclyl portion of the -L-cycloalkyl, —N($R^5$)heterocyclyl, and -L-heterocyclyl are optionally substituted with one or more $R^2$;

each $R^2$ is independently oxo, cyano, halogen, —PO$_3$(C1-C3 alkyl)$_2$, alkoxy, hydroxyalkyl, heteroalkyl, aralkyl, haloalkyl, —COOR$^5$, —Y$^2$-haloalkyl, —Y$^1$—C1-C6 alkyl, —Y$^2$—C1-C6 alkyl, -L-cycloalkyl, -L-heteroaryl, -L-heterocyclyl, —Y$^1$-heterocyclyl, —Y$^2$—heterocyclyl, -L-N($R^5$)$_2$, —O-L-N($R^5$)$_2$, —C(CF$_3$)N($R^5$)$_2$, —Y$^1$—N($R^5$)$_2$, or —Y$^2$—N($R^5$)$_2$ wherein the ring portion of the aralkyl, -L-cycloalkyl, -L-heteroaryl, -L-heterocyclyl and —Y$^1$-heterocyclyl is optionally substituted with one or more $R^4$;

$R^3$ is independently C1-C3 alkyl or halogen;

each $R^4$ is oxo, cyano, hydroxyl, alkoxy, halogen, haloalkyl, hydroxyalkyl, heteroalkyl, cycloalkyl, -L-N($R^5$)$_2$, C1-C6 alkyl or —Y$^1$-heterocyclyl, wherein —Y$^1$-heterocyclyl is optionally substituted with one or more $R^7$;

L is a bond or C1-C4 alkylene;

$Y^1$ is a bond, —C(O)—, or —NHC(O)—;

$Y^2$ is a bond, —S—, —SO—, —SO$_2$—, or —NR$^5$SO$_2$—, each $R^5$ is independently hydrogen or C1-C3 alkyl;

$R^6$ is independently hydrogen, C1-C3 alkyl, halogen, haloalkyl, hydroxyalkyl, or heteroalkyl;

each $R^7$ is independently oxo, cyano, hydroxyl, alkoxy, halogen, haloalkyl, hydroxyalkyl, heteroalkyl, cycloalkyl, -L-N($R^5$)$_2$, or C1-C6 alkyl and n is 1 or 2.

In one embodiment for compounds of Formula (I), Z is O or S. In one embodiment, X is O, CR$^5$, CR$^5$OH or C($R^5$)$_2$, wherein when X is O, ====== is a single bond; when X is C($R^5$)$_2$' ====== is a single bond; when X is CR$^5$OH, ====== is a single bond; or when X is CR$^{5'}$ ====== is a double bond. In one embodiment, n is one. In one embodiment, n is two.

In one embodiment for compounds of Formula (I), Z is O, X is O, n is one and ====== is a single bond. In another embodiment, Z is O, X is CR$^5$ and ====== is a double bond. In one embodiment, Z is O, X is C($R^5$)$_2$' n is one, and ====== is a single bond. In one embodiment, Z is O, X is CR$^5$OH, n is one, and ====== is a single bond. In another embodiment, Z is O, X is C($R^5$)$_2$' n is two, and ====== is a single bond. In yet another embodiment, Z is S, X is C($R^5$)$_2$' n is one, and ====== is a single bond.

In one embodiment for compounds of Formula (I), $R^1$ is aryl, which is optionally substituted with one or more $R^2$. In certain embodiments, the aryl is phenyl, which is optionally substituted with one or more $R^2$.

In one embodiment for compounds of Formula (I), the aryl is substituted with a single $R^2$ group. In one embodiment, the aryl is substituted with two $R^2$ groups. In one embodiment, the aryl is substituted with three $R^2$ groups. Exemplary aryl $R^2$ groups include halogen, hydroxyl, haloalkyl, —Y$^1$—C1-C6 alkyl, —Y$^2$—C1-C6 alkyl, -L-N($R^5$)$_2$, —Y$^1$—N($R^5$)$_2$, —Y$^2$—N($R^5$)$_2$, —Y$^2$-haloalkyl, -L-heterocyclyl, or —Y$^1$-heterocyclyl, wherein the heterocyclyl portion of the -L-heterocyclyl and —Y$^1$-heterocyclyl is optionally substituted with one or more $R^4$.

In one embodiment for compounds of Formula (I), $R^1$ is phenyl substituted with —Y$^2$—C1-C6 alkyl. In one embodiment, $Y^2$ is a bond and the C1-C6 alkyl is methyl, ethyl or isopropyl. In one embodiment, $R^1$ is phenyl substituted with the —Y$^2$—C1-C6 alkyl, wherein $Y^2$ is —SO$^2$— and the C1-C6 alkyl is methyl. In one embodiment, $R^1$ is phenyl, which is disubstituted with methyl and —Y$^2$—C1-C6 alkyl, wherein $Y^2$ is —SO$^2$— and the C1-C6 alkyl is methyl.

In one embodiment for compounds of Formula (I), $R^1$ is phenyl substituted one $R^2$, wherein $R^2$ is a cyano group.

In one embodiment for compounds of Formula (I), $R^1$ is phenyl substituted one $R^2$, wherein $R^2$ is -L-heteroaryl. In certain embodiments, the -L-heteroaryl is tetrazolyl. In one embodiment, $R^1$ is phenyl substituted one $R^2$, wherein $R^2$ is PO$_3$(C1-C3 alkyl)$_2$. In one embodiment, $R^1$ is phenyl substituted one $R^2$, wherein $R^2$ is —COOR$^5$. In one embodiment, le is phenyl substituted one $R^2$, wherein $R^2$ is —O-L-N($R^5$)$_2$. In one embodiment, $R^1$ is phenyl substituted one $R^2$, wherein $R^2$ is aralkyl.

In one embodiment for compounds of Formula (I), $R^1$ is phenyl substituted with at least one $R^2$, wherein $R^2$ is -L-N($R^5$)$_2$. In one embodiment, L is a bond. In one embodiment, L is methylene. In one embodiment, each $R^5$ is independently hydrogen. In one embodiment, each $R^5$ is independently C1-C3 alkyl. In one embodiment, each C1-C3 alkyl is methyl. In one embodiment, one $R^5$ is C1-C3 alkyl and the other is hydrogen. In one embodiment, the one C1-C3 alkyl is methyl. In one embodiment, $R^1$ is phenyl substituted with -L-N($R^5$)$_2$ and further substituted with one or more halogen and/or C1-C6 alkyl.

In one embodiment for compounds of Formula (I), $R^1$ is phenyl substituted with one $R^2$, wherein $R^2$ is —Y$^1$—N($R^5$)$_2$. In certain embodiments, $Y^1$ is —C(O)— and each $R^5$ is C1-C3 alkyl. In one embodiment, each C1-C3 alkyl is methyl. In one embodiment, $Y^1$ is —C(O)— and each $R^5$ is hydrogen. In one embodiment, $Y^1$ is —C(O)— and one $R^5$ is C1-C3 alkyl and the other is hydrogen. In one embodiment, the one C1-C3 alkyl is methyl. In one embodiment, $R^1$ is phenyl substituted with —Y$^1$—N($R^5$)$_2$ and further substituted with one or more halogen and/or C1-C6 alkyl.

In one embodiment for compounds of Formula (I), $R^1$ is phenyl substituted with the —Y$^2$-haloalkyl, wherein $Y^2$ is —S— or —SO$^2$— and the haloalkyl is trifluoromethyl.

In one embodiment for compounds of Formula (I), $R^1$ is phenyl substituted with at least one -L-heterocyclyl or —Y$^1$-heterocyclyl, each heterocyclyl optionally substituted with one or more $R^4$. In one embodiment, $R^1$ is phenyl substituted with one $R^2$, wherein $R^2$ is —Y$^1$-heterocyclyl optionally substituted with one or more $R^4$. In one embodiment, $Y^1$ is —C(O)— and the heterocyclyl is piperazinyl optionally substituted with C1-C3 alkyl.

In certain embodiments for compounds of Formula (I), the $R^2$ group is -L-heterocyclyl optionally substituted with one or more $R^4$. In one embodiment, L is methylene and the heterocyclyl is pyrrolidinyl, piperdinyl, piperazinyl or 4-methyl-piperazinyl. In one embodiment, L is methylene and the heterocyclyl is azetindyl, pyrrolidinyl, piperdinyl, piperazinyl, piperazinone, tetrahydropyranyl, morpholinyl, thiomorpholinyl or diazapanyl, each optionally substituted with one or more $R^4$. Exemplary $R^4$ groups include oxo, halogen, hydroxyalkyl and C1-C3 alkyl.

In one embodiment for compounds of Formula (I), $R^1$ is phenyl substituted with —Y$^1$-heterocyclyl optionally substituted with one or more $R^4$. In certain embodiments, $Y^1$ is —C(O)— and the heterocyclyl is azetidinyl, pyrrolidinyl, piperdinyl, piperazinyl or 4-methyl-piperazinyl, each optionally further substituted with one or more halogen.

In one embodiment for compounds of Formula (I), $R^1$ is phenyl substituted with -L-heteroaryl optionally substituted with one or more $R^4$. In certain embodiments, the -L-heteroaryl is tetrazolyl.

In one embodiment for compounds of Formula (I), $R^1$ is phenyl substituted with $PO_3(C1-C3\ alkyl)_2$. In another embodiment, $R^1$ is phenyl substituted with —$COOR^5$. In one embodiment, $R^1$ is phenyl substituted with hydroxyalkyl, —O-L-$N(R^5)_2$ or aralkyl.

In one embodiment for compounds of Formula (I), $R^1$ is heteroaryl, which is optionally substituted with one or more $R^2$. In certain embodiments, the heteroaryl is pyrazolyl, imidazolyl, oxazolyl, isoxazolyl, thiazolyl, triazinyl, pyridyl, pyridinyl-2-one, pyrazinyl, pyridazinyl, pyrimidinyl, or 5,6-dihydro-4H-pyrrolo[1,2-b]pyrazolyl, each of which is optionally substituted with one or more $R^4$.

In one embodiment for compounds of Formula (I), the heteroaryl is substituted with a single $R^2$ group. In one embodiment, the heteroaryl is substituted with two $R^2$ groups. In one embodiment, the heteroaryl is substituted with three $R^2$ groups. Exemplary heteroaryl $R^2$ groups include amino, cyano, halogen, alkoxy, hydroxyalkyl, heteroalkyl, haloalkyl, —$Y^2$— haloalkyl, —$Y^1$—C1-C6 alkyl, —$Y^2$—C1-C6 alkyl, -L-cycloalkyl, -L-heterocyclyl, —$Y^1$-heterocyclyl, -L-$N(R^5)_2$, or —$Y^1$—$N(R^5)_2$, wherein the ring of the -L-cycloalkyl, -L-heteroaryl, -L-heterocyclyl and —$Y^1$-heterocyclyl is optionally substituted with one or more $R^4$.

In one embodiment for compounds of Formula (I), $R^4$ is amino, hydroxyl, cyano, alkoxy, or halogen. In one embodiment, —$R^7$ is C1-C3 alkyl. In one embodiment, $R^4$ is halogen, wherein the halogen is fluorine or chlorine. In one embodiment, $R^4$ is alkoxy, wherein the alkoxy is methoxy or ethoxy. In one embodiment, $R^4$ is cycloalkyl, wherein the cycloalkyl is cyclopropyl. In one embodiment, the $R^4$ group is further substituted with one or more independently selected $R^7$.

In another embodiment for compounds of Formula (I), $R^4$ is heteroaryl and each $R^2$ is independently hydroxyalkyl, heteroalkyl or haloalkyl. In certain embodiments, the hydroxyalkyl is hydroxymethyl, hydroxyethyl or 2-methyl, 2-hydroxypropyl. In certain embodiments, the heteroalkyl is methoxymethyl or methoxyethyl. In certain embodiments, the haloalkyl is fluoromethyl, difluoromethyl, trifluoromethyl, fluoroethyl, difluoroethyl, or trifluoroethyl.

In certain embodiments for compounds of Formula (I), $R^1$ is heteroaryl and $R^2$ is -L-C1-C6 alkyl, wherein $Y^1$ is a bond and the C1-C6 alkyl is methyl, ethyl or isopropyl. In one embodiment, $R^2$ is —$Y^1$—C1-C6 alkyl, wherein $Y^1$ is a —C(O)— and the C1-C6 alkyl is methyl, ethyl or isopropyl. In other embodiments, $Y^1$ is —NHC(O)- and the C1-C6 alkyl portion is methyl.

In one embodiment for compounds of Formula (I), $R^1$ is heteroaryl and $R^2$ is —$Y^2$—C1-C6 alkyl, wherein —$Y^2$ is —$SO_2$— and the C1-C6 alkyl is methyl. In another embodiment, $R^2$ is —$Y^2$—C1-C6 alkyl, wherein —$Y^2$ is —S— and the C1-C6 alkyl is methyl.

In one embodiment for compounds of Formula (I), $R^1$ is heteroaryl and $R^2$ is —$Y^1$-heterocyclyl, which is optionally substituted with one or more $R^4$. In one embodiment, $Y^1$ is a bond. In another embodiment, $Y^1$ is —C(O)—. In one embodiment, $Y^1$ is a bond and the heterocyclyl is azetidinyl, oxetanyl, tetrahydrofuranyl, tetrahydropyranyl, pyrrolidinyl, piperdinyl, piperazinyl or 4-methyl-piperazinyl. In one embodiment, $R^4$ is C1-C3 alkyl. In one embodiment, the C1-C3 alkyl is further substituted with one or more independently selected $R^7$. In one embodiment, $R^4$ is halogen.

In one embodiment for compounds of Formula (I), the heteroaryl is substituted with at least one $R^2$ that is -L-heterocyclyl, which is optionally substituted with one or more $R^4$. In one embodiment, L is ethylene and the heterocyclyl is pyrrolidinyl, piperdinyl, piperazinyl or 4-methyl-piperazinyl. In one embodiment, L is methylene and the heterocyclyl is azetindyl, pyrrolidinyl, piperdinyl, piperazinyl, piperazinone, tetrahydropyranyl, morpholinyl, thiomorpholinyl or diazapanyl, each optionally substituted with one or more $R^4$.

In one embodiment for compounds of Formula (I), the $R^4$ group is independently -L-$N(R^5)_2$, hydroxyl, cyano, alkoxy, or halogen. In one embodiment, $R^4$ is C1-C3 alkyl. In one embodiment, $R^4$ is halogen, wherein the halogen is fluorine or chlorine. In one embodiment, $R^4$ is alkoxy, wherein the alkoxy is methoxy or ethoxy. In one embodiment, $R^4$ is cycloalkyl, wherein the cycloalkyl is cyclopropyl. In one embodiment, $R^4$ is -L-$N(R^5)_2$. In one embodiment, L is a bond. In one embodiment, L is methylene. In one embodiment, each $R^5$ is independently hydrogen. In one embodiment, each $R^5$ is independently C1-C3 alkyl. In one embodiment, each C1-C3 alkyl is methyl. In one embodiment, one $R^5$ is C1-C3 alkyl and the other is hydrogen. In one embodiment, the one C1-C3 alkyl is methyl.

In one embodiment for compounds of Formula (I), $R^1$ is heteroaryl and $R^2$ is -L-$N(R^5)_2$. In one embodiment, L is a bond. In one embodiment, L is methylene, ethylene or propylene. In one embodiment, each $R^5$ is independently C1-C3 alkyl. In one embodiment, each C1-C3 alkyl is methyl. In one embodiment, one $R^5$ is C1-C3 alkyl and the other is hydrogen. In one embodiment, the one C1-C3 alkyl is methyl. In one embodiment, each $R^5$ is independently hydrogen.

In one embodiment for compounds of Formula (I), $R^1$ is heteroaryl and $R^2$ is -L-heteroaryl, which is optionally substituted with one or more $R^4$. In one embodiment, L is a bond. In one embodiment, L is C1-C3 alkylene. In one embodiment, the C1-C3 alkylene is methylene. In certain embodiments, the heteroaryl of the -L-heteroaryl is pyrazolyl, pyridyl, pyrimidinyl, pyrazinyl, triazinyl, thiazolyl or pyridazinyl. In one embodiment, the heteroaryl of the -L-heteroaryl is pyridyl. In certain embodiments, the heteroaryl of the -L-heteroaryl is further substituted with one or more independently selected $R^7$.

In one embodiment for compounds of Formula (I), $R^1$ is heteroaryl which is substituted with two $R^2$ groups independently selected from two —$Y^1$—C1-C6 alkyl groups; —$Y^1$—C1-C6 alkyl and alkoxy; —$Y^1$—C1-C6 alkyl and cycloalkyl; —$Y^1$—C1-C6 alkyl and haloalkyl; —$Y^1$—C1-C6 alkyl and amino; two alkoxy groups; alkoxy and halogen; alkoxy and cyano, and amino and haloalkyl. In certain embodiments, $R^2$ is —$Y^1$—C1-C6 alkyl, wherein each $Y^1$ is a bond and each C1-C6 alkyl is methyl, ethyl or isopropyl. In one embodiment, the cycloalkyl is cyclopropyl. In one embodiment, the alkoxy is methoxy. In one embodiment, the halogen is fluorine or chlorine. In one embodiment, the haloalkyl is trifluoromethyl or trifluoroethyl.

In one embodiment for compounds of Formula (I), $R^1$ is -L-heterocyclyl optionally substituted with one or more $R^2$. In one embodiment, L is a bond and the heterocyclyl is tetrahydrofuranyl, piperdinyl, piperazinyl or morpholinyl. In one embodiment, L is a methylene and the heterocyclyl is azetidinyl, pyrrolidinyl or 3-$\lambda^2$-azabicyclo[3.1.0]hexanyl. In certain embodiments, the heterocyclyl is substituted with one or more $R^4$ independently selected from oxo, halogen, alkoxy, hydroxyl and —$Y^1$—C1-C6 alkyl, wherein Y is a bond or —C(O)—.

In one embodiment for compounds of Formula (I), n is zero. In one embodiment, n is one and $R^3$ is halogen. In certain embodiments, the halogen is fluorine or chlorine. In one embodiment, the halogen is fluorine.

In one embodiment for compounds of Formula (I), $R^6$ is hydrogen, C1-C3 alkyl, halogen, haloalkyl, hydroxyalkyl, or heteroalkyl. In certain embodiments, $R^6$ is hydrogen. In other embodiments, $R^6$ is methyl, ethyl or propyl.

In one embodiment for compounds of Formula (I), the cyclyl portion of $R^4$ group is substituted with one $R^7$ group. In certain embodiments, $R^7$ is oxo, hydroxyl, alkoxy, halogen, haloalkyl, hydroxyalkyl, heteroalkyl, cycloalkyl, -L-N$(R^5)_2$ or C1-C3 alkyl. In certain embodiments, $R^7$ is C1-C3 alkyl, wherein the C1-C3 alkyl is methyl, ethyl or isopropyl. In certain embodiments, $R^7$ is halogen, wherein the halogen is fluorine or chlorine. In certain embodiments, $R^7$ is oxo.

In one embodiment for compounds of Formula (I), the cyclyl portion of $R^4$ group is substituted with two $R^7$ groups. In certain embodiments, the two $R^7$ groups are each halogen, wherein each halogen is fluorine.

In one embodiment, the compound of Formula (I) is:

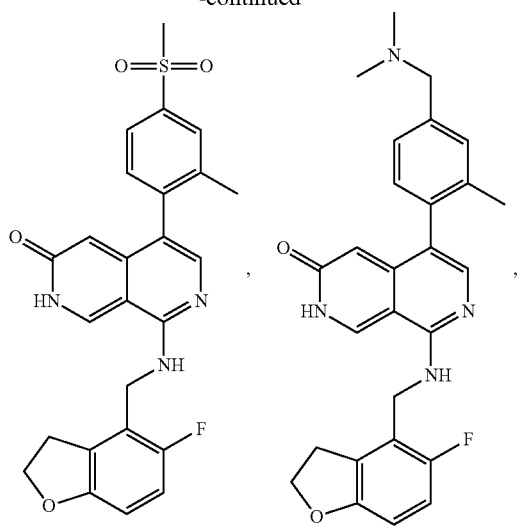

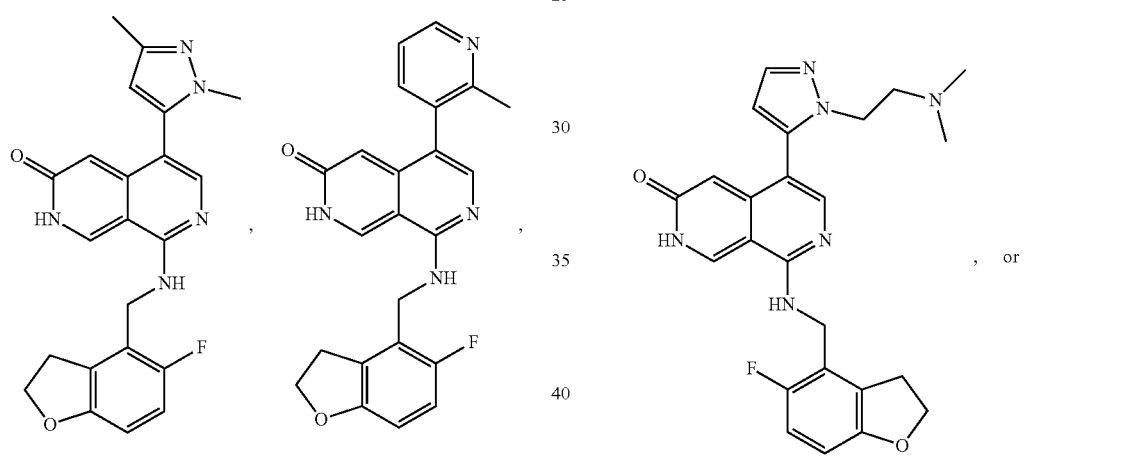

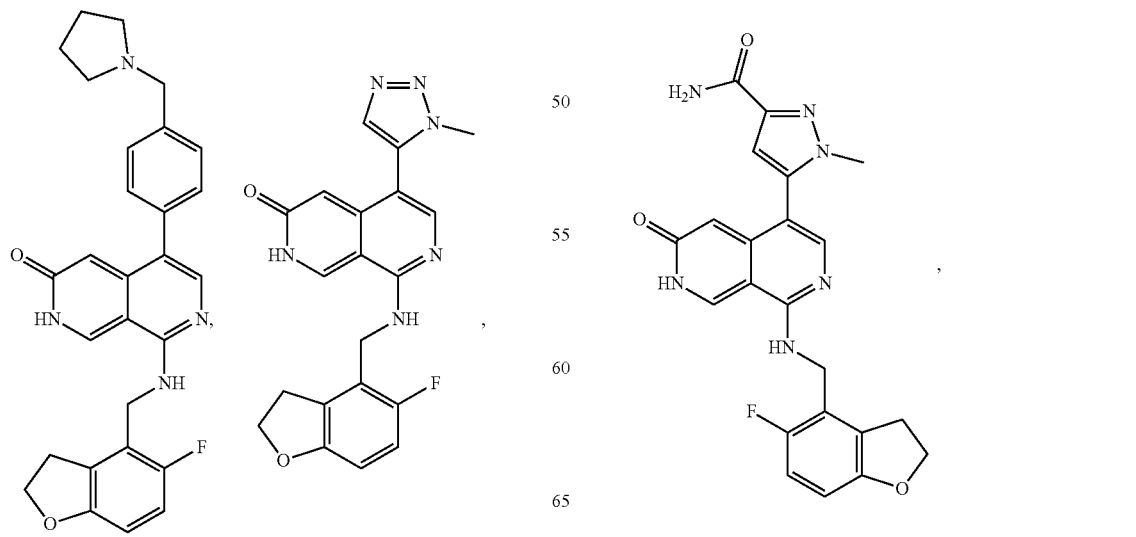

In another aspect of the invention, compounds are provided represented by Formula (II):

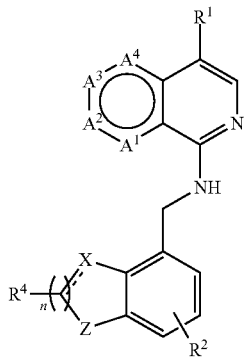

Formula (II)

and pharmaceutically acceptable salts thereof:
wherein;

═══ represents a single or a double bond;
$A^1$, $A^2$, $A^3$ and $A^4$ are each independently N or $CR^4$, wherein no more than two of $A^1$, $A^2$, $A^3$ and $A^4$ are N;
Z is O or S;
X is O, $CR^5$, $CR^5OH$, or $C(R^5)_2$, wherein:
when X is O, ═══ is a single bond;
when X is $C(R^5)_2$, ═══ is a single bond;
when X is $CR^5OH$, ═══ is a single bond; or
when X is $CR^{5'}$ ═══ is a double bond;
$R^1$ is aryl, heteroaryl, -L-cycloalkyl, —$N(R^5)$heterocyclyl, or -L-heterocyclyl, wherein the aryl, the heteroaryl and the cyclyl portion of the -L-cycloalkyl, —$N(R^5)$heterocyclyl, and -L-heterocyclyl are optionally substituted with one or more $R^3$;
$R^2$ is independently C1-C3 alkyl or halogen;
each $R^3$ is independently oxo, cyano, halogen, —$PO_3$(C1-C3 alkyl)$_2$, alkoxy, hydroxyalkyl, heteroalkyl, aralkyl, haloalkyl, —$COOR^5$, —$Y^2$-haloalkyl, —$Y^1$—C1-C6 alkyl, —$Y^2$—C1-C6 alkyl, -L-cycloalkyl, -L-heteroaryl, -L-heterocyclyl, —$Y^1$-heterocyclyl, —$Y^2$—heterocyclyl, -L-$N(R^5)_2$, —O-L-$N(R^5)_2$, —$C(CF_3)N(R^5)_2$, —$Y^1$—$N(R^5)_2$, or —$Y^2$—$N(R^5)_2$ wherein the ring portion of the aralkyl, -L-cycloalkyl, -L-heteroaryl, -L-heterocyclyl and —$Y^1$-heterocyclyl is optionally substituted with one or more independently selected $R^6$;
$R^4$ is hydrogen, C1-C3 alkyl, halogen, haloalkyl, hydroxyalkyl, or heteroalkyl;
L is a bond or C1-C4 alkylene;
$Y^1$ is a bond, —C(O)—, or —NHC(O)—;
$Y^2$ is a bond, —S—, —SO—, —$SO_2$—, or —$NR^5SO_2$—;
each $R^5$ is independently hydrogen or C1-C3 alkyl;
each $R^6$ is oxo, cyano, hydroxyl, alkoxy, halogen, haloalkyl, hydroxyalkyl, heteroalkyl, cycloalkyl, -L-$N(R^5)_2$, C1-C6 alkyl or —$Y^1$-heterocyclyl, wherein —$Y^1$-heterocyclyl is optionally substituted with one or more $R^7$;
each $R^7$ is independently hydrogen, C1-C3 alkyl, halogen, haloalkyl, hydroxyalkyl, or heteroalkyl;
each $R^4$ is independently hydrogen, alkoxy, heteroalkyl, —$N(R^5)_2$, heteroalkylN$(R^5)_2$, C1-C3 alkyl, —S—C1-C3 alkyl or aryl; and
n is 1 or 2.

In one embodiment for compounds of Formula (II), $A^3$ is N. In certain embodiments, $A^3$ is N and $A^1$, $A^2$, and $A^4$ are each $CR^4$. In one embodiment, the $R^4$ groups at $A^1$ and $A^2$ are hydrogen, and the $R^4$ group at $A^4$ is alkoxy. In another embodiment for compounds of Formula (II), $A^2$ and $A^4$ are each $CR^4$ and $A^1$ and $A^3$ are each N. In certain embodiments, $A^1$ and $A^3$ are each N, the $R^4$ group at $A^4$ is hydrogen and the $R^4$ group at $A^2$ is alkoxy.

In one embodiment for compounds of Formula (II), $A^2$ is N and $A^1$, $A^3$, and $A^4$ are each $CR^4$. In certain embodiments, $A^2$ is N, the $R^4$ group at each of $A^1$ and $A^4$ is hydrogen and the $R^4$ group at $A^3$ is alkoxy, heteroalkyl, —$N(R^5)_2$, heteroalkylN$(R^5)_2$, C1-C3 alkyl, —S—C1-C3 alkyl or aryl.

In another embodiment for compounds of Formula (II), $A^2$ and $A^4$ are each N and $A^1$ and $A^3$ are each $CR^4$. In certain embodiments, $A^2$ and $A^4$ are each N, the $R^4$ group at $A^1$ is hydrogen, and the $R^4$ group at $A^3$ is alkoxy, heteroalkyl, —$N(R^5)_2$, heteroalkylN$(R^5)_2$, C1-C3 alkyl, —S—C1-C3 alkyl or aryl.

In another embodiment for compounds of Formula (II), $A^4$ is N and $A^1$, $A^2$, and $A^3$ are each $CR^4$. In certain embodiments, $A^4$ is N, the $R^4$ groups at $A^1$ and $A^2$ are each hydrogen, and the $R^4$ group at $A^3$ is alkoxy.

In one embodiment for compounds of Formula (II),

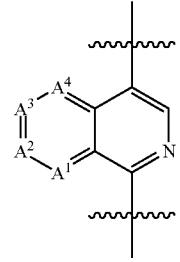

is selected from the group consisting of:

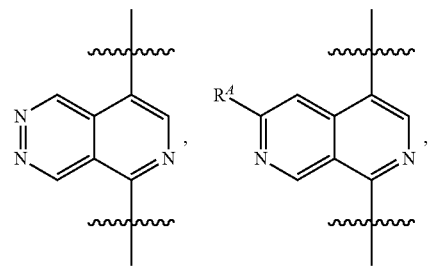

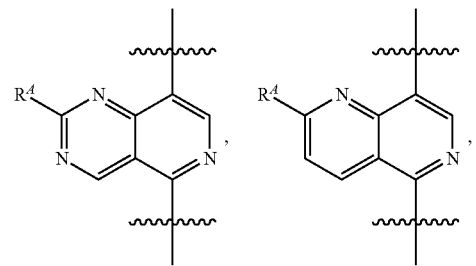

-continued

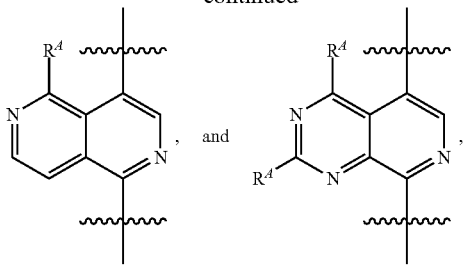

wherein each $R^4$ is as defined in Formula (II).

In one embodiment for compounds of Formula (II), Z is O or S. In one embodiment, X is O, $CR^5$, $CR^5OH$ or $C(R^5)_2$, wherein when X is O, ====== is a single bond; when X is $C(R^5)_2$,' ====== is a single bond; when X is $CR^5OH$, ====== is a single bond; or when X is $CR^{5'}$ ====== is a double bond. In one embodiment, n is one. In one embodiment, n is two.

In one embodiment for compounds of Formula (II), Z is O, X is O, n is one and ====== is a single bond. In another embodiment, Z is O, X is $CR^5$ and ====== is a double bond. In one embodiment, Z is O, X is $C(R^5)_2$ n is one, and ====== is a single bond. In one embodiment, Z is O, X is $CR^5OH$, n is one, and ====== is a single bond. In another embodiment, Z is O, X is $C(R^5)_2$' n is two, and ====== is a single bond. In yet another embodiment, Z is S, X is $C(R^5)_2$,' n is one, and ====== is a single bond.

In one embodiment for compounds of Formula (II), $R^1$ is aryl, which is optionally substituted with one or more $R^3$. In certain embodiments, the aryl is phenyl, which is optionally substituted with one or more $R^3$.

In one embodiment for compounds of Formula (II), the aryl is substituted with a single $R^3$ group. In one embodiment, the aryl is substituted with two $R^3$ groups. In one embodiment, the aryl is substituted with three $R^3$ groups. Exemplary aryl $R^3$ groups include halogen, hydroxyl, haloalkyl, $—Y^1—C1-C6$ alkyl, $—Y^2—C1-C6$ alkyl, -L-N$(R^5)_2$, $—Y^1—N(R^5)_2$, $—Y^2—N(R^5)_2$, $—Y^2$-haloalkyl, -L-heterocyclyl, or $—Y^1$-heterocyclyl, wherein the heterocyclyl portion of the -L-heterocyclyl and $—Y^1$-heterocyclyl is optionally substituted with one or more independently selected $R^6$.

In one embodiment for compounds of Formula (II), $R^1$ is phenyl substituted with $—Y^2—C1-C6$ alkyl. In one embodiment, $Y^2$ is a bond and the C1-C6 alkyl is methyl, ethyl or isopropyl. In one embodiment, $R^1$ is phenyl substituted with the $—Y^2—C1-C6$ alkyl, wherein $Y^2$ is $—SO^2—$ and the C1-C6 alkyl is methyl. In one embodiment, $R^1$ is phenyl, which is disubstituted with methyl and $—Y^2—C1-C6$ alkyl, wherein $Y^2$ is $—SO^2—$ and the C1-C6 alkyl is methyl.

In one embodiment for compounds of Formula (II), $R^1$ is phenyl substituted one $R^3$, wherein $R^3$ is a cyano group.

In one embodiment for compounds of Formula (II), $R^1$ is phenyl substituted one $R^3$, wherein $R^3$ is -L-heteroaryl. In certain embodiments, the -L-heteroaryl is tetrazolyl. In one embodiment, $R^1$ is phenyl substituted one $R^3$, wherein $R^4$ is $PO_3$(C1-C3 alkyl)$_2$. In one embodiment, $R^1$ is phenyl substituted one $R^3$, wherein $R^4$ is $—COOR^5$. In one embodiment, $R^1$ is phenyl substituted one $R^3$, wherein $R^4$ is $—O-L-$ $N(R^5)_2$, wherein L is C1-C4 alkylene. In one embodiment, $R^1$ is phenyl substituted one $R^3$, wherein $R^3$ is aralkyl.

In one embodiment for compounds of Formula (II), $R^1$ is phenyl substituted with at least one $R^3$, wherein $R^3$ is -L-N$(R^5)_2$. In one embodiment, L is a bond. In one embodiment, L is methylene. In one embodiment, each $R^5$ is independently hydrogen. In one embodiment, each $R^5$ is independently C1-C3 alkyl. In one embodiment, each C1-C3 alkyl is methyl. In one embodiment, one $R^5$ is C1-C3 alkyl and the other is hydrogen. In one embodiment, the one C1-C3 alkyl is methyl. In one embodiment, $R^1$ is phenyl substituted with -L-N$(R^5)_2$ and further substituted with one or more halogen and/or C1-C6 alkyl.

In one embodiment for compounds of Formula (II), $R^1$ is phenyl substituted with one $R^3$, wherein $R^3$ is $—Y^1—N(R^5)_2$. In certain embodiments, $Y^1$ is $—C(O)—$ and each $R^5$ is C1-C3 alkyl. In one embodiment, each C1-C3 alkyl is methyl. In one embodiment, $Y^1$ is $—C(O)—$ and each $R^5$ is hydrogen. In one embodiment, $Y^1$ is $—C(O)—$ and one $R^5$ is C1-C3 alkyl and the other is hydrogen. In one embodiment, the one C1-C3 alkyl is methyl. In one embodiment, $R^1$ is phenyl substituted with $—Y^1—N(R^5)_2$ and further substituted with one or more halogen and/or C1-C6 alkyl.

In one embodiment for compounds of Formula (II), $R^1$ is phenyl substituted with the $—Y^2$-haloalkyl, wherein $Y^2$ is $—S—$ or $—SO^2—$ and the haloalkyl is trifluoromethyl.

In one embodiment for compounds of Formula (II), $R^1$ is phenyl substituted with at least one -L-heterocyclyl or $—Y^1$-heterocyclyl, each heterocyclyl optionally substituted with one or more independently selected $R^6$. In one embodiment, $R^1$ is phenyl substituted with one $R^3$, wherein $R^3$ is $—Y^1$-heterocyclyl optionally substituted with one or more independently selected $R^6$. In one embodiment, $Y^1$ is $—C(O)—$ and the heterocyclyl is piperazinyl optionally substituted with C1-C3 alkyl.

In certain embodiments for compounds of Formula (II), the $R^3$ group is -L-heterocyclyl optionally substituted with one or more $R^6$. In one embodiment, L is methylene and the heterocyclyl is pyrrolidinyl, piperdinyl, piperazinyl or 4-methyl-piperazinyl. In one embodiment, L is methylene and the heterocyclyl is azetindyl, pyrrolidinyl, piperdinyl, piperazinyl, piperazinone, tetrahydropyranyl, morpholinyl, thiomorpholinyl or diazapanyl, each optionally substituted with one or more independently selected $R^6$. Exemplary $R^7$ groups include oxo, halogen, hydroxyalkyl and C1-C3 alkyl.

In one embodiment for compounds of Formula (II), $R^1$ is phenyl substituted with $—Y^1$-heterocyclyl optionally substituted with one or more independently selected $R^6$. In certain embodiments, $Y^1$ is $—C(O)—$ and the heterocyclyl is azetidinyl, pyrrolidinyl, piperdinyl, piperazinyl or 4-methyl-piperazinyl, each optionally further substituted with one or more halogen.

In one embodiment for compounds of Formula (II), $R^1$ is phenyl substituted with -L-heteroaryl optionally substituted with one or more independently selected $R^6$. In certain embodiments, the -L-heteroaryl is tetrazolyl.

In one embodiment for compounds of Formula (II), $R^1$ is phenyl substituted with $PO_3$(C1-C3 alkyl)$_2$. In another embodiment, $R^1$ is phenyl substituted with $—COOR^5$. In one embodiment, $R^1$ is phenyl substituted with hydroxyalkyl, $—O-L-N(R^5)_2$ or aralkyl.

In one embodiment for compounds of Formula (II), $R^1$ is heteroaryl, which is optionally substituted with one or more independently selected $R^3$. In certain embodiments, the heteroaryl is pyrazolyl, imidazolyl, oxazolyl, isoxazolyl, thiazolyl, triazinyl, pyridyl, pyridinyl-2-one, pyrazinyl, pyridazinyl, pyrimidinyl, or 5,6-dihydro-4H-pyrrolo[1,2-b]

pyrazolyl, each of which is optionally substituted with one or more independently selected $R^3$.

In one embodiment for compounds of Formula (II), the heteroaryl is substituted with a single $R^3$ group. In one embodiment, the heteroaryl is substituted with two $R^3$ groups. In one embodiment, the heteroaryl is substituted with three $R^3$ groups. Exemplary heteroaryl $R^3$ groups include amino, cyano, halogen, alkoxy, hydroxyalkyl, heteroalkyl, haloalkyl, —$Y^2$-haloalkyl, —$Y^1$—C1-C6 alkyl, —$Y^2$—C1-C6 alkyl, -L-cycloalkyl, -L-heteroaryl, -L-heterocyclyl, —$Y^1$-heterocyclyl, -L-N($R^5$)$_2$, or —$Y^1$—N($R^5$)$_2$, wherein the ring of the -L-cycloalkyl, -L-heteroaryl, -L-heterocyclyl and —$Y^1$-heterocyclyl is optionally substituted with one or more independently selected $R^6$.

In one embodiment for compounds of Formula (II), $R^6$ is amino, hydroxyl, cyano, alkoxy, or halogen. In one embodiment, $R^6$ is C1-C3 alkyl. In one embodiment, $R^6$ is halogen, wherein the halogen is fluorine or chlorine. In one embodiment, $R^6$ is alkoxy, wherein the alkoxy is methoxy or ethoxy. In one embodiment, $R^6$ is cycloalkyl, wherein the cycloalkyl is cyclopropyl.

In another embodiment for compounds of Formula (II), $R^1$ is heteroaryl and each $R^3$ is independently hydroxyalkyl, heteroalkyl or haloalkyl. In certain embodiments, the hydroxyalkyl is hydroxymethyl, hydroxyethyl or 2-methyl, 2-hydroxypropyl. In certain embodiments, the heteroalkyl is methoxymethyl or methoxyethyl. In certain embodiments, the haloalkyl is fluoromethyl, difluoromethyl, trifluoromethyl, fluoroethyl, difluoroethyl, or trifluoroethyl.

In certain embodiments for compounds of Formula (II), $R^1$ is heteroaryl and $R^3$ is —$Y^1$—C1-C6 alkyl, wherein $Y^1$ is a bond and the C1-C6 alkyl is methyl, ethyl or isopropyl. In one embodiment, $R^4$ is —$Y^1$—C1-C6 alkyl, wherein $Y^1$ is a —C(O)— and the C1-C6 alkyl is methyl, ethyl or isopropyl. In other embodiments, $Y^1$ is —NHC(O)- and the C1-C6 alkyl portion is methyl.

In one embodiment for compounds of Formula (II), $R^1$ is heteroaryl and $R^3$ is —$Y^2$—C1-C6 alkyl, wherein $Y^2$ is —$SO_2$— and the C1-C6 alkyl is methyl. In another embodiment, $R^4$ is —$Y^2$—C1-C6 alkyl, wherein $Y^2$ is —S— and the C1-C6 alkyl is methyl.

In one embodiment for compounds of Formula (II), $R^1$ is heteroaryl and $R^3$ is —$Y^1$-heterocyclyl, which is optionally substituted with one or more independently selected $R^6$. In one embodiment, $Y^1$ is a bond. In another embodiment, $Y^1$ is —C(O)—. In one embodiment, $Y^1$ is a bond and the heterocyclyl is azetidinyl, oxetanyl, tetrahydrofuranyl, tetrahydropyranyl, pyrrolidinyl, piperdinyl, piperazinyl or 4-methyl-piperazinyl. In one embodiment, $R^6$ is C1-C3 alkyl. In one embodiment, $R^6$ is halogen.

In one embodiment for compounds of Formula (II), the heteroaryl is substituted with at least one $R^3$ that is -L-heterocyclyl, which is optionally substituted with one or more $R^6$. In one embodiment, L is ethylene and the heterocyclyl is pyrrolidinyl, piperdinyl, piperazinyl or 4-methyl-piperazinyl. In one embodiment, L is methylene and the heterocyclyl is azetindyl, pyrrolidinyl, piperdinyl, piperazinyl, piperazinone, tetrahydropyranyl, morpholinyl, thiomorpholinyl or diazapanyl, each optionally substituted with one or more independently selected $R^6$.

In one embodiment for compounds of Formula (II), the $R^6$ is independently -L-N($R^5$)$_2$, hydroxyl, cyano, alkoxy, or halogen. In one embodiment, $R^6$ is C1-C3 alkyl. In one embodiment, $R^6$ is halogen, wherein the halogen is fluorine or chlorine. In one embodiment, $R^6$ is alkoxy, wherein the alkoxy is methoxy or ethoxy. In one embodiment, $R^7$ is cycloalkyl, wherein the cycloalkyl is cyclopropyl. In one embodiment, $R^6$ is -L-N($R^5$)$_2$. In one embodiment, L is a bond. In one embodiment, L is methylene. In one embodiment, each $R^5$ is independently hydrogen. In one embodiment, each $R^5$ is independently C1-C3 alkyl. In one embodiment, each C1-C3 alkyl is methyl. In one embodiment, one $R^5$ is C1-C3 alkyl and the other is hydrogen. In one embodiment, the one C1-C3 alkyl is methyl.

In one embodiment for compounds of Formula (II), $R^1$ is heteroaryl and $R^6$ is -L-N($R^5$)$_2$. In one embodiment, L is a bond. In one embodiment, L is methylene, ethylene or propylene. In one embodiment, each $R^5$ is independently C1-C3 alkyl. In one embodiment, each C1-C3 alkyl is methyl. In one embodiment, one $R^5$ is C1-C3 alkyl and the other is hydrogen. In one embodiment, the one C1-C3 alkyl is methyl. In one embodiment, each $R^5$ is independently hydrogen.

In one embodiment for compounds of Formula (II), $R^1$ is heteroaryl and $R^3$ is -L-heteroaryl, which is optionally substituted with one or more independently selected $R^6$. In one embodiment, L is a bond. In one embodiment, L is C1-C3 alkylene. In one embodiment, the C1-C3 alkylene is methylene. In certain embodiments, the heteroaryl of the -L-heteroaryl is pyrazolyl, pyridyl, pyrimidinyl, pyrazinyl, triazinyl, thiazolyl or pyridazinyl. In one embodiment, the heteroaryl of the -L-heteroaryl is pyridyl.

In one embodiment for compounds of Formula (II), $R^1$ is heteroaryl which is substituted with two $R^3$ groups independently selected from two —$Y^1$—C1-C6 alkyl groups; —$Y^1$—C1-C6 alkyl and alkoxy; —$Y^1$—C1-C6 alkyl and cycloalkyl; —$Y^1$—C1-C6 alkyl and haloalkyl; —$Y^1$—C1-C6 alkyl and amino; two alkoxy groups; alkoxy and halogen; alkoxy and cyano, and amino and haloalkyl. In certain embodiments, $R^3$ is —$Y^1$—C1-C6 alkyl, wherein each $Y^1$ is a bond and each C1-C6 alkyl is methyl, ethyl or isopropyl. In one embodiment, the cycloalkyl is cyclopropyl. In one embodiment, the alkoxy is methoxy. In one embodiment, the halogen is fluorine or chlorine. In one embodiment, the haloalkyl is trifluoromethyl or trifluoroethyl.

In one embodiment for compounds of Formula (II), $R^1$ is -L-heterocyclyl optionally substituted with one or more independently selected $R^3$. In one embodiment, L is a bond and the heterocyclyl is tetrahydrofuranyl, piperdinyl, piperazinyl or morpholinyl. In one embodiment, L is a methylene and the heterocyclyl is azetidinyl, pyrrolidinyl or 3-$\lambda^2$-azabicyclo[3.1.0]hexanyl. In certain embodiments, the heterocyclyl is substituted with one or more $R^3$ independently selected from oxo, halogen, alkoxy, hydroxyl and —$Y^1$—C1-C6 alkyl, wherein $Y^1$ is a bond or —C(O)—.

In one embodiment, the compound of Formula (II) is:
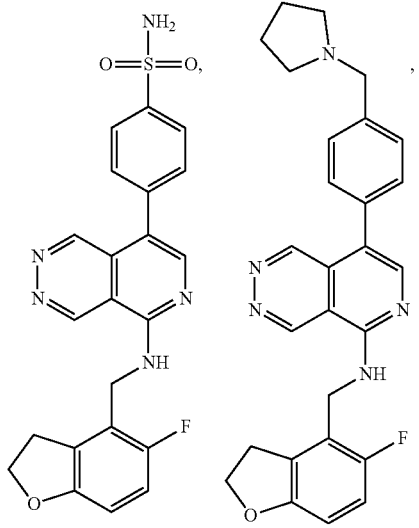
-continued
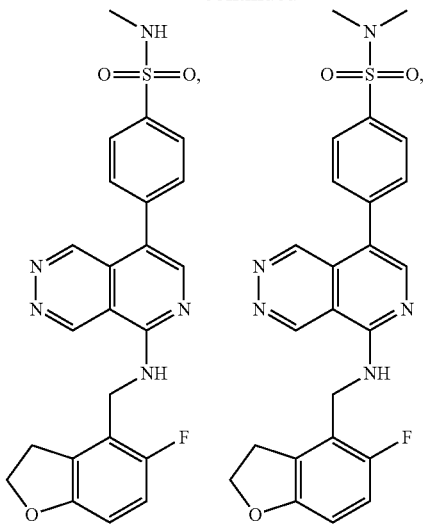

23
-continued
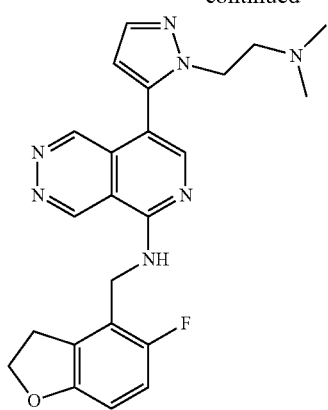
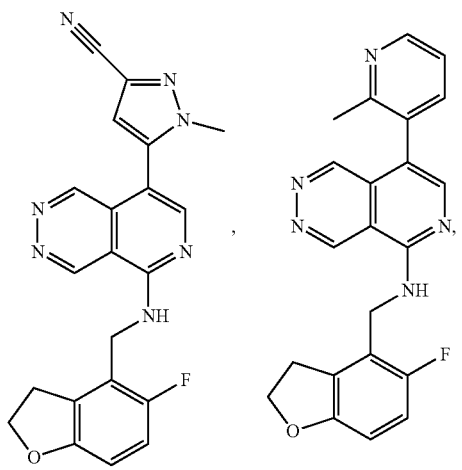
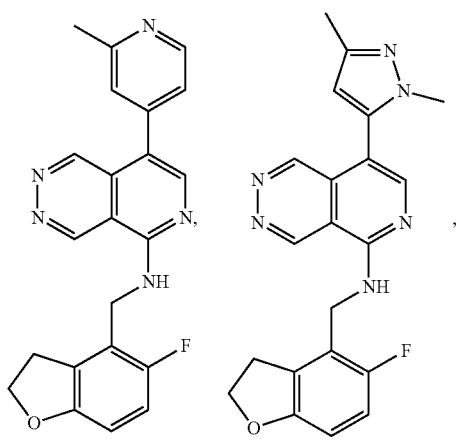
24
-continued
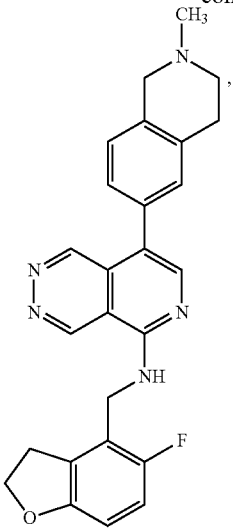 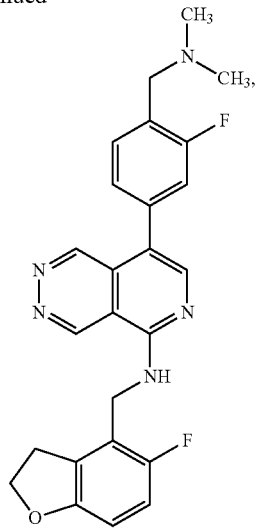
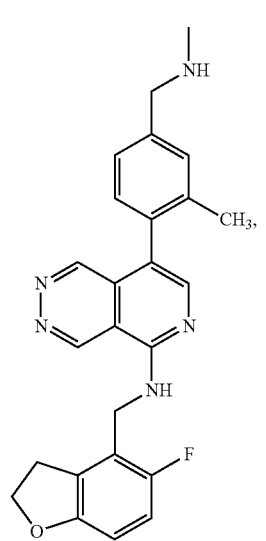 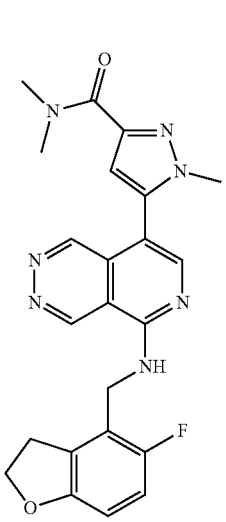
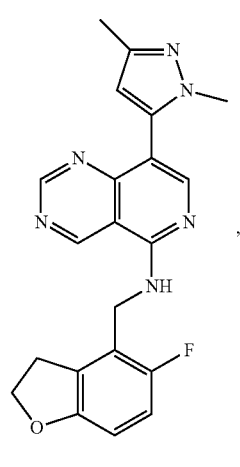 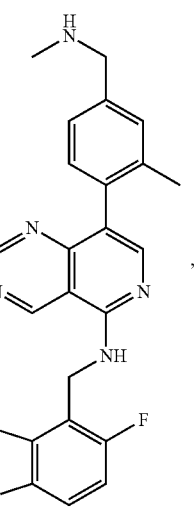

25
-continued
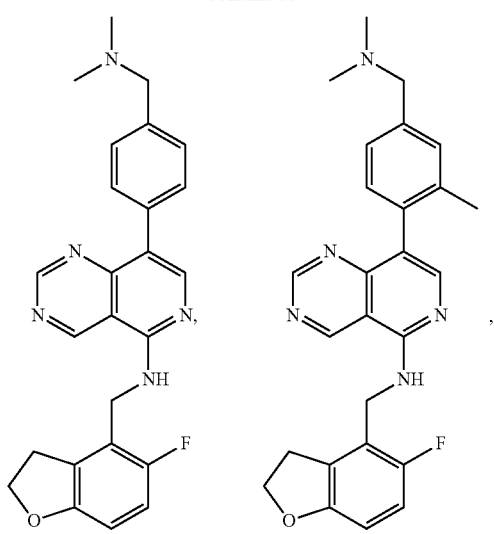
26
-continued
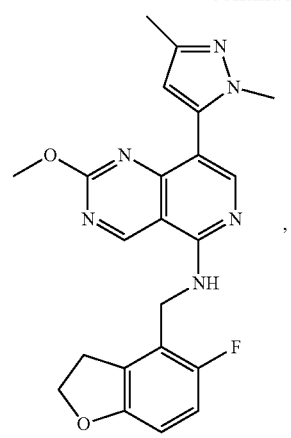
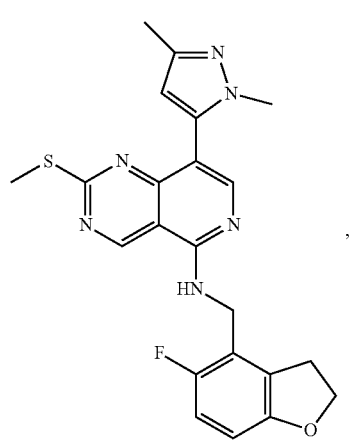
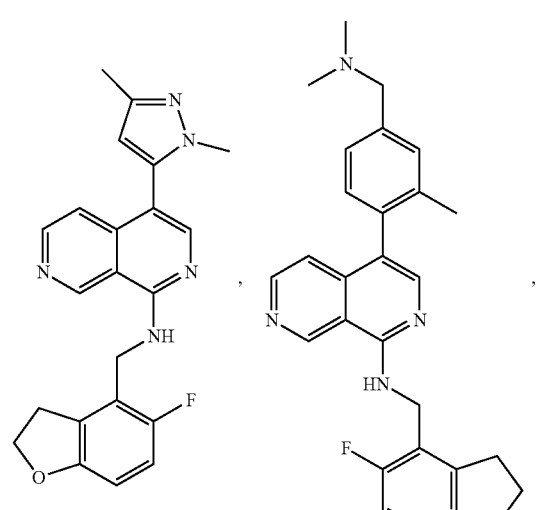

27
-continued
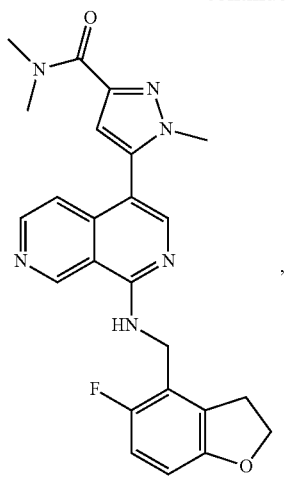
,
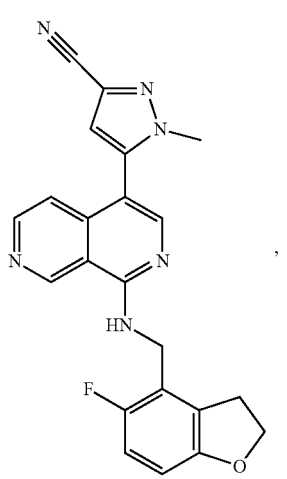
,
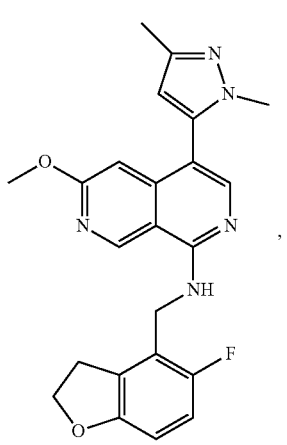
,
28
-continued
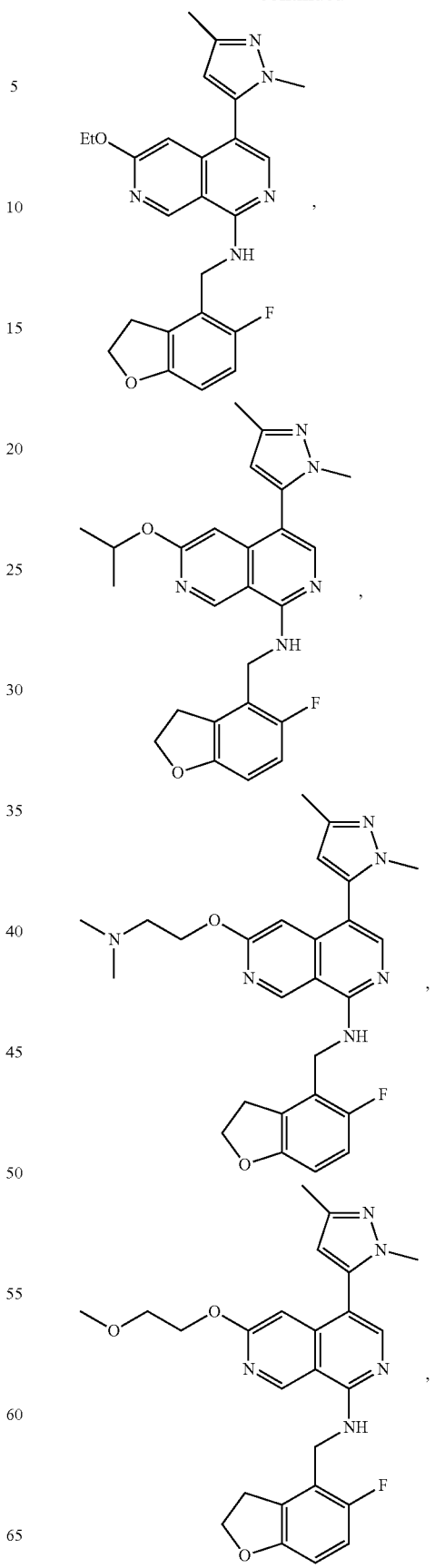

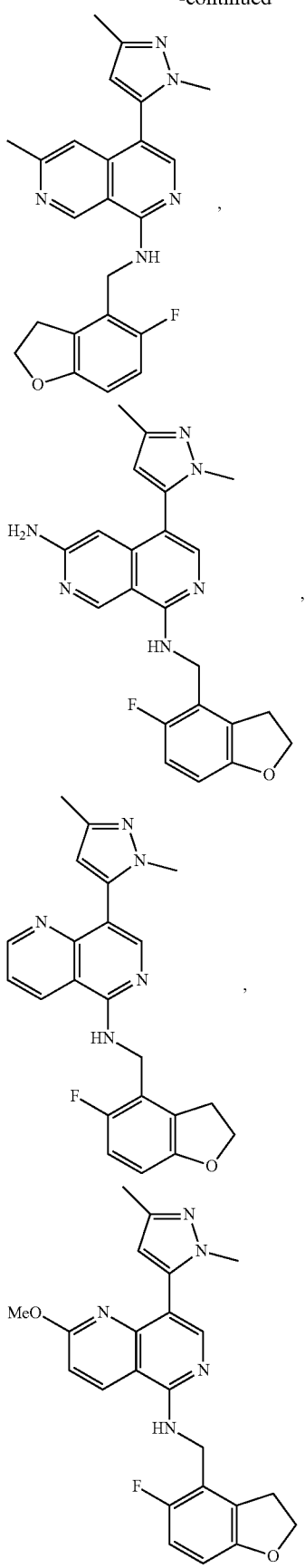
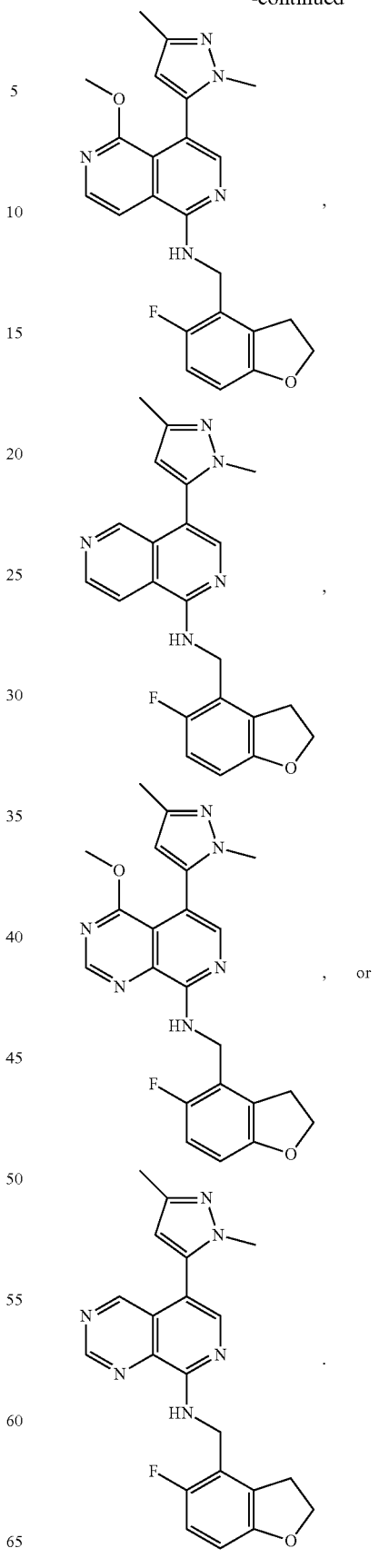

In one aspect of the invention, the compound is:

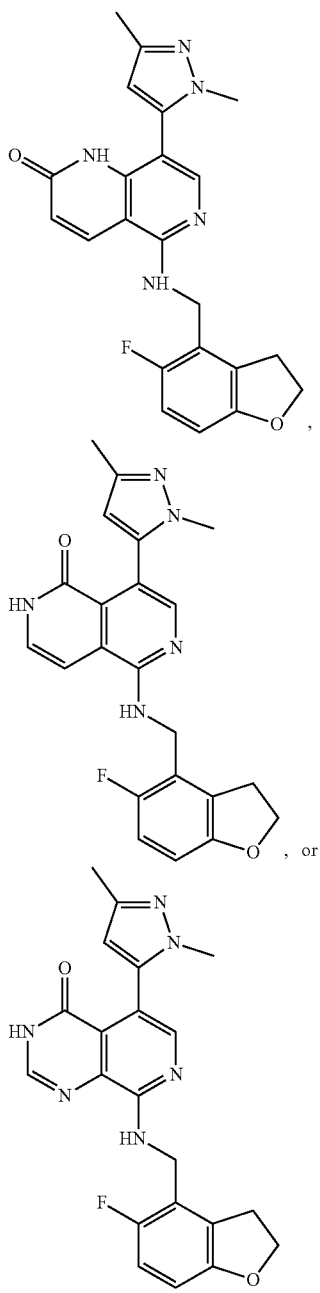

The compounds of the present invention can be used in pharmaceutical compositions.

Pharmaceutical Compositions

In another aspect, the invention provides pharmaceutical compositions comprising a PRC2 inhibitor according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain embodiments, compounds of the invention are administered intravenously in a hospital setting. In certain other embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

As used herein, the term "pharmaceutically acceptable salts" refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. A dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods described herein.

Methods of Use

In yet another aspect, the invention provides for methods for inhibiting PRC2 activity in a cell, comprising contacting the cell in which inhibition of PRC2 activity is desired with a therapeutically effective amount of a compound of the present invention, including Formula (I) and Formula (II), pharmaceutically acceptable salts thereof or pharmaceutical compositions containing the compound or pharmaceutically acceptable salt thereof.

The compositions and methods provided herein are particularly deemed useful for inhibiting PRC2 activity in a cell. In one embodiment, a cell in which inhibition of PRC2 activity is desired is contacted with a therapeutically effective amount of a compound of the present invention, including Formula (I) and Formula (II), to negatively modulate the activity of PRC2. In other embodiments, a therapeutically effective amount of pharmaceutically acceptable salt or pharmaceutical compositions containing the compound of Formula (I) and Formula (II) may be used.

By negatively modulating the activity of PRC2, particularly in cases for cells overexpressing the EZH2 enzyme or somatic mutations that activate the EZH2 enzyme, the methods are designed to restore normal cellular transcription expression patterns, e.g., by altering methylation pattern of H3K27, to inhibition undesired cellular proliferation resulting from enhanced PRC2 activity within the cell. The cells may be contacted in a single dose or multiple doses in accordance with a particular treatment regimen to affect the desired negative modulation of PRC2. The degree of mono- and dimethylation of histone H3K27 may be monitored in the cell using well known methods, including those described in Example A below, to assess the effectiveness of treatment and dosages may be adjusted accordingly by the attending medical practitioner.

In another aspect, methods of treating cancer comprising administering to a patient having cancer a therapeutically effective amount of a compound of the present invention, including Formula (I) and Formula (II), pharmaceutically acceptable salts thereof or pharmaceutical compositions comprising the compound or pharmaceutically acceptable salts thereof are provided.

The compositions and methods provided herein may be used for the treatment of a wide variety of cancer including tumors such as prostate, breast, brain, skin, cervical carcinomas, testicular carcinomas, etc More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is diffuse large B-cell lymphoma (DLBCL).

The concentration and route of administration to the patient will vary depending on the cancer to be treated. The compounds, pharmaceutically acceptable salts thereof and pharmaceutical compositions comprising such compounds and salts also may be co-administered with other antineoplastic compounds, e.g., chemotherapy, or used in combination with other treatments, such as radiation or surgical intervention, either as an adjuvant prior to surgery or postoperatively. The degree of mono- and dimethylation of histone H3K27 may be monitored in the patient using well known methods, including those described in Example A below, to access the effectiveness of treatment, along with other prognostic or biological factors, and dosages may be adjusted accordingly by the attending medical practitioner.

GENERAL REACTION SCHEME, INTERMEDIATES AND EXAMPLES

General Reaction Schemes

The compounds of the present invention may be prepared using commercially available reagents and intermediates in the synthetic methods and reaction schemes described herein, or may be prepared using other reagents and conventional methods well known to those skilled in the art.

For instance, intermediates for compounds and compounds of the present invention, including Formula (I) and Formula (II), may be prepared according to General Reaction Schemes I-IV:

General Reaction Scheme I

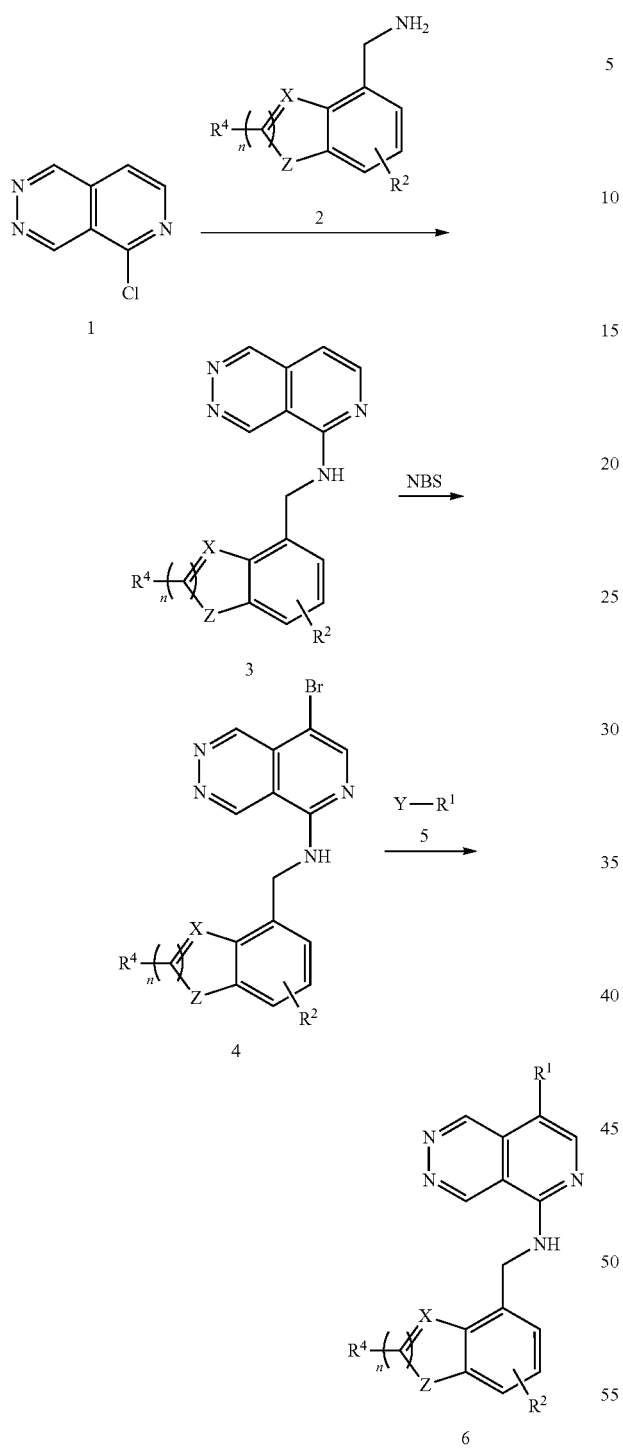

General Reaction Scheme II pound 4. The halide Compound 4 can then undergo a metal mediated reaction with a coupling partner, such as a boronic acid derivative, —Y—$R^1$ 5 in the presence of a suitable base, e.g., sodium carbonate, to form title compound Compound 6.

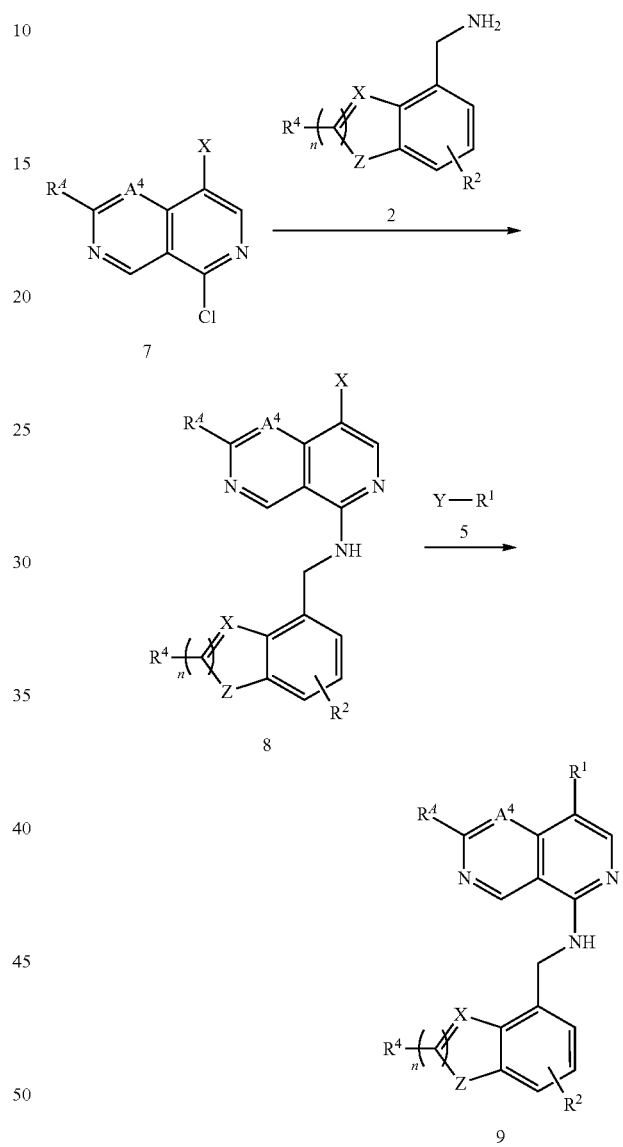

For General Reaction Scheme I, Compound 6 is an example of Formula (II) wherein $A^2$ and $A^3$ are both Nitrogen, and $A^1$ and $A^4$ are both $CR^A$, wherein $R^A$ is H. In this General Reaction Scheme I, 5-chloropyrido[3,4-d]pyridazine 1 is reacted with an amine such as $R^2$ optionally substituted intermediate amine 2, this reaction could for example be a nucleophilic substitution, to yield Compound 3. Compound 3 is then treated with a halogenating reagent, such as NBS, to provide the corresponding halide Compound 4. The halide Compound 4 can then undergo a metal mediated reaction with a coupling partner, such as a boronic acid derivative, —Y—$R^1$ 5 in the presence of a suitable base, e.g., sodium carbonate, to form title compound Compound 6.

For General Reaction Scheme II, Compound 9 is an example of Formula (II) wherein $A^2$ is Nitrogen, $A^4$ is either Nitrogen or $CR^A$, and both $A^1$ and $A^3$ are $CR^A$, wherein $R^A$ is H. In General Reaction Scheme II, 5-chloro-8-halopyrido [4,3-d]pyrimidine 7, where X can be Bromine or Iodine, is reacted with an amine such as $R^2$ optionally substituted intermediate amine 2, this reaction could for example be a nucleophilic substitution, to yield Compound 8. The halide Compound 8 can then undergo a metal mediated reaction with a coupling partner, such as a boronic acid derivative, Y—$R^1$ 5 in the presence of a suitable base, e.g., sodium carbonate, to form title compound, Compound 9.

General Reaction Scheme III

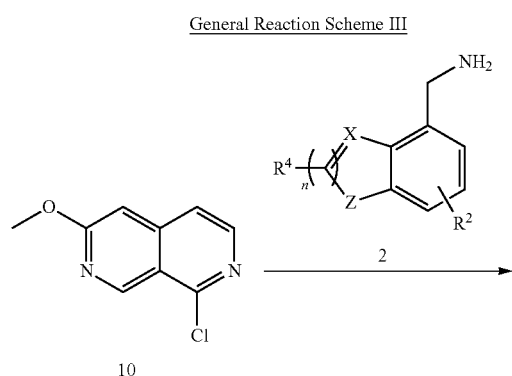

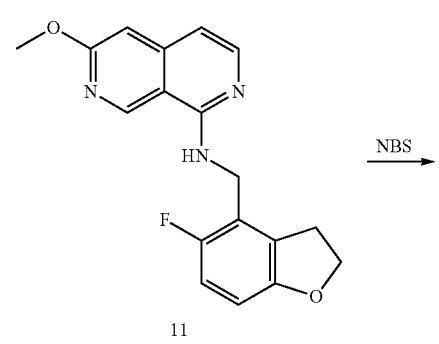

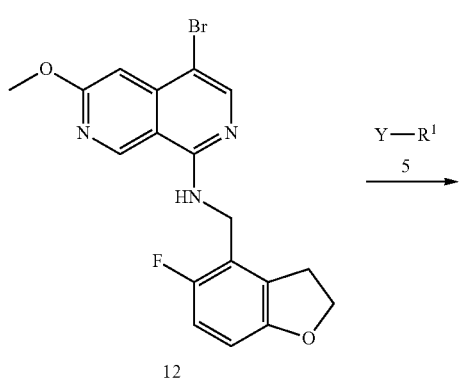

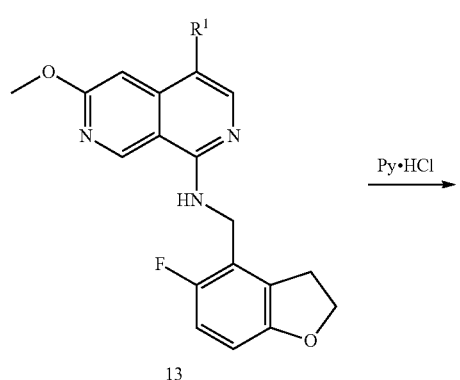

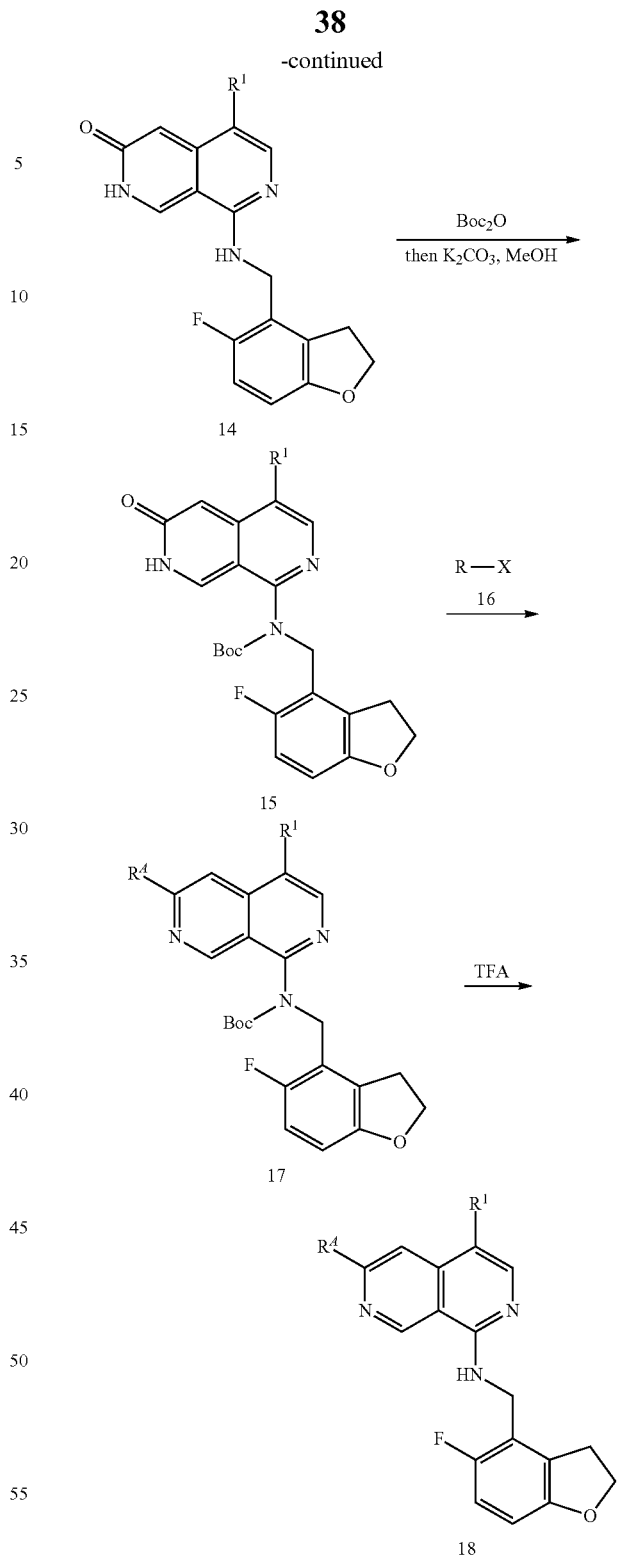

For General Reaction Scheme III, Compound 18 is an example of Formula (II) wherein $A^2$ is Nitrogen, $A^1$ and $A^4$ are both $CR^A$ wherein $R^A$ is H, and $A^3$ is $CR^A$ as defined in Formula (II). In General Reaction Scheme II, 1-chloro-6-methoxy-2,7-naphthyridine 10 is reacted with an amine such as $R^2$ optionally substituted intermediate amine 2, this reaction could for example be a nucleophilic substitution, to yield Compound 11. Compound 11 is then treated with a halogenating reagent, such as NBS, to provide the corresponding halide Compound 12. The halide Compound 12 can then undergo a metal mediated reaction with a coupling partner, such as a boronic acid derivative, Y—R$^1$ 5 in the presence of a suitable base, e.g., sodium carbonate, to form Compound 13. Compound 13 can then be treated with a weak acid, such as pyridine hydrochloride, to form Compound 14. Compound 14 can then be transformed to the monocarbamate via treatment with a decarbonate such as Boc2O and further treatment with a base such a potassium carbonate, within a protic solvent, for example methanol, to provide the monoprotected Compound 15. Compound 15 can be reacted with a halide R—X 16, this reaction could for example be a nucleophilic substitution reaction, to give Compound 17. The protecting group on Compound 17 could then be removed with an acid, such as TFA, to form the title compound, Compound 18.

General Reaction Scheme IV

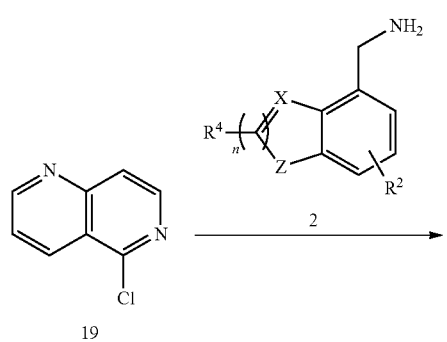

For General Reaction Scheme IV, Compound 22 is an example of Formula (II) wherein A$^4$ is Nitrogen, and A$^1$-A$^3$ are all three CR$^A$ wherein R$^A$ is H. In General Reaction Scheme IV, 5-chloro-1,6-naphthyridine 19 is reacted with an amine such as R$^2$ optionally substituted intermediate amine 2, this reaction could for example be a nucleophilic substitution, to yield Compound 20. Compound 20 is then treated with a halogenating reagent, such as NB S, to provide the corresponding halide Compound 21. The halide Compound 20 can then undergo a metal mediated reaction with a coupling partner, such as a boronic acid derivative, Y—R$^1$ 5 in the presence of a suitable base, e.g., sodium carbonate, to form title compound, Compound 22.

Intermediate A-1

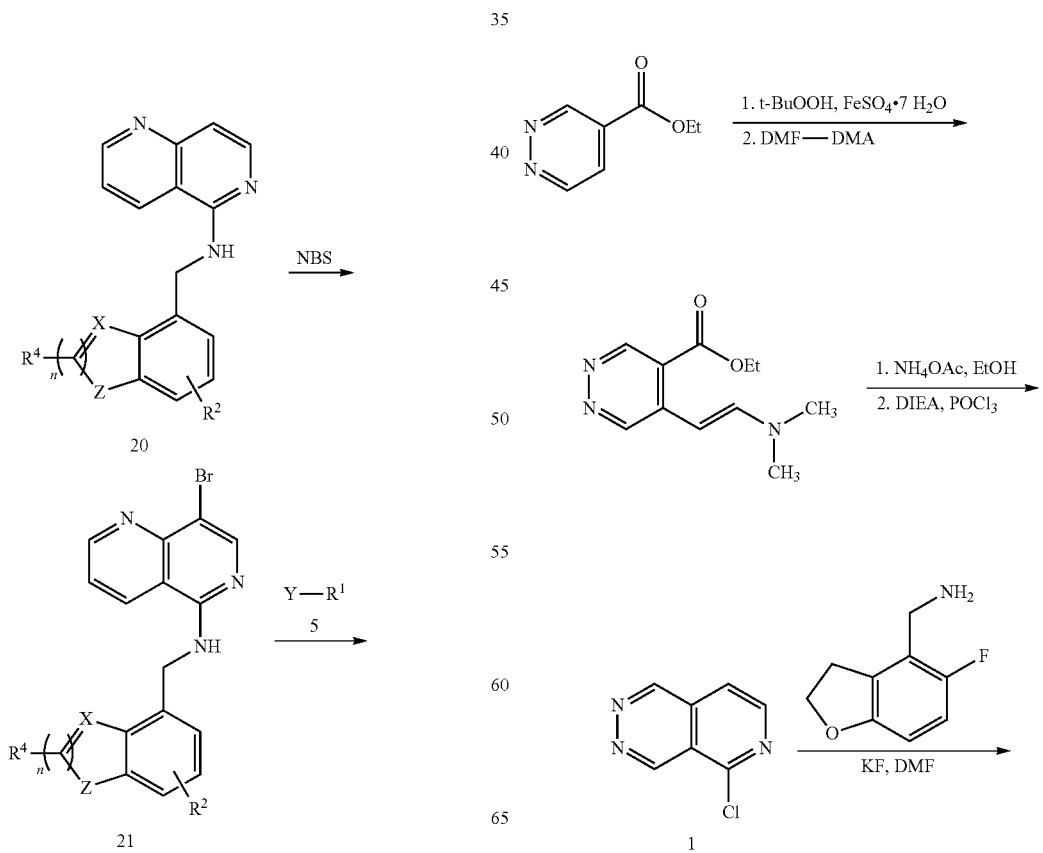

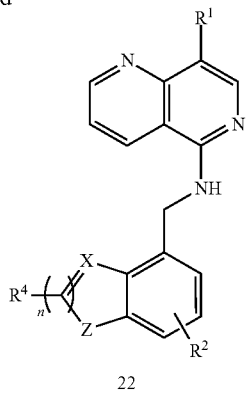

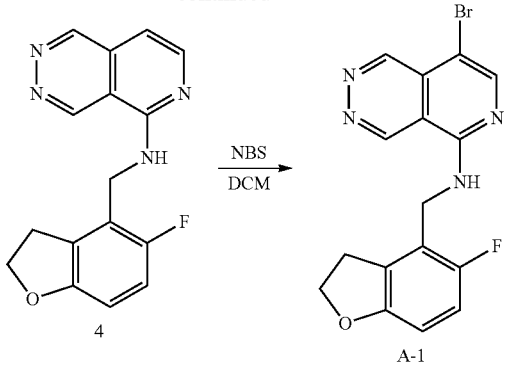

An exemplary Intermediate A, Intermediate A-1 (Compound 4 of General Reaction Scheme 1), may be used to synthesize compounds of Formula (II) wherein $A^2$ and $A^3$ are both Nitrogen, and $A^1$ and $A^4$ are both $CR^4$, where $R^4$ is H.

Step A: To a stirred solution of ethyl pyridazine-4-carboxylate (3.00 g, 19.7 mmol, 1.00 equiv.) in $H_2SO_4$ (75.0 mL, concentrated) at 15° C. was added 2-hydroperoxy-2-methyl-propane (5.33 g, 59.2 mmol, 5.67 mL, 3.00 equiv.) and a saturated aqueous solution of $FeSO_4 \cdot 7H_2O$ (16.5 g, 59.2 mmol, 3.00 equiv.) drop-wise simultaneously. After addition the mixture was stirred at 15° C. for 5 hours. The reaction mixture was then adjusted to pH=7 with $NH_3 \cdot H_2O$ and extracted with ethyl acetate (50.0 mL×3). The combined organic phases were washed with brine (100 mL×3), dried, and concentrated. The residue was purified by column chromatography ($SiO_2$, petroleum ether/ethyl acetate=10/1 to 2/1) to give ethyl 5-methylpyridazine-4-carboxylate (2.80 g, 16.9 mmol, 85.5% yield) as red oil.

A mixture of ethyl 5-methylpyridazine-4-carboxylate (2.80 g, 16.9 mmol, 1.00 equiv.) in DMF-DMA (20.1 g, 169 mmol, 22.4 mL, 10.0 equiv.) was stirred at 120° C. for 5 hours. The reaction mixture was then concentrated in vacuum. The residue was purified by column chromatography ($SiO_2$, petroleum ether/ethyl acetate=3/1 to 0/1) to give ethyl 5 ethyl (E)-5-(2-(dimethylamino)vinyl)pyridazine-4-carboxylate (2.80 g, 12.7 mmol, 75.1% yield) as a yellow solid.

Step B: To a solution of ethyl (E)-5-(2-(dimethylamino)vinyl)pyridazine-4-carboxylate (2.80 g, 12.7 mmol, 1.00 equiv.) in ethanol (50.0 mL) was added $NH_4OAc$ (9.75 g, 127 mmol, 10.0 equiv.) and the mixture was stirred at 90° C. for 1 hour. The reaction mixture was concentrated in vacuo. The residue was triturated with water, and the precipitate was dried in vacuum to give pyrido[3,4-d]pyridazin-5(6H)-one (1.50 g, 10.2 mmol, 80.6% yield) as a gray solid.

$^1$H NMR (400 MHz, DMSO-$d_6$) δ=11.55 (br s, 1H), 9.58 (d, J=1.6 Hz, 1H), 9.56 (s, 1H), 7.72 (d, J=7.2 Hz, 1H), 6.66 (d, J=6.8 Hz, 1H).

A mixture of pyrido[3,4-d]pyridazin-5(6H)-one (500 mg, 3.40 mmol, 1.00 equiv.) in $POCl_3$ (13.2 g, 86.1 mmol, 8.00 mL, 25.3 equiv.) and DIPEA (1.10 g, 8.50 mmol, 1.48 mL, 2.50 equiv.) was stirred at 100° C. for 1 hour. The reaction mixture was then poured into ice water and extracted with DCM (50.0 mL×2). The combined organic phases were washed with an aqueous solution of sodium bicarbonate and brine, then dried, and evaporated to give the crude product. The residue was purified by column chromatography ($SiO_2$, petroleum ether/ethyl acetate=4/1 to 2/1) to give 5-chloropyrido[3,4-d]pyridazine, Compound 1 (100 mg, 556 μmol, 16.4% yield, 92.0% purity) as a yellow solid, LC-MS [M+1]:166.1.

Step C: To a solution of 5-chloropyrido[3,4-d]pyridazine (125 mg, 695 μmol, 1.00 equiv.) in D-MF (3.00 mL) was added KF (161 mg, 2.78 mmol, 65.1 μL, 4.00 equiv.) and (5-fluoro-2,3-dihydrobenzofuran-4-yl)methanamine (Compound 4, 174 mg, 1.04 mmol, 1.50 equiv.), and the mixture was stirred at 120° C. for 1 hr under a nitrogen atmosphere. The reaction mixture was diluted with ethyl acetate (40.0 mL), washed with brine (20.0 mL×3), and the combined organic phases were dried and concentrated in vacuum. The crude product was purified by prep-TLC ($SiO_2$, dichloromethane/methanol=20/1) to give N-((5-fluoro-2,3-dihydrobenzofuran-4-yl)methyl)pyrido[3,4-d]pyridazin-5-amine (140 mg, 473 μmol, 68.0% yield) as a yellow solid. LC-MS [M+1]: 297.0.

Intermediate A-1: To a solution of N-((5-fluoro-2,3-dihydrobenzofuran-4-yl)methyl)pyrido[3,4-d]pyridazin-5-amine (0.12 g, 405 μmol, 1.00 equiv.) in DCM (6.00 mL) was added NBS (72.0 mg, 405 μmol, 1.00 equiv.) at 0° C. The mixture was stirred at 0° C. for 30 minutes. The reaction mixture was then quenched with water (2 mL), the organic phase was separated, dried over sodium sulfate, and concentrated in vacuum. The residue was purified by column chromatography ($SiO_2$, petroleum ether/ethyl acetate=3/1 to 1/0) to give 8-bromo-N-((5-fluoro-2,3-dihydrobenzofuran-4-yl)methyl)pyrido[3,4-d]pyridazin-5-amine (140 mg, 373 μmol, 92.1% yield) as a yellow solid. LC-MS [M+1]: 375.1.

Intermediate A-2

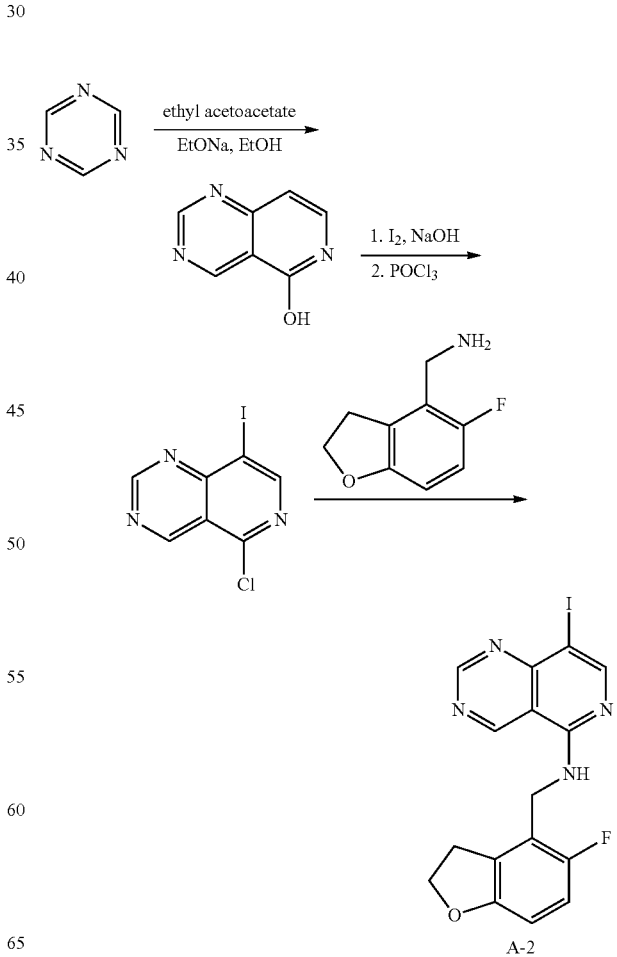

An exemplary Intermediate A, Intermediate A-2, may be used to synthesize compounds of Formula (II) wherein $A^2$ and $A^4$ are both Nitrogen, and $A^1$ and $A^3$ are both $CR^A$, where $R^A$ is H.

Step A: A mixture of ethyl 3-oxobutanoate (8.03 g, 61.8 mmol, 7.79 mL, 1.00 equiv.) and 1,3,5-triazine (5.00 g, 61.7 mmol, 1.00 equiv.) were added to a solution of freshly prepared sodium ethoxide (1.68 g, 24.7 mmol, 0.40 equiv.) in ethanol (18.0 mL) at 20° C. The reaction was heated at 90° C. for 3 hours under a nitrogen atmosphere, then the ethanol was removed under vacuum. Water (50.0 mL) was added to the reaction mixture and then the pH was adjusted with concentrated HCl until the solution was at pH=3. The mixture was filtered and solid was washed with acetone (20.0 mL) and dried to give pyrido[4,3-d]pyrimidin-5-ol (1.4 g, 9.52 mmol, 15.43% yield) as a yellow solid.

$^1$H NMR (400 MHz, DMSO-$d_6$) δ=11.87 (br, s, 1H), 9.41 (s, 1H), 9.32 (s, 1H), 7.72 (d, J=7.2 Hz, 1H), 6.57 (d, J=7.2 Hz, 1H).

Step B: $I_2$ (1.10 g, 4.34 mmol, 874 µL, 1.28 equiv.) was added to a suspension of pyrido[4,3-d]pyrimidin-5-ol (500 mg, 3.40 mmol, 1.00 equiv.) in sodium hydroxide (0.40 M, 17.0 mL, 2.00 equiv.). The reaction mixture was heated at 80° C. for 18 hours. The mixture was then cooled to 20° C. and the resulting precipitate was filtered. The collected solid was washed with water (15.0 mL), dried, and concentrated to give 8-iodopyrido[4,3-d]pyrimidin-5-ol (800 mg, 2.93 mmol, 86.22% yield) as a yellow solid.

$^1$H NMR (400 MHz, DMSO-$d_6$) δ=12.17 (br s, 1H), 9.42 (s, 1H), 9.33 (s, 1H), 8.13 (s, 1H).

A solution of 8-iodopyrido[4,3-d]pyrimidin-5-ol (300 mg, 1.10 mmol, 1.00 equiv.) in $POCl_3$ (14.9 g, 96.9 mmol, 9.00 mL, 88.1 equiv.) was heated at 100° C. for 48 hours. The reaction mixture was concentrated under reduced pressure and the residue was poured into ice water (10.0 mL). The resulting mixture treated with potassium carbonate (2 M, 10.0 mL) and extracted with ethyl acetate (20.0 mL×3). The combined organic layers were dried over sodium sulfate, filtered, and concentrated under reduced pressure to give 5-chloro-8-iodo-pyrido[4,3-d]pyrimidine (300 mg, 1.03 mmol, 93.67% yield) as a yellow solid which used without further purification.

Intermediate A-2: To a mixture of (5-fluoro-2,3-dihydrobenzofuran-4-yl)methanamine (86.0 mg, 515 µmol, 1.50 equiv.) and 5-chloro-8-iodo-pyrido[4,3-d]pyrimidine (100 mg, 343 µmol, 1.00 equiv.) in DMF (1.00 mL) was added potassium fluoride (59.8 mg, 1.03 mmol, 24.1 µL, 3.00 equiv.) in one portion at 20° C. under a $N_2$ atmosphere. The mixture was stirred at 120° C. for 2 hrs. Water (5.00 mL) was added to the reaction mixture and then extracted with ethyl acetate (5.00 mL×3), the combined organic phase was dried and concentrated to give N-[(5-fluoro-2,3-dihydrobenzofuran-4-yl)methyl]-8-iodopyrido[4,3-d]pyrimidin-5-amine (100 mg, 237 µmol, 69.0% yield) as a yellow solid.

$^1$H NMR (400 MHz, CDCl$_3$) δ=9.35 (s, 1H), 9.11 (s, 1H), 8.66 (s, 1H), 6.80-6.74 (t, J=8.8, 1H), 6.58 (dd, J=4.0, 8.4 Hz, 1H), 5.96 (t, J=4.4, 1H), 4.74 (d, J=5.6 Hz, 2H), 4.58-4.53 (m, 3H), 3.32 (t, J=8.8 Hz, 2H).

Intermediate A-3

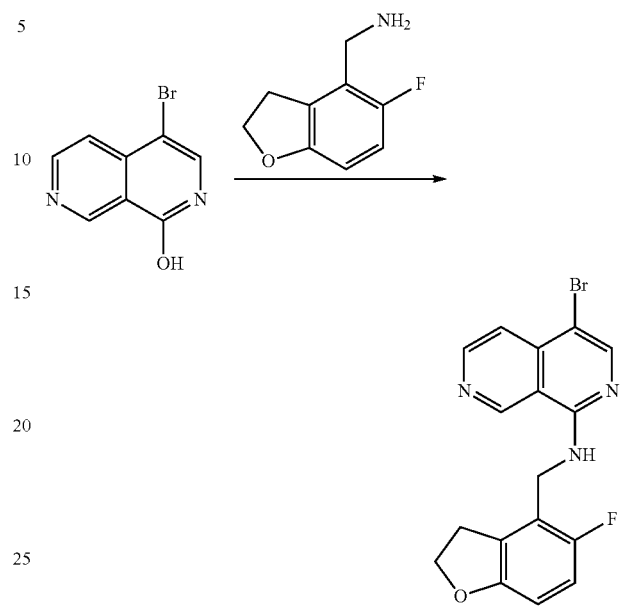

An exemplary Intermediate A, Intermediate A-3, may be used to synthesize compounds of Formula (II) wherein $A^2$ is Nitrogen, and $A^1$, $A^3$, and $A^4$ are all $CR^A$, where $R^A$ is H.

To a solution of 4-bromo-1-chloro-2,7-naphthyridine (100 mg, 411 µmol, 1.00 equiv.) and (5-fluoro-2,3-dihydrobenzofuran-4-yl)methanamine (82.5 mg, 493 µmol, 1.20 equiv.) in DMF (1.00 mL) was added DIEA (106 mg, 821 µmol, 143 µL, 2.00 equiv.). The mixture was stirred at 85° C. for 1 hour. After completion of the reaction, the mixture was triturated in water (5.00 mL), and the solids were filtered, collected, and dried under vacuum to give 4-bromo-N-[(5-fluoro-2,3-dihydrobenzofuran-4-yl)methyl]-2,7-naphthyridin-1-amine (130 mg) as a gray solid which was used without further purification. LC-MS [M+1]: 374.0.

Intermediate A-4

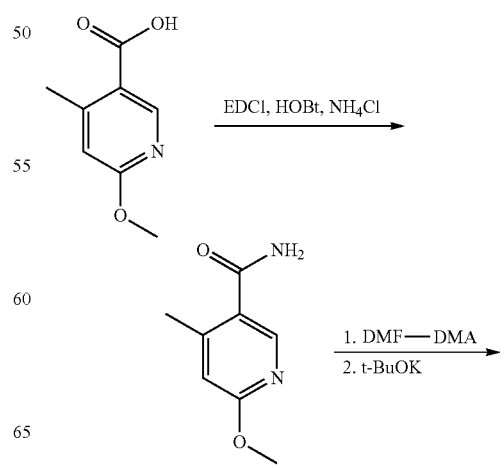

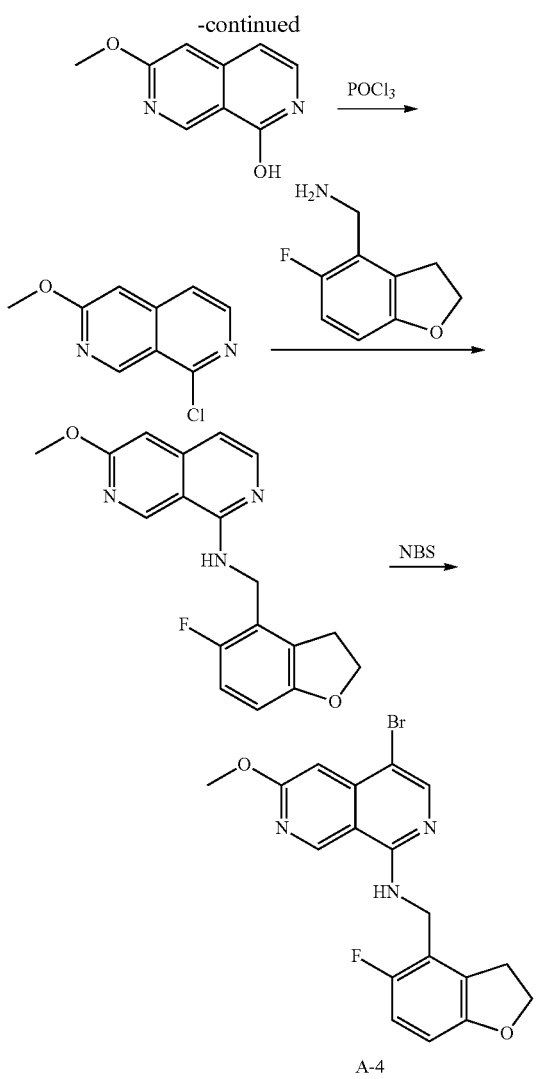

An exemplary Intermediate A, Intermediate A-4 (Compound 12 of General Reaction Scheme III), may be used to synthesize compounds of Formula (II) wherein $A^2$ is N, $A^1$ and $A^4$ are both $CR^A$ wherein this example $R^A$ is H, and $A^3$ is $CR^A$ wherein this example $R^A$ is alkoxy.

Step A: To a mixture of 6-methoxy-4-methylnicotinic acid (1.00 g, 5.98 mmol, 1.00 equiv.) and 4-methylmorpholine (1.51 g, 15.0 mmol, 1.64 mL, 2.50 equiv.) in DMF (20.0 mL) was added ammonium chloride (1.92 g, 36.0 mmol, 6.00 equiv.), EDCI (1.72 g, 8.97 mmol, 1.50 equiv.) and HOBt (1.21 g, 8.97 mmol, 1.50 equiv.) in one portion at 25° C. under an N2 atmosphere. The mixture was stirred at 25° C. for 2 hours. After this time, water (20.0 mL) was added to the reaction mixture and then extracted with ethyl acetate (10.0 mL×5). The combined organic phases were washed with brine, dried over sodium sulfate, filtered, and concentrated to give a residue. The residue was triturated with petroleum ether (10.0 mL) to give a suspension, filtered, and the filter cake was washed with petroleum ether (3 mL), then collected and concentrated to give 6-methoxy-4-methylnicotinamide (800 mg, 4.81 mmol, 80.5% yield) as an off-white solid.

$^1$H NMR (400 MHz, DMSO-d$_6$) δ=8.22 (s, 1H), 7.72 (s, br, 1H), 7.35 (s, br, 1H), 6.69 (s, 1H), 3.92-3.80 (m, 3H), 2.37 (s, 3H).

Step B: A mixture of 6-methoxy-4-methylnicotinamide (800 mg, 4.81 mmol, 1.00 equiv.) and DMF-DMA (12.9 g, 108 mmol, 14.4 mL, 22.5 equiv.) in a medium pressure flask was heated to 115° C. for 1 hour. DMF-DMA was removed under reduce pressure to give a residue. The residue was triturated with petroleum ether (2.00 mL) to give N-((dimethylamino)methylene)-6-methoxy-4-methylnicotinamide (900 mg, 4.07 mmol, 84.5% yield) as a white solid.

$^1$H NMR (400 MHz, CDCl$_3$) δ=9.02 (s, 1H), 8.50 (s, 1H), 6.49 (s, 1H), 3.89 (s, 3H), 3.10 (d, J=5.6 Hz, 6H), 2.55 (s, 3H).

To a solution of N-((dimethylamino)methylene)-6-methoxy-4-methylnicotinamide (800 mg, 3.62 mmol, 1.00 equiv.) in THF (16 mL) was added t-BuOK (1.00 M, 4.70 mL, 1.30 equiv.). The reaction mixture was stirred for 3 hrs at 80° C., then water (10 mL) was added to the reaction mixture and further acidified to pH=5 with HCl (2.00 M). The reaction was extracted with ethyl acetate (5 mL×8). The organic phase was separated, dried, and then concentrated to give 6-methoxy-2,7-naphthyridin-1-ol (500 mg, 2.84 mmol, 78.5% yield) as a white solid.

$^1$H NMR (400 MHz, CD$_3$OD) δ=9.14 (s, 1H), 7.27 (d, J=7.2 Hz, 1H), 6.89 (s, 1H), 6.54 (d, J=7.6 Hz, 1H), 4.04 (s, 3H).

Step C: A solution of 6-methoxy-2,7-naphthyridin-1-ol (500 mg, 2.84 mmol, 1.00 equiv.) and DIEA (733 mg, 5.68 mmol, 988 µL 2.00 equiv.) in phosphorus oxychloride (8.25 g, 53.8 mmol, 5.00 mL, 19.0 equiv.) was stirred at 100° C. for 2 hours. Phosphorus oxychloride was removed under reduce pressure to give a reside, then ethyl acetate (10.0 mL) was added to the reaction mixture and then quenched the reaction with ice-water (2.00 mL). The organic phase was separated and washed with saturated sodium bicarbonate (10.0 mL), then brine (10.0 mL), dried, and concentrated to give crude 1-chloro-6-methoxy-2,7-naphthyridine (500 mg) as a yellow solid.

Step D: To a mixture of 1-chloro-6-methoxy-2,7-naphthyridine (500 mg, 2.57 mmol, 1.00 equiv.) and (5-fluoro-2,3-dihydrobenzofuran-4-yl)methanamine (472 mg, 2.83 mmol, 1.10 equiv.) in DMF (1.00 mL) was added DIEA (996 mg, 7.71 mmol, 1.34 mL, 3.00 equiv.) in one portion at 20° C. under an N$_2$ atmosphere. The mixture was stirred at 100° C. for 2 hours. The reaction mixture was quenched by addition water (3.00 mL) at 20° C., and then diluted with ethyl acetate (3 mL) and extracted with ethyl acetate (3.00 mL×3). The combined organic layers were washed with brine (10.0 mL), dried over anhydrous sodium sulfate, filtered and concentrated under reduced pressure to give a residue. The residue was purified by column (SiO$_2$, petroleum ether/ethyl acetate=1/1) to give N-((5-fluoro-2,3-dihydrobenzofuran-4-yl)methyl)-6-methoxy-2,7-naphthyridin-1-amine (400 mg, 1.03 mmol, 40.2% yield, 84.0% purity) as a white solid.

$^1$H NMR (400 MHz, CDCl$_3$) δ=8.87 (s, 1H), 7.99 (d, J=6.0 Hz, 1H), 6.89-6.81 (m, 1H), 6.79 (s, 1H), 6.76 (d, J=5.6 Hz, 1H), 6.68-6.61 (m, 1H), 5.72 (br s, 1H), 4.82 (d, J=5.6 Hz, 2H), 4.64-4.55 (m, 3H), 4.02 (s, 3H), 3.38 (t, J=8.8 Hz, 2H).

Intermediate A-4: A mixture of N-((5-fluoro-2,3-dihydrobenzofuran-4-yl)methyl)-6-methoxy-2,7-naphthyridin-1-amine (120 mg, 369 µmol, 1.00 equiv.) and NBS (45.0 mg, 253 µmol, 0.07 equiv.) in dichloromethane (1.50 mL) was stirred at 0° C. for 0.5 hour. The reaction mixture was evaporated to give a residue. The residue was purified by prep-TLC (SiO$_2$, petroleum ether/ethyl acetate=1/1) to give 4-bromo-N-((5-fluoro-2,3-dihydrobenzofuran-4-yl)

methyl)-6-methoxy-2,7-naphthyridin-1-amine (180 mg, 445 µmol, 85.2% yield) as a light yellow solid. LC-MS [M+1]: 404.0.

Intermediate A-5

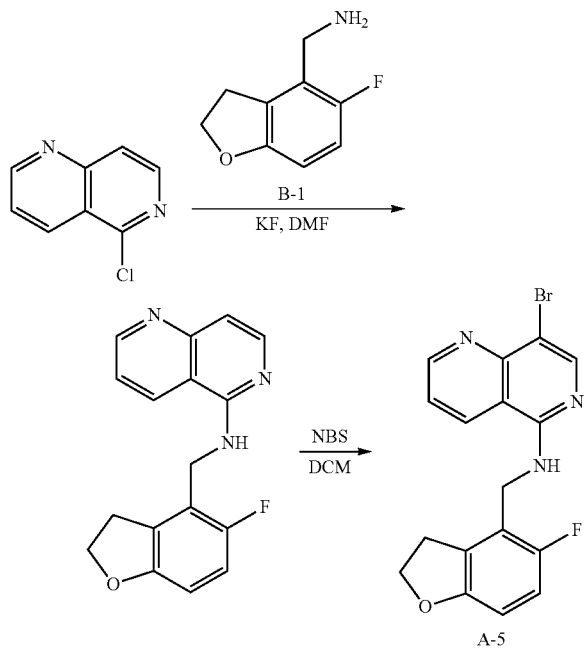

An exemplary Intermediate A, Intermediate A-5 (Compound 21 of General Reaction Scheme IV, may be used to synthesize compounds of Formula (II) wherein $A^4$ is Nitrogen, $A^1$-$A^3$ are all three $CR^4$, wherein $R^4$ is H.

Step A: To a solution of 5-chloro-1,6-naphthyridine (60.0 mg, 365 µmol, 1.00 equiv.) in dimethyl sulfoxide (1.00 mL) was added potassium fluoride (42.4 mg, 729 µmol, 17.1 µL, 2.00 equiv.) and (5-fluoro-2,3-dihydrobenzofuran-4-yl) methanamine (73.1 mg, 437 µmol, 1.20 equiv.). The mixture was stirred at 130° C. for 1 hour. The mixture was poured into ice-water (5.00 mL) and stirred for 15 min. The aqueous phase was extracted with ethyl acetate (5.00 mL×3). The combined organic phase was washed with brine (5.00 mL×3), dried with anhydrous sodium sulfate, filtered and concentrated in vacuum. The residue was purified by prep-TLC ($SiO_2$, petroleum ether/ethyl acetate=3/1) to give N-((5-fluoro-2,3-dihydrobenzofuran-4-yl)methyl)-1,6-naphthyridin-5-amine (70.0 mg, 237 µmol, 65.0% yield) as a white solid.

$^1$H NMR (400 MHz, DMSO-$d_6$) δ=8.91 (dd, J=1.6, 4.4 Hz, 1H), 8.72 (d, J=8.4 Hz, 1H), 8.08 (d, J=6.0 Hz, 1H), 7.98 (t, J=5.2 Hz, 1H), 7.48 (dd, J=4.4, 8.4 Hz, 1H), 6.98 (d, J=6.0 Hz, 1H), 6.93-6.86 (m, 1H), 6.64 (dd, J=4.0, 8.8 Hz, 1H), 4.69 (d, J=5.2 Hz, 2H), 4.49 (t, J=8.8 Hz, 2H), 3.24 (t, J=8.8 Hz, 2H). LC-MS [M+1]: 295.9.

To a solution of N-((5-fluoro-2,3-dihydrobenzofuran-4-yl)methyl)-1,6-naphthyridin-5-amine (50.0 mg, 169 µmol, 1.00 equiv.) in DCM (0.50 mL) was added N-bromosuccinimide (27.1 mg, 152 µmol, 0.90 equiv.). The mixture was stirred at 0° C. for 1 hour. The mixture was concentrated in vacuum to give a residue. The residue was purified by prep-TLC ($SiO_2$, petroleum ether/ethyl acetate=2/1) to give 8-bromo-N-((5-fluoro-2,3-dihydrobenzofuran-4-yl) methyl)-1,6-naphthyridin-5-amine (52.0 mg, 139 µmol, 82.1% yield) as a white solid.

$^1$H NMR (400 MHz, DMSO-$d_6$) δ=9.03 (dd, J=1.2, 4.4 Hz, 1H), 8.79 (dd, J=1.2, 8.4 Hz, 1H), 8.32 (s, 1H), 8.23 (br t, J=5.2 Hz, 1H), 7.61 (dd, J=4.4, 8.4 Hz, 1H), 6.94-6.86 (m, 1H), 6.65 (dd, J=4.0, 8.8 Hz, 1H), 4.67 (d, J=5.2 Hz, 2H), 4.50 (t, J=8.8 Hz, 2H), 3.23 (t, J=8.8 Hz, 2H).

Intermediate B-1

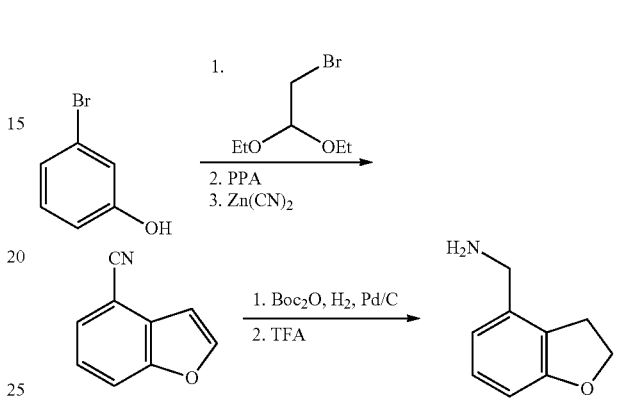

An exemplary Intermediate B, Intermediate B-1, may be used to synthesize compounds of Formula I or Formula II wherein Z is O, n is one, X is $C(R^5)_2$, and ═══ is a single bond. A mixture of 3-bromophenol (10.0 g, 57.8 mmol, 1.00 equiv) and 2-bromo-1,1-diethoxy-ethane (13.7 g, 69.4 mmol, 10.4 mL, 1.20 equiv) in DMF (100 mL) was added potassium carbonate (24.0 g, 173 mmol, 3.00 equiv). The resultant mixture was stirred at 110° C. for 12 h under a nitrogen atmosphere. The reaction mixture was diluted with petroleum ether (100 mL) and washed with brine (50.0 mL×4), dried over anhydrous sodium sulfate, filtered and concentrated under reduced pressure to give a residue. The crude material was purified by column chromatography (petroleum ether) to afford 1-bromo-3-(2,2-diethoxyethoxy) benzene (17.0 g, 48.2 mmol, 83.4% yield, 82.0% purity) as a light yellow oil.

$^1$H NMR (400 MHz, CDCl$_3$) δ=7.17-7.07 (m, 3H), 6.88-6.84 (m, 1H), 4.82 (t, J=5.2 Hz, 1H), 3.99 (d, J=5.2 Hz, 2H), 3.80-3.74 (m, 1H), 3.80-3.73 (m, 2H), 3.68-3.61 (m, 2H), 1.25 (t, J=7.2 Hz, 6H).

To a solution of polyphosphoric acid (21.5 g, 63.6 mmol, 1.50 equiv) in toluene (80.0 mL) was added 1-bromo-3-(2, 2-diethoxyethoxy)benzene (15.0 g, 42.5 mmol, 1.00 equiv) at 90° C. The mixture was stirred at 90° C. for 2 h and then concentrated under reduced pressure to give a residue. The crude material was purified by column chromatography (petroleum ether) to afford 4-bromobenzofuran (5.20 g, 13.2 mmol, 31.0% yield, 50.0% purity) as a yellow oil.

$^1$H NMR (400 MHz, CDCl$_3$) δ=7.70 (s, 1H), 7.67 (d, J=2.0 Hz, 1H), 7.61 (d, J=2.4 Hz, 1H), 7.47 (d, J=8.4 Hz, 2H), 7.41 (d, J=8.0 Hz, 1H), 7.37 (dd, J=1.6, 8.4 Hz, 1H), 7.21-7.15 (m, 1H), 6.85-6.80 (m, 1H), 6.78-6.73 (m, 1H).

To a solution of 4-bromobenzofuran (5.20 g, 13.2 mmol, 1.00 equiv) in DMAC (50.0 mL) was added zinc cyanide (6.85 g, 58.3 mmol, 4.42 equiv) and Pd(PPh$_3$)$_4$ (1.52 g, 1.32 mmol, 0.100 equiv). The mixture was stirred at 140° C. for 12 h under a nitrogen atmosphere. The reaction mixture was diluted with ethyl acetate (80.0 mL), washed with brine (50.0 mL×3), dried over anhydrous sodium sulfate, filtered and concentrated under reduced pressure to give a residue.

The crude material was purified by column chromatography (petroleum ether/ethyl acetate=50/1 to 0/1) to afford benzofuran-4-carbonitrile (1.60 g, 10.1 mmol, 76.2% yield, 90.0% purity) as a light-yellow oil.

1H NMR (400 MHz, CDCl3) δ=7.80 (d, J=2.0 Hz, 1H), 7.75 (d, J=8.4 Hz, 1H), 7.60 (d, J=8.0 Hz, 1H), 7.38 (t, J=8.4 Hz, 1H), 7.03-7.00 (m, 1H).

To a solution of benzofuran-4-carbonitrile (750 mg, 4.72 mmol, 1.00 equiv) in methyl alcohol (10.0 mL) was added Boc$_2$O (3.09 g, 14.2 mmol, 3.00 equiv) and Pd/C (4.72 mmol, 10.0 w. %, 1.00 equiv). The mixture was stirred at 30° C. for 24 h under hydrogen (50.0 psi). The reaction mixture was filtered and concentrated under reduced pressure to give the crude material, which was purified by column chromatography (petroleum ether/ethyl acetate=1/0 to 50/1) to afford tert-butyl N-(2,3-dihydrobenzofuran-4-ylmethyl) carbamate (140 mg, 562 μmol, 11.9% yield) as a colorless oil.

$^1$H NMR (400 MHz, CDCl$_3$) δ=7.10 (t, J=8.0 Hz, 1H), 6.74 (dd, J=8.0, 14.0 Hz, 2H), 4.75 (br s, 1H), 4.59 (t, J=8.8 Hz, 2H), 4.28 (br d, J=5.6 Hz, 2H), 3.20 (t, J=8.8 Hz, 2H), 1.47 (s, 9H).

To a solution of tert-butyl N-(2,3-dihydrobenzofuran-4-ylmethyl) carbamate (140 mg, 562 μmol, 1.00 equiv) in DCM (2.00 mL) was added TFA (640 mg, 5.62 mmol, 416 μL, 10.0 equiv). The mixture was stirred at 25° C. for 1 h. The reaction mixture was diluted with DCM (10.0 mL) and was added to a saturated potassium carbonate aqueous solution (10.0 mL). The biphasic mixture was stirred at 25° C. for 0.5 h. The organic phase was separated, dried over sodium sulfate, concentrated in vacuo to afford 2,3-dihydrobenzofuran-4-ylmethanamine (80.0 mg, 483 μmol, 85.9% yield, 90.0% purity) as a yellow solid.

1H NMR (400 MHz, CDCl3) δ=7.13 (t, J=8.0 Hz, 1H), 6.84 (d, J=7.6 Hz, 1H), 6.72 (d, J=8.0 Hz, 1H), 4.60 (t, J=8.8 Hz, 2H), 3.82 (s, 2H), 3.20 (t, J=8.8 Hz, 2H).

Intermediate B-2

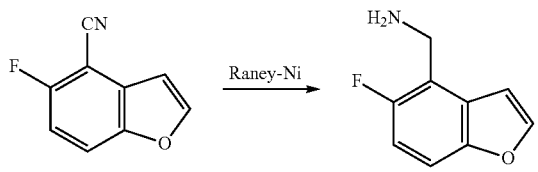 [SMILES: N#Cc1c(F)ccc2occc12 ; NCc1c(F)ccc2occc12]

A second exemplary Intermediate B, Intermediate B-2, may be used to synthesize compounds of Formula (I) or Formula (II) wherein Z is O, n is one, X is CR$^5$, and ------ is a double bond. To a mixture of 5-fluorobenzofuran-4-carbonitrile (250 mg, 1.47 mmol, 1.00 equiv) and Raney-Ni (126 mg, 1.47 mmol, 1.00 equiv) in methyl alcohol (6.60 mL) was added ammonium hydroxide (1.60 mL). The mixture was purged with nitrogen and stirred at 25° C. for 12 h under a hydrogen atmosphere. The reaction mixture was filtered and concentrated under reduced pressure to afford (5-fluorobenzofuran-4-yl) methanamine (220 mg, 1.20 mmol, 81.3% yield, 90.0% purity) as a brown oil.

$^1$H NMR (400 MHz, CDCl$_3$) δ=7.67 (s, 1H), 7.33 (br d, J=5.6 Hz, 1H), 7.04 (br t, J=9.6 Hz, 1H), 6.90 (s, 1H), 4.54-3.78 (m, 2H).

Intermediate B-3

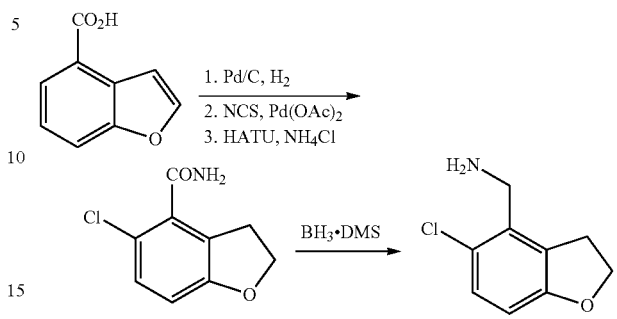

A third exemplary Intermediate B, Intermediate B-3, may be used to synthesize compounds of formula I wherein Z is O, n is one, X is C(R$^5$)$_2$, and ------ is a single bond. To a solution of benzofuran-4-carboxylic acid (900 mg, 5.55 mmol, 1 equiv) in MeOH (9.00 mL) was added palladium on activated carbon (20.0 mg, 555 μmol, 10.0 wt %, 0.10 equiv) under nitrogen. The vessel was evacuated and purged with hydrogen several times. The mixture was stirred at 25° C. for 12 h under hydrogen (50.0 psi). The reaction mixture was filtered and the filtrate was concentrated in vacuo to afford 2,3-dihydrobenzofuran-4-carboxylic acid (750 mg, 3.66 mmol, 65.9% yield, 80.0% purity) as a white solid.

$^1$H NMR (400 MHz, DMSO-d$_6$) δ=7.38 (d, J=8.0 Hz, 1H), 7.20 (t, J=8.0 Hz, 1H), 6.97 (d, J=8.0 Hz, 1H), 4.54 (t, J=8.8 Hz, 2H), 3.45 (br t, J=8.8 Hz, 2H).

To a solution of 2,3-dihydrobenzofuran-4-carboxylic acid (750 mg, 3.66 mmol, 1.00 equiv) in DMF (1.00 mL) was added Pd(OAc)$_2$ (82.1 mg, 366 μmol, 0.10 equiv) and NCS (586 mg, 4.39 mmol, 1.20 equiv). The reaction was stirred at 110° C. for 12 h under an atmosphere of nitrogen. The reaction mixture was filtered and concentrated in vacuo and the resultant residue was purified by silica gel chromatography (petroleum ether/ethyl acetate=5/1 to dichloromethane/methanol=10/1) to afford 5-chloro-2,3-dihydrobenzofuran-4-carboxylic acid (600 mg, crude) as a yellow oil. LC-MS: [M+1] 198.9.

To a solution of 5-chloro-2,3-dihydrobenzofuran-4-carboxylic acid (600 mg, 3.02 mmol, 1.00 equiv) in DMF (5.00 mL) was added ammonium chloride (242 mg, 4.53 mmol, 1.50 equiv), HATU (2.30 g, 6.04 mmol, 2.00 equiv), DIEA (1.17 g, 9.06 mmol, 1.58 mL, 3.00 equiv). The reaction mixture was stirred at 25° C. for 12 h and concentrated in vacuo to give the crude material, which was purified by silica gel chromatography (petroleum ether/ethyl acetate=10/1 to 1/1) to afford 5-chloro-2,3-dihydrobenzofuran-4-carboxamide (700 mg, 2.83 mmol, 93.8% yield, 80.0% purity) as a white solid.

$^1$H NMR (400 MHz, DMSO-d$_6$) δ=7.87 (br s, 1H), 7.63 (br s, 1H), 7.17 (d, J=8.4 Hz, 1H), 6.79 (d, J=8.4 Hz, 1H), 4.58 (t, J=8.8 Hz, 2H), 3.18 (t, J=8.8 Hz, 2H).

To a solution of 5-chloro-2,3-dihydrobenzofuran-4-carboxamide (300 mg, 1.21 mmol, 1.00 equiv) in THF (5.00 mL) was added dropwise BH$_3$-DMS (10.0 M, 607 μL, 5.00 equiv). The reaction was stirred at 70° C. for 2.5 h, quenched with Me-0H (5.00 mL) and concentrated in vacuo to provide a residue. To the residue was added water (20.0 mL) and the mixture was extracted with DCM (20.0 mL×3). The combined organic phase was washed with brine (20.0 mL×2), dried over anhydrous sodium sulfate, filtered and concentrated to afford (5-chloro-2,3-dihydrobenzofuran-4-yl)methanamine (240 mg, crude) as a brown oil. LC-MS: [M−16] 167.1.

Intermediate B-4

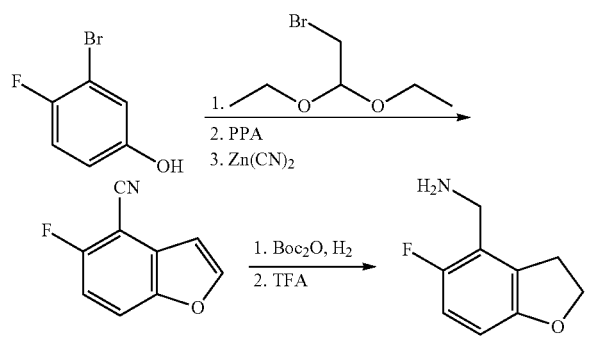

A fourth exemplary Intermediate B, Intermediate B-4, may be used to synthesize compounds of formula I wherein Z is O, n is one, X is C(R⁵)₂, and ------ is a single bond. To a solution of 3-bromo-4-fluoro-phenol (100 g, 524 mmol, 1.00 equiv) and 2-bromo-1,1-diethoxy-ethane (124 g, 628 mmol, 94.5 mL, 1.20 equiv) in DMF (600 mL) was added potassium carbonate (217 g, 1.57 mol, 3.00 equiv). The mixture was stirred at 110° C. for 12 h under an atmosphere of nitrogen. The reaction mixture was diluted with ethyl acetate (500 mL), washed with brine (500 ml×5) and concentrated at reduced pressure to provide a residue. The residue was purified by column chromatography (petroleum ether/ethyl acetate=1/0 to 20/1) to afford 2-bromo-4-(2,2-diethoxyethoxy)-1-fluoro-benzene (171 g, 501 mmol, 95.7% yield, 90.0% purity) as a light-yellow oil.

$^1$H NMR (400 MHz, CDCl₃) δ=7.12 (dd, J=2.8, 5.6 Hz, 1H), 7.06-6.98 (m, 1H), 6.84 (td, J=3.2, 9.2 Hz, 1H), 4.81 (t, J=5.2 Hz, 1H), 3.96 (d, J=5.2 Hz, 2H), 3.81-3.72 (m, 2H), 3.68-3.59 (m, 2H), 1.25 (t, J=7.2 Hz, 6H).

To a solution of PPA (254 g, 752 mmol, 1.50 equiv) in toluene (1.30 L) was added 2-bromo-4-(2,2-diethoxyethoxy)-1-fluoro-benzene (171 g, 501 mmol, 1.00 equiv) at 90° C. The mixture was stirred at 95° C. for 2 h and concentrated at reduced pressure to provide a residue. The residue was purified by column chromatography (petroleum ether) to give 4-bromo-5-fluoro-benzofuran (87.3 g, 203 mmol, 40.5% yield, 50.0% purity) as a yellow oil. To a mixture of 4-bromo-5-fluoro-benzofuran (85.5 g, 398 mmol, 1.00 equiv) and 6-bromo-5-fluoro-benzofuran (85.5 g, 398 mmol, 1.00 equiv) in DMAC (1.50 L) was added zinc cyanide (31.1 g, 264 mmol, 0.67 equiv) and Pd(PPh₃)₄ (23.0 g, 19.9 mmol, 0.05 equiv). The mixture was stirred at 90° C. for 12 h under an atmosphere of nitrogen. The reaction mixture was diluted with ethyl acetate (1.00 L) and filtered. The filtrate was washed with brine (1.00 L×3) and the organic layer was concentrated at reduced pressure to provide a residue. The residue was purified by column chromatography (petroleum ether/ethyl acetate=1/0 to 50/1) to afford 4-bromo-5-fluoro-benzofuran (78 g, crude) as a white solid.

To a solution of 4-bromo-5-fluoro-benzofuran (87.3 g, 203 mmol, 1.00 equiv) in DMAC (600 mL) was added zinc cyanide (94.6 g, 805 mmol, 3.97 equiv) and Pd(PPh₃)₄ (23.5 g, 20.3 mmol, 0.10 equiv). The mixture was stirred at 110° C. for 12 h under an atmosphere of nitrogen. The reaction mixture was diluted with ethyl acetate (500 mL), washed with brine (400 mL×5), dried over anhydrous sodium sulfate, filtered and concentrated at reduced pressure to provide a residue. The residue was purified by column chromatography (petroleum ether/ethyl acetate=1/0 to 50/1) to afford 5-fluorobenzofuran-4-carbonitrile (20.0 g, 118 mmol, 58.1% yield, 95.0% purity) as a white solid.

$^1$H NMR (400 MHz, CDCl₃) δ=7.84 (d, J=2.0 Hz, 1H), 7.73-7.67 (m, 1H), 7.14 (t, J=9.2 Hz, 1H), 7.02-6.96 (m, 1H).

To a solution of 5-fluorobenzofuran-4-carbonitrile (19.6 g, 116 mmol, 1.00 equiv) in methyl alcohol (1.00 L) was added di-tert-butyl dicarbonate (75.7 g, 347 mmol, 3.00 equiv) and Pd/C 10 w. % (1.16 g). The mixture was stirred at 35° C. for 24 h under an atmosphere of hydrogen gas (50.0 psi). The reaction mixture was filtered and concentrated at reduced pressure to provide a residue. The residue was purified by column chromatography (petroleum ether/ethyl acetate=1/0 to 3/1) to afford tert-butyl N-[(5-fluoro-2,3-dihydrobenzofuran-4-yl)methyl]carbamate (22.0 g, 78.2 mmol, 67.7% yield, 95.0% purity) as a white solid.

$^1$H NMR (400 MHz, CDCl₃) δ=6.82-6.76 (m, 1H), 6.62 (dd, J=4.0, 8.8 Hz, 1H), 4.88 (br s, 1H), 4.60 (t, J=8.8 Hz, 2H), 4.30 (br d, J=6.0 Hz, 2H), 3.30 (br t, J=8.8 Hz, 2H), 1.44 (s, 9H).

To a solution of tert-butyl N-[(5-fluoro-2,3-dihydrobenzofuran-4-yl)methyl] carbamate (22.0 g, 78.2 mmol, 1.00 equiv) in DCM (200 mL) was added TFA (89.2 g, 782 mmol, 57.9 mL, 10.0 equiv). The mixture was stirred at 25° C. for 0.5 h and subsequently quenched with satd aq potassium carbonate (200 mL). The mixture was allowed to stir at 25° C. for 0.5 hour. The organic phase was separated and dried over sodium sulfate, concentrated in vacuo to afford (5-fluoro-2,3-dihydrobenzofuran-4-yl)methanamine (13.0 g, 73.9 mmol, 94.5% yield, 95.0% purity) as a light yellow oil.

$^1$H NMR (400 MHz, CDCl₃) δ=6.85-6.76 (m, 1H), 6.60 (dd, J=4.0, 8.8 Hz, 1H), 4.61 (t, J=8.8 Hz, 2H), 3.82 (s, 2H), 3.24 (t, J=8.8 Hz, 2H).

Alternatively, Intermediate B-2 may be prepared on a large scale as follows:

To a solution of 3-bromo-4-fluorophenol (1.00 kg, 5.24 mol, 1.00 equiv) and Cs₂CO₃ (3.41 kg, 10.5 mol, 2.00 equiv) in DMF (5.00 L) was added compound 2-bromo-1,1-diethoxyethane (1.24 kg, 6.28 mol, 1.20 equiv) in one portion. The suspension was stirred at 110° C. for 12 h. TLC (petroleum ether/ethyl acetate=10/1, R$_f$=0.50) indicated that the reaction was complete. The reaction mixture was filtered, diluted with water (15.0 L) and extracted with MTBE (5.00 L×2). The combined organic layers were washed with brine (3.00 L), dried over Na₂SO₄, filtered and concentrated under reduced pressure to give compound 2-bromo-4-(2,2-diethoxyethoxy)-1-fluorobenzene (1.61 kg, crude) as a yellow oil.

Two reactions were conducted in parallel on the same scale and combined during the workup. To a mixture of polyphosphoric acid (1.30 kg) in toluene (2.40 L) was added 2-bromo-4-(2,2-diethoxyethoxy)-1-fluorobenzene (800 g, 2.60 mol, 1.00 equiv) in one portion at 90° C. The mixture was stirred at 90° C. for 3 h. TLC (petroleum ether/EtOAc=10/1, R$_f$=0.6) indicated that the reaction was complete. The two reactions were combined prior to work up. The mixture was poured into water (6.00 L) and extracted with MTBE (6.00 L×2). The combined organic layer was washed with brine (5.00 L×2), dried over anhydrous Na₂SO₄, filtered and concentrated in vacuo. The residue was purified by silica gel chromatography (petroleum ether/

EtOAc=1/0 to 100/1) to give a ~1:1 mixture of 4-bromo-5-fluorobenzofuran and 6-bromo-5-fluorobenzofuran (800 g, 3.72 mol, 71.4% yield) as a brown oil.

Two reactions were conducted in parallel on the same scale and combined during the workup. To a mixture of 4-bromo-5-fluorobenzofuran (150 g, 698 mmol, 1.00 equiv) and 6-bromo-5-fluorobenzofuran (150 g, 698 mmol, 1.00 equiv) in DMA (2.40 L) was added Zn(CN)$_2$ (49.2 g, 419 mmol, 0.60 equiv) and Pd(PPh$_3$)$_4$ (40.3 g, 34.9 mmol, 0.05 equiv) in one portion at 25° C. under N$_2$. The mixture was stirred at 90° C. for 12 h. TLC (petroleum ether/EtOAc=10/1) indicated the consumption of the undesired isomer (6-bromo-5-fluorobenzofuran). The two reactions were combined prior to work up. The mixture was diluted with EtOAc (5.00 L) and filtered. The filtrate was poured into water (8.00 L) and the mixture was extracted with EtOAc (3.00 L×2). The combined organic phase was washed with brine (4.00 L×2), dried over anhydrous Na$_2$SO$_4$, filtered and concentrated under reduced pressure. The residue was purified by silica gel chromatography (petroleum ether/EtOAc=1/0 to 5/1) to give compound 4-bromo-5-fluorobenzofuran (340 g) as a yellow oil.

Two reactions were conducted in parallel on the same scale and combined during the workup. To a mixture of compound 4-bromo-5-fluorobenzofuran (170 g, 791 mmol, 1.00 equiv) in DMA (1.30 L) was added Zn(CN)$_2$ (92.8 g, 791 mmol, 1.00 equiv.) and Pd(PPh$_3$)$_4$ (91.4 g, 79.1 mmol, 0.10 equiv) in one portion at 25° C. under N$_2$. The resultant mixture was stirred at 120° C. for 12 h. TLC (petroleum ether/EtOAc=10/1) indicated that the reaction was complete. The two reactions were combined prior to work up and the mixture was poured into water (3.00 L) and EtOAc (4.00 L), filtered, and the filtrate was extracted with EtOAc (2.00 L×2). The combined organic layer was washed with brine (3.00 L×2), dried over anhydrous Na$_2$SO$_4$, filtered and concentrated in vacuo. The residue was purified by silica gel chromatography (petroleum ether/EtOAc=1/0 to 50/1) to afford compound 5-fluorobenzofuran-4-carbonitrile (120 g, 745 mmol, 47.1% yield) as a yellow oil.

$^1$H NMR (400 MHz, CD$_3$OD) δ 8.06 (d, J=2.0 Hz, 1H), 7.82-7.86 (m, 1H), 7.23-7.28 (m, 1H), 7.02 (d, J=2.0 Hz, 1H).

Two reactions were conducted in parallel on the same scale and combined during the workup. To a solution of compound 5-fluorobenzofuran-4-carbonitrile (60.0 g, 372 mmol, 1.00 equiv) in MeOH (1.50 L) was added Boc$_2$O (122 g, 559 mmol, 1.50 equiv) and Pd/C (12.0 g, 10 wt %) under N$_2$. The suspension was evacuated and purged with H2 several times and the mixture was stirred under H$_2$ (50 psi) at 50° C. for 12 h. TLC (petroleum ether/EtOAc=10/1) indicated that the reaction was complete. The two reactions were combined prior to work up and filtered. The filtrate was concentrated to afford a residue that was triturated with petroleum ether (500 mL), filtered, and dried at 45° C. under vacuum to provide tert-butyl ((5-fluoro-2,3-dihydrobenzofuran-4-yl)methyl)carbamate (100 g, 374 mmol, 50.2% yield) as a white solid.

$^1$H NMR (400 MHz, CDCl$_3$) δ 6.76-6.81 (m, 1H), 6.60-6.63 (m, 1H), 4.60 (t, J=8.8 Hz, 2H), 4.29-4.31 (m, 2H), 3.30 (t, J=8.8 Hz, 2H), 1.44 (s, 9H).

Two reactions were conducted in parallel on the same scale and combined during the workup. To a mixture of tert-butyl ((5-fluoro-2,3-dihydrobenzofuran-4-yl)methyl)carbamate (50.0 g, 187 mmol, 1.00 equiv) in EtOAc (400 mL) was added HCl/EtOAc (300 mL, 4M) in one portion at 25° C. under N$_2$. The resultant mixture was stirred for 4 h at which time TLC (petroleum ether/EtOAc=5/1) indicated that the reaction was complete. The two reactions were combined prior to work up, filtered, and the filter cake was washed by MTBE (100 mL×2). The filter cake was dissolved in water (200 mL) and the pH was adjusted to 9 with sat.aq. K$_2$CO$_3$ at 0° C. prior to extraction with DCM (200 mL×4). The combined organic phase was washed with brine (200 mL×2), dried over anhydrous Na$_2$SO$_4$, filtered and concentrated in vacuo to afford (5-fluoro-2,3-dihydrobenzofuran-4-yl)methanamine (50.0 g, 299 mmol, 79.9% yield) as a brown oil.

$^1$H NMR (400 MHz, DMSO-d$_6$) δ 8.57 (br. s., 3H), 6.97 (m, 1H), 6.77-6.80 (m, 1H), 4.55-4.59 (m, 2H), 3.94 (s, 2H), 3.37-3.42 (m, 2H).

Intermediate B-5

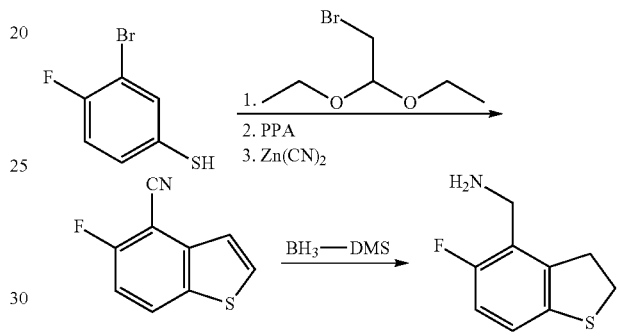

A fifth exemplary Intermediate B, Intermediate B-5, may be used to synthesize compounds of formula I wherein Z is S, n is one, X is C(R$^5$)$_2$, and ------ is a single bond. A mixture of 3-bromo-4-fluoro-benzenethiol (4.50 g, 21.7 mmol, 1.00 equiv), 2-bromo-1,1-diethoxy-ethane (4.71 g, 23.9 mmol, 3.60 mL, 1.10 equiv), and potassium carbonate (3.60 g, 26.1 mmol, 1.20 equiv) in DMF (50.0 mL) was purged with nitrogen. The mixture was stirred at 80° C. for 0.5 h under an atmosphere of nitrogen. The mixture was concentrated in vacuo to provide a residue, which was purified by column chromatography (petroleum ether/ethyl acetate, 20/1 to 5/1) to afford 2-bromo-4-(2,2-diethoxyethylsulfanyl)-1-fluoro-benzene (6.2 g, 19.2 mmol, 88.3% yield) as a colorless liquid.

$^1$H NMR (400 MHz, CDCl$_3$) δ=7.63 (dd, J=2.4, 6.4 Hz, 1H), 7.32 (ddd, J=2.4, 4.4, 8.8 Hz, 1H), 7.03 (t, J=8.4 Hz, 1H), 4.63 (t, J=5.6 Hz, 1H), 3.72-3.65 (m, 2H), 3.57-3.51 (m, 2H), 3.08 (d, J=5.6 Hz, 2H), 1.20 (t, J=7.2 Hz, 6H).

To a solution of polyphosphoric acid (39 g, 710 μL, 1.00 equiv) in chlorobenzene (70.0 mL) was added 2-bromo-4-(2,2-diethoxyethylsulfanyl)-1-fluoro-benzene (5.9 g, 18.3 mmol, 1.00 equiv) and the resultant mixture was stirred at 130° C. for 12 h. The mixture was concentrated in vacuo to provide a residue. The residue was purified by column chromatography (petroleum ether) to afford 4-bromo-5-fluoro-benzothiophene (2.50 g, 10.8 mmol, 29.8% yield, 50% purity) as a colorless liquid.

$^1$H NMR (400 MHz, CDCl$_3$) δ=7.75 (dd, J=4.4, 8.8 Hz, 1H), 7.61 (d, J=5.6 Hz, 1H), 7.49 (d, J=5.6 Hz, 1H), 7.17 (t, J=8.8 Hz, 1H).

To a solution of 4-bromo-5-fluoro-benzothiophene (1.25 g, 5.41 mmol, 1.00 equiv) in DMAC (12.0 mL) was added zinc cyanide (953 mg, 8.11 mmol, 515 μL, 1.50 equiv) and Pd(PPh$_3$)$_4$ (938 mg, 811 μmol, 0.150 equiv). The mixture was stirred at 100° C. for 12 h under an atmosphere of nitrogen. Water (50.0 mL) was added and the mixture was extracted with ethyl acetate (80.0 mL×3). The combined organic layer was concentrated in vacuo to provide a residue. The residue was purified by column chromatography (petroleum ether) to afford 5-fluorobenzothiophene-4-carbonitrile (530 mg, 2.99 mmol, 27.7% yield) as a white solid.

$^1$H NMR (400 MHz, CDCl$_3$) δ=8.05 (dd, J=4.4, 8.8 Hz, 1H), 7.80 (d, J=5.6 Hz, 1H), 7.57 (d, J=5.6 Hz, 1H), 7.23 (t, J=8.8 Hz, 1H).

To a mixture of 5-fluorobenzothiophene-4-carbonitrile (300 mg, 1.69 mmol, 1.00 equiv) in THF (2.00 mL) was added BH$_3$-Me$_2$S (10 M, 677 μL, 4.00 equiv) at 0° C. and the mixture was stirred for 6 h at 75° C. The mixture was cooled to room temperature and was quenched with ethanol (10.0 mL) and the pH was adjusted to 3 with aq HCl (2 M). The mixture was concentrated in vacuo to provide a residue to which water (20.0 mL) was added. The aqueous mixture was extracted with ethyl acetate (40.0 mL×4) and the combined organic layer was concentrated to afford (5-fluorobenzothiophen-4-yl)methanamine (150 mg, 828 μmol, 48.9% yield) as a yellow solid.

Intermediate B-6

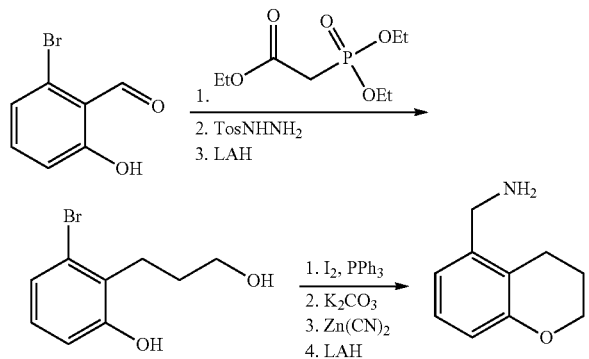

A sixth exemplary Intermediate B, Intermediate B-6, may be used to synthesize compounds of formula I wherein Z is O, n is two, X is C(R$^5$)$_2$, and ------ is a single bond.

To a solution of 2-bromo-6-hydroxy-benzaldehyde (0.30 g, 1.49 mmol, 1.00 equiv.) and ethyl 2-diethoxyphosphorylacetate (669 mg, 2.98 mmol, 592 μL, 2.00 equiv.) in DMF (3.00 mL) was added NaH (119 mg, 2.98 mmol, 60% purity, 2.00 equiv.) at rt under a nitrogen atmosphere. The resultant mixture was stirred at 40° C. for 12 h. The reaction mixture was diluted with ethyl acetate (50.0 mL) and quenched with water (10.0 mL). The combined organic phase was washed with brine (30.0 mL×3), dried over sodium sulfate, filtered and concentrated in vacuo. The crude residue was purified by column chromatography (SiO$_2$, Petroleum ether/Ethyl acetate=10/1 to 4/1) to afford ethyl (E)-3-(2-bromo-6-hydroxy-phenyl)prop-2-enoate (380 mg, 1.37 mmol, 92.0% yield, 98.0% purity) as a white solid.

$^1$H NMR (400 MHz, CD$_3$OD) δ=8.02 (d, J=16.0 Hz, 1H), 7.15 (dd, J=1.2, 8.0 Hz, 1H), 7.06 (t, J=8.0 Hz, 1H), 6.97 (d, J=16.0 Hz, 1H), 6.86 (d, J=8.0 Hz, 1H), 4.56 (s, 1H), 4.25 (q, J=7.2 Hz, 2H), 1.33 (t, J=7.2 Hz, 3H).

To a solution of ethyl (E)-3-(2-bromo-6-hydroxy-phenyl)prop-2-enoate (380 mg, 1.37 mmol, 1.00 equiv.) in THF (5.00 mL) and water (5.00 mL) was added NaOAc (225 mg, 2.75 mmol, 2.00 equiv.) and 4-methylbenzenesulfonohydrazide (512 mg, 2.75 mmol, 2.00 equiv.). The mixture was stirred at 70° C. for 12 h. The mixture was cooled to rt and extracted with ethyl acetate (20.0 mL×2). The combined organic phase was washed with brine (30.0 mL×3), dried over sodium sulfate, filtered and concentrated in vacuo. The crude residue was purified by column chromatography (SiO$_2$, petroleum ether/ethyl acetate=20/1 to 10/1) to afford ethyl 3-(2-bromo-6-hydroxy-phenyl)propanoate (380 mg, 1.32 mmol, 96.2% yield, 95.0% purity) as a light-yellow oil.

$^1$H NMR (400 MHz, CDCl$_3$) δ=8.27 (s, 1H), 7.14 (dd, J=1.2, 8.0 Hz, 1H), 6.99 (t, J=8.0 Hz, 1H), 6.93-6.88 (m, 1H), 4.17 (q, J=7.2 Hz, 2H), 3.50 (s, 1H), 3.10-3.03 (m, 2H), 2.87-2.79 (m, 2H), 1.28-1.24 (m, 3H).

To a solution of ethyl 3-(2-bromo-6-hydroxy-phenyl)propanoate (0.10 g, 348 μmol, 1.00 equiv.) in THF (2.00 mL) was added LAH (39.6 mg, 1.04 mmol, 3.00 equiv.) at 0° C. The mixture was stirred at rt for 2 h. The reaction mixture was quenched with water (0.50 mL) and was diluted with DCM (30.0 mL). The mixture was dried over magnesium sulfate, filtered and concentrated in vacuo. The crude residue was purified by prep-TLC (SiO$_2$, PE:EA=2:1) to afford 3-bromo-2-(3-hydroxypropyl)phenol (70.0 mg, 297 μmol, 85.4% yield, 98.0% purity) as a yellow oil.

$^1$H NMR (400 MHz, CDCl$_3$) δ=7.66 (br s, 1H), 7.14 (dd, J=1.2, 8.0 Hz, 1H), 6.97 (t, J=8.0 Hz, 1H), 6.84 (dd, J=1.2, 8.0 Hz, 1H), 3.64 (t, J=5.6 Hz, 2H), 3.03-2.94 (m, 2H), 2.01-1.90 (m, 2H).

Iodine (3.30 g, 13.0 mmol, 2.62 mL, 1.65 equiv.) was added to a solution of imidazole (2.42 g, 35.5 mmol, 4.50 equiv.) and PPh$_3$ (3.72 g, 14.2 mmol, 1.80 equiv.) in DCM (40.0 mL) at 0° C. The reaction mixture was stirred for 15 min followed by the dropwise addition of a solution of 3-bromo-2-(3-hydroxypropyl)phenol (1.85 g, 7.89 mmol, 1.00 equiv.) in DCM (10.0 mL). The reaction mixture was protected from light and stirred for 12 h at rt. The mixture was diluted with DCM (50.0 mL) and washed with brine (40.0 mL×2). The combined organic phase was dried over sodium sulfate, filtered and concentrated in vacuo. The crude material was purified by column chromatography (SiO$_2$, petroleum ether/ethyl acetate=1/0 to 20/1) to afford 3-bromo-2-(3-iodopropyl)phenol (2.10 g, 6.16 mmol, 78.1% yield) as a white solid.

To a solution of 3-bromo-2-(3-iodopropyl)phenol (2.10 g, 6.16 mmol, 1.00 equiv.) in acetone (50.0 mL) was added K$_2$CO$_3$ (1.70 g, 12.3 mmol, 2.00 equiv.). The mixture was stirred at 50° C. for 12 h. The reaction mixture was filtered and concentrated in vacuo. The crude material was purified by column chromatography (SiO$_2$, petroleum ether) to afford 5-bromochromane (1.20 g, 5.63 mmol, 91.5% yield, 100% purity) as a light-yellow oil.

A mixture of 5-bromochromane (0.10 g, 469 μmol, 1.00 equiv.), Zn(CN)$_2$ (110 mg, 939 μmol, 2.00 equiv.), Pd(PPh$_3$)$_4$ (81.4 mg, 70.4 μmol, 0.15 equiv.) in DMAC (1.00 mL) was purged with nitrogen. The mixture was stirred at 100° C. for 8 h. The reaction mixture was diluted with ethyl acetate (20.0 mL) and washed with brine (15.0 mL×3). The combined organic phase was dried over sodium sulfate, filtered and concentrated in vacuo. The crude material was purified by prep-TLC (SiO$_2$, PE:EA=10:1) to afford chromane-5-carbonitrile (60.0 mg, 377 μmol, 80.3% yield) as a light-yellow oil.

$^1$H NMR (400 MHz, CDCl$_3$) δ=7.22-7.18 (m, 1H), 7.18-7.13 (m, 1H), 7.02 (dd, J=1.2, 8.0 Hz, 1H), 4.28-4.19 (m, 2H), 2.97 (t, J=6.4 Hz, 2H), 2.16-2.02 (m, 2H).

To a solution of chromane-5-carbonitrile (60.0 mg, 377 μmol, 1.00 equiv.) in THF (3.00 mL) was added LAH (57.2 mg, 1.51 mmol, 4.00 equiv.) at 0° C. The mixture was stirred at rt for 2 h. The reaction mixture was quenched with water (1.00 mL) and diluted with DCM (30 mL). The mixture was dried with magnesium sulfate and filtered. The filtrate was concentrated in vacuo to afford chroman-5-ylmethanamine (70.0 mg, crude) as a light-yellow oil.

Intermediate B-7

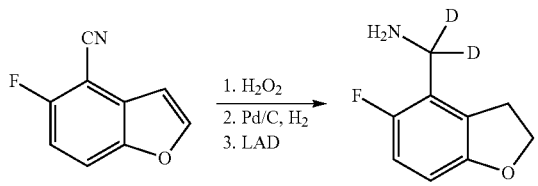 [SMILES: N#Cc1c(F)ccc2occc12 ; [2H]C([2H])(N)c1c(F)ccc2c1CCO2]

A seventh exemplary Intermediate B, Intermediate B-7, may be used to synthesize compounds of formula I wherein Z is O, n is one, X is C(R⁵)₂, ------ is a single bond, and two hydrogens have been substituted with deuteriums.

To a solution of 5-fluorobenzofuran-4-carbonitrile (2.00 g, 12.4 mmol, 1.00 equiv) in dimethyl sulfoxide (20.0 mL) was added hydrogen peroxide (7.04 g, 62.1 mmol, 5.96 mL, 30% purity, 5.00 equiv) and potassium carbonate (1.72 g, 12.4 mmol, 1.00 equiv) at 0° C. The mixture was stirred at 25° C. for 1 h. The residue was poured into ice-water (5.00 mL) and stirred for 10 min. The mixture was filtered and concentrated under vacuum to give 5-fluorobenzofuran-4-carboxamide (1.80 g, 10.1 mmol, 81.0% yield) as a white solid.

$^1$H NMR (400 MHz, DMSO-d$_6$) δ=8.11 (d, J=2.0 Hz, 1H), 7.81 (br s, 1H), 7.73 (dd, J=4.0, 8.8 Hz, 2H), 7.23 (dd, J=9.2, 10.4 Hz, 1H), 7.10 (d, J=1.2 Hz, 1H).

A solution of 5-fluorobenzofuran-4-carboxamide (1.80 g, 10.1 mmol, 1.00 equiv) in methyl alcohol (4.00 mL) was charged with hydrogen (50 psi) and Pd/C (500 mg, 50% purity). The mixture was stirred at 35° C. for 12 h. The mixture was filtered and concentrated under vacuum to give 5-fluoro-2,3-dihydrobenzofuran-4-carboxamide (1.60 g, 8.83 mmol, 87.9% yield) as a white solid. LC-MS [M+1]: 182.2.

$^1$H NMR (400 MHz, DMSO-d$_6$) δ=7.82-7.55 (m, 2H), 6.96 (t, J=8.8 Hz, 1H), 6.79 (dd, J=4.0, 8.8 Hz, 1H), 4.54 (t, J=8.8 Hz, 2H), 3.25 (t, J=8.8 Hz, 2H).

To a solution of 5-fluoro-2,3-dihydrobenzofuran-4-carboxamide (1.60 g, 8.83 mmol, 1.00 equiv) in tetrahydrofuran (20.0 mL) was added lithium aluminumdeuteride (670 mg, 17.7 mmol, 911 µL, 2.00 equiv) at 0° C. The mixture was stirred at 60° C. for 12 h. The mixture was quenched with water (1.60 mL) (stirred for 15 min), followed by sodium hydroxide (1.50 mL, 15% aq.) (15 min) and water (4.80 mL) (30 min). The suspension was filtered and concentrated in vacuo to give a residue. The residue was purified by prep-HPLC (basic conditions) to afford (5-fluoro-2,3-dihydrobenzofuran-4-yl)methan-d2-amine (0.80 g, 4.56 mmol, 51.6% yield, 96.4% purity) as a red oil.

$^1$H NMR (400 MHz, CHLOROFORM-d) δ=6.82-6.76 (m, 1H), 6.59 (dd, J=4.0, 8.8 Hz, 1H), 4.59 (t, J=8.8 Hz, 2H), 3.23 (t, J=8.8 Hz, 2H).

Intermediate B-8

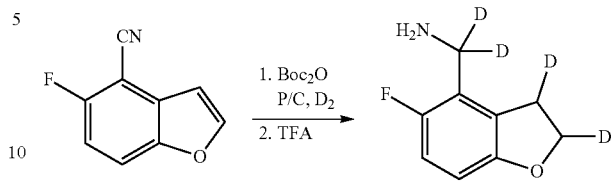

A eighth exemplary Intermediate B, Intermediate B-8, may be used to synthesize compounds of formula I wherein Z is O, n is one, X is C(R⁵)₂, ------ is a single bond, and two hydrogens in the linker and two hydrogens on the furan portion have been substituted with deuteriums.

To a solution of 5-fluorobenzofuran-4-carbonitrile (100 mg, 620 µmol, 1.00 equiv) in methanol-d₄ (1.00 mL) was added di-tert-butyl dicarbonate (135 mg, 620 µmol, 143 µL, 1.00 equiv) and palladium on carbon (100 mg, 10.0 w %, 0.09 equiv). The mixture was stirred at 35° C. for 12 h under a deuterium gas atmosphere (15 psi). The reaction was filtered and concentrated at reduced pressure to give tert-butyl ((5-fluoro-2,3-dihydrobenzofuran-4-yl-2,3-d2) methyl-d2)carbamate (45.0 mg, 166 µmol, 26.7% yield) as a white solid.

$^1$H NMR (400 MHz, CDCl$_3$) δ=6.82-6.76 (m, 1H), 6.62 (dd, J=3.6, 8.4 Hz, 1H), 4.86 (br s, 1H), 4.57 (br d, J=10.0 Hz, 1H), 3.27 (br d, J=6.8 Hz, 1H), 1.46-1.41 (s, 9H).

To a solution of tert-butyl ((5-fluoro-2,3-dihydrobenzofuran-4-yl-2,3-d2)methyl-d2)carbamate (40.0 mg, 147 µmol, 1.00 equiv) in dichloromethane (2.00 mL) was added trifluoroacetic acid (109 µL, 1.47 mmol, 10.0 equiv). The mixture was stirred at 25° C. for 1 h. and subsequently was concentrated at reduced pressure to give a residue. The residue was added to saturated sodium bicarbonate (2.00 mL) and stirred for 5 min. The aqueous phase was extracted with ethyl acetate (2.00 mL×3). The combined organic phase was washed with brine (2.00 mL×3), dried with anhydrous sodium sulfate, filtered and concentrated at reduced pressure to afford dideuterio-(2,3-dideuterio-5-fluoro-2,3-dihydrobenzofuran-4-yl)methanamine (25.0 mg, crude) as a white solid, which was used without further purification.

Intermediate B-9

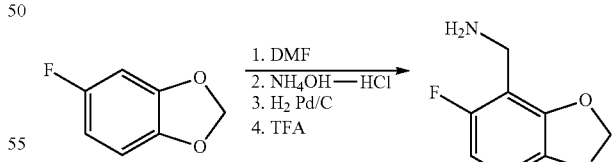

A ninth exemplary Intermediate B, Intermediate B-9, may be used to synthesize compounds of formula I wherein Z is O, n is one, X is O, and ------ is a single bond.

To a solution of 5-fluoro-1,3-benzodioxole (500 mg, 3.57 mmol, 1.00 equiv) in THF (5.00 mL) was added n-BuLi (2.50 M, 1.57 mL, 1.10 equiv) dropwise at −78° C. The mixture was stirred at −78° C. for 15 min followed by the dropwise addition of DMF (235 mg, 3.21 mmol, 247 µL, 0.90 equiv) and continued stirring at −78° C. for 0.5 h. The mixture was poured into saturated ammonium chloride aqueous solution (5.00 mL) and stirred for 15 min. The aqueous phase was extracted with ethyl acetate (6.00 mL×2). The combined organic phase was washed with brine (6.00 mL×3), dried with anhydrous sodium sulfate, filtered and concentrated under reduced pressure to give 5-fluoro-1,3-benzodioxole-4-carbaldehyde (370 mg, 2.20 mmol, 61.7% yield) as a white solid.

$^1$H NMR (400 MHz, DMSO-$d_6$) δ=10.07 (s, 1H), 7.12 (dd, J=4.4, 8.4 Hz, 1H), 6.72 (dd, J=8.8, 11.6 Hz, 1H), 6.17 (s, 2H).

To a solution of 5-fluoro-1,3-benzodioxole-4-carbaldehyde (200 mg, 1.19 mmol, 1.00 equiv) in ethyl alcohol (6.00 mL) was added hydroxylamine-hydrochloride (248 mg, 3.57 mmol, 3.00 equiv) and triethylamine (827 μL, 5.95 mmol, 5.00 equiv). The mixture was stirred at 15° C. for 0.5 h and the mixture was concentrated under reduced pressure to give a residue. The residue was triturated with water (3.00 mL×2) and filtered, the filter cake was collected and dried under reduced pressure to give 5-fluoro-1,3-benzodioxole-4-carbaldehyde oxime (200 mg, 1.09 mmol, 91.8% yield) as a white solid.

$^1$H NMR (400 MHz, DMSO-$d_6$) δ=11.68 (s, 1H), 8.08 (s, 1H), 6.91 (br dd, J=4.0, 8.4 Hz, 1H), 6.77-6.65 (m, 1H), 6.12 (s, 2H).

To a solution of 5-fluoro-1,3-benzodioxole-4-carbaldehyde oxime (280 mg, 2.07 mmol, 1.00 equiv) in methyl alcohol (3.00 mL) was added Pd/C (2.07 mmol, 10% purity, 1.00 equiv) and di-tert-butyl dicarbonate (906 mg, 4.15 mmol, 953 μL, 2.00 equiv). The mixture was stirred at 25° C. for 12 h under a hydrogen atmosphere (15 psi). The mixture was filtered and concentrated under reduced pressure to give a residue. The residue was purified by column chromatography (SiO$_2$, petroleum ether/ethyl acetate=1/0 to 2/1) to afford tert-butyl N-[(5-fluoro-1,3-benzodioxol-4-yl)methyl]carbamate (350 mg, 1.71 mmol, 82.3% yield) as a white solid. LC-MS [M−55]: 214.1.

To a solution of tert-butyl ((5-fluorobenzo[d][1,3]dioxol-4-yl)methyl)carbamate (85.0 mg, 316 μmol, 1.00 equiv) in DCM (1.00 mL) was added TFA (0.30 mL). The mixture was stirred at 25° C. for 0.5 h. The reaction mixture was neutralized with saturated aq potassium carbonate (5.00 mL) and stirred for 30 min. The aqueous phase was extracted with DCM (5.00 mL×2). The combined organic phase was washed with brine (5.00 mL×2), dried with anhydrous sodium sulfate, filtered and concentrated under reduced pressure to give (5-fluorobenzo[d][1,3]dioxol-4-yl)methanamine (45.0 mg, 266 μmol, 84.3% yield) as a yellow oil.

$^1$H NMR (400 MHz, CDCl$_3$) δ=6.63 (dd, J=4.4, 8.4 Hz, 1H), 6.52 (dd, J=8.4, 10.4 Hz, 1H), 6.00 (s, 2H), 3.89 (s, 2H).

Intermediate C-1

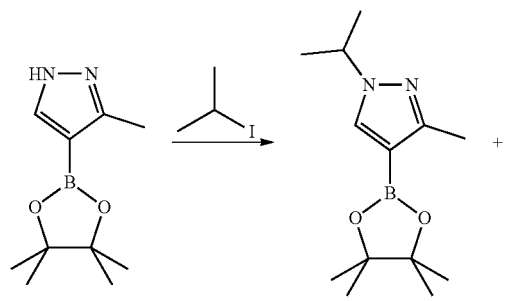

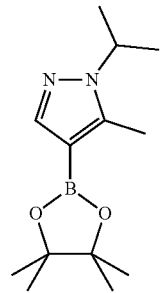

An exemplary Intermediate C, Intermediate C-1, may be used to synthesize compounds of Formula (I) or Formula (II) wherein R$^1$ is a disubstituted heteroaryl. A mixture of 3-methyl-4-(4,4,5,5-tetramethyl-1,3,2-dioxaborolan-2-yl)-1H-pyrazole (370 mg, 1.78 mmol, 1.00 equiv), 2-iodopropane (907 mg, 5.33 mmol, 533 uL, 3.00 equiv) and cesium carbonate (2.32 g, 7.11 mmol, 4.00 equiv) in acetonitrile (7.00 mL) was purged with nitrogen and subsequently stirred at 90° C. for 4 h. The reaction mixture was filtered and concentrated under reduced pressure to provide a residue. The crude material was purified by column chromatography (petroleum ether/ethyl acetate, 1/0 to 3/1) to afford a mixture of 1-isopropyl-3-methyl-4-(4,4,5,5-tetramethyl-1,3,2-dioxaborolan-2-yl)pyrazole (170 mg, 34.4% yield, 90.0% purity) and 1-isopropyl-5-methyl-4-(4,4,5,5-tetramethyl-1,3,2-dioxaborolan-2-yl)pyrazole (170 mg, 34.4% yield, 90.0% purity) as a light yellow oil. LC-MS [M+1]: 251.4.

$^1$H NMR (400 MHz, CDCl$_3$) δ=7.73 (s, 0.6H), 7.65 (s, 1H), 4.50-4.36 (m, 2H), 2.45 (s, 2H), 2.40 (s, 3H), 1.50-1.44 (m, 12H), 1.31 (s, 22H).

Intermediate C-2

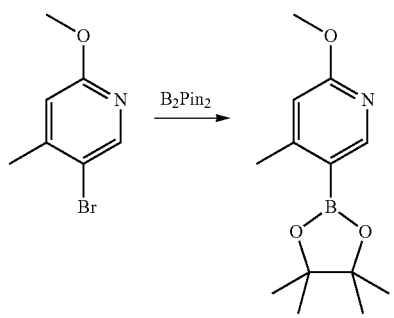

A second exemplary Intermediate C, Intermediate C-2, may be used to synthesize compounds of formula I and formula II, wherein R$^1$ is disubstituted heteroaryl. A mixture of 5-bromo-2-methoxy-4-methyl-pyridine (350 mg, 1.73 mmol, 1.00 equiv), bis(pinacolato)diboron (2.20 g, 8.66 mmol, 5.00 equiv), potassium acetate (527 mg, 5.37 mmol, 3.10 equiv), Pd(dppf)Cl$_2$ (127 mg, 173 μmol, 0.10 equiv) in dioxane (5.00 mL) was purged with nitrogen and stirred at 90° C. for 3 h. The residue was diluted with ethyl acetate (3.00 mL) and extracted with ethyl acetate (2.00 mL×3). The combined organic layers were washed with brine (2.00 mL×3), dried over anhydrous sodium sulfate, filtered and concentrated under reduced pressure to give a residue. The crude material was purified by column chromatography (petroleum ether/ethyl acetate, 100/1 to 20/1) to afford 2-methoxy-4-methyl-5-(4,4,5,5-tetramethyl-1,3,2-dioxaborolan-2-yl)pyridine (150 mg, 546 μmol, 31.5% yield, 90.6% purity) as a white solid.

$^1$H NMR (400 MHz, CDCl$_3$) δ=8.47 (s, 1H), 6.51 (s, 1H), 3.93 (s, 3H), 2.45 (s, 3H), 1.33 (s, 12H).

Intermediate C-3

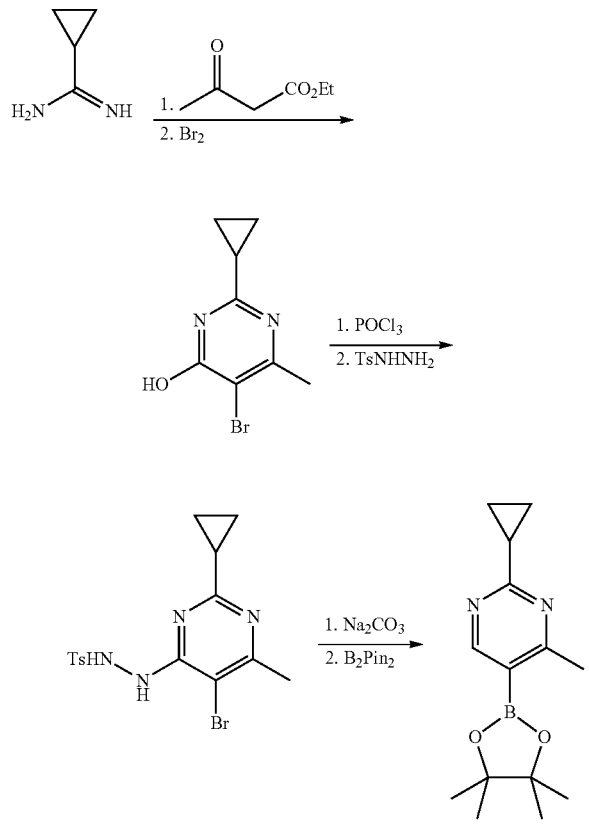

A third exemplary Intermediate C, Intermediate C-3, may be used to synthesize compounds of formula I or formula II wherein R$^1$ is disubstituted heteroaryl. A mixture of cyclopropanecarboxamidine-HCl (5.00 g, 59.4 mmol, 1.00 equiv), ethyl 3-oxobutanoate (7.74 g, 59.4 mmol, 7.51 mL, 1.00 equv), sodium ethoxide (8.09 g, 119 mmol, 2.00 equiv) in ethanol (500 mL) was purged with nitrogen and subsequently stirred at 25° C. for 12 h. The residue was dissolved in water (25.0 mL) and the pH was adjusted to ~4 with HCl (1 M). After cooling to 5° C., the solid was collected and dried under reduced pressure to give 2-cyclopropyl-6-methyl-pyrimidin-4-ol (4.00 g, 26.6 mmol, 44.8% yield, 100% purity) as a white solid. LC-MS [M+1]: 151.3.

$^1$H NMR (400 MHz, DMSO-d$_6$) δ=12.45 (s, 1H), 5.93 (s, 1H), 2.07 (s, 3H), 1.90-1.85 (m, 1H), 1.00-0.97 (m, 4H).

A mixture of 2-cyclopropyl-6-methyl-pyrimidin-4-ol (4.00 g, 26.6 mmol, 1.00 equiv), bromine (4.34 g, 27.2 mmol, 1.40 mL, 1.00 equiv), potassium hydroxide (1.49 g, 26.6 mmol, 1.00 equiv) in water (32.6 mL) was stirred at 25° C. for 2 h under a nitrogen atmosphere. The solid was filtered to give 5-bromo-2-cyclopropyl-6-methyl-pyrimidin-4-ol (2.76 g, 9.31 mmol, 35.0% yield, 77.3% purity) as a white solid. LC-MS [M+3]: 231.0.

A mixture of 5-bromo-2-cyclopropyl-6-methyl-pyrimidin-4-ol (2.50 g, 8.44 mmol, 1.00 equiv) and dimethyl formamide (1.54 g, 21.1 mmol, 1.62 mL, 2.50 equiv) in toluene (36.9 mL) was added dropwise a solution of phosphorus oxychloride (1.57 g, 10.2 mmol, 951 μL, 1.21 equiv) in toluene (9.20 mL) at 0° C. The mixture was subsequently stirred at 25° C. for 3 h under a nitrogen atmosphere. The mixture was poured into sodium carbonate (1.00 M, 55.2 mL) and extracted with ethyl acetate (10.0 mL×3). The combined organic phase was concentrated to afford compound 5-bromo-4-chloro-2-cyclopropyl-6-methyl-pyrimidine (2.31 g, 4.51 mmol, 53.5% yield, 48.4% purity) as a yellow oil. LC-MS [M+3]: 249.1.

A mixture of 5-bromo-4-chloro-2-cyclopropyl-6-methyl-pyrimidine (2.31 g, 9.33 mmol, 1.00 equiv), 4-methylbenzenesulfonohydrazide (5.91 g, 31.7 mmol, 3.40 equiv) in chloroform (4.30 mL) was stirred at 90° C. for 16 h under a nitrogen atmosphere. The solid was filtered and rinsed with dichloromethane (20.0 mL) to afford N-(5-bromo-2-cyclopropyl-6-methyl-pyrimidin-4-yl)-4-methyl-benzenesulfonohydrazide (1.60 g, 4.02 mmol, 43.1% yield, 99.8% purity) as a white solid. LC-MS [M+3]: 399.2.

$^1$H NMR (400 MHz, DMSO-d$_6$) δ=10.08 (br s, 1H), 7.64 (d, J=8.4 Hz, 2H), 7.34 (d, J=8.0 Hz, 2H), 2.44 (br s, 3H), 2.37 (s, 3H), 2.05-1.83 (m, 1H), 1.05-0.90 (m, 2H), 0.87-0.75 (m, 2H).

A mixture of N'-(5-bromo-2-cyclopropyl-6-methyl-pyrimidin-4-yl)-4-methyl-benzenesulfonohydrazide (1.60 g, 4.02 mmol, 1.00 equiv) and aqueous sodium carbonate (0.57 M, 90.6 mL, 12.8 equiv) was stirred at 90° C. for 1 h under a nitrogen atmosphere. The mixture was diluted with ethyl acetate (50.0 mL) and the organic phase was separated and concentrated to afford 5-bromo-2-cyclopropyl-4-methyl-pyrimidine (620 mg, 2.59 mmol, 64.6% yield, 89.2% purity) as a brown oil. LC-MS [M+1]: 213.2.

$^1$H NMR (400 MHz, CDCl$_3$) δ=8.49 (s, 1H), 2.56 (s, 3H), 2.25-2.08 (m, 1H), 1.19-0.99 (m, 4H).

A mixture of 5-bromo-2-cyclopropyl-4-methyl-pyrimidine (580 mg, 2.43 mmol, 1.00 equiv),4,4,5,5-tetramethyl-2-(4,4,5,5-tetramethyl-1,3,2-dioxaborolan-2-yl)-1,3,2-dioxaborolane (863 mg, 3.40 mmol, 1.40 equiv), potassium acetate (715 mg, 7.28 mmol, 3.00 equiv), and Pd(dppf)Cl$_2$ (88.8 mg, 121 μmol, 0.05 equiv) in dioxane (5.00 mL) was purged with nitrogen and was subsequently stirred at 90° C. for 4 h under a nitrogen atmosphere. The residue was diluted with water (3.00 mL) and extracted with ethyl acetate (2.00 mL×3). The combined organic layers were washed with brine (2.00 mL×3), dried over anhydrous sodium sulfate, filtered and concentrated under reduced pressure to give a residue. The crude material was purified by column chromatography (petroleum ether/ethyl acetate, 100/1 to 10/1) to afford 2-cyclopropyl-4-methyl-5-(4,4,5,5-tetramethyl-1,3,2-dioxaborolan-2-yl)pyridine (1.00 g, 1.92 mmol, 79.2% yield, 50.0% purity) as a yellow oil.

$^1$H NMR (400 MHz, CDCl$_3$) δ=8.73 (s, 1H), 2.62 (s, 3H), 2.27-2.14 (m, 1H), 1.34 (s, 12H), 1.18-1.13 (m, 2H), 1.07-1.01 (m, 2H).

Intermediate C-4

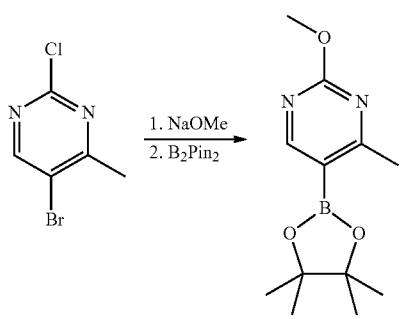

A fourth exemplary Intermediate C, Intermediate C-4, may be used to synthesize compounds of formula I or formula II, wherein $R^1$ is disubstitued heteroaryl. A mixture of sodium (111 mg, 4.82 mmol, 1.00 equiv) in methanol (772 mg, 24.1 mmol, 975. μL, 5.00 equiv) was stirred at 25° C. for 0.5 h. To this solution was added 5-bromo-2-chloro-4-methyl-pyrimidine (1.00 g, 4.82 mmol, 1.00 equiv) and the mixture was stirred at 25° C. for 2 h. The reaction was quenched upon the addition of water (5 mL). The aqueous phase was extracted with ethyl acetate (10.0 mL×3) and the combined organic phase was washed with brine (10.0 mL×3), dried over anhydrous $Na_2SO_4$, filtered and concentrated in vacuo to afford 5-bromo-2-methoxy-4-methyl-pyrimidine (500 mg, 2.46 mmol, 51.1% yield) as a red oil. LC-MS: [M+1] 203.1.

To a solution of 5-bromo-2-methoxy-4-methyl-pyrimidine (500 mg, 2.46 mmol, 1.00 equiv), 4,4,5,5-tetramethyl-2-(4,4,5,5-tetramethyl-1,3,2-dioxaborolan-2-yl)-1,3,2-dioxaborolane (813 mg, 3.20 mmol, 1.30 equiv) and potassium acetate (483 mg, 4.93 mmol, 2.00 equiv) in dioxane (5.00 mL) was added $Pd(dppf)Cl_2$ (180 mg, 246 μmol, 0.10 equiv) under nitrogen. The resultant mixture was stirred at 105° C. for 2 h. The mixture was concentrated in vacuo to give the crude material, which was purified by column chromatography (petroleum ether/ethyl acetate, 1/0 to 1:1) to afford 2-methoxy-4-methyl-5-(4,4,5,5-tetramethyl-1,3,2-dioxaborolan-2-yl)pyrimidine (150 mg, 539 μmol, 21.9% yield, 90.0% purity) as a red oil.

$^1$H NMR (400 MHz, MeOD) δ=8.69 (s, 1H), 4.03 (s, 3H), 2.65 (s, 3H), 1.38 (s, 12H).

Intermediate C-5

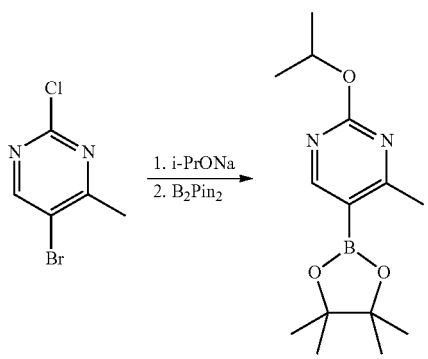

A fifth exemplary Intermediate C, Intermediate C-5, may be used to synthesize compounds of formula I or formula II, wherein $R^1$ is disubstitued heteroaryl. To a solution of isopropanol (869 mg, 14.5 mmol, 1.11 mL, 3.00 equiv) in THF (10.0 mL) was added portionwise NaH (578 mg, 14.5 mmol, 60.0% purity, 3.00 equiv) at 0° C. The mixture was stirred at 0° C. for 0.5 h. Subsequent to the addition of 5-bromo-2-chloro-4-methyl-pyrimidine (1.00 g, 4.82 mmol, 1.00 equiv) the mixture was allowed to stir at 25° C. for 3 h. The mixture was poured into water (20.00 mL) and the aqueous phase was extracted with ethyl acetate (20.0 mL×3). The combined organic phase was washed with brine (20.0 mL×3), dried over anhydrous $Na_2SO_4$, filtered and concentrated to provide 5-bromo-2-isopropoxy-4-methyl-pyrimidine (600 mg, 2.60 mmol, 53.9% yield) as a yellow oil.

To a solution of 5-bromo-2-isopropoxy-4-methyl-pyrimidine (300 mg, 1.30 mmol, 1.00 equiv), 4,4,5,5-tetramethyl-2-(4,4,5,5-tetramethyl-1,3,2-dioxaborolan-2-yl)-1,3,2-dioxaborolane (429 mg, 1.69 mmol, 1.30 equiv) and potassium acetate (255 mg, 2.60 mmol, 2.00 equiv) in dioxane (5.00 mL) was added $Pd(dppf)Cl_2$ (95.0 mg, 130 μmol, 0.10 equiv). The mixture was stirred at 105° C. for 2 h under an atmosphere of nitrogen. The mixture was concentrated in vacuo to provide the crude material, which was purified by column chromatography (petroleum ether/ethyl acetate, 1/1 to dichloromethane:methanol, 10/1) to afford 2-isopropoxy-4-methyl-5-(4,4,5,5-tetramethyl-1,3,2-dioxaborolan-2-yl)pyrimidine (60.0 mg, 216 μmol, 16.6% yield) as a white oil. LC-MS: [M+1] 279.3.

Intermediate C-6

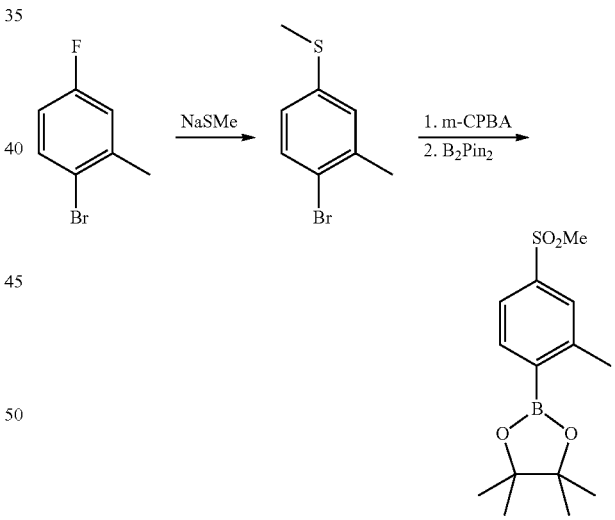

A sixth exemplary Intermediate C, Intermediate C-6, may be used to synthesize compounds of formula I or formula II, wherein $R^1$ is disubstitued aryl. To a solution of 1-bromo-4-fluoro-2-methyl-benzene (1.00 g, 5.29 mmol, 1.00 equiv) in DMF (10.0 mL) was added NaSMe (869 mg, 5.29 mmol, 1.00 equiv). The mixture was stirred at 50° C. for 12 h. The reaction mixture was diluted with ethyl acetate (50.0 mL) and the organic layer was washed with brine (40.0 mL×3), dried over anhydrous sodium sulfate, filtered and concentrated under reduced pressure to afford 1-bromo-2-methyl-4-methylsulfanyl-benzene (900 mg, crude) as a light yellow oil.

¹H NMR (400 MHz, CD₃OD) δ=7.42 (d, J=8.4 Hz, 1H), 7.17 (d, J=2.0 Hz, 1H), 6.97 (dd, J=2.0, 8.4 Hz, 1H), 2.45 (s, 3H), 2.35 (s, 3H).

To a solution of 1-bromo-2-methyl-4-methylsulfanyl-benzene (900 mg, 4.15 mmol, 1.00 equiv) in DCM (9.00 mL) was added m-CPBA (1.43 g, 8.29 mmol, 2.00 equiv) at 0° C. The reaction mixture was stirred at 25° C. for 2 h. The reaction mixture was diluted with DCM (20.0 mL), washed with satd aq potassium carbonate (20.0 mL×3), brine (20.0 mL×2), and the organic phase was concentrated under reduced pressure to give a residue. The crude material was purified by column chromatography (petroleum ether/ethyl acetate, 1/0 to 3/1) to afford 1-bromo-2-methyl-4-methylsulfonyl-benzene (370 mg, 1.41 mmol, 34.0% yield, 95.0% purity) as a white solid.

¹H NMR (400 MHz, MeOD) δ=7.87 (d, J=1.6 Hz, 1H), 7.82 (d, J=8.4 Hz, 1H), 7.66 (dd, J=2.0, 8.4 Hz, 1H), 3.12 (s, 3H), 2.50 (s, 3H).

A mixture of 1-bromo-2-methyl-4-methylsulfonyl-benzene (170 mg, 648 µmol, 1.00 equiv), potassium acetate (127 mg, 1.30 mmol, 2.00 equiv), Pd(dppf)Cl₂ (47.4 mg, 64.8 µmol, 0.100 equiv) and 4,4,5,5-tetramethyl-2-(4,4,5,5-tetramethyl-1,3,2-dioxaborolan-2-yl)-1,3,2-dioxaborolane (247 mg, 972 µmol, 1.50 equiv) in dioxane (3.00 mL) was purged with nitrogen. The resultant reaction mixture was stirred at 105° C. for 1 h. The mixture was filtered and concentrated under reduced pressure to give a residue. The crude material was purified by prep-TLC (petroleum ether/ethyl acetate, 5/1) to afford 4,4,5,5-tetramethyl-2-(2-methyl-4-methylsulfonyl-phenyl)-1,3,2-dioxaborolane (110 mg, 338 µmol, 52.1% yield, 90.9% purity) as a colorless oil. LC-MS [M+1]: 296.9.

Intermediate C-7

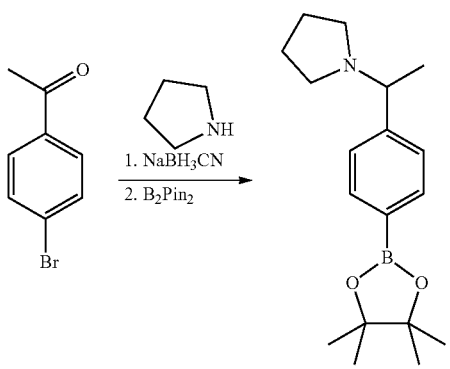

A seventh exemplary Intermediate C, Intermediate C-7, may be used to synthesize compounds of formula I or formula II, wherein R¹ is a monosubstitued aryl. To a solution of 1-(4-bromophenyl)ethanone (1.00 g, 5.02 mmol, 1.00 equiv), pyrrolidine (1.79 g, 25.1 mmol, 2.10 mL, 5.00 equiv) in methanol (16.0 mL) was added NaBH₃CN (347 mg, 5.53 mmol, 1.10 equiv). The mixture was stirred at 20° C. for 24 h. To the mixture was added water (4.00 mL) and the aqueous phase was extracted with ethyl acetate (5.00 mL). The combined organic phase was washed with brine (2.00 mL), dried over anhydrous Na₂SO₄, filtered and concentrated to afford 1-[1-(4-bromophenyl)ethyl]pyrrolidine (1.00 g, 3.93 mmol, 78.3% yield) as a yellow oil.

To a solution of 1-[1-(4-bromophenyl)ethyl]pyrrolidine (400 mg, 1.57 mmol, 1.00 equiv), 4,4,5,5-tetramethyl-2-(4,4,5,5-tetramethyl-1,3,2-dioxaborolan-2-yl)-1,3,2-dioxaborolane (799 mg, 3.15 mmol, 2.00 equiv) and potassium acetate (308 mg, 3.15 mmol, 2.00 equiv) in dioxane (2.00 mL) was added Pd(dppf)Cl₂ (115 mg, 157 µmol, 0.100 equiv). The reaction mixture was stirred at 105° C. for 2 h under an atmosphere of nitrogen. The mixture was concentrated in vacuo to give a residue. The crude material was purified by column chromatography (petroleum ether/ethyl acetate, 1/0 to 1/1) to afford 1-[1-[4-(4,4,5,5-tetramethyl-1,3,2-dioxaborolan-2-yl)phenyl]ethyl]pyrrolidine (110 mg) as a red oil.

Intermediate C-8

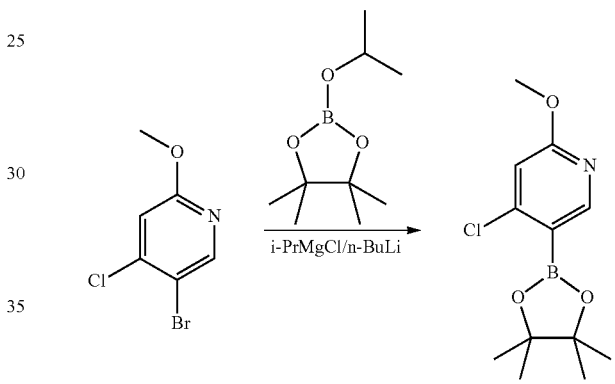

An eighth exemplary Intermediate C, Intermediate C-8, may be used to synthesize compounds of formula I or formula II, wherein R¹ is a disubstitued heteroaryl. To a solution of n-butyllithium (2.50 M, 1.80 mL, 1.00 equiv) was added dropwise over one min to i-PrMgCl (2.00 M, 1.12 mL, 0.500 equiv) in THF (12 mL) at 0° C. under a nitrogen atmosphere. The mixture was stirred at 0° C. for 5 min followed by the addition of 5-bromo-4-chloro-2-methoxypyridine (1.00 g, 4.50 mmol, 1.00 equiv) after which the mixture was stirred at 0° C. for 45 min. To this solution was added 2-isopropoxy-4,4,5,5-tetramethyl-1,3,2-dioxaborolane (836 mg, 4.50 mmol, 917 uL, 1.00 equiv) and the mixture stirred for an additional 15 min prior to stirring at 20° C. for 3 h. The reaction mixture was quenched by the addition of satd aq ammonium chloride (20.0 mL) at 20° C. and was extracted with ethyl acetate (20.0 mL×3). The combined organic layers were washed with brine (10.0 mL), dried over anhydrous sodium sulfate, filtered and concentrated under reduced pressure to afford 4-chloro-2-methoxy-5-(4,4,5,5-tetramethyl-1,3,2-dioxaborolan-2-yl)pyridine (1.00 g, 3.71 mmol, 82.5% yield) as a gray solid, which used for the next step without further purification.

¹H NMR (400 MHz, CDCl₃) δ=8.47 (s, 1H), 6.77 (s, 1H), 3.97 (s, 3H), 1.38 (s, 12H).

Intermediate C-9

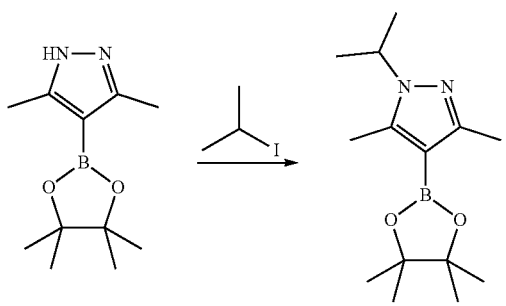

A ninth exemplary Intermediate C, Intermediate C-9 may be used to synthesize compounds of formula I or formula II, wherein $R^1$ is a trisubstitued heteroaryl. A mixture of 3,5-dimethyl-4-(4,4,5,5-tetramethyl-1,3,2-dioxaborolan-2-yl)-1H-pyrazole (100 mg, 450 μmol, 1.00 equiv), isopropyl iodide (306 mg, 1.80 mmol, 180 μL, 4.00 equiv) and cesium carbonate (587 mg, 1.80 mmol, 4.00 equiv) in acetonitrile (3.00 mL) was purged with nitrogen and subsequently stirred at 65° C. for 4 h. The mixture was filtered and the solvent was removed in vacuo to afford 1-isopropyl-3,5-dimethyl-4-(4,4,5,5-tetramethyl-1,3,2-dioxaborolan-2-yl)pyrazole (100 mg, 368 μmol, 81.8% yield, 97.3% purity) as a green oil. LC-MS [M+1]: 265.

Intermediate C-10

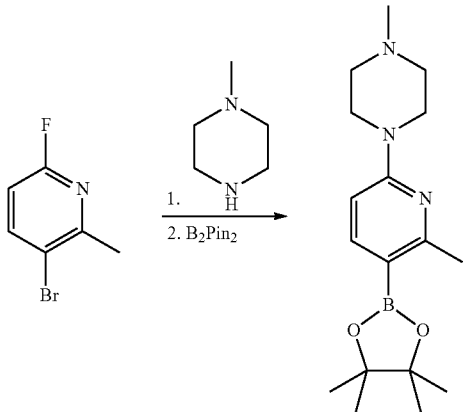

A tenth exemplary Intermediate C, Intermediate C-10, may be used to synthesize compounds of formula I or formula II, wherein $R^1$ is a disubstitued heteroaryl. A mixture of 3-bromo-6-fluoro-2-methyl-pyridine (1.00 g, 5.26 mmol, 1.00 equiv) and N-methylpiperazine (685 mg, 6.84 mmol, 759 μL, 1.30 equiv) was stirred at 110° C. for 12 h. The mixture was diluted with ethyl acetate (50.0 mL), washed with brine (20.0 mL×3), dried over anhydrous $Na_2SO_4$, filtered and concentrated to provide 1-(5-bromo-6-methyl-2-pyridyl)-4-methyl-piperazine (1.10 g, 4.07 mmol, 77.4% yield) as a yellow solid. LC-MS [M+1]: 272.1.

To a solution of 1-(5-bromo-6-methyl-2-pyridyl)-4-methyl-piperazine (400 mg, 1.48 mmol, 1.00 equiv), 4,4,5,5-tetramethyl-2-(4,4,5,5-tetramethyl-1,3,2-dioxaborolan-2-yl)-1,3,2-dioxaborolane (752 mg, 2.96 mmol, 2.00 equiv) and potassium acetate (291 mg, 2.96 mmol, 2.00 equiv) in dioxane (2.00 mL) was added Pd(dppf)Cl$_2$ (108 mg, 148 μmol, 0.100 equiv). The reaction was stirred at 105° C. for 2 h under an atmosphere of nitrogen. The mixture was concentrated in vacuo to give a residue. The crude material was purified by prep-TLC (DCM/MeOH=10/1) to afford compound 1-methyl-4-(6-methyl-5-(4,4,5,5-tetramethyl-1,3,2-dioxaborolan-2-yl)pyridin-2-yl)piperazine (210 mg, 662 μmol, 44.7% yield) as a brown oil. LC-MS [M+1]: 318.3.

Intermediate C-11

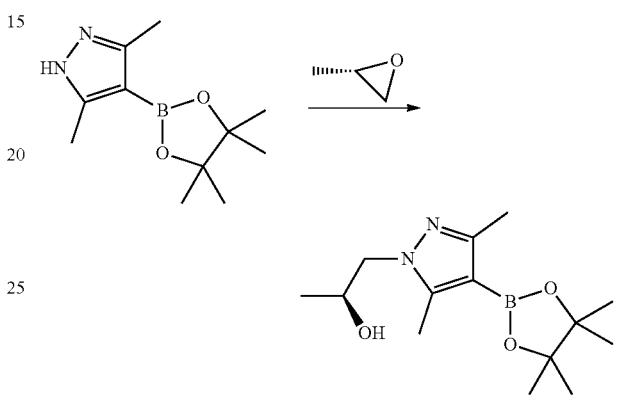

An eleventh exemplary Intermediate C, Intermediate C-11, may be used to synthesize compounds of formula I or formula II, wherein $R^1$ is a trisubstitued heteroaryl. To a solution of 3,5-dimethyl-4-(4,4,5,5-tetramethyl-1,3,2-dioxaborolan-2-yl)-1H-pyrazole (100 mg, 450 μmol, 1.00 equiv), (2S)-2-methyloxirane (392 mg, 6.75 mmol, 473 μL, 15.0 equiv) was added cesium carbonate (29.3 mg, 90.1 μmol, 0.20 equiv). The reaction mixture was stirred at 50° C. for 16 h and was subsequently concentrated under vacuum to give a residue. The crude residue was purified by prep-TLC (SiO$_2$, petroleum ether:ethyl acetate=1:1) to afford (2S)-1-[3,5-dimethyl-4-(4,4,5,5-tetramethyl-1,3,2-dioxaborolan-2-yl)pyrazol-1-yl]propan-2-ol (56.0 mg, 44.4% yield) as a yellow oil. LC-MS [M+1]: 281.3.

Intermediate C-12

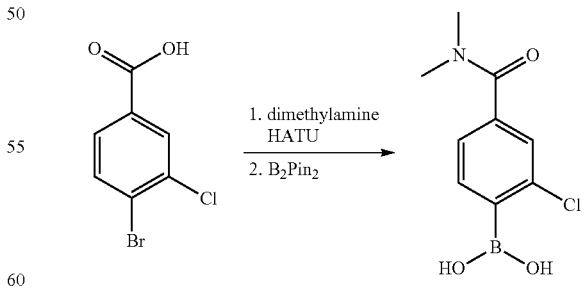

A twelfth exemplary Intermediate C, Intermediate C-12, may be used to synthesize compounds of formula I or formula II, wherein $R^1$ a disubstitued aryl. To a solution of 4-bromo-3-chloro-benzoic acid (300 mg, 1.27 mmol, 1.00 equiv), DIEA (490 mg, 3.79 mmol, 660 μL, 3.00 equiv) and N,N-dimethylamine (2.00 M in THF, 1.27 mL, 2.00 equiv)

in DMF (3.00 mL) was added HATU (727 mg, 1.91 mmol, 1.50 equiv). The mixture was stirred at room temperature for 2 h and the reaction mixture was subsequently quenched upon the addition water (15.0 mL). The mixture was extracted with dichloromethane (20.0 mL×3). The combined organic layer was washed with water (30.0 mL) and concentrated to provide the crude mixture. The resultant residue was purified by column chromatography (SiO$_2$, petroleum ether/ethyl acetate=5/1 to 2/1) to afford 4-bromo-3-chloro-N,N-dimethyl-benzamide (430 mg, 983 μmol, 77.0% yield, 60.0% purity) as a white solid. LC-MS [M+1]: 264.0.

$^1$H NMR (400 MHz, CDCl$_3$) δ=7.67 (d, J=8.2 Hz, 1H), 7.53 (d, J=1.6 Hz, 1H), 7.18 (dd, J=2.0, 8.4 Hz, 1H), 3.11 (s, 3H), 2.99 (s, 3H).

To a solution of 4-bromo-3-chloro-N,N-dimethyl-benzamide (150 mg, 343 μmol, 1.00 equiv), 4,4,5,5-tetramethyl-2-(4,4,5,5-tetramethyl-1,3,2-dioxaborolan-2-yl)-1,3,2-dioxaborolane (870 mg, 3.43 mmol, 10.0 equiv) and potassium acetate (67.0 mg, 683 μmol, 2.00 equiv) in dioxane (10.0 mL) was added Pd(PPh$_3$)$_2$Cl$_2$ (24.0 mg, 34.2 μmol, 0.10 equiv). The vessel was flushed with nitrogen and the mixture was stirred at 100° C. for 1 h. The reaction mixture was cooled to rt and filtered through a pad of Celite. Purification by prep-TLC (SiO$_2$, petroleum ether/ethyl acetate=2/1) afforded [2-chloro-4-(dimethylcarbamoyl)phenyl]boronic acid (200 mg) as a yellow solid. LC-MS [M+1]: 228.0.

Intermediate C-13

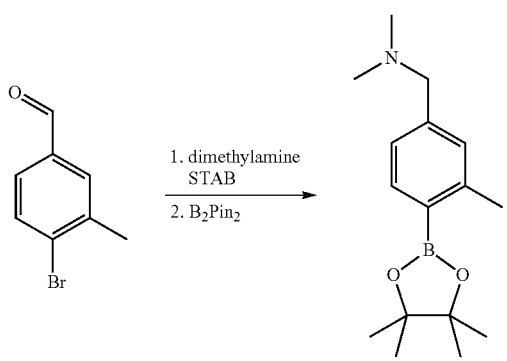

A thirteenth exemplary Intermediate C, Intermediate C-13, may be used to synthesize compounds of formula I or formula II, wherein R$^1$ is a disubstitued aryl. A mixture of 4-bromo-3-methyl-benzaldehyde (500 mg, 2.51 mmol, 1.00 equiv) and N,N-dimethylamine (2 M in THF, 6.3 mL, 12.6 mmol, 5.00 equiv) in methanol (10.0 mL) was stirred at 40° C. for 30 min. Subsequently, sodium triacetoxyborohydride (1.60 g, 7.54 mmol, 3.00 equiv) was added and the mixture was stirred for another 3 h. The solution was concentrated under reduced pressure to give a residue. The crude residue was purified by column chromatography (petroleum ether/ethyl acetate=1/0 to 0/1 then dichloromethane/methanol=20/1 to 10/1) to afford 1-(4-bromo-3-methyl-phenyl)-N,N-dimethyl-methanamine (570 mg) as a brown oil.

$^1$H NMR (400 MHz, CD$_3$OD) δ=7.61 (d, J=8.0 Hz, 1H), 7.38 (d, J=1.6 Hz, 1H), 7.16 (dd, J=1.6, 8.0 Hz, 1H), 3.96 (s, 2H), 2.63 (s, 6H), 2.42 (s, 3H).

A mixture of 1-(4-bromo-3-methyl-phenyl)-N,N-dimethyl-methanamine (470 mg, 2.06 mmol, 1.00 equiv), 4,4,4',4',5,5,5',5'-octamethyl-2,2'-bi(1,3,2-dioxaborolane) (785 mg, 3.09 mmol, 1.50 equiv), potassium acetate (404 mg, 4.12 mmol, 2.00 equiv) and Pd(dppf)Cl$_2$ (151 mg, 206 μmol, 0.100 equiv) in dioxane (8.00 mL) was purged with nitrogen and allowed to stir at 105° C. for 2 h. The mixture was concentrated under reduced pressure to give a residue. The residue was purified by column chromatography (dichloromethane/methanol=50/1 to 10/1) to afford N,N-dimethyl-1-[3-methyl-4-(4,4,5,5-tetramethyl-1,3,2-dioxaborolan-2-yl)phenyl]methanamine (70.0 mg, 185 μmol, 8.99% yield, 72.8% purity) as a brown oil. LC-MS [M+1]: 275.6.

Intermediate C-14

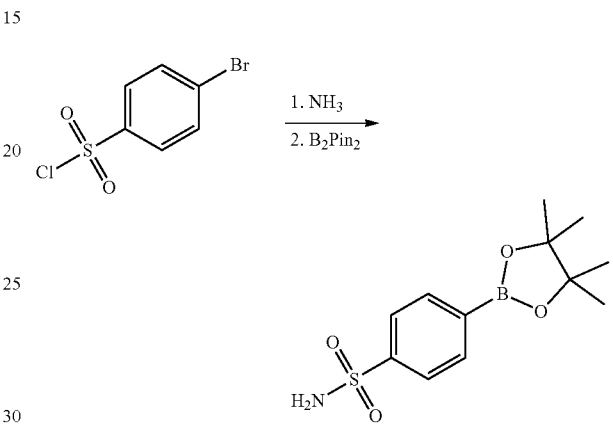

A fourteenth exemplary Intermediate C, Intermediate C-14, may be used to synthesize compounds of formula I or formula II, wherein R$^1$ is a monosubstitued aryl. To a solution of 4-bromobenzenesulfonyl chloride (200 mg, 783 μmol, 1.00 equiv) in THF (2.00 mL) was added ammonia (7 N in MeOH, 224 μL, 1.57 mmol, 2.00 equiv). The reaction mixture was stirred at 25° C. for 30 min. The mixture was concentrated in vacuo to provide a residue that was poured into water (10.0 mL). The aqueous phase was extracted with ethyl acetate (10.0 mL×3) and the combined organic phase was washed with brine (3.00 mL×3), dried with anhydrous sodium sulfate, filtered and concentrated to give 4-bromobenzenesulfonamide (180 mg, 762 μmol, 97.4% yield) as a white solid.

$^1$H NMR (400 MHz, DMSO-d$_6$) δ=7.82-7.72 (m, 4H), 7.46 (s, 2H).

To a solution of 4-bromobenzenesulfonamide (100 mg, 424 μmol, 1.00 equiv) and 4,4,5,5-tetramethyl-2-(4,4,5,5-tetramethyl-1,3,2-dioxaborolan-2-yl)-1,3,2-dioxaborolane (129 mg, 508 μmol, 1.20 equiv) in DMSO (2.00 mL) was added potassium acetate (83.1 mg, 847 μmol, 2.00 equiv) and Pd(dppf)Cl$_2$ (31.0 mg, 42.4 μmol, 0.10 equiv) under an atmosphere of nitrogen. The mixture was stirred at 80° C. for 3 h and was subsequently concentrated under vacuum to give a residue. The residue was poured into water (10.0 mL) and the aqueous phase was extracted with ethyl acetate (10.0 mL×3). The combined organic phase was washed with brine (5.00 mL×3), dried with anhydrous sodium sulfate, filtered and concentrated to afford 4-(4,4,5,5-tetramethyl-1,3,2-dioxaborolan-2-yl)benzenesulfonamide (95.0 mg, 336 μmol, 79.2% yield) as a red solid.

$^1$H NMR (400 MHz, CDCl$_3$) δ=7.96-7.88 (m, 4H), 7.26 (s, 2H), 1.35 (s, 12H).

Intermediate C-15

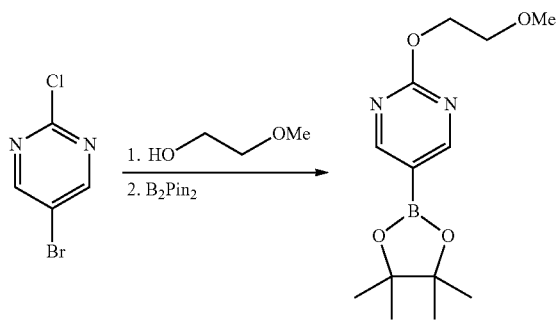 [SMILES: Clc1ncc(Br)cn1 ; COCCO ; COCCOc1ncc(B2OC(C)(C)C(C)(C)O2)cn1]

A fifteenth exemplary Intermediate C, Intermediate C-15, may be used to synthesize compounds of formula I or formula II, wherein $R^1$ is a monosubstitued heteroaryl. To a solution of 2-methoxyethanol (236 mg, 3.10 mmol, 245 μL, 1.50 equiv) in tetrahydrofuran (2.00 mL) was added portionwise sodium hydride (99.3 mg, 60.0%, 2.48 mmol, 1.20 equiv) at 0° C. The mixture was stirred at this temperature for 45 min followed by the dropwise addition of 5-bromo-2-chloro-pyrimidine (400 mg, 2.07 mmol, 1.00 equiv) at room temperature. The resulting mixture was stirred for an additional 4 h. The mixture was filtered and concentrated in vacuo to give a residue. The residue was purified by prep-TLC (petroleum ether/ethyl acetate=10/1) to afford 5-bromo-2-(2-methoxyethoxy)pyrimidine (150 mg, 644 μmol, 31.1% yield) as a white solid.

$^1$H NMR (400 MHz, CD$_3$OD) δ=8.54 (s, 2H), 4.42-4.37 (m, 2H), 3.68-3.62 (m, 2H), 3.30 (s, 3H).

A mixture of 5-bromo-2-(2-methoxyethoxy)pyrimidine (150 mg, 644 μmol, 1.00 equiv), 4,4,5,5-tetramethyl-2-(4,4,5,5-tetramethyl-1,3,2-dioxaborolan-2-yl)-1,3,2-dioxaborolane (327 mg, 1.29 mmol, 2.00 equiv), potassium acetate (126 mg, 1.29 mmol, 2.00 equiv), Pd(dppf)Cl$_2$ (47.1 mg, 64.4 μmol, 0.10 equiv) in dioxane (1.00 mL) was purged with nitrogen stirred at 100° C. for 2 h. The reaction was filtered and concentrated in vacuo to give a residue. The residue was purified by prep-TLC (petroleum ether/ethyl acetate=1/1) to afford 2-(2-methoxyethoxy)-5-(4,4,5,5-tetramethyl-1,3,2-dioxaborolan-2-yl)pyrimidine (130 mg, 464 μmol, 72.1% yield) as a yellow oil.

$^1$H NMR (400 MHz, CDCl$_3$) δ=8.83-8.79 (m, 2H), 4.61-4.54 (m, 2H), 3.82-3.76 (m, 2H), 3.44 (s, 3H), 1.36 (s, 12H).

Intermediate C-16

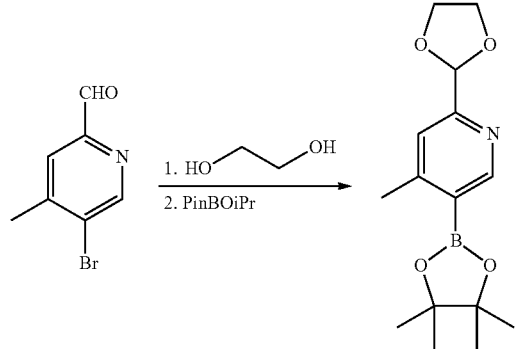

A sixteenth exemplary Intermediate C, Intermediate C-16, may be used to synthesize compounds of formula I or formula II, wherein $R^1$ is a disubstitued heteroaryl. To a solution of ethylene glycol (310 mg, 5.00 mmol, 280 μL, 2.00 equiv), 5-bromo-4-methyl-pyridine-2-carbaldehyde (500 mg, 2.50 mmol, 1.00 equiv) in toluene (20.0 mL) was added p-toluenesulfonic acid (47.6 mg, 250 μmol, 0.10 equiv). The mixture was stirred at 110° C. for 12 h and was subsequently concentrated in vacuo to give a residue. The residue was purified by column chromatography (SiO$_2$, petroleum ether/ethyl acetate=1/0 to 5:1) to afford 5-bromo-2-(1,3-dioxolan-2-yl)-4-methylpyridine (320 mg, 1.24 mmol, 49.6% yield) as a colorless oil.

$^1$H NMR (400 MHz, CDCl$_3$) δ=8.64 (s, 1H), 7.42 (s, 1H), 5.80 (s, 1H), 4.19-4.14 (m, 2H), 4.10-4.05 (m, 2H), 2.42 (s, 3H).

To a solution of 5-bromo-2-(1,3-dioxolan-2-yl)-4-methylpyridine (300 mg, 1.23 mmol, 1.00 equiv) in diethyl ether (20.0 mL) was added n-butyllithium (2.5 M, 737 μL, 1.50 equiv) at –78° C. under a nitrogen atmosphere. The mixture was stirred at –78° C. for 0.5 h followed by the addition of 2-isopropoxy-4,4,5,5-tetramethyl-1,3,2-dioxaborolane (457 mg, 2.46 mmol, 501 μL, 2.00 equiv). The mixture was warmed to 0° C. and stirred for an additional 1.5 h. The mixture was quenched with water (15.0 mL) and the resulting mixture was extracted with ethyl acetate (20.0 mL×2). The combined organic phase was dried over sodium sulfate, filtered and concentrated under reduced pressure to afford 2-(1,3-dioxolan-2-yl)-4-methyl-5-(4,4,5,5-tetramethyl-1,3,2-dioxaborolan-2-yl)pyridine (150 mg, crude) as a yellow oil. LC-MS [M+1]: 292.15.

Intermediate C-17

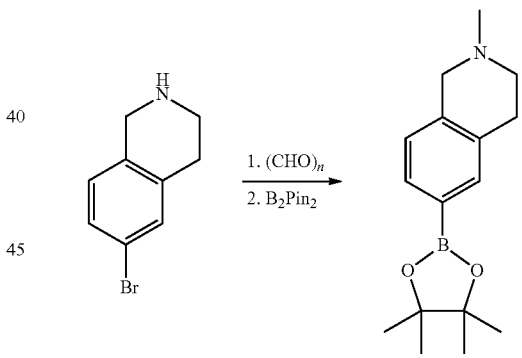

A seventeenth exemplary Intermediate C, Intermediate C-17, may be used to synthesize compounds of formula I or formula II, wherein $R^1$ is a monosubstitued bicyclic heteroaryl. A mixture of paraformaldehyde (350 mg, 3.63 mmol, 2.20 equiv) in methanol (1.00 mL) was stirred at 60° C. for 1 h and then cooled to 40° C. To the mixture was added AcOH (1 drop) and 6-bromo-1,2,3,4-tetrahydroisoquinoline (350 mg, 1.65 mmol, 1.00 equiv) followed by NaCNBH$_3$ (114 mg, 1.82 mmol, 1.1 equiv). The mixture was stirred at 40° C. for 1 h and was subsequently filtered and concentrated in vacuo to give a residue. The residue was purified by prep-TLC (petroleum ether/ethyl acetate=2/1) to afford 6-bromo-2-methyl-3,4-dihydro-1H-isoquinoline (360 mg, 1.59 mmol, 96.5% yield) as a yellow oil.

$^1$H NMR (400 MHz, CD$_3$OD) δ=7.32 (s, 1H), 7.28 (dd, J=2.0, 8.4 Hz, 1H), 7.00 (d, J=8.0 Hz, 1H), 3.57 (s, 2H), 2.94 (t, J=6.0 Hz, 2H), 2.75-2.72 (m, 2H), 2.46 (s, 3H).

A mixture of 6-bromo-2-methyl-3,4-dihydro-1H-isoquinoline (220 mg, 973 µmol, 1.00 equiv), 4,4,5,5-tetramethyl-2-(4,4,5,5-tetramethyl-1,3,2-dioxaborolan-2-yl)-1,3,2-dioxaborolane (494 mg, 1.95 mmol, 2.00 equiv), potassium acetate (191 mg, 1.95 mmol, 2.00 equiv), Pd(dppf)Cl$_2$ (71.2 mg, 97.3 µmol, 0.10 equiv) in dioxane (3.00 mL) was purged with nitrogen and subsequently stirred at 100° C. for 2 h. The mixture was filtered and concentrated in vacuo to give a residue. The residue was purified by prep-TLC (petroleum ether/ethyl acetate=2/1) to afford 2-methyl-6-(4,4,5,5-tetramethyl-1,3,2-dioxaborolan-2-yl)-3,4-dihydro-1H-isoquinoline (150 mg, crude) as a white solid.

Intermediate C-18

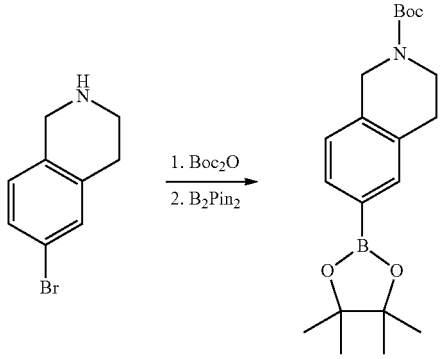 [SMILES: Brc1ccc2c(c1)CCNC2 ; CC(C)(C)OC(=O)N1CCc2cc(B3OC(C)(C)C(C)(C)O3)ccc2C1]

An eighteenth exemplary Intermediate C, Intermediate C-18, may be used to synthesize compounds of formula I or formula II, wherein R$^1$ is a N-protected bicyclic heteroaryl. To a solution of 6-bromo-1,2,3,4-tetrahydroisoquinoline (400 mg, 1.89 mmol, 1.00 equiv) in tetrahydrofuran (2.00 mL) was added Boc$_2$O (617 mg, 2.83 mmol, 1.50 equiv) and dimethylaminopyridine (46.1 mg, 377 µmol, 0.20 equiv). The mixture was stirred at 25° C. for 3 h and was subsequently filtered and concentrated in vacuo to give a residue. The residue was purified by column chromatography (SiO$_2$, Petroleum ether/Ethyl acetate=20/1 to 3/1) to afford tert-butyl 6-bromo-3,4-dihydro-1H-isoquinoline-2-carboxylate (150 mg, 480 µmol, 25.5% yield) as a white solid.

$^1$H NMR (400 MHz, CD$_3$OD) δ=7.38-7.32 (m, 2H), 7.07 (d, J=8.0 Hz, 1H), 4.52 (br s, 2H), 3.64 (br t, J=6.0 Hz, 2H), 2.84 (t, J=6.0 Hz, 2H), 1.51 (s, 9H).

A mixture of tert-butyl 6-bromo-3,4-dihydro-1H-isoquinoline-2-carboxylate (140 mg, 448 µmol, 1.00 equiv), 4,4,5,5-tetramethyl-2-(4,4,5,5-tetramethyl-1,3,2-dioxaborolan-2-yl)-1,3,2-dioxaborolane (228 mg, 897 µmol, 2.00 equiv), Pd(dppf)Cl$_2$ (32.8 mg, 44.8 µmol, 0.10 equiv), potassium acetate (88.0 mg, 897 µmol, 2.00 equiv) in dioxane (1.00 mL) was purged with nitrogen and subsequently stirred at 100° C. for 2 h. The mixture was filtered and concentrated in vacuo to give a residue. The residue was purified by prep-TLC (petroleum ether/ethyl acetate=2/1) to afford tert-butyl 6-(4,4,5,5-tetramethyl-1,3,2-dioxaborolan-2-yl)-3,4-dihydro-1H-isoquinoline-2-carboxylate (100 mg, 278 µmol, 62.1% yield) as a yellow oil.

$^1$H NMR (400 MHz, CD$_3$OD) δ=7.58-7.54 (m, 2H), 7.13 (d, J=8.0 Hz, 1H), 4.58 (br s, 2H), 3.65 (br t, J=6.0 Hz, 2H), 2.84 (t, J=6.0 Hz, 2H), 1.35 (s, 12H), 1.19 (br s, 1H), 1.22 (s, 9H).

Intermediate C-19

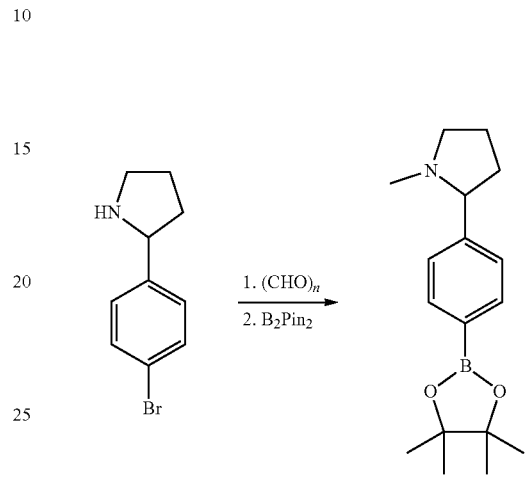

A nineteenth exemplary Intermediate C, Intermediate C-19, may be used to synthesize compounds of formula I or formula II, wherein R$^1$ is a monosubstitued aryl. A mixture of paraformaldehyde (133 mg, 4.42 mmol, 122 µL, 10.0 equiv) and methyl alcohol (1.00 mL) was stirred at 60° C. for 1 h and then cooled to 0° C. To the mixture was added acetic acid (52.5 mg, 874 µmol, 0.05 mL, 1.98 equiv) and 2-(4-bromophenyl)pyrrolidine (100 mg, 442 µmol, 1.00 equiv). The mixture was allowed to stir for 1 h at room temperature prior to the addition of sodium cyanoborohydride (83.4 mg, 1.33 mmol, 3.00 equiv) and an additional hour of stirring. The mixture was filtered and concentrated under reduced pressure to give a residue. The residue was purified by prep-TLC (SiO$_2$, petroleum ether/ethyl acetate=3/1) to afford 2-(4-bromophenyl)-1-methyl-pyrrolidine (100 mg, 413 µmol, 93.3% yield, 99.1% purity) as a white solid. LC-MS [M+1]: 240.1.

$^1$H NMR (400 MHz, CDCl$_3$) δ=7.48-7.41 (m, 2H), 7.26-7.21 (m, 2H), 3.33-3.14 (m, 1H), 3.02 (t, J=8.4 Hz, 1H), 2.29 (q, J=9.2 Hz, 1H), 2.16 (s, 3H), 2.06-1.89 (m, 1H), 1.86-1.77 (m, 1H), 1.76-1.69 (m, 2H).

A mixture of 2-(4-bromophenyl)-1-methyl-pyrrolidine (48.0 mg, 200 µmol, 1.00 equiv), bis(pinacolato)diboron (76.1 mg, 300 µmol, 1.50 equiv), potassium acetate (58.9 mg, 600 µmol, 3.00 equiv), Pd(dppf)Cl$_2$ (14.6 mg, 20.0 µmol, 0.10 equiv) in dioxane (1.00 mL) was purged with nitrogen and then stirred at 90° C. for 2 h. The mixture was filtered and concentrated under reduced pressure to provide a residue. The residue was purified by prep-TLC (SiO$_2$, petroleum ether/ethyl acetate=3/1) to afford 1-methyl-2-[4-(4,4,5,5-tetramethyl-1,3,2-dioxaborolan-2-yl)phenyl]pyrrolidine (23.0 mg, 73.3 µmol, 36.7% yield, 91.5% purity) as a white solid. LC-MS [M+1]: 288.0.

Intermediate C-20

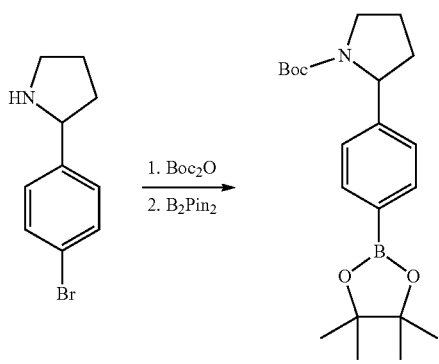 [SMILES: Brc1ccc(C2CCCN2)cc1 ; CC(C)(C)OC(=O)N1CCCC1c1ccc(B2OC(C)(C)C(C)(C)O2)cc1]

A twentieth exemplary Intermediate C, Intermediate C-20, may be used to synthesize compounds of formula I or formula II, wherein $R^1$ is a monosubstituted aryl. A mixture of 2-(4-bromophenyl)pyrrolidine (50.0 mg, 221 μmol, 1.00 equiv), di-tert-butyl dicarbonate (57.9 mg, 265 μmol, 1.20 equiv) and dimethylaminopyridine (2.70 mg, 22.1 μmol, 0.10 equiv) in tetrahydrofuran (1.00 mL) was purged with nitrogen and then was stirred at 25° C. for 2 h. The mixture was filtered and concentrated under reduced pressure. The resultant residue was purified by prep-TLC (SiO$_2$, petroleum ether/ethyl acetate=10/1) to afford tert-butyl 2-(4-bromophenyl)pyrrolidine-1-carboxylate (55.0 mg, 163 μmol, 73.6% yield, 96.5% purity) as a yellow oil. LC-MS [M–55]: 272.1.

A mixture of tert-butyl 2-(4-bromophenyl)pyrrolidine-1-carboxylate (46.6 mg, 138 μmol, 1.00 equiv), bis(pinacolato)diboron (52.5 mg, 207 μmol, 1.50 equiv), potassium acetate (40.6 mg, 414 μmol, 3.00 equiv) and Pd(dppf)Cl$_2$ (10.1 mg, 13.8 μmol, 0.10 equiv) in dioxane (1.00 mL) was purged with nitrogen and then stirred at 90° C. for 2 h. The mixture was filtered and concentrated under reduced pressure. The residue was purified by prep-TLC (SiO$_2$, petroleum ether/ethyl acetate=5/1) to afford tert-butyl 2-[4-(4,4,5,5-tetramethyl-1,3,2-dioxaborolan-2-yl)phenyl]pyrrolidine-1-carboxylate (45.0 mg, 102 μmol, 74.3% yield, 85.0% purity) as a yellow solid. LC-MS [M–55]: 318.2.

$^1$H NMR (400 MHz, CDCl$_3$) δ=7.75 (br d, J=7.6 Hz, 2H), 7.17 (br d, J=7.6 Hz, 2H), 4.80 (br s, 1H), 3.63 (br s, 2H), 2.32 (br s, 1H), 1.98-1.75 (m, 3H), 1.58 (s, 9H), 1.35 (br s, 12H).

Intermediate C-21

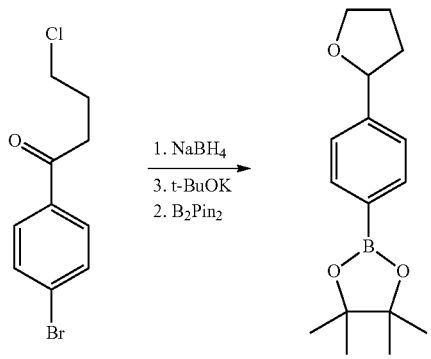

A twenty first exemplary Intermediate C, Intermediate C-21, may be used to synthesize compounds of formula I or formula II, wherein $R^1$ is a monosubstitued heteroaryl. To a solution of a 1-(4-bromophenyl)-4-chloro-butan-1-one (1.00 g, 3.82 mmol, 1.00 equiv) in methanol (13.0 mL) was added portionwise NaBH$_4$ (300 mg, 7.93 mmol, 2.07 equiv) at room temperature. The mixture was allowed to stir at room temperature for 2 h and was subsequently quenched by the addition of water (10.0 mL). The mixture was diluted with dichloromethane (20 mL) and the organic layer was washed with water and brine, dried over anhydrous sodium sulfate, filtered and concentrated under reduced pressure to afford the crude product 1-(4-bromophenyl)-4-chloro-butan-1-ol (1.00 g, 3.79 mmol, 99.2% yield) as a light yellow oil.

$^1$H NMR (400 MHz, CDCl$_3$) δ=7.49 (d, J=8.4 Hz, 2H), 7.24 (d, J=8.4 Hz, 2H), 4.71 (br t, J=6.0 Hz, 1H), 3.54 (s, 2H), 2.01-1.72 (m, 4H).

A solution of 1-(4-bromophenyl)-4-chloro-butan-1-ol (500 mg, 1.90 mmol, 1.00 equiv) and t-BuOK (1.0 M in THF, 1.90 mL, 1.00 equiv) was stirred for 2 h at room temperature. The reaction was quenched with water and extracted with ether (2×20.0 ml). The combined organic phase was dried over anhydrous sodium sulfate, filtered and concentrated under reduced pressure to provide 2-(4-bromophenyl)tetrahydrofuran (420 mg, 1.85 mmol, 97.5% yield) as a white solid.

$^1$H NMR (400 MHz, CDCl$_3$) δ=7.49-7.42 (m, 2H), 7.24-7.18 (m, 2H), 4.85 (t, J=7.2 Hz, 1H), 4.13-4.05 (m, 1H), 3.97-3.90 (m, 1H), 2.38-2.27 (m, 1H), 2.06-1.95 (m, 2H), 1.80-1.70 (m, 1H).

To a mixture of 2-(4-bromophenyl)tetrahydrofuran (150 mg, 661 μmol, 1.00 equiv) and 4,4,5,5-tetramethyl-2-(4,4,5,5-tetramethyl-1,3,2-dioxaborolan-2-yl)-1,3,2-dioxaborolane (252 mg, 992 μmol, 1.50 equiv), potassium acetate (195 mg, 1.99 mmol, 3.01 equiv) in dioxane (5.00 mL) was added Pd(dppf)Cl$_2$ (48.3 mg, 66.0 μmol, 0.10 equiv). The mixture was stirred at 105° C. for 1 h, cooled to room temperature and filtered through a pad of Celite. The filtrate was concentrated to give a residue that was purified by prep-TLC (SiO$_2$, petroleum ether/ethyl acetate=2/1) to afford 4,4,5,5-tetramethyl-2-(4-tetrahydrofuran-2-ylphenyl)-1,3,2-dioxaborolane (240 mg, 639 μmol, 96.8% yield, 73% purity) as a colorless oil. LC-MS [M+1]: 275.1.

$^1$H NMR (400 MHz, CDCl$_3$) δ=7.78 (d, J=8.4 Hz, 2H), 7.34 (d, J=7.6 Hz, 2H), 4.92 (t, J=7.2 Hz, 1H), 4.17-4.06 (m, 1H), 4.00-3.90 (m, 1H), 2.41-2.27 (m, 1H), 2.09-1.91 (m, 2H), 1.85-1.73 (m, 1H), 1.35 (s, 12H).

Intermediate C-22

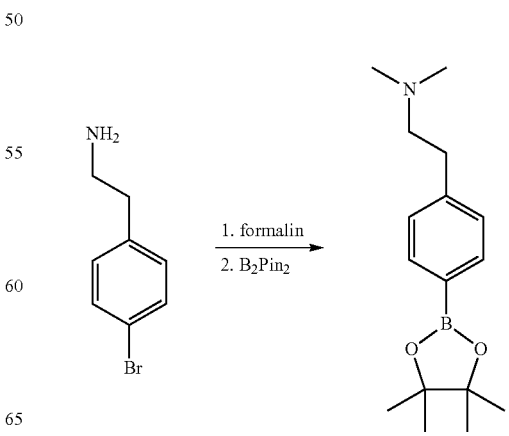

A twenty second exemplary Intermediate C, Intermediate C-22, may be used to synthesize compounds of formula I or formula II, wherein $R^1$ is a monosubstituted aryl. To a cooled solution of 2-(4-bromophenyl)ethanamine (200 mg, 1.0 mmol, 155 µL, 1.00 equiv) in formalin (300 mg, 9.99 mmol, 275 µL, 10.0 equiv) was added HCOOH (5.00 mL) and the solution was stirred at 110° C. for 16 h under nitrogen. The reaction mixture was concentrated to give a residue. To the residue was added HCl (3 N, 1.00 mL) and the mixture was washed with ethyl acetate (310 mL). The aqueous phase was basified to pH=14 with NaOH (10 N, 1.00 mL) and then extracted with ethyl acetate (3×15.0 mL). The combined organic phase was washed with brine (2×15.0 mL), dried over anhydrous sodium sulfate, and concentrated in vacuo to afford 2-(4-bromophenyl)-N,N-dimethyl-ethanamine (200 mg, 877 µmol, 87.7% yield) as a colorless oil.

1H NMR (400 MHz, CDCl$_3$) δ=7.40 (d, J=8.4 Hz, 2H), 7.09 (d, J=8.4 Hz, 2H), 2.73 (d, J=8.4 Hz, 2H), 2.56-2.48 (m, 2H), 2.29 (s, 6H).

A mixture of 2-(4-bromophenyl)-N,N-dimethyl-ethanamine (160 mg, 701 µmol, 1.00 equiv), 4,4,5,5-tetramethyl-2-(4,4,5,5-tetramethyl-1,3,2-dioxaborolan-2-yl)-1,3,2-dioxaborolane (268 mg, 1.06 mmol, 1.50 equiv), Pd(dppf)Cl$_2$ (51.2 mg, 70.0 µmol, 0.10 equiv), potassium acetate (206 mg, 2.10 mmol, 3.00 equiv) in dioxane (8.00 mL) was purged with nitrogen and was stirred at 100° C. for 1 h. The mixture was concentrated to give a residue that was purified by prep-TLC (SiO$_2$, dichloromethane/methanol=10/1) to afford N,N-dimethyl-2-[4-(4,4,5,5-tetramethyl-1,3,2-dioxaborolan-2-yl)phenyl]ethanamine (350 mg, crude) as a black oil. LC-MS [M+1]: 276.2.

Intermediate C-23

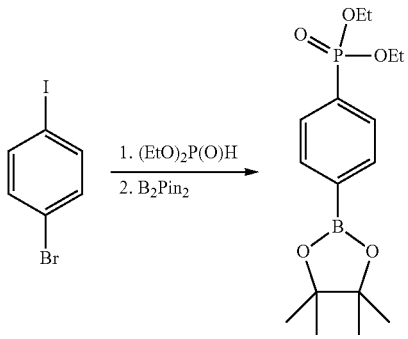

A twenty third exemplary Intermediate C, Intermediate C-23, may be used to synthesize compounds of formula I or formula II, wherein $R^1$ is a monosubstitued aryl. To a solution of 1-bromo-4-iodo-benzene (200 mg, 707 µmol, 1.00 equiv), diethyl phosphite (97.6 mg, 707 µmol, 91.2 µL, 1.00 equiv) in tetrahydrofuran (2.00 mL) was added Pd(OAc)$_2$ (4.76 mg, 21.2 µmol, 0.03 equiv), potassium acetate (9.02 mg, 91.9 µmol, 0.13 equiv), DPPF (23.5 mg, 42.4 µmol, 0.06 equiv) and triethylamine (107 mg, 1.06 mmol, 147 µL, 1.50 equiv). The vessel was flushed with nitrogen and stirred at 68° C. for 1 h. The mixture was concentrated in vacuo to give a residue. The residue was purified by prep-TLC (SiO$_2$, petroleum ether/ethyl acetate=1/1) to afford 1-bromo-4-diethoxyphosphoryl-benzene (110 mg, 341 µmol, 48.2% yield, 90.8% purity) as a red solid. LC-MS [M+3]: 294.9.

$^1$H NMR (400 MHz, CDCl$_3$) δ=7.73-7.57 (m, 4H), 4.22-3.99 (m, 4H), 1.32 (t, J=7.2 Hz, 6H).

To a solution of 1-bromo-4-diethoxyphosphoryl-benzene (100 mg, 341 µmol, 1.00 equiv), 4,4,5,5-tetramethyl-2-(4,4,5,5-tetramethyl-1,3,2-dioxaborolan-2-yl)-1,3,2-dioxaborolane (104 mg, 409 µmol, 1.20 equiv) in dioxane (2.00 mL) was added Pd(dppf)Cl$_2$ (24.9 mg, 34.1 µmol, 0.10 equiv) and potassium acetate (67.0 mg, 682 µmol, 2.00 equiv) under a nitrogen atmosphere. The mixture was stirred at 100° C. for 2 h and was subsequently concentrated in vacuo to give a residue. The residue was purified by prep-TLC (SiO$_2$, petroleum ether/ethyl acetate=1/1) to afford 2-(4-diethoxyphosphorylphenyl)-4,4,5,5-tetramethyl-1,3,2-dioxaborolane (55.0 mg, 162 µL, 47.4% yield) as a red oil.

$^1$H NMR (400 MHz, CDCl$_3$) δ=7.93-7.87 (m, 2H), 7.85-7.76 (m, 2H), 4.21-4.01 (m, 4H), 1.36 (s, 12H), 1.32 (t, J=7.2 Hz, 6H).

Intermediate C-24

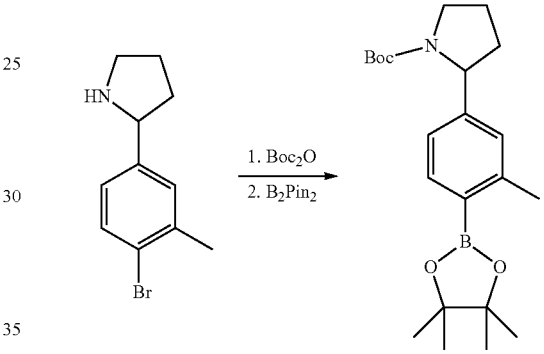

A twenty fourth exemplary Intermediate C, Intermediate C-24, may be used to synthesize compounds of formula I or formula II, wherein $R^1$ is a disubstituted aryl. To a solution of 2-(4-bromo-3-methyl-phenyl)pyrrolidine (500 mg, 2.08 mmol, 1.00 equiv) in dichloromethane (5.00 mL) was added Boc$_2$O (1.05 g, 4.79 mmol, 1.10 mL, 2.30 equiv) and dimethylaminopyridine (25.4 mg, 208 µmol, 0.10 equiv). The mixture was stirred at 25° C. for 1 h and was subsequently filtered and concentrated under reduced pressure to give a residue. The residue was purified by column chromatography (SiO$_2$, petroleum ether/ethyl acetate=30/1 to 20/1) to afford tert-butyl 2-(4-bromo-3-methyl-phenyl)pyrrolidine-1-carboxylate (600 mg, 84.7% yield) as a yellow oil.

$^1$H NMR (400 MHz, CD$_3$OD) δ=7.46 (br d, J=8.4 Hz, 1H), 7.10 (d, J=1.6 Hz, 1H), 6.92 (dd, J=1.6, 8.0 Hz, 1H), 4.73 (br s, 1H), 3.65-3.51 (m, 2H), 2.37 (s, 3H), 2.34-2.27 (m, 1H), 1.93-1.82 (m, 2H), 1.82-1.73 (m, 1H), 1.45 (br s, 3H), 1.24-1.13 (m, 6H).

A mixture of 4,4,5,5-tetramethyl-2-(4,4,5,5-tetramethyl-1,3,2-dioxaborolan-2-yl)-1,3,2-dioxaborolane (268 mg, 1.06 mmol, 1.20 equiv), tert-butyl 2-(4-bromo-3-methyl-phenyl)pyrrolidine-1-carboxylate (300 mg, 882 µmol, 1.00 equiv), Pd(dppf)Cl$_2$ (64.1 mg, 88.2 µL, 0.10 equiv) and potassium acetate (173 mg, 1.76 mmol, 2.00 equiv) in dioxane (3.00 mL) was purged with nitrogen and then the mixture was stirred at 100° C. for 1.5 h. The reaction mixture was filtered and concentrated under reduced pressure to give a residue. The residue was purified by column chromatography (SiO$_2$, petroleum ether/ethyl acetate=20/1 to 10/1) to afford tert-butyl 2-[3-methyl-4-(4,4,5,5-tetramethyl-1,3,2-dioxaborolan-2-yl)phenyl]pyrrolidine-1-carboxylate (260 mg, 76.1% yield) as a white solid.

$^1$H NMR (400 MHz, CDCl$_3$) δ=7.68 (br d, J=7.6 Hz, 1H), 7.0-6.94 (m, 2H), 4.98-4.66 (m, 1H), 3.61 (br s, 2H), 2.52 (s, 3H), 2.36 (br s, 1H), 1.93-1.76 (m, 3H), 1.35 (br s, 12H), 1.29-1.25 (m 3H), 1.21 (br s, 6H).

Intermediate C-25

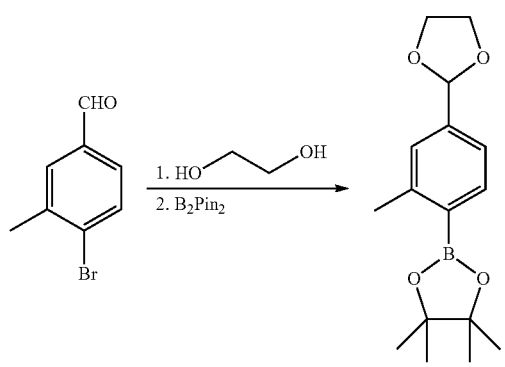

A twenty fifth exemplary Intermediate C, Intermediate C-25, may be used to synthesize compounds of formula I or formula II, wherein R$^1$ is a disubstitued aryl. To a solution of 4-bromo-3-methyl-benzaldehyde (2.00 g, 10.1 mmol, 1.00 equiv) in toluene (100 mL) was added Ts-OH—H$_2$O (191 mg, 1.00 mmol, 0.10 equiv) and ethylene glycol (1.25 g, 20.1 mmol, 1.12 mL, 2.00 equiv). The mixture was stirred at 130° C. for 12 h prior to cooling to room temperature. The pH was adjusted to 9 with DMAP and then concentrated in vacuo. The residue was purified by column chromatography (neutral Al$_2$O$_3$, petroleum ether/ethyl acetate=1/0 to 100/1) to afford 2-(4-bromo-3-methyl-phenyl)-1,3-dioxolane (2.30 g, 9.46 mmol, 94.2% yield) as a yellow oil.

$^1$H NMR (400 MHz, CDCl$_3$) δ=7.54 (d, J=8.4 Hz, 1H), 7.36 (d, J=1.6 Hz, 1H), 7.17 (dd, J=2.4, 8.0 Hz, 1H), 5.76 (s, 1H), 4.15-4.08 (m, 2H), 4.08-4.00 (m, 2H), 2.42 (s, 3H).

A mixture of 2-(4-bromo-3-methyl-phenyl)-1,3-dioxolane (2.50 g, 10.3 mmol, 1.00 equiv), Pin$_2$B$_2$ (3.39 g, 13.4 mmol, 1.30 equiv), KOAc (2.02 g, 20.6 mmol, 2.00 equiv) and Pd(dppf)Cl$_2$ (376 mg, 514 μmol, 0.05 equiv) in dioxane (30.0 mL) was purged with N$_2$ and then stirred at 100° C. for 6 h. The mixture was concentrated in vacuo. The residue was purified by column chromatography (neutral Al$_2$O$_3$, petroleum ether/ethyl acetate=1/0 to 50/1) to afford 2-[4-(1,3-dioxolan-2-yl)-2-methyl-phenyl]-4,4,5,5-tetramethyl-1,3,2-dioxaborolane (2.60 g, 8.96 mmol, 87.1% yield) as a green oil.

$^1$H NMR (400 MHz, CDCl$_3$) δ=7.78 (d, J=7.6 Hz, 1H), 7.29-7.25 (m, 2H), 5.81 (s, 1H), 4.15-4.08 (m, 2H), 4.07-4.01 (m, 2H), 2.56 (s, 3H), 1.35 (s, 12H).

Intermediate C-26

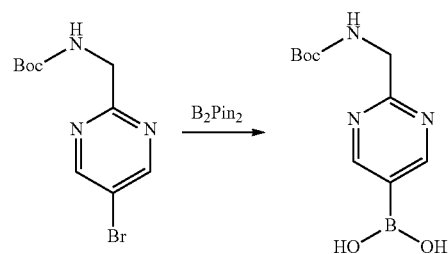

A twenty sixth exemplary Intermediate C, Intermediate C-26, may be used to synthesize compounds of formula I or formula II, wherein R$^1$ is a monosubstitued heteroaryl. A mixture of tert-butyl N-[(5-bromopyrimidin-2-yl)methyl]carbamate (100 mg, 347 μmol, 1.00 equiv), Pin$_2$B$_2$ (176 mg, 694 μmol, 2.00 equiv), KOAc (68.1 mg, 694 μmol, 2.00 equiv) and Pd(dppf)Cl$_2$ (25.4 mg, 34.7 μmol, 0.10 equiv) in dioxane (2.00 mL) was purged with N$_2$ and then stirred at 100° C. for 2 h. The reaction mixture was filtered and concentrated in vacuo to afford [2[(tert-butoxycarbonylamino)methyl]pyrimidin-5-yl]boronic acid (100 mg, crude) as a red oil. LC-MS [M−55]: 198.1.

Intermediate C-27

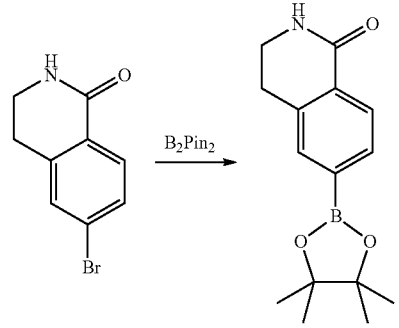

A twenty seventh exemplary Intermediate C, Intermediate C-27, may be used to synthesize compounds of formula I or formula II, wherein R$^1$ a monosubstitued bicyclic heteroaryl. A mixture of 6-bromo-3,4-dihydro-2H-isoquinolin-1-one (150 mg, 664 μmol, 1.00 equiv), 4,4,5,5-tetramethyl-2-(4,4,5,5-tetramethyl-1,3,2-dioxaborolan-2-yl)-1,3,2-dioxaborolane (253 mg, 996 μmol, 1.50 equiv), Pd(dppf)Cl$_2$ (48.55 mg, 66.35 μmol, 0.10 equiv), potassium acetate (195 mg, 1.99 mmol, 3.00 equiv) in dioxane (5.00 mL) was purged with nitrogen and then stirred at 95° C. for 2 h. The reaction mixture was cooled and filtered through a pad of Celite and the filtrate was concentrated to give a residue. The residue was purified by column chromatography (SiO$_2$, petroleum ether/ethyl acetate=3/1 to 1/1) to afford 6-(4,4,5,5-tetramethyl-1,3,2-dioxaborolan-2-yl)-3,4-dihydro-2H-isoquinolin-1-one (180 mg, 659 μmol, 99.32% yield) as an off-white solid. LC-MS [M+1]: 274.1.

$^1$H NMR (400 MHz, CDCl$_3$) δ=8.07 (d, J=8.0 Hz, 1H), 7.80 (d, J=7.6 Hz, 1H), 7.67 (s, 1H), 6.04 (s, 1H), 3.57 (dt, J=2.8, 6.4 Hz, 2H), 3.02 (t, J=6.4 Hz, 2H), 1.37 (s, 12H).

Intermediate C-28

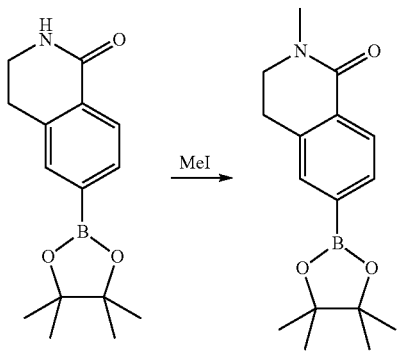 [SMILES: "MeI" ; CC1(C)OB(c2ccc3c(c2)CCNC3=O)OC1(C)C ; CN1CCc2cc(B3OC(C)(C)C(C)(C)O3)ccc2C1=O]

A twenty eighth exemplary Intermediate C, Intermediate C-28, may be used to synthesize compounds of formula I or formula II, wherein $R^1$ is a disubstitued bicyclic heteroaryl. To a suspension of NaH (79.1 mg, 60%, 1.98 mmol, 2.00 equiv) in DMF (3.00 mL) at 0° C. was added dropwise a solution of 6-(4,4,5,5-tetramethyl-1,3,2-dioxaborolan-2-yl)-3,4-dihydro-2H-isoquinolin-1-one (270 mg, 989 μmol, 1.00 equiv) in DMF. The mixture was stirred at this temperature for an additional 30 min prior to the dropwise addition of $CH_3I$ (1.40 g, 9.89 mmol, 615 μL, 10.0 equiv) at 0° C. The mixture was allowed to warm to room temperature and stirred for 3 h. The reaction was quenched upon the addition of 20.0 mL of water followed by extraction with diethyl ether (3×30.0 mL). The combined organic layer was washed with water (50.0 mL), dried over sodium sulfate, filtered and concentrated under reduced pressure to afford 2-methyl-6-(4,4,5,5-tetramethyl-1,3,2-dioxaborolan-2-yl)-3,4-dihydroisoquinolin-1-one (300 mg, crude) as a black oil. LC-MS [M+1]: 288.1.

$^1$H NMR (400 MHz, $CHCl_3$-d) δ=8.07 (d, J=7.6 Hz, 1H), 7.77 (d, J=7.6 Hz, 1H), 7.63 (s, 1H), 3.56 (t, J=6.8 Hz, 2H), 3.16 (s, 3H), 3.01 (t, J=6.8 Hz, 2H), 1.36 (s, 12H).

Intermediate C-29

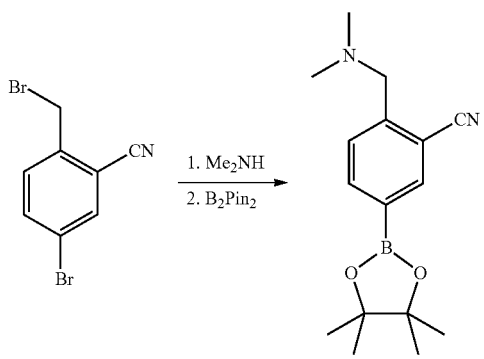

A twenty ninth exemplary Intermediate C, Intermediate C-29, may be used to synthesize compounds of formula I or formula II, wherein $R^1$ is a disubstitued aryl. A mixture of 5-bromo-2-(bromomethyl)benzonitrile (100 mg, 364 μmol, 1.00 equiv), diisopropylethylamine (141 mg, 1.09 mmol, 190 μL, 3.00 equiv) and dimethylamine (2.00 M, 1.82 mL, 10.0 equiv) in dimethyl formamide (2.00 mL) was stirred at room temperature for 3 h. The reaction mixture was diluted with water 5.00 mL and extracted with ethyl acetate (5.00 mL×3). The combined organic layer was washed with brine (3.00 mL×3), dried over sodium sulfate, filtered and concentrated under reduced pressure to give a residue. The residue was purified by prep-TLC (petroleum ether/ethyl acetate=3/1) to afford 5-bromo-2-[(dimethylamino)methyl] benzonitrile (50.0 mg, 209 μmol, 57.5% yield) as a yellow oil. LC-MS [M+1]: 239.2.

$^1$H NMR (400 MHz, $CDCl_3$) δ=7.77 (d, J=2.0 Hz, 1H), 7.69 (dd, J=2.0, 8.4 Hz, 1H), 7.46 (d, J=8.4 Hz, 1H), 3.59 (s, 2H), 1.59 (br s, 6H).

A mixture of 5-bromo-2-[(dimethylamino)methyl]benzonitrile (30.0 mg, 125 μmol, 1.00 equiv), bis(pinacolato) diboron (63.7 mg, 251 μmol, 2.00 equiv), potassium acetate (36.9 mg, 376 μmol, 3.00 equiv) and Pd(dppf)$Cl_2 \cdot CH_2Cl_2$ (3.07 mg, 3.76 μmol, 0.03 equiv) in dioxane (1.00 mL) was purged with nitrogen and then stirred at 90° C. for 4 h. The mixture was filtered and concentrated under reduced pressure to give the crude product 2-[(dimethylamino)methyl]-5-(4,4,5,5-tetramethyl-1,3,2-dioxaborolan-2-yl)benzonitrile (40.0 mg) as a black oil which was used in the next step without further purification.

Intermediate C-30

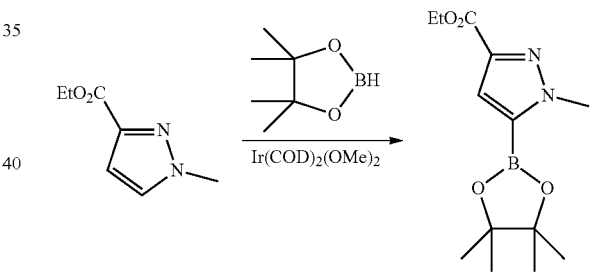

A thirtieth exemplary Intermediate C, Intermediate C-30, may be used to synthesize compounds of formula I or formula II, wherein $R^1$ is a disubstituted heteroaryl. To a solution of Ir(COD)$_2$(OMe)$_2$ (5.00 mg, 7.54 μmol, 0.02 equiv) and 4,4,5,5-tetramethyl-1,3,2-dioxaborolane (68.5 mg, 535 μmol, 77.7 μL, 1.50 equiv) in n-pentane (0.50 mL) was added 4-tert-butyl-2-(4-tert-butyl-2-pyridyl)pyridine (5.00 mg, 18.6 μL, 0.05 equiv) and the mixture was stirred at 25° C. for 20 minutes. To this mixture was added a solution of methyl 1-methylpyrazole-3-carboxylate (50.0 mg, 357 μmol, 1.00 equiv) in n-pentane (0.50 mL) and THF (0.50 mL) and the mixture was stirred at 25° C. for 24 h. The mixture was partitioned between ethyl acetate (10.0 mL) and water (10.0 mL). The organic phase was dried over anhydrous sodium sulfate and concentrated to afford the crude product methyl 1-methyl-5-(4,4,5,5-tetramethyl-1,3,2-dioxaborolan-2-yl)pyrazole-3-carboxylate (50.0 mg, 113 μmol, 31.6% yield, 60.0% purity) as a black oil.

$^1$H NMR (400 MHz, $CDCl_3$) δ=7.28 (s, 1H), 4.15 (s, 3H), 3.93 (s, 3H), 1.35 (s, 12H).

Intermediate C-31

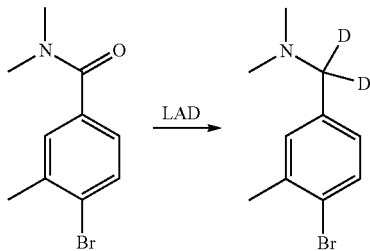

A thirty first exemplary Intermediate C, Intermediate C-31, may be used to synthesize compounds of formula I or formula II, wherein $R^1$ is a disubstitued aryl, in which one substituent has two hydrogens replaced with deuteriums. To a solution of 4-bromo-N,N,3-trimethyl-benzamide (500 mg, 2.07 mmol, 1.00 equiv) in THF (5.00 mL) was added lithium tetradeuterioalumanide (235 mg, 6.20 mmol, 3.00 equiv). The mixture was stirred at 0° C. for 1.5 h and subsequently was warmed to room temperature and allowed to stir for another hour. The reaction mixture was cooled to 0° C. and diluted with THF (10.0 mL). The reaction was quenched upon the dropwise addition of deuterium oxide (0.24 mL), 15% NaOD solution in deuterium oxide (0.24 mL) at 0° C., and finally deuterium oxide (0.72 mL). The mixture was stirred at room temperature for 10 min, dried over sodium sulfate, filtered and concentrated under reduced pressure to give a residue. The residue was purified by column chromatography (SiO$_2$, dichloromethane/methanol=50/1 to 20/1) to afford 1-(4-bromo-3-methyl-phenyl)-1,1-dideuterio-N,N-dimethyl-methanamine (220 mg, crude) as a brown oil. LC-MS [M+1]: 232.1.

Intermediate C-32

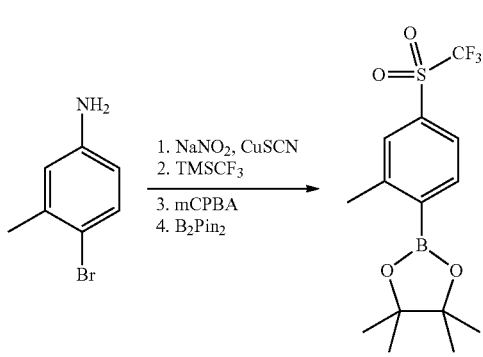

A thirty second exemplary Intermediate C, Intermediate C-32, may be used to synthesize compounds of formula I or formula II, wherein $R^1$ is a disubstitued aryl. To a solution of 4-bromo-3-methyl-aniline (4.00 g, 21.5 mmol, 1.00 equiv) in concentrated sulfuric acid (40.0 mL) and water (40.0 mL) was added sodium nitrite (1.62 g, 23.4 mmol, 1.09 equiv) at 0° C. and the mixture was stirred for 90 min. Subsequently, potassium thiocyanate (2.82 g, 29.0 mmol, 2.82 mL, 1.35 equiv) in water (16.0 mL) and thiocyanato-copper (6.80 g, 55.9 mmol, 2.60 equiv) was then added to the suspension at 5° C. After stirring at 5° C. for 2 h, the mixture was allowed to stir at room temperature for 10 h. The mixture was filtered and concentrated under reduced pressure to give a residue. The residue was purified by column chromatography (SiO$_2$, petroleum ether) to afford (4-bromo-3-methyl-phenyl) thiocyanate (2.00 g, 8.77 mmol, 40.8% yield) as a yellow oil.

$^1$H NMR (400 MHz, CDCl$_3$) δ=7.52 (d, J=8.4 Hz, 1H), 7.33 (d, J=2.4 Hz, 1H), 7.14 (dd, J=2.4, 8.4 Hz, 1H), 2.36 (s, 3H).

A mixture of (4-bromo-3-methyl-phenyl) thiocyanate (500 mg, 2.19 mmol, 1.00 equiv), trimethyl(trifluoromethyl) silane (1.00 g, 7.04 mmol, 3.21 equiv) and tetrabutylammonium fluoride (1.00 M, 701 µL, 0.32 equiv) in tetrahydrofuran (1.00 mL) was stirred at room temperature for 4 h. The mixture was filtered and concentrated under reduced pressure. The residue was purified by column chromatography (SiO$_2$, petroleum ether) to afford 1-bromo-2-methyl-4-(trifluoromethylsulfanyl)benzene (450 mg, 1.66 mmol, 75.7% yield) as a colorless oil.

$^1$H NMR (400 MHz, CDCl$_3$) δ=7.59 (d, J=8.0 Hz, 1H), 7.52 (d, J=2.0 Hz, 1H), 7.34 (dd, J=2.4, 8.0 Hz, 1H), 2.44 (s, 3H).

A mixture of 1-bromo-2-methyl-4-(trifluoromethylsulfanyl)benzene (450 mg, 1.66 mmol, 1.00 equiv) and m-chloroperbenzoic acid (2.02 g, 85.0%, 9.96 mmol, 6.00 equiv) in chloroform (10.0 mL) was stirred at room temperature for 2 h. The mixture was heated to 60° C. and allowed to stir for an additional 10 h. The mixture was diluted with saturated sodium bicarbonate (15.0 mL) and extracted with dichloromethane (5.00 mL×3). The combined organic phase was washed with sodium sulfite (5.00 mL), brine (5.00 mL), dried over sodium sulfate, filtered and concentrated under pressure to give a residue. The residue was purified by column chromatography (SiO$_2$, petroleum ether) to afford 1-bromo-2-methyl-4-(trifluoromethylsulfonyl) benzene (400 mg, 1.32 mmol, 79.5% yield) as a white solid.

$^1$H NMR (400 MHz, CDCl$_3$) δ=7.88 (d, J=2.0 Hz, 1H), 7.86 (d, J=8.4 Hz 1H), 7.71 (dd, J=2.4, 8.4 Hz, 1H), 2.55 (s, 3H).

A mixture of 1-bromo-2-methyl-4-(trifluoromethylsulfonyl)benzene (100 mg, 330 µmol, 1.00 equiv), bis(pinacolato) diboron (168 mg, 660 µmol, 2.00 equiv), potassium acetate (97.1 mg, 990 µmol, 3.00 equiv) and Pd(dppf)Cl$_2$ (24.1 mg, 33.0 µmol, 0.10 equiv) in dioxane (2.00 mL) was purged with nitrogen and then stirred at 90° C. for 2 h. The mixture was filtered and concentrated under reduced pressure to afford 4,4,5,5-tetramethyl-2-[2-methyl-4-(trifluoromethylsulfonyl)phenyl]-1,3,2-dioxaborolane (200 mg, crude) as a black solid that was used into the next step without further purification.

Intermediate C-33

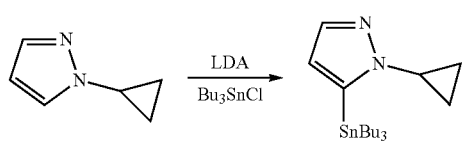

A thirty third exemplary Intermediate C, Intermediate C-33, may be used to synthesize compounds of formula I or formula II, wherein $R^1$ is a monosubstituted heteroaryl. To a solution of diisopropylamine (243 mg, 2.40 mmol, 339 µL, 1.30 equiv) in THF (4.00 mL) was added dropwise n-BuLi (2.50 M, 961 µL, 1.30 equiv) at −78° C. and then the reaction was stirred at −78° C. for 30 mins. 1-cyclopropylpyrazole (200 mg, 1.85 mmol, 1.00 equiv) was added and the reaction was stirred at −78° C. for 1 h. Tributyl(chloro)stannane (602 mg, 1.85 mmol, 498 uL, 1.00 equiv) was added drop-wise and the reaction was stirred at −78° C. for another 30 min. The reaction mixture was partitioned between ethyl acetate (5.00 mL) and saturated ammonium chloride (5.00 mL). The organic phase was separated, washed with brine (5.00 mL), dried over sodium sulfate, filtered and concentrated under reduced pressure to give tributyl-(2-cyclopropylpyrazol-3-yl)stannane (1.00 g, crude) as a colorless oil which used for the next step without further purification.

$^1$H NMR (400 MHz, CDCl$_3$) δ=7.51 (d, J=1.6 Hz, 1H), 6.32 (d, J=1.6 Hz, 1H), 3.54-3.49 (m, 1H), 1.61-1.50 (m, 6H), 1.37-1.31 (m, 6H), 1.21-1.13 (m, 6H), 0.97-0.89 (m, 13H).

Intermediate C-34

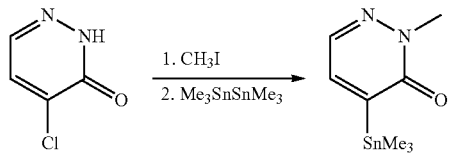

A thirty fourth exemplary Intermediate C, Intermediate C-44, may be used to synthesize compounds of formula I or formula II, wherein R$^1$ is a disubstitued heteroaryl. To a solution of 4-chloropyridazin-3-ol (300 mg, 2.30 mmol, 1.00 equiv) and methyl iodide (3.26 g, 23.0 mmol, 1.43 mL, 10.0 equiv) in dioxane (6.00 mL) was added silver oxide (533 mg, 2.30 mmol, 1.00 equiv). The mixture was stirred at 60° C. for 5 h. The mixture was filtered and concentrated in vacuo to provide a residue. The residue was purified by prep-TLC (SiO$_2$, petroleum ether/ethyl acetate=1/1) to afford 4-chloro-2-methyl-pyridazin-3-one (110 mg, 761 μmol, 33.1% yield) as a yellow solid.

$^1$H NMR (400 MHz, DMSO-d$_6$) δ=7.87 (d, J=4.4 Hz, 1H), 7.78 (d, J=4.4 Hz, 1H), 3.72 (s, 3H).

To a solution of 4-chloro-2-methyl-pyridazin-3-one (110 mg, 761 μmol, 1.00 equiv) and hexamethylditin (998 mg, 3.04 mmol, 631 μL, 4.00 equiv) in dioxane (2.00 mL) was added Pd(PPh$_3$)$_4$ (87.93 mg, 76.09 μmol, 0.10 equiv) under nitrogen. The mixture was stirred at 110° C. for 2 h and was subsequently filtered and concentrated in vacuo. The residue was purified by prep-TLC (SiO$_2$, petroleum ether/ethyl acetate=1/1) to afford 2-methyl-4-trimethylstannyl-pyridazin-3-one (130 mg, 476 μmol, 62.6% yield) as a white solid.

$^1$H NMR (400 MHz, CD$_3$OD) δ=7.79 (d, J=3.6 Hz, 1H), 7.51 (d, J=3.6 Hz, 1H), 3.73 (s, 3H), 0.32 (s, 9H).

Intermediate C-35

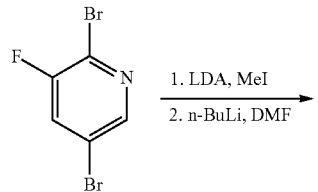

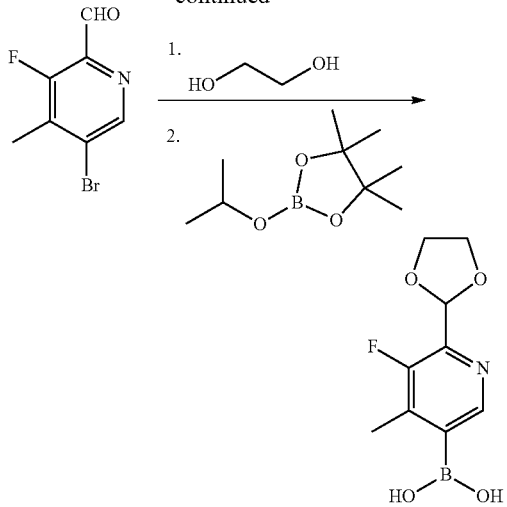

A thirty fifth exemplary Intermediate C, Intermediate C-35, may be used to synthesize compounds of formula I or formula II, wherein R$^1$ is a trisubstitued heteroaryl. To a solution of 2,5-dibromo-3-fluoro-pyridine (0.50 g, 1.96 mmol, 1.00 equiv) in THF (10.0 mL) was added n-BuLi (2.50 M, 1.18 mL, 1.50 equiv) dropwise at −65° C. The mixture was stirred at −65° C. for 0.5 h followed by the addition of N-isopropylpropan-2-amine (397 mg, 3.92 mmol, 554 μL, 2.00 equiv) one portion and stirring at this temperature for an additional 30 min. To this mixture was added methyl iodide (334 mg, 2.35 mmol, 147 μL, 1.20 equiv) and the mixture was allowed to stir at −65° C. for 1 h. The reaction mixture was quenched by the addition of satd aq NH$_4$Cl (10.0 mL) and the resulting mixture was extracted with ethyl acetate (20.0 mL×3). The combined organic phase was washed with brine (30.0 mL×2), dried over anh sodium sulfate, filtered and concentrated under reduced pressure to give the crude residue. The residue was purified by prep-HPLC (acidic conditions) to afford 2,5-dibromo-3-fluoro-4-methyl-pyridine (300 mg, 1.12 mmol, 56.9% yield) as a yellow solid. LC-MS [M+1]: 269.7.

To a solution of 2,5-dibromo-3-fluoro-4-methyl-pyridine (0.80 g, 2.97 mmol, 1.00 equiv) in THF (10.0 mL) was added n-BuLi (2.5 M, 1.19 mL, 1.00 equiv) at −65° C. and the resultant mixture was stirred for 0.5 h followed by the dropwise addition of DMF (326 mg, 4.46 mmol, 343 μL, 1.50 equiv). After an additional 30 min of stirring at −65° C. the reaction mixture was quenched with satd aq NH$_4$Cl (5.00 mL) and the resulting mixture was extracted with ethyl acetate (30.0 mL×2). The combined organic phase was washed with brine (30.0 mL×2), dried over anh sodium sulfate, filtered and concentrated under reduced pressure to give the crude residue. The residue was purified by column chromatography (SiO$_2$, petroleum ether/ethyl acetate=1/0 to 100/1) to afford 5-bromo-3-fluoro-4-methyl-pyridine-2-carbaldehyde (300 mg, 1.38 mmol, 46.3% yield) as a yellow solid.

$^1$H NMR (400 MHz, CDCl$_3$) δ=10.20 (d, J=0.8 Hz, 1H), 8.69 (s, 1H), 2.48 (d, J=2.4 Hz, 3H).

To a solution of 5-bromo-3-fluoro-4-methyl-pyridine-2-carbaldehyde (300 mg, 1.38 mmol, 1.00 equiv) in Tol. (10.0 mL) was added TsOH—H$_2$O (26.2 mg, 138 μmol, 0.10 equiv) and ethylene glycol (171 mg, 2.75 mmol, 14 μL, 2.00 equiv). The mixture was stirred at 120° C. for 2 h. The reaction mixture was concentrated under reduced pressure to provide a crude residue. The residue was purified by column chromatography (SiO$_2$, petroleum ether/ethyl acetate=1/0 to 100/1) to afford 5-bromo-2-(1,3-dioxolan-2-yl)-3-fluoro-4-methyl-pyridine (250 mg, 954 µmol, 69.3% yield) as a colorless oil.

$^1$H NMR (400 MHz, CDCl$_3$) δ=8.49 (s, 1H), 6.13 (s, 1H), 4.32-4.20 (m, 2H), 4.14-4.04 (m, 2H), 2.39 (d, J=2.4 Hz, 3H).

To a solution of 5-bromo-2-(1,3-dioxolan-2-yl)-3-fluoro-4-methyl-pyridine (450 mg, 1.72 mmol, 1.00 equiv) in Et$_2$O (10.0 mL) was added dropwise n-BuLi (2.5 M, 756 µL, 1.10 equiv) at –70° C. The mixture was stirred for 0.5 h at –70° C. f and subsequently 2-isopropoxy-4,4,5,5-tetramethyl-1,3,2-dioxaborolane (639 mg, 3.43 mmol, 701 µL, 2.00 equiv) was added. The mixture was stirred at –70° C. for 1 h and was quenched with satd aq NH$_4$Cl (10 mL). The mixture was extracted with DCM (30 mL×3) and the combined organic phase was washed with brine (50.0 mL×2), dried over sodium sulfate, filtered and concentrated under reduced pressure to give a crude solid. The crude material was purified by prep-TLC (SiO$_2$, petroleum ether/ethyl acetate=1/1) to afford [6-(1,3-dioxolan-2-yl)-5-fluoro-4-methyl-3-pyridyl]boronic acid (220 mg, 940 µmol, 54.8% yield, 97.0% purity) as a light yellow oil. LC-MS [M+1]: 228.0.

Intermediate C-36

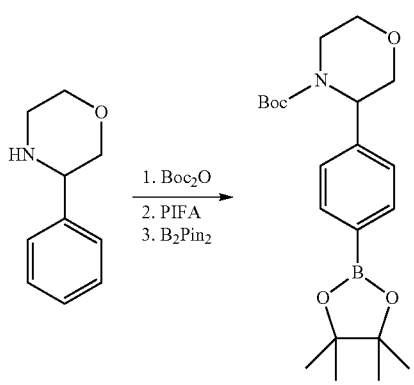

A thirty sixth exemplary Intermediate C, Intermediate C-36, may be used to synthesize compounds of formula I or formula II, wherein R$^1$ is a monosubstitued aryl. To a solution of 3-phenylmorpholine (500 mg, 3.06 mmol, 1.00 equiv) in tetrahydrofuran (5.00 mL) was added triethylamine (512 µL, 3.68 mmol, 1.20 equiv) and di-tert-butyl dicarbonate (669 mg, 3.06 mmol, 704 µL, 1.00 equiv.). The mixture was stirred at 20° C. for 1 h. The mixture was concentrated under reduced pressure to give a residue (1.30 g, crude) that was used in the next step directly.

To a solution of tert-butyl 3-phenylmorpholine-4-carboxylate (580 mg, 2.20 mmol, 1.00 equiv) in dichloromethane (6.00 mL) was added phenyl-λ$^3$-iodanediyl bis(2,2,2-trifluoroacetate) (1.04 g, 2.42 mmol, 1.10 equiv) and iodine (559 mg, 2.20 mmol, 444 µL, 1.00 equiv). The reaction mixture was stirred at 20° C. for 2 h. The mixture was diluted with sodium bicarbonate solution (20.0 mL) and extracted with dichloromethane (10.0 mL×3). The combined organic layer was washed with saturated sodium thiosulfate solution (20.0 mL), brine (20 mL), dried over anhydrous sodium sulfate, filtered and concentrated under reduced pressure to give a residue. The residue was purified by column chromatography (SiO$_2$, petroleum ether/ethyl acetate=1/0 to 10/1) to afford tert-butyl 3-(4-iodophenyl)morpholine-4-carboxylate (260 mg, 668 µL, 30.3% yield) as a white oil.

$^1$H NMR (400 MHz, DMSO-d$_6$) δ=7.73 (br d, J=8.4 Hz, 2H), 7.16 (br d, J=8.0 Hz, 2H), 4.92 (br s, 1H), 4.20 (br d, J=12.0 Hz, 1H), 3.84-3.78 (m, 1H), 3.76-3.65 (m, 2H), 3.50-3.40 (m, 1H), 3.04-2.93 (m, 1H), 1.39 (s, 9H).

A mixture of tert-butyl 3-(4-iodophenyl)morpholine-4-carboxylate (260 mg, 668 µmol, 1.00 equiv), 4,4,5,5-tetramethyl-2-(4,4,5,5-tetramethyl-1,3,2-dioxaborolan-2-yl)-1,3,2-dioxaborolane (254 mg, 1.00 mmol, 1.50 equiv), potassium acetate (131 mg, 1.34 mmol, 2.00 equiv) and Pd(dppf)Cl$_2$ (48.9 mg, 66.8 µmol, 0.10 equiv) in dioxane (2.00 mL) was purged with and subsequently stirred at 100° C. for 2 h under a nitrogen atmosphere. The mixture was filtered and concentrated at reduced pressure to give a residue. The residue was purified by column chromatography (SiO$_2$, petroleum ether/ethyl acetate=1/0 to 10/1) to afford tert-butyl 3-[4-(4,4,5,5-tetramethyl-1,3,2-dioxaborolan-2-yl)phenyl]morpholine-4-carboxylate (100 mg, 257 µmol, 38.5% yield) as white oil.

$^1$H NMR (400 MHz, DMSO-d$_6$) δ=7.67 (d, J=8.0 Hz, 2H), 7.37 (d, J=7.6 Hz, 2H), 4.98 (br s, 1H), 4.29-4.23 (m, 1H), 3.86-3.66 (m, 3H), 3.51-3.42 (m, 1H), 3.07-2.96 (m, 1H), 1.41-1.38 (m, 9H), 1.30 (s, 12H).

Intermediates C-37-C-38

Characterization of Intermediates C36-C38

| Int. # | Structure | $^1$H NMR |
|---|---|---|
| C-37 | 5-((dimethylamino)methyl)-2-(4,4,5,5-tetramethyl-1,3,2-dioxaborolan-2-yl)benzonitrile | $^1$H NMR (400 MHz, CD$_3$OD) δ = 10.03 (s, 1H), 8.41 (s, 1H), 8.16-8.10 (m, 2H). |

| Int. # | Structure | ¹H NMR |
|---|---|---|
| C-38 | 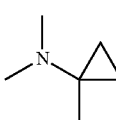 N,N-dimethyl-1-(4-(4,4,5,5-tetramethyl-1,3,2-dioxaborolan-2-yl)phenyl)cyclopropan-1-amine | ¹H NMR (400 MHz, DMSO-d₆) δ = 7.64 (d, J = 8.4 Hz, 2H), 7.27 (d, J = 7.6 Hz, 2H), 3.92 (s, 2H), 2.11 (s, 6H), 1.29 (s, 12H), 0.88-0.79 (m, 2H), 0.76-0.67 (m, 2H). LC-MS [M + 1]: 288.2. |
| C-39 | 1-(4-(4,4,5,5-tetramethyl-1,3,2-dioxaborolan-2-yl)-1H-pyrazol-1-yl)propan-2-ol | ¹H NMR (400 MHz, methanol-d₄) δ = 7.84 (s, 1H), 7.68 (s, 1H), 4.16-4.04 (m, 3H), 1.31 (s, 12H), 1.16-1.12 (m, 3H). LC-MS [M + 1]: 253.3. |
| C-40 | tert-butyl (S)-2-(4-(4,4,5,5-tetramethyl-1,3,2-dioxaborolan-2-yl)phenyl)pyrrolidine-1-carboxylate | ¹H NMR (400 MHz, CDCl₃) δ = 7.74 (br d, J = 7.6 Hz, 2H), 7.17 (br d, J = 7.6 Hz, 2H), 4.79 (br s, 1H), 3.63 (br s, 2H), 2.31 (br s, 1H), 1.94-1.73 (m, 3H), 1.35 (s, 12H), 1.19 (s, 9H). |
| C-41 | 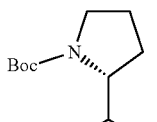 tert-butyl (R)-2-(4-(4,4,5,5-tetramethyl-1,3,2-dioxaborolan-2-yl)phenyl)pyrrolidine-1-carboxylate | LC-MS [M − 55]: 318.2. |
| C-42 | 1-methyl-2-(4-(4,4,5,5-tetramethyl-1,3,2-dioxaborolan-2-yl)phenyl)azetidine | LC-MS [M + 1]: 274.1. |
| C-43 | 4-(4-(4,4,5,5-tetramethyl-1,3,2-dioxaborolan-2-yl)phenyl)azetidin-2-one | LC-MS [M + 1]: 274.1. |

| Int. # | Structure | ¹H NMR |
|---|---|---|
| C-44 | tert-butyl 3-(4-(4,4,5,5-tetramethyl-1,3,2-dioxaborolan-2-yl)phenyl)morpholine-4-carboxylate | ¹H NMR (400 MHz, DMSO-d₆) δ = 7.67 (d, J = 8.0 Hz, 2H), 7.37 (d, J = 7.6 Hz, 2H), 4.98 (br s, 1H), 4.29-4.23 (m, 1H), 3.86-3.66 (m, 3H), 3.51-3.42 (m, 1H), 3.07-2.96 (m, 1H), 1.41-1.38 (m, 9H), 1.30 (s, 12H). |
| C-45 | methyl 1-methyl-5-(4,4,5,5,-tetramethyl-1,3,2-dioxaborolan-2-yl)-1H-pyrazole-3-carboxylate | ¹H NMR (400 MHz, CDCl₃) δ = 7.28 (s, 1H), 4.15 (s, 3H), 3.93 (s, 3H), 1.35 (s, 12H). |

The following Examples are intended to illustrate further certain embodiments of the invention and are not intended to limit the scope of the invention.

Example 1

4-(5-4(5-fluoro-2,3-dihydrobenzofuran-4-yl)methyl)amino)pyrido[3,4-d]pyridazin-8-yl)benzenesulfonamide

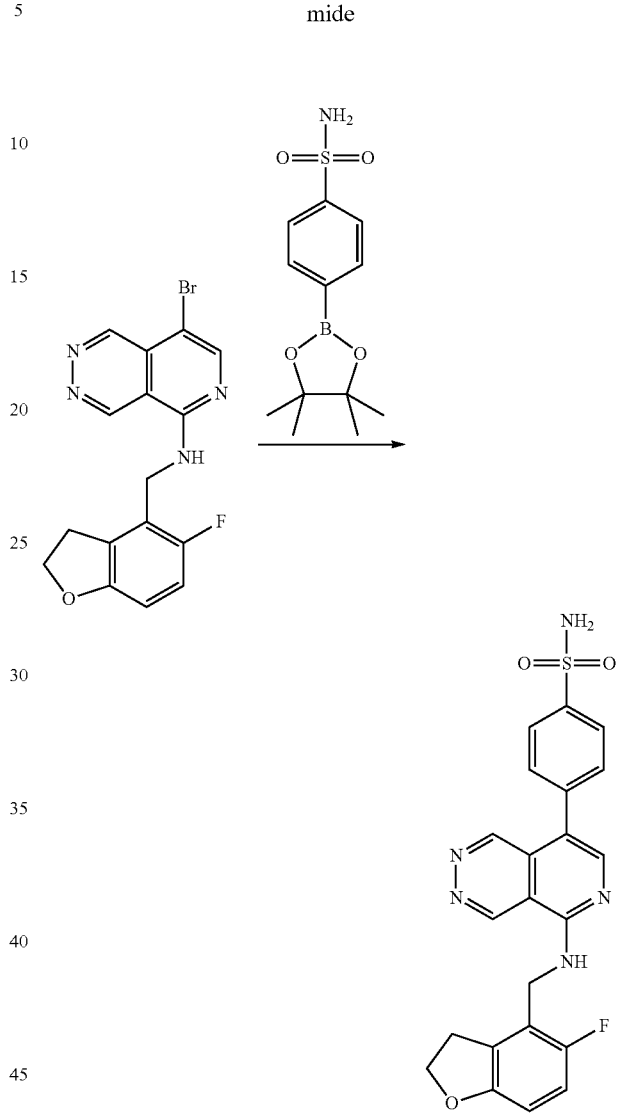

A mixture of Intermediate A-1 (30.0 mg, 80.0 μmol, 1.00 equiv.), 4-(4,4,5,5-tetramethyl-1,3,2-dioxaborolan-2-yl)benzenesulfonamide (45.3 mg, 160 μmol, 2.00 equiv.), sodium bicarbonate (20.2 mg, 240 μmol, 9.33 μL, 3.00 equiv.) and Pd(dppf)Cl₂ (5.85 mg, 8.00 μmol, 0.10 equiv.) in dioxane (1.00 mL) and water (0.20 mL) was degassed and purged with nitrogen 3 times, and then stirred at 100° C. for 2 hours under a nitrogen atmosphere. The mixture was filtered and concentrated under reduced pressure to give the crude product which was purified by prep-HPLC [column: Waters Xbridge 150*25 5μ; mobile phase: phase A-water (10 mM NH₄HCO₃), phase B—ACN] B %: 25%-55%] to give title compound 4-(5-(((5-fluoro-2,3-dihydrobenzofuran-4-yl)methyl)amino)pyrido[3,4-d]pyridazin-8-yl)benzenesulfonamide (18.3 mg, 37.0 μmol, 46.3% yield, 91.2% purity) as an off-white solid. LC-MS [M+1]: 452.0.

¹H NMR (400 MHz, DMSO-d₆) δ=10.03 (s, 1H), 9.41 (s, 1H), 8.77 (br t, J=4.8 Hz, 1H), 8.44 (s, 1H), 7.96 (d, J=8.4 Hz, 2H), 7.76 (d, J=8.4 Hz, 2H), 7.46 (br s, 2H), 6.93 (t,

J=9.2 Hz, 1H), 6.67 (dd, J=3.6, 8.4 Hz, 1H), 4.76 (br d, J=4.8 Hz, 2H), 4.53 (t, J=8.4 Hz, 2H), 3.32-3.28 (m, 2H).

Examples 2-14 were prepared following the procedure set forth in Example 1 and using the general reactions schemes and intermediates described herein.

TABLE 1

Characterization of EXAMPLES 2-14

| Ex. # | Structure | Analytical Data |
|---|---|---|
| 2 | 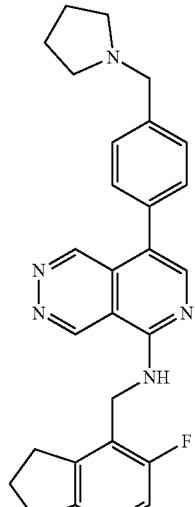<br>N-((5-fluoro-2,3-dihydrobenzo-furan-4-yl)methyl)-8-(4-(pyrrolidin-1-ylmethyl)phenyl)pyrido[3,4-d]pyridazin-5-amine | $^1$H NMR (400 MHz, CDCl$_3$) δ = 9.56 (s, 1H), 9.47 (s, 1H), 8.44 (s, 1H), 7.51 (d, J = 8.0 Hz, 2H), 7.41 (d, J = 8.0 Hz, 2H), 6.87 (t, J = 8.8 Hz, 1H), 6.67 (dd, J = 4.0, 8.8 Hz, 1H), 6.00 (br s, 1H), 4.88 (d, J = 5.2 Hz, 2H), 4.63 (t, J = 8.8 Hz, 2H), 3.74 (s, 2H), 3.43 (t, J = 8.8 Hz, 2H), 2.61 (br s, 4H), 1.85 (br s, 4H). LC-MS [M + 1]: 456.3. |
| 3 | 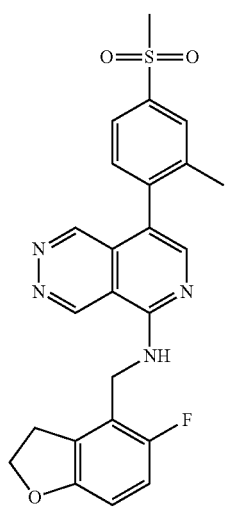<br>N-((5-fluoro-2,3-dihydro-benzofuran-4-yl)methyl)-8-(2-methyl-4-(methylsulfonyl)phenyl)pyrido[3,4-d]pyridazin-5-amine | $^1$H NMR (400 MHz, CD$_3$OD) δ = 10.25 (s, 1H), 9.09 (d, J = 0.8 Hz, 1H), 8.72 (s, 1H), 8.06 (s, 1H), 7.97 (dd, J = 1.6, 8.0 Hz, 1H), 7.60 (d, J = 8.0 Hz, 1H), 6.94-6.85 (m, 1H), 6.68 (dd, J = 4.0, 8.8 Hz, 1H), 4.98-4.92 (m, 2H), 4.62 (t, J = 8.8 Hz, 2H), 3.45 (t, J = 8.8 Hz, 2H), 3.23 (s, 3H), 2.28 (s, 3H). LC-MS [M + 1]: 465.0. |

TABLE 1-continued

Characterization of EXAMPLES 2-14

| Ex. # | Structure | Analytical Data |
|---|---|---|
| 4 | 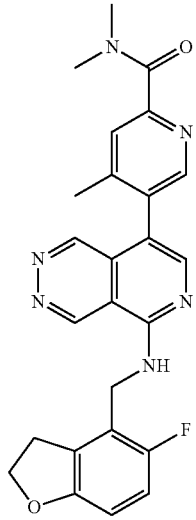<br>5-(5-(((5-fluoro-2,3-dihydrobenzofuran-4-yl)methyl)amino)pyrido[3,4-d]pyridazin-8-yl)-N,N,4-trimethylpicolinamide | $^1$H NMR (400 MHz, CDCl$_3$) δ = 9.52 (s, 1H), 9.07 (s, 1H), 8.43 (s, 1H), 8.33 (s, 1H), 7.69 (s, 1H), 6.92-6.86 (m, 1H), 6.69 (dd, J = 4.0, 8.4 Hz, 1H), 6.16 (br t, J = 5.2 Hz, 1H), 4.93-4.85 (m, 2H), 4.65 (t, J = 8.8 Hz, 2H), 3.44 (t, J = 8.4 Hz, 2H), 3.20 (s, 6H), 2.20 (s, 3H). LC-MS [M + 1]: 459.3. |
| 5 | 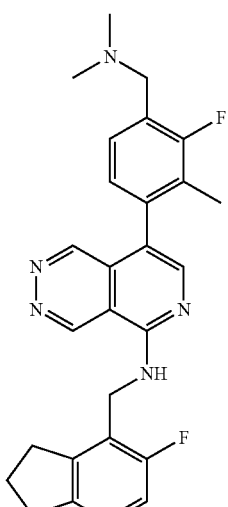<br>8-(4-((dimethylamino)methyl)-3-fluoro-2-methylphenyl)-N-((5-fluoro-2,3-dihydrobenzofuran-4-yl)methyl)pyrido[3,4-d]pyridazin-5-amine | $^1$H NMR (400 MHz, DMSO-d$_6$) δ = 10.54 (br s, 1H), 10.21 (s, 1H), 9.07 (d, J = 1.2 Hz, 1H), 9.03 (br s, 1H), 8.39 (s, 1H), 7.64 (t, J = 7.6 Hz, 1H), 7.26 (d, J = 7.6 Hz, 1H), 6.98-6.90 (m, 1H), 6.69 (dd, J = 4.0, 8.4 Hz, 1H), 4.83-4.69 (m, 2H), 4.55 (t, J = 8.4 Hz, 2H), 4.41 (br d, J = 4.8 Hz, 2H), 3.37-3.31 (m, 2H), 2.82 (t, J = 4.0 Hz, 6H), 2.01 (d, J = 2.4 Hz, 3H). LC-MS [M + 1]: 462.1. |

TABLE 1-continued

Characterization of EXAMPLES 2-14

| Ex. # | Structure | Analytical Data |
|---|---|---|
| 6 | 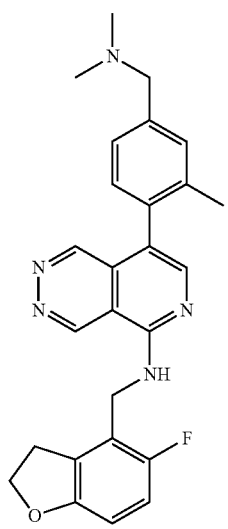<br>8-(4-((dimethylamino)methyl)-2-methylphenyl)-N-((5-fluoro-2,3-dihdyrobenzofuran-4-yl)methyl)pyrido[3,4-d]pyridazin-5-amine | $^{1}$H NMR (400 MHz, CD$_3$OD) δ = 9.86 (s, 1H), 8.93 (s, 1H), 8.32 (s, 1H), 7.40 (s, 1H), 7.33 (d, J = 7.6 Hz, 1H), 7.26 (d, J = 7.6 Hz, 1H), 6.86 (t, J = 9.2 Hz, 1H), 6.64 (dd, J = 3.6, 8.4 Hz, 1H), 4.87-4.71 (m, 2H), 4.58 (t, J = 8.8 Hz, 2H), 3.59 (s, 2H), 3.39 (br t, J = 8.8 Hz, 2H), 2.35 (s, 6H), 2.12 (s, 3H). LC-MS [M + 1]: 444.0. |
| 7 | 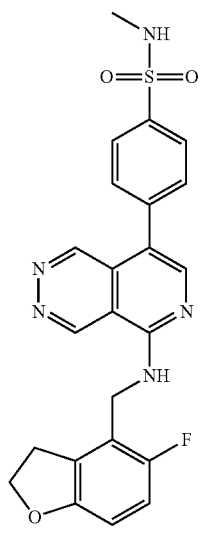<br>4-(5-(((5-fluoro-2,3-dihydro-benzofuran-4-yl)methyl)amino)pyrido[3,4-d]pyridazin-8-yl)-N-methylbenzenesulfonamide | $^{1}$H NMR (400 MHz, CDCl$_3$) δ = 9.51 (s, 2H), 8.45 (s, 1H), 8.04 (d, J = 8.4 Hz, 2H), 7.64 (d, J = 8.4 Hz, 2H), 6.92-6.83 (m, 1H), 6.68 (dd, J = 4.4, 8.8 Hz, 1H), 6.14 (br s, 1H), 4.90 (d, J = 5.6 Hz, 2H), 4.64 (t, J = 8.8 Hz, 2H), 4.43 (br d, J = 4.8 Hz, 1H), 3.43 (t, J = 8.8 Hz, 2H), 2.79 (d, J = 5.2 Hz, 3H). LC-MS [M + 1]: 466.3. |

TABLE 1-continued

Characterization of EXAMPLES 2-14

| Ex. # | Structure | Analytical Data |
|---|---|---|
| 8 | 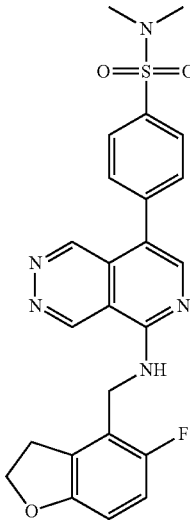<br>4-(5-(((5-fluoro-2,3-dihydrobenzo-furan-4-yl)methyl)amino)pyrido[3,4-d]pyridazin-8-yl)-N,N-dimethyl-benzenesulfonamide | $^1$H NMR (400 MHz, DMSO-d$_6$) δ = 10.03 (d, J = 1.2 Hz, 1H), 9.46 (d, J = 1.2 Hz, 1H), 8.78 (t, J = 5.2 Hz, 1H), 8.46 (s, 1H), 7.93-7.84 (m, 2H), 7.84-7.78 (m, 2H), 6.98-6.85 (m, 1H), 6.67 (dd, J = 4.0, 8.4 Hz, 1H), 4.76 (d, J = 5.2 Hz, 2H), 4.53 (t, J = 8.8 Hz, 2H), 3.32-3.28 (m, 2H), 2.68 (s, 6H). LC-MS [M + 1]: 480.2. |
| 9 | 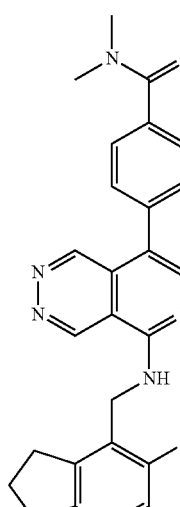<br>4-(5-(((5-fluoro-2,3-dihydrobenzo-furan-4-yl)methyl)amino)pyrido[3,4-d]pyridazin-8-yl)-N,N-dimethyl-benzamide | $^1$H NMR (400 MHz, DMSO-d$_6$) δ = 10.01 (s, 1H), 9.43 (s, 1H), 8.68 (br s, 1H), 8.42 (s, 1H), 7.61-7.54 (m, 4H), 6.93 (br t, J = 9.2 Hz, 1H), 6.67 (br dd, J = 3.6, 8.4 Hz, 1H), 4.76 (br d, J = 4.4 Hz, 2H), 4.53 (br t, J = 8.8 Hz, 2H), 3.32-3.31 (m, 2H), 3.01 (br s, 6H). LC-MS [M + 1]: 444.3. |

TABLE 1-continued

Characterization of EXAMPLES 2-14

| Ex. # | Structure | Analytical Data |
|---|---|---|
| 10 | 5-(5-(((5-fluoro-2,3-dihydro-benzofuran-4-yl)methyl)amino)pyrido[3,4-d]pyridazin-8-yl)-N,N-dimethylpyridine-2-sulfonamide | $^1$H NMR (400 MHz, DMSO-$d_6$) δ = 10.04 (s, 1H), 9.49 (s, 1H), 8.94 (br s, 1H), 8.87 (br s, 1H), 8.51 (s, 1H), 8.30 (br d, J = 7.2 Hz, 1H), 8.03 (br d, J = 8.4 Hz, 1H), 6.93 (br t, J = 10.0 Hz, 1H), 6.72-6.66 (m, 1H), 4.77 (br s, 2H), 4.54 (br t, J = 8.8 Hz, 2H), 3.31-3.28 (m, 2H), 2.87 (s, 6H). LC-MS [M + 1]: 481.2. |
| 11 | N-((5-fluoro-2,3-dihydrobenzo-furan-4-yl)methyl)-8-(2-methyl-pyridin-3-yl)pyrido[3,4-d]pyridazin-5-amine | $^1$H NMR (400 MHz, DMSO-$d_6$) δ = 10.02 (d, J = 0.8 Hz, 1H), 8.92 (d, J = 1.2 Hz, 1H), 8.67 (br t, J = 4.4 Hz, 1H), 8.57 (dd, J = 1.6, 4.8 Hz, 1H), 8.31 (s, 1H), 7.68 (dd, J = 1.6, 7.6 Hz, 1H), 7.37 (dd, J = 4.8, 7.6 Hz, 1H), 6.97-6.87 (m, 1H), 6.68 (dd, J = 4.0, 8.8 Hz, 1H), 4.85-4.63 (m, 2H), 4.53 (t, J = 8.8 Hz, 2H), 3.28-3.22 (m, 2H), ), 2.25 (s, 3H). LC-MS [M + 1]: 388.2 |

TABLE 1-continued

Characterization of EXAMPLES 2-14

| Ex. # | Structure | Analytical Data |
|---|---|---|
| 12 | 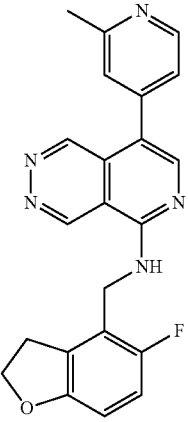<br>N-((5-fluoro-2,3-dihydrobenzo-furan-4-yl)methyl)-8-(2-methyl-pyridin-4-yl)pyrido[3,4-d]pyridazin-5-amine | $^1$H NMR (400 MHz, CDCl$_3$) δ = 9.56 (d, J = 1.2 Hz, 1H), 9.50 (d, J = 1.2 Hz, 1H), 8.66 (d, J = 4.8 Hz, 1H), 8.44 (s, 1H), 7.28-7.27 (m, 1H), 7.22 (d, J = 5.2 Hz, 1H), 6.87 (t, J = 10.0 Hz, 1H), 6.68 (dd, J = 4.0, 8.8 Hz, 1H), 6.16 (br t, J = 5.6 Hz, 1H), 4.90 (d, J = 5.6 Hz, 2H), 4.64 (t, J = 8.8 Hz, 2H), 3.43 (t, J = 8.8 Hz, 2H), 2.68 (s, 3H). LC-MS [M + 1]: 388.3. |
| 13 | 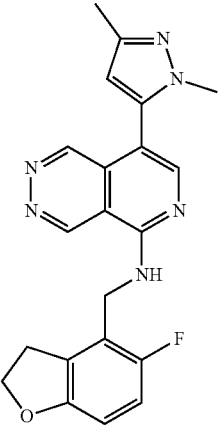<br>8-(1,3-dimethyl-1H-pyrazol-5-yl)-N-((5-fluoro-2,3-dihydrobenzo-furan-4-yl)methyl)pyrido[3,4-d]pyridazin-5-amine | $^1$H NMR (400 MHz, DMSO-d$_6$) δ = 10.01 (s, 1H), 9.17 (s, 1H), 8.78 (br s, 1H), 8.40 (s, 1H), 6.93 (br t, J = 9.2 Hz, 1H), 6.68 (br dd, J = 4.0, 8.8 Hz, 1H), 6.25 (s, 1H), 4.76 (br d, J = 4.8 Hz, 2H), 4.53 (br t, J = 8.8 Hz, 2H), 3.59 (s, 3H), 3.28-3.20 (m, 2H), 2.23 (s, 3H). LC-MS [M + 1]: 391.3. |
| 14 | 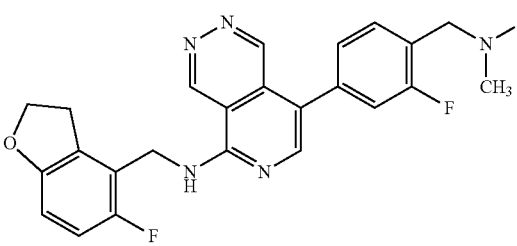<br>8-(4-((dimethylamino)methyl)-3-fluorophenyl)-N-((5-fluoro-2,3-dihydrobenzofuran-4-yl)methyl)pyrido[3,4-d]pyridazin-5-amine | $^1$H NMR (400 MHz, DMSO-d$_6$) δ = 10.00 (d, J = 1.2 Hz, 1H), 9.42 (d, J = 0.8 Hz, 1H), 8.67 (t, J = 4.8 Hz, 1H), 8.41 (s, 1H), 7.53 (t, J = 7.6 Hz, 1H), 7.42-7.31 (m, 2H), 6.96-6.88 (m, 1H), 6.67 (dd, J = 4.0, 8.8 Hz, 1H), 4.75 (d, J = 4.4 Hz, 2H), 4.53 (t, J = 8.8 Hz, 2H), 3.52 (s, 2H), 3.29-3.28 (m, 2H), 2.21 (s, 6H). LC-MS [M + 1]: 448.3. |

Example 15

5-(5-(((5-fluoro-2,3-dihydrobenzofuran-4-yl)methyl)amino)pyrido[3,4-d]pyridazin-8-yl)-N,N,1-trimethyl-1H-pyrazole-3-carboxamide

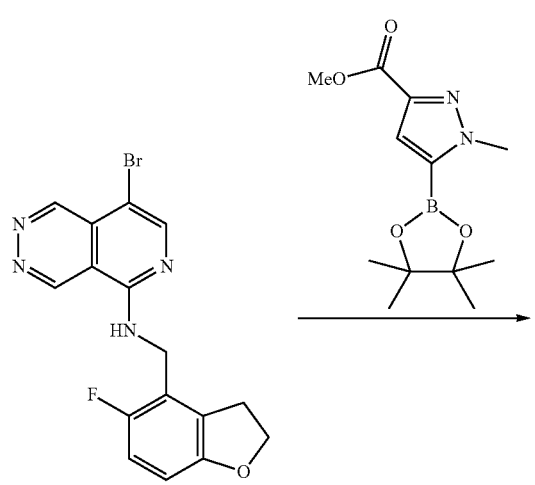

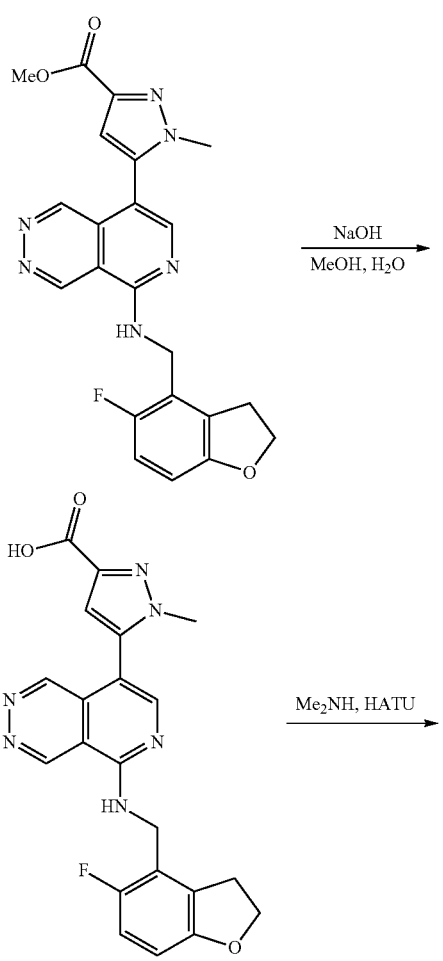

Step A: A mixture of 8-bromo-N-((5-fluoro-2,3-dihydrobenzofuran-4-yl)methyl)pyrido[3,4-d]pyridazin-5-amine (130 mg, 346 μmol, 1.00 equiv.), methyl 1-methyl-5-(4,4,5,5-tetramethyl-1,3,2-dioxaborolan-2-yl)-1H-pyrazole-3-carboxylate (230 mg, 866 μmol, 2.50 equiv.), bis(tri-tert-butylphosphine)palladium(0) (35.4 mg, 69.3 μmol, 0.20 equiv.) and potassium carbonate (239 mg, 1.73 mmol, 5.00 equiv.) in dioxane (3.00 mL) and water (0.50 mL), was degassed and purged with nitrogen 3 times. The mixture was then stirred at 90° C. for 1 hour under a nitrogen atmosphere. After completion of the reaction, the reaction mixture was filtered and concentrated in vacuo to give a residue. The residue was purified by column chromatography ($SiO_2$, petroleum ether/ethyl acetate=3/1 to 1/1) to give the product methyl 5-(5-(((5-fluoro-2,3-dihydrobenzofuran-4-yl)methyl)amino)pyrido[3,4-d]pyridazin-8-yl)-1-methyl-1H-pyrazole-3-carboxylate (160 mg, crude) as a light yellow solid.

$^1$H NMR (400 MHz, DMSO-$d_6$) δ=10.03 (d, J=1.2 Hz, 1H), 9.16 (d, J=1.2 Hz, 1H), 8.88 (s, 1H), 8.46 (s, 1H), 6.98 (s, 1H), 6.93 (t, J=8.8 Hz, 1H), 6.68 (dd, J=4.0, 8.8 Hz, 1H), 4.77 (d, J=5.2 Hz, 2H), 4.54 (t, J=8.8 Hz, 2H), 3.83 (s, 3H), 3.76 (s, 3H), 3.39-3.33 (m, 2H).

Step B: To a solution of methyl 5-(5-4(5-fluoro-2,3-dihydrobenzofuran-4-yl)methyl)amino)pyrido[3,4-d]pyridazin-8-yl)-1-methyl-1H-pyrazole-3-carboxylate (140 mg, 322 μmol, 1.00 equiv.) in methanol (5.00 mL) was added sodium hydroxide (1.00 M in water, 967 μL, 3.00 equiv.) until the solution was adjusted to pH >12. The mixture was stirred at 50° C. for 1 hour. After completion of the reaction, the mixture was acidified to pH=7 with hydrochloric acid solution (1.00 M in water). During this period, a white precipitate was formed and the suspension was filtered, the cake was collected and dried under vacuum to give crude product 5-(5-(((5-fluoro-2,3-dihydrobenzofuran-4-yl)methyl)amino)pyrido[3,4-d]pyridazin-8-yl)-1-methyl-1H-pyrazole-3-carboxylic acid (120 mg, 285 μmol, 88.6% yield) as a yellow solid which was used without further purification.

$^1$H NMR (400 MHz, DMSO-$d_6$) δ=12.72 (s, 1H), 10.03 (d, J=1.2 Hz, 1H), 9.16 (d, J=1.2 Hz, 1H), 8.87 (t, J=5.2 Hz, 1H), 8.46 (s, 1H), 6.91 (m, 2H), 6.68 (dd, J=4.0, 8.8 Hz, 1H), 4.77 (d, J=4.8 Hz, 2H), 4.54 (t, J=8.8 Hz, 2H), 3.74 (s, 3H), 3.30-3.29 (m, 2H).

Example 15: To a solution of 5-(5-(((5-fluoro-2,3-dihydrobenzofuran-4-yl)methyl)amino)pyrido[3,4-d]pyridazin-8- yl)-1-methyl-1H-pyrazole-3-carboxylic acid (30.0 mg, 71.4 μmol, 1.00 equiv.) and dimethylamine hydrochloride (25.3 mg, 214 μmol, 36.0 μL, 3.00 eq., hydrochloride) in DMF (1.00 mL) was added diisopropylethylamine (46.1 mg, 357 μmol, 62.0 μL, 5.00 equiv.) and HATU (40.70 mg, 107 μmol, 1.50 equiv.), the mixture was stirred at 25° C. for 1 hour. After completion of the reaction, the mixture was triturated with water (20.0 mL). The suspension was filtered, and the cake was dried under reduced pressure to give the crude product. The crude product was purified by prep-HPLC [column: Phenomenex Synergi C18 150×25×10 um; mobile phase: phase A—water (0.05% HCl), phase B—ACN; B %: 18%-48%] to give 5-[5-[(5-fluoro-2,3-dihydrobenzofuran-4-yl)methylamino]pyrido [3,4-d]pyridazin-8-yl]-N,N,1-trimethyl-pyrazole-3-carboxamide (12.4 mg, 27.6 μmol, 38.7% yield, 99.7% purity) as a yellow solid. LC-MS [M+1]: 448.0.

$^1$H NMR (400 MHz, CD$_3$OD) δ=10.19 (d, J=1.2 Hz, 1H), 9.31 (d, J=1.2 Hz, 1H), 8.81 (s, 1H), 6.88-6.77 (m, 2H), 6.60 (dd, J=4.0, 8.8 Hz, 1H), 4.87 (s, 2H), 4.54 (t, J=8.8 Hz, 2H), 3.77 (s, 3H), 3.42-3.33 (m, 5H), 3.09 (s, 3H).

Example 16

5-(5-(((5-fluoro-2,3-dihydrobenzofuran-4-yl)methyl)amino)pyrido[3,4-d]pyridazin-8-yl)-1-methyl-1H-pyrazole-3-carbonitrile

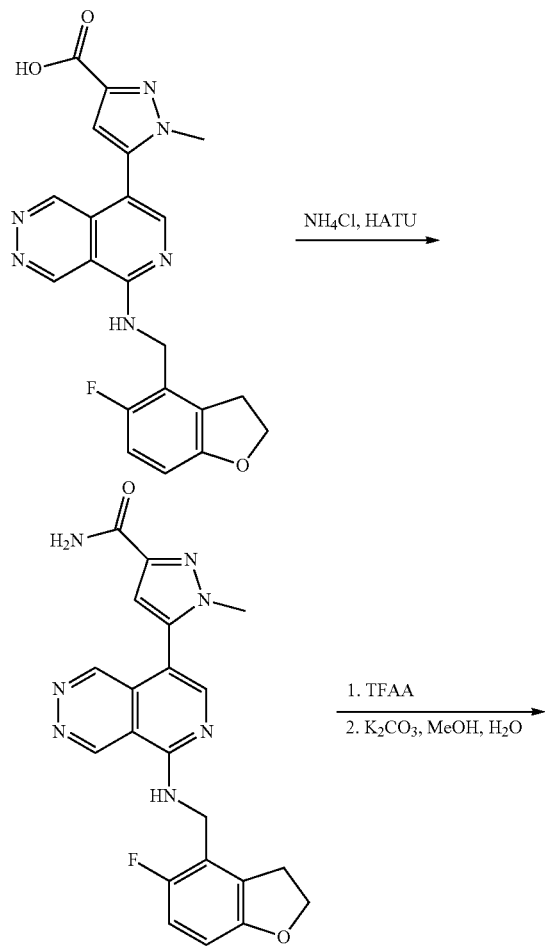

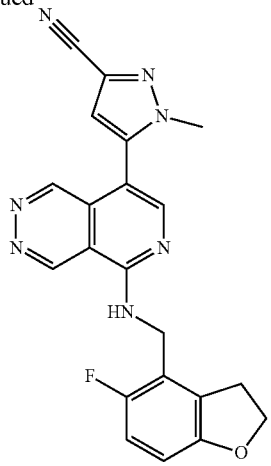

Step A: To a solution of 5-[5-[(5-fluoro-2,3-dihydrobenzofuran-4-yl) methylamino]pyrido[3,4-d]pyridazin-8-yl]-1-methyl-pyrazole-3-carboxylic acid (Example 15, Step B; 50.0 mg, 119 μmol, 1.00 equiv.) and ammonium chloride (19.0 mg, 355 μmol, 2.99 equiv.) in DMF (2.00 mL) was added diisopropylethylamine (50.0 mg, 387 μmol, 67.4 μL, 3.25 equiv.) and HATU (67.8 mg, 178 μmol, 1.50 equiv.). The mixture was stirred at 25° C. for 1 hour. After completion of the reaction, the reaction mixture was triturated with water (20.0 mL). The suspension was filtered and the cake was collected and dried under reduced pressure to give the crude product 5-(5-(((5-fluoro-2,3-dihydrobenzofuran-4-yl)methyl)amino)pyrido[3,4-d]pyridazin-8-yl)-1-methyl-1H-pyrazole-3-carboxamide (40.0 mg, 95.4 μmol, 80.2% yield) as a yellow solid.

$^1$H NMR (400 MHz, DMSO-d$_6$) δ=10.02 (d, J=1.2 Hz, 1H), 9.17 (d, J=1.2 Hz, 1H), 8.85 (t, J=5.2 Hz, 1H), 8.45 (s, 1H), 7.57 (s, 1H), 7.26 (s, 1H), 7.00-6.89 (m, 1H), 6.83 (s, 1H), 6.68 (dd, J=4.0, 8.4 Hz, 1H), 4.76 (d, J=4.8 Hz, 2H), 4.53 (t, J=8.8 Hz, 2H), 3.73 (s, 3H), 3.33-3.31 (m, 3H).

Example 16: To a mixture of 55-(5-(((5-fluoro-2,3-dihydrobenzofuran-4-yl)methyl)amino)pyrido[3,4-d]pyridazin-8-yl)-1-methyl-1H-pyrazole-3-carboxamide (30.0 mg, 71.53 μmol, 1.00 equiv.) and triethylamine (146 mg, 1.44 mmol, 201 μL, 20.2 equiv.) in anhydrous THF (0.50 mL) was added trifluoroacetic anhydride (135 mg, 643 μmol, 89.4 μL, 8.99 equiv.) at 0° C. The resulting mixture was warmed to 25° C. and stirred for 0.5 hour. The reaction mixture was diluted with water (10.0 mL) and extracted with ethyl acetate (15.0 mL×3), the combined organic layers were washed with brine (20.0 mL×2), dried over anhydrous sodium sulfate, filtered and concentrated under reduced pressure to give N-(8-(3-cyano-1-methyl-1H-pyrazol-5-yl)pyrido[3,4-d]pyridazin-5-yl)-2,2,2-trifluoro-N-((5-fluoro-2,3-dihydrobenzofuran-4-yl)methyl)acetamide (40.0 mg). The compound was dissolved in methanol (0.80 mL), and potassium carbonate (20.0 mg, 144 μmol, 2.00 equiv.) in water (0.20 mL) was added to the methanol solution. The mixture was stirred at 15° C. for 30 minutes, then the reaction mixture was filtered and concentrated under reduced pressure to give a residue. The residue was purified by prep-HPLC [column: Phenomenex Synergi C18 150×30 mm×4 um; mobile phase: phase A—water (0.05% HCl), phase B—ACN) B %: 40%-60%] to give 5-[5-[(5-fluoro-2,3-dihydrobenzofuran-4-yl)methylamino]pyrido[3,4-d]

pyridazin-8-yl]-1-methyl-pyrazole-3-carbonitrile (20.3 mg, 50.3 μmol, 70.4% yield, 99.5% purity) as a yellow solid. LC-MS [M+1]: 402.2.

¹H NMR (400 MHz, CD₃OD) δ=10.24 (d, J=1.2 Hz, 1H), 9.32 (d, J=0.8 Hz, 1H), 8.84 (s, 1H), 7.08 (s, 1H), 6.88 (t, J=9.2 Hz, 1H), 6.67 (dd, J=4.0, 8.8 Hz, 1H), 4.94 (s, 2H), 4.61 (t, J=8.8 Hz, 2H), 3.87 (s, 3H), 3.44 (t, J=8.8 Hz, 2H).

Example 17

N-((5-fluoro-2,3-dihydrobenzofuran-4-yl)methyl)-8-(2-methyl-1,2,3,4-tetrahydroisoquinolin-6-yl)pyrido[3,4-d]pyridazin-5-amine

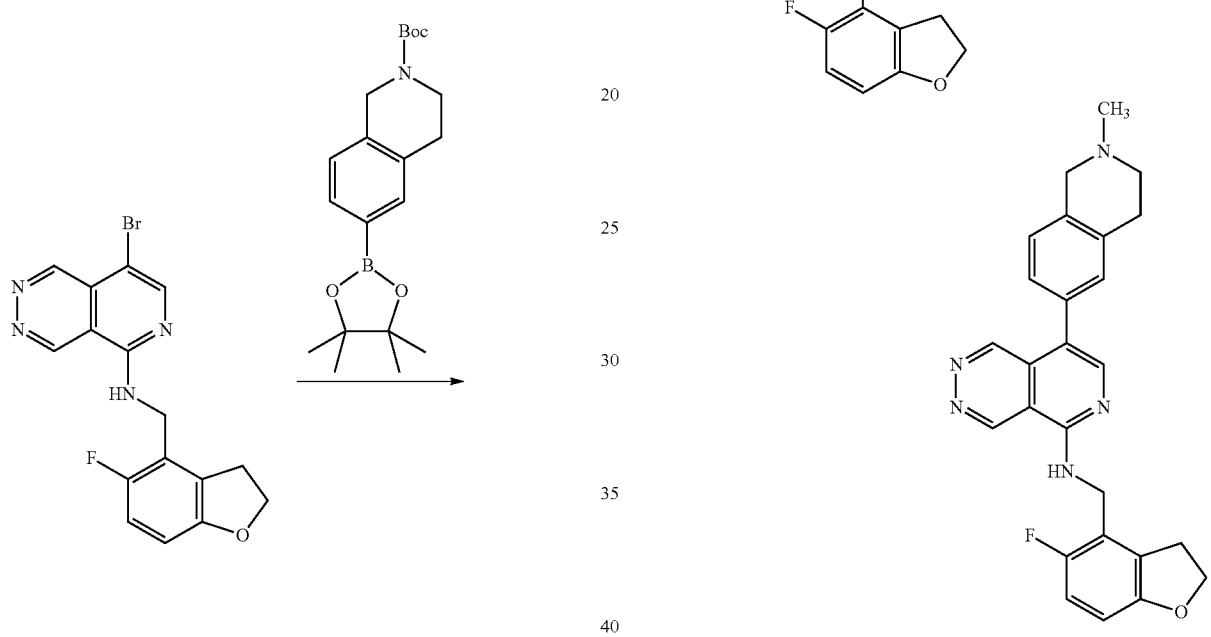

Step A: A mixture of tert-butyl 6-(4,4,5,5-tetramethyl-1,3,2-dioxaborolan-2-yl)-3,4-dihydroisoquinoline-2(1H)-carboxylate (57.5 mg, 160 μmol, 1.20 equiv.), 8-bromo-N-((5-fluoro-2,3-dihydrobenzofuran-4-yl)methyl)pyrido[3,4-d]pyridazin-5-amine (50.0 mg, 133 μmol, 1.00 equiv.), sodium bicarbonate (33.6 mg, 399 μmol, 15.5 μL, 3.00 equiv) and Pd(dppf)Cl₂ (9.75 mg, 13.3 μmol, 0.10 equiv) in dioxane (1.00 mL) and water (0.20 mL) was degassed and purged with nitrogen 3 times, and then the mixture was stirred at 100° C. for 1 hour under a nitrogen atmosphere. The reaction mixture was filtered and concentrated under reduced pressure to give a residue. The residue was purified by prep-TLC (SiO₂, petroleum ether/ethyl acetate=0/1) to give tert-butyl 6-(5-(((5-fluoro-2,3-dihydrobenzofuran-4-yl)methyl)amino)pyrido[3,4-d]pyridazin-8-yl)-3,4-dihydroisoquinoline-2(1H)-carboxylate (60.0 mg, 85.3% yield) as a yellow solid. LC-MS [M+1]: 527.9.

Step B: To a solution of tert-butyl 6-(5-(((5-fluoro-2,3-dihydrobenzofuran-4-yl)methyl)amino)pyrido[3,4-d]pyridazin-8-yl)-3,4-dihydroisoquinoline-2(1H)-carboxylate (50.0 mg, 94.8 μmol, 1.00 equiv) in DCM (2.00 mL) was added trifluoroacetic acid (924 mg, 8.10 mmol, 0.60 mL, 85.5 equiv.). The mixture was stirred at 25° C. for 1 hour. The reaction mixture adjusted to pH=9 with potassium carbonate aqueous solution in water (3.00 mL) and extracted with dichloromethane/methanol=10/1 (5.00 mL×3). The combined organic layers were washed with brine (5.00 mL×2), dried over sodium sulfate, filtered and concentrated under reduced pressure to give N-((5-fluoro-2,3-dihydrobenzofuran-4-yl)methyl)-8-(1,2,3,4-tetrahydroisoquinolin-6-yl)pyrido[3,4-d]pyridazin-5-amine (30.0 mg, crude) as a yellow solid.

¹H NMR (400 MHz, CD₃OD) δ=9.81 (d, J=1.2 Hz, 1H), 9.38 (d, J=1.2 Hz, 1H), 8.38 (s, 1H), 7.27-7.21, (m, 3H), 6.90-6.78 (m, 1H), 6.61 (dd, J=3.6, 8.4 Hz, 1H), 4.84-4.83 (m, 1H), 4.55 (t, J=8.8 Hz, 2H), 4.06 (s, 2H), 3.36 (t, J=8.8 Hz, 2H), 3.16 (t, J=6.0 Hz, 2H), 2.93 (t, J=6.0 Hz, 2H).

Example 17: A mixture of N-((5-fluoro-2,3-dihydrobenzofuran-4-yl)methyl)-8-(1,2,3,4-tetrahydroisoquinolin-6-yl)pyrido[3,4-d]pyridazin-5-amine (30.0 mg, 70.2 μmol, 1.00 equiv.), acetic acid (4.21 mg, 70.2 μmol, 4.01 μL, 1.00 equiv.) and paraformaldehyde (90.0 mg) in methanol (1.00 mL) was stirred at 45° C. for 0.5 hours, and then sodium triacetoxyborohydride (44.6 mg, 210 μmol, 3.00 equiv.) was added to the mixture. The reaction was stirred at 45° C. for 1 hour under a nitrogen atmosphere. The mixture was then filtered and concentrated under reduced pressure to give a residue. The residue was purified by prep-HPLC [column: Xtimate C18 10 u 250 mm×80 mm; mobile phase: phase A—water (0.05% ammonia hydroxide v/v), phase B—ACN; B %:40%-60%] to give N-((5-fluoro-2,3-dihydrobenzofuran-4-yl)methyl)-8-(2-methyl-1,2,3,4-tetrahydroisoquinolin-6-yl)pyrido[3,4-d]pyridazin-5-amine (7.17 mg, 22.6% yield, 97.8% purity) as a yellow solid. LC-MS [M+1]: 442.3.

¹H NMR (400 MHz, DMSO-d₆) δ=9.99 (d, J=0.8 Hz, 1H), 9.40 (d, J=1.2 Hz, 1H), 8.59 (t, J=5.2 Hz, 1H), 8.36 (s, 1H), 7.28-7.23 (m, 2H), 7.22-7.18 (m, 1H), 6.92 (t, J=8.8 Hz, 1H), 6.67 (dd, J=4.0, 8.8 Hz, 1H), 4.75 (d, J=4.8 Hz, 2H), 4.53 (t, J=8.4 Hz, 2H), 3.56 (s, 2H), 3.29-3.28 (m, 2H), 2.90 (br t, J=5.6 Hz, 2H), 2.64 (br t, J=5.6 Hz, 2H), 2.37 (s, 3H).

Example 18

8-(1-(2-(dimethylamino)ethyl)-1H-pyrazol-5-yl)-N-((5-fluoro-2,3-dihydrobenzofuran-4-yl)methyl)pyrido[3,4-d]pyridazin-5-amine

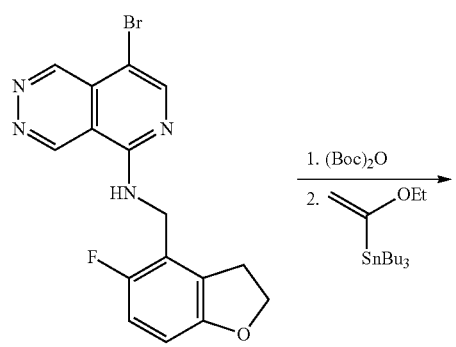

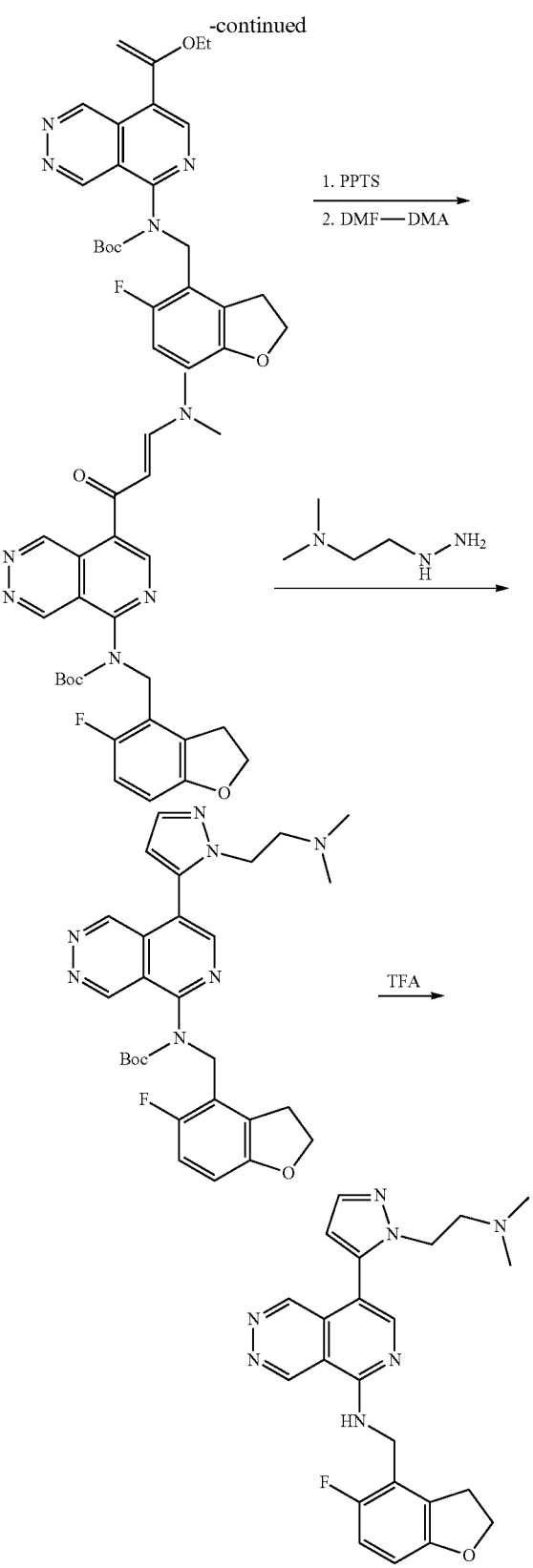

Step A: To a solution of 8-bromo-N-((5-fluoro-2,3-dihydrobenzofuran-4-yl)methyl)pyrido[3,4-d]pyridazin-5-amine (100 mg, 267 μmol, 1.00 equiv) in THF (1.00 mL) was added DMAP (3.26 mg, 26.7 μmol, 0.10 equiv) and di-tertbutyl dicarbonate (87.3 mg, 400 μmol, 91.9 μL, 1.50 equiv.). The mixture was stirred at 80° C. for 30 minutes, then concentrated in vacuo to give a residue. The residue was triturated with petroleum ether (5.00 mL) to give tert-butyl (8-bromopyrido[3,4-d]pyridazin-5-yl)((5-fluoro-2,3-dihydrobenzofuran-4-yl)methyl)carbamate (90.0 mg, 190 μmol, 71.0% yield) as a yellow solid.

$^1$H NMR (400 MHz, CDCl$_3$) δ=9.80 (d, J=1.2 Hz, 1H), 9.33 (d, J=0.4 Hz, 1H), 8.92 (s, 1H), 6.63-6.57 (m, 1H), 6.55-6.50 (m, 1H), 5.23 (s, 2H), 4.58 (t, J=8.8 Hz, 2H), 3.35 (br t, J=8.4 Hz, 2H), 1.33 (s, 9H).

To a solution of tert-butyl (8-bromopyrido[3,4-d]pyridazin-5-yl)((5-fluoro-2,3-dihydrobenzofuran-4-yl) methyl)carbamate (90.0 mg, 189 μmol, 1.00 equiv.) in dioxane (1.00 mL) was added Pd(PPh$_3$)$_2$Cl$_2$ (13.3 mg, 18.9 μmol, 0.10 equiv.) and tributyl(1-ethoxyvinyl)tin (68.4 mg, 189 μmol, 63.9 μL, 1.00 equiv.) under a nitrogen atmosphere. The mixture was stirred at 100° C. for 1 hour. After this time potassium fluoride solution (3.00 mL) was added and stirred for 15 minutes at 25° C. The aqueous phase was extracted with ethyl acetate (3.00 mL×2). The combined organic phases were washed with brine (3.00 mL×2), dried with anhydrous sodium sulfate, filtered and concentrated in vacuum. The residue was purified by prep-TLC (SiO$_2$, petroleum ether/ethyl acetate=1/1) to give tert-butyl (8-(1-ethoxyvinyl)pyrido[3,4-d]pyridazin-5-yl)((5-fluoro-2,3-dihydrobenzofuran-4-yl)methyl)carbamate (85.0 mg, 182 μmol, 96.2% yield) as a yellow solid.

$^1$H NMR (400 MHz, CDCl$_3$) δ=9.93 (d, J=1.2 Hz, 1H), 9.36 (d, J=1.2 Hz, 1H), 8.85 (s, 1H), 6.64-6.58 (m, 1H), 6.54-6.50 (m, 1H), 5.25 (s, 2H), 4.65 (d, J=2.8 Hz, 1H), 4.60 (d, J=2.8 Hz, 1H), 4.56 (t, J=8.8 Hz, 2H), 4.13-4.06 (m, 2H), 3.34 (br t, J=8.2 Hz, 2H), 1.33 (s, 9H), 0.93 (t, J=7.2 Hz, 3H).

Step B: To a solution of tert-butyl (8-(1-ethoxyvinyl) pyrido[3,4-d]pyridazin-5-yl)((5-fluoro-2,3-dihydrobenzofuran-4-yl)methyl)carbamate (85.0 mg, 182 μmol, 1.00 equiv) in DMF (1.00 mL) and water (0.50 mL) was added pyridinium p-toluenesulfonate (91.6 mg, 364 μmol, 2.00 equiv), and the mixture was stirred at 25° C. for 1 hour. The residue was poured into water (6.00 mL) and stirred for 15 minutes. The aqueous phase was extracted with ethyl acetate (6.00 mL×3). The combined organic phases were washed with brine (6.00 mL×3), dried with anhydrous sodium sulfate, filtered and concentrated in vacuo. The residue was by prep-TLC (SiO$_2$, petroleum ether/ethyl acetate=1/1) to give tert-butyl (8-acetylpyrido[3,4-d]pyridazin-5-yl)((5-fluoro-2,3-dihydrobenzofuran-4-yl)methyl)carbamate (70.0 mg, 160 μmol, 87.6% yield) as a yellow solid.

$^1$H NMR (400 MHz, DMSO-d$_6$) δ=10.34 (d, J=1.2 Hz, 1H), 9.51 (s, 1H), 9.32 (s, 1H), 6.79-6.69 (m, 1H), 6.57 (dd, J=4.0, 8.8 Hz, 1H), 5.23 (s, 2H), 4.52 (t, J=8.8 Hz, 2H), 3.30-3.25 (m, 2H), 2.80 (s, 3H), 1.26 (s, 9H).

To a solution of tert-butyl (8-acetylpyrido[3,4-d]pyridazin-5-yl)((5-fluoro-2,3-dihydrobenzofuran-4-yl) methyl)carbamate (70.0 mg, 194 μmol, 1.00 equiv.) in DMF-DMA (1.00 mL) was stirred at 100° C. for 1 hour. The mixture was concentrated in vacuo to give a residue. The residue was purified by prep-TLC (SiO$_2$, petroleum ether/ ethyl acetate=0/1) to give tert-butyl (E)-(8-(3-(dimethylamino)acryloyl)pyrido[3,4-d]pyridazin-5-yl)((5-fluoro-2,3-dihydrobenzofuran-4-yl)methyl)carbamate (70.0 mg, 142 μmol, 88.8% yield) as a yellow solid.

$^1$H NMR (400 MHz, CDCl$_3$) δ=10.20 (br s, 1H), 9.37 (d, J=1.2 Hz, 1H), 9.00 (s, 1H), 7.84 (br s, 1H), 6.63-6.56 (m, 1H), 6.55-6.49 (m, 1H), 5.57 (d, J=12.4 Hz, 1H), 5.27 (s, 2H), 4.57 (t, J=8.8 Hz, 2H), 3.36 (br t, J=8.8 Hz, 2H), 3.24 (s, 3H), 2.99 (s, 3H), 1.32 (s, 9H).

Step C: To a solution of tert-butyl (E)-(8-(3-(dimethylamino)acryloyl)pyrido[3,4-d]pyridazin-5-yl)((5-fluoro-2,3-dihydrobenzofuran-4-yl)methyl)carbamate (70.0 mg, 142 μmol, 1.00 equiv.) in ethanol (1.00 mL) was added 2-hydrazineyl-N, N-dimethylethan-1-amine (17.6 mg, 170 μmol, 1.20 equiv.). The mixture was stirred at 80° C. for 1 hour, then the mixture was concentrated in vacuo to give tert-butyl (8-(1-(2-(dimethylamino)ethyl)-1H-pyrazol-5-yl)pyrido[3, 4-d]pyridazin-5-yl)((5-fluoro-2,3-dihydrobenzofuran-4-yl) methyl)carbamate (35.0 mg, 65.6 μmol, crude) as a yellow solid which was used without further purification.

Example 18: To a solution tert-butyl (8-(1-(2-(dimethylamino)ethyl)-1H-pyrazol-5-yl)pyrido[3,4-d]pyridazin-5-yl) ((5-fluoro-2,3-dihydrobenzofuran-4-yl)methyl)carbamate (20.0 mg, 37.5 μmol, 1.00 equiv.) in DCM (1.00 mL) was added TFA (0.30 mL). The mixture was stirred at 25° C. for 1 hour. The mixture was adjusted to pH=8 with ammonium hydroxide and concentrated in vacuo to give a residue. The residue was purified by prep-HPLC (column: Waters Xbridge 150×25 mm×5 um; mobile phase: phase A—water (10 mM NH$_4$HCO$_3$), phase B—ACN; B %: 20%-50%] to give 8-(1-(2-(dimethylamino)ethyl)-1H-pyrazol-5-yl)-N-((5-fluoro-2,3-dihydrobenzofuran-4-yl)methyl)pyrido[3,4-d]pyridazin-5-amine (9.00 mg, 20.5 μmol, 54.7% yield, 98.7% purity) as a yellow solid. LC-MS [M+1]: 434.3.

$^1$H NMR (400 MHz, CDCl$_3$) δ=9.47 (s, 1H), 9.27 (s, 1H), 8.41 (s, 1H), 7.70 (d, J=1.2 Hz, 1H), 6.88 (t, J=9.2 Hz, 1H), 6.68 (dd, J=4.0, 8.8 Hz, 1H), 6.37 (d, J=1.6 Hz, 1H), 6.19 (br s, 1H), 4.89 (d, J=5.6 Hz, 2H), 4.63 (t, J=8.8 Hz, 2H), 4.05 (t, J=6.4 Hz, 2H), 3.42 (t, J=8.8 Hz, 2H), 2.64 (t, J=6.4 Hz, 2H), 1.95 (s, 6H).

Example 19

N-((5-fluoro-2,3-dihydrobenzofuran-4-yl)methyl)-8-(2-methyl-4-((methylamino)methyl)phenyl)pyrido[3,4-d]pyridazin-5-amine

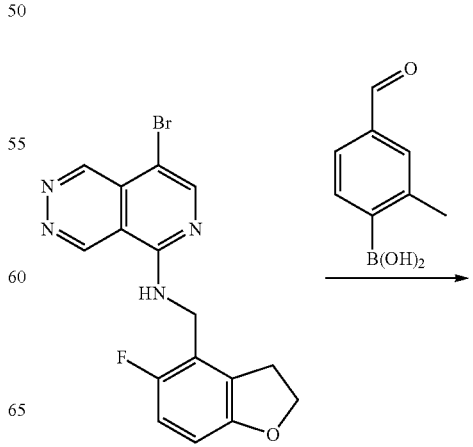

-continued

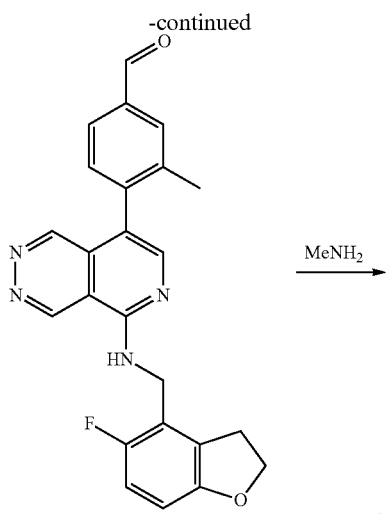

MeNH₂ →

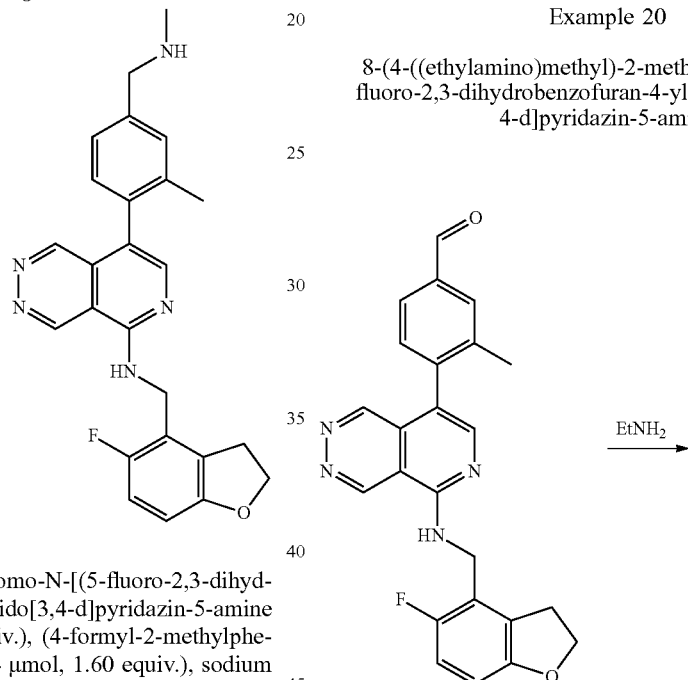

Step A: A mixture of 8-bromo-N-[(5-fluoro-2,3-dihydrobenzofuran-4-yl) methyl]pyrido[3,4-d]pyridazin-5-amine (60.0 mg, 152 μmol, 1.00 equiv.), (4-formyl-2-methylphenyl)boronic acid (40.0 mg, 244 μmol, 1.60 equiv.), sodium bicarbonate (25.6 mg, 305 μmol, 11.9 μL, 2.00 equiv.) and Pd(dppf)Cl₂ (11.2 mg, 15.2 μmol, 0.10 equiv.) in a mixture of dioxane (1.50 mL) and water (0.30 mL) was degassed and purged with nitrogen 3 times, then the mixture was stirred at 100° C. for 1 hour under a nitrogen atmosphere. The reaction mixture was cooled and filtered through a pad of celite, and the filtrate was evaporated to give a residue. The residue was purified by prep-TLC (SiO₂, dichloromethane/methanol=10/1) to give 4-(5-(((5-fluoro-2,3-dihydrobenzofuran-4-yl)methyl)amino)pyrido[3,4-d]pyridazin-8-yl)-3-methylbenzaldehyde (60.0 mg, 124 μmol, 81.7% yield, 86.0% purity) as a yellow solid.

Example 19: To a solution of 4-(5-(((5-fluoro-2,3-dihydrobenzofuran-4-yl)methyl)amino)pyrido[3,4-d]pyridazin-8-yl)-3-methylbenzaldehyde (20.0 mg, 41.5 μmol, 1.00 equiv.), methylamine (2.00 M in THF, 104 μL, 5.00 equiv.), and titanium (IV) isopropoxide (35.4 mg, 125 μmol, 36.8 μL, 3.00 equiv.) in 1,2-dichloromethane (1.00 mL) was adjusted to pH=6-7 with acetic acid (2.49 mg, 41.50 μmol, 2.37 μL, 1.00 equiv.), then the reaction mixture was stirred for 30 minutes, then sodium triacetoxyborohydride (17.6 mg, 83.0 μmol, 2.00 equiv.) was added and the reaction was stirred at 25° C. for 1.5 hours. The reaction mixture was diluted with ammonium chloride solution (20.0 mL) and the suspension was filtered, the filtrate was extracted with ethyl acetate (20.0 mL×2). The combined organic layers were washed with saturated aqueous sodium chloride solution (30.0 mL), dried over anhydrous sodium sulfate and concentrated under reduced pressure to give residue. The residue was purified by prep-HPLC [column: Phenomenex Synergi C18 150×25×10 um; mobile phase: phase A—water (0.05% HCl), phase B—ACN; B %: 20%-40%] to give N-((5-fluoro-2,3-dihydrobenzofuran-4-yl)methyl)-8-(2-methyl-4-((methylamino)methyl)phenyl)pyrido[3,4-d]pyridazin-5-amine (11.6 mg, 24.9 μmol, 60.0% yield, hydrochloride) as a yellow solid. LC-MS [M+1]: 430.3.

¹H NMR (400 MHz, CD₃OD) δ=10.28 (s, 1H), 9.01 (d, J=0.8 Hz, 1H), 8.67 (s, 1H), 7.59 (s, 1H), 7.54-7.48 (m, 1H), 7.42 (d, J=8.0 Hz, 1H), 6.92-6.84 (m, 1H), 6.67 (dd, J=4.0, 8.8 Hz, 1H), 4.87-4.97 (m, 2H), 4.60 (t, J=8.8 Hz, 2H), 4.28 (s, 2H), 3.43 (t, J=8.8 Hz, 2H), 2.79 (s, 3H), 2.20 (s, 3H).

Example 20

8-(4-((ethylamino)methyl)-2-methylphenyl)-N-((5-fluoro-2,3-dihydrobenzofuran-4-yl)methyl)pyrido[3,4-d]pyridazin-5-amine EtNH₂ →

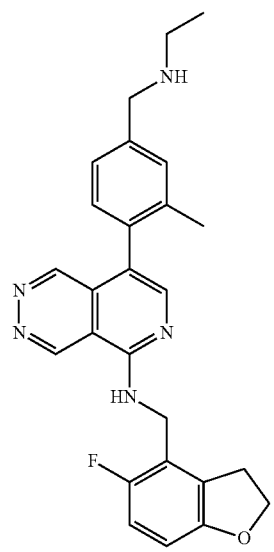

To a solution of 4-(5-(((5-fluoro-2,3-dihydrobenzofuran-4-yl)methyl)amino)pyrido[3,4-d]pyridazin-8-yl)-3-methylbenzaldehyde (Example 19, Step A; 30.0 mg, 72.4 µmol, 1.00 equiv.), ethylamine (16.3 mg, 362 µmol, 5.00 equiv.) and tetraisopropoxytitanium (61.7 mg, 217 µL, 64.1 µL, 3.00 equiv.) in 1,2-dichloromethane (1.00 mL) was adjusted to pH between 5-6 with acetic acid (8.69 mg, 145 µmol, 8.28 µL, 2.00 equiv.), and the reaction mixture was stirred at 40° C. for 0.5 hour. After this time, sodium triacetoxyborohydride (30.7 mg, 145 µmol, 2.00 equiv.) was added, and the reaction mixture was stirred at 40° C. for another 1 hour. The reaction mixture was diluted with ammonium chloride solution (20.0 mL) and the suspension was filtered, and the filtrate was extracted with ethyl acetate (20.0 mL×3). The combined organic layers were washed with brine (30.0 mL), dried over anhydrous sodium sulfate and concentrated under reduced pressure to give residue. The residue was purified by prep-HPLC [column: Waters Xbridge 150×25 mm×5 um; mobile phase: phase A—water (10 mM NH$_4$HCO$_3$) phase B—ACN; B %: 27%-51%] to give 8-(4-((ethylamino)methyl)-2-methylphenyl)-N-((5-fluoro-2,3-dihydrobenzofuran-4-yl)methyl)pyrido[3,4-d]pyridazin-5-amine (8.50 mg, 19.1 µmol, 26.4% yield, 99.6% purity) as a white solid. LC-MS [M+1]: 444.4.

$^1$H NMR (400 MHz, CD$_3$OD) δ=9.83 (d, J=1.6 Hz, 1H), 8.90 (d, J=1.2 Hz, 1H), 8.29 (s, 1H), 7.40 (s, 1H), 7.33 (d, J=7.6 Hz, 1H), 7.23 (d, J=7.6 Hz, 1H), 6.89-6.81 (m, 1H), 6.62 (dd, J=4.0, 8.8 Hz, 1H), 4.79-4.83 (m, 2H), 4.56 (t, J=8.8 Hz, 2H), 3.84 (s, 2H), 3.37 (t, J=8.8 Hz, 2H), 2.77-2.68 (m, 2H), 2.10 (s, 3H), 1.19 (t, J=7.2 Hz, 3H).

Example 21

N-((5-fluoro-2,3-dihydrobenzofuran-4-yl)methyl)-8-(4-((methylamino)methyl)phenyl)pyrido[3,4-d]pyridazin-5-amine

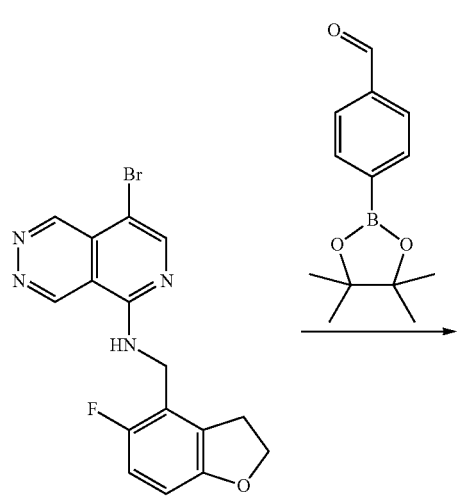

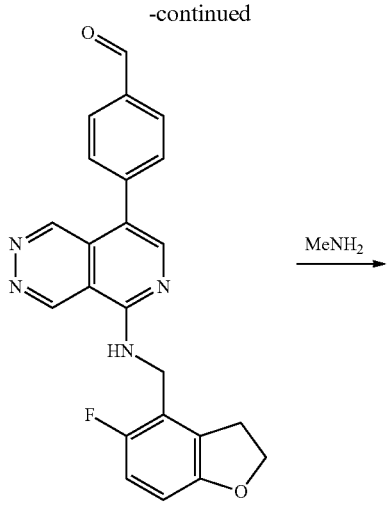

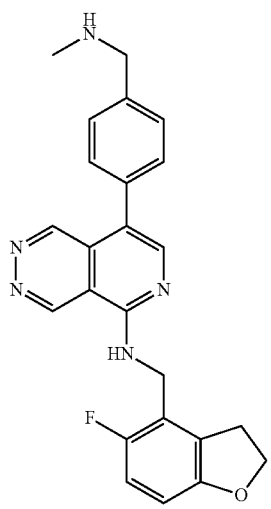

Step A: A mixture of 8-bromo-N-[(5-fluoro-2,3-dihydrobenzofuran-4-yl) methyl]pyrido[3,4-d]pyridazin-5-amine (40.0 mg, 106 µmol, 1.00 equiv), 4-(4,4,5,5-tetramethyl-1,3,2-dioxaborolan-2-yl) benzaldehyde (49.5 mg, 213 µmol, 2.00 equiv.), Pd(dppf)Cl$_2$ (7.80 mg, 10.7 µmol, 0.10 equiv.) and sodium bicarbonate (26.9 mg, 320 µmol, 12.4 µL, 3.00 equiv.) in dioxane (2.00 mL) and water (0.40 mL) was degassed and then heated to 80° C. for 12 hours under a nitrogen atmosphere. The reaction mixture was poured into water (10.0 mL) and extracted with ethyl acetate (20.0 mL×3). The combined organic phases were washed with brine (10.0 mL), dried over anhydrous sodium sulfate, concentrated in vacuo to give a 4-(5-4(5-fluoro-2,3-dihydrobenzofuran-4-yl)methyl)amino)pyrido[3,4-d]pyridazin-8-yl)benzaldehyde (40.0 mg, crude) as a brown solid which used for the next step without further purification. LC-MS [M+1]: 401.1.

Example 21: Methylamine (2.00 M, in THF, 374 μL, 10 equiv.) was added to a mixture of 4-(5-(((5-fluoro-2,3-dihydrobenzofuran-4-yl)methyl)amino)pyrido[3,4-d]pyridazin-8-yl)benzaldehyde (30.0 mg, 75.0 μmol, 1.00 equiv) and AcOH (1 drop) in THF (1 mL), and the reaction mixture was stirred at 15° C. for 30 minutes. After this time sodium triacetoxyborohydride (47.6 mg, 225 μmol, 3.00 equiv) was added to the mixture, and the mixture was degassed and purged with nitrogen 3 times and stirred at 15° C. for 3 hours under a nitrogen atmosphere. The reaction was filtered, and the filtrate was concentrated and purified by prep-HPLC [column: Phenomenex Synergi C18 150×30 mm×4 um; mobile phase: phase A—water (0.05% HCl), phase B—ACN; B %:17%-37%] to give N-((5-fluoro-2,3-dihydrobenzofuran-4-yl)methyl)-8-(4-((methylamino)methyl)phenyl)pyrido[3,4-d]pyridazin-5-amine (6.00 mg, 14.4 μmol, 19.3% yield, 100% purity) as a yellow solid. LC-MS [M+1]: 416.1.

$^1$H NMR (400 MHz, CD$_3$OD) δ=10.24 (s, 1H), 9.47 (d, J=1.2 Hz, 1H), 8.83 (s, 1H), 7.79-7.67 (m, 4H), 6.94-6.84 (m, 1H), 6.68 (dd, J=4.0, 8.8 Hz, 1H), 4.93 (s, 2H), 4.62 (t, J=8.8 Hz, 2H), 4.34 (s, 2H), 3.43 (t, J=8.8 Hz, 2H), 2.81 (s, 3H).

Example 22

8-(1,3-dimethyl-1H-pyrazol-5-yl)-N-((5-fluoro-2,3-dihydrobenzofuran-4-yl)methyl)pyrido[4,3-d]pyrimidin-5-amine

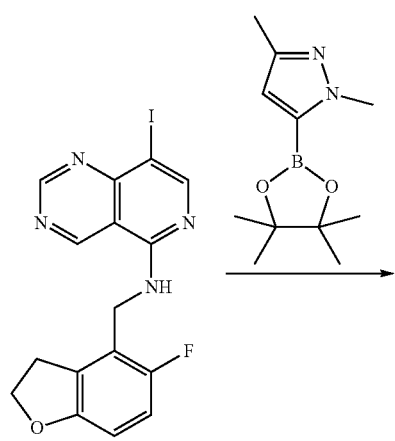

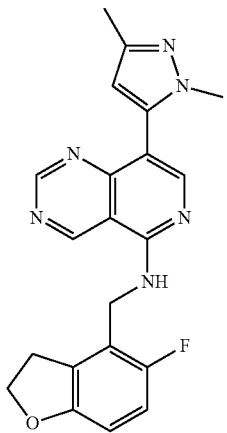

A mixture of Intermediate A-2 (50.0 mg, 118 μmol, 1.00 equiv.), 1,3-dimethyl-5-(4,4,5,5-tetramethyl-1,3,2-dioxaborolan-2-yl)pyrazole (52.6 mg, 237 μmol, 2.00 equiv.), Pd(dppf)Cl$_2$ (8.67 mg, 11.8 μmol, 0.10 equiv.) and sodium carbonate (37.7 mg, 355 μmol, 3.00 equiv.) in dioxane (2.00 mL) and water (0.40 mL) was de-gassed and then heated to 80° C. for 12 hours under N$_2$ atmosphere. The reaction mixture was poured into water (10.0 mL) and extracted with dichloromethane/methanol (10/1) (20.0 mL×3). The organic phase was washed with brine (10.0 mL), dried over anhydrous sodium sulfate, concentrated in vacuum to give a residue which purified by prep-HPLC (column: Xtimate C18 150*25 mm*5 μm; mobile phase: [water (0.05% ammonia hydroxide v/v)-ACN]; B %: 28%-58%, 10 min) and then lyophilization to give title compound 8-(1,3-dimethyl-1H-pyrazol-5-yl)-N-((5-fluoro-2,3-dihydrobenzofuran-4-yl)methyl)pyrido[4,3-d]pyrimidin-5-amine (16.0 mg, 40.0 μmol, 33.8% yield, 97.6% purity) as a yellow solid. LC-MS [M+1]: 391.3.

$^1$H NMR (400 MHz, DMSO-d$_6$) δ=9.89 (s, 1H), 9.29 (s, 1H), 8.79 (br s, 1H), 8.31 (s, 1H), 6.93 (t, J=9.6 Hz, 1H), 6.68 (dd, J=4.0, 8.8 Hz, 1H), 6.10 (s, 1H), 4.75 (br d, J=2.4 Hz, 2H), 4.54 (t, J=8.8 Hz, 2H), 3.52 (s, 3H), 3.32-3.29 (m, 2H), 2.19 (s, 3H).

Examples 23-25 were prepared following the procedure set forth in Example 22 and using the general reactions schemes and intermediates described herein.

TABLE 2

Characterization of EXAMPLES 23-25

| Ex. # | Structure | Analytical Data |
|---|---|---|
| 23 | 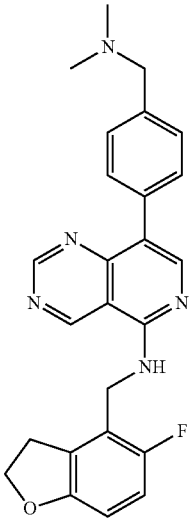<br>8-(4-((dimethylamino)methyl)phenyl)-N-((5-fluoro-2,3-dihydrobenzofuran-4-yl)methyl)pyrido[4,3-d]pyrimidin-5-amine | $^1$H NMR (400 MHz, DMSO-$d_6$) δ = 9.88 (s, 1H), 9.30 (s, 1H), 8.61 (br s, 1H), 8.40 (s, 1H), 7.59 (br d, J = 8.0 Hz, 2H), 7.34 (br d, J = 8.0 Hz, 2H), 6.93 (br t, J = 9.2 Hz, 1H), 6.67 (dd, J = 3.6, 8.8 Hz, 1H), 4.75 (br d, J = 4.0 Hz, 2H), 4.53 (br t, J = 8.8 Hz, 2H), 3.42 (s, 2H), 3.32-3.30 (m, 2H), 2.18 (s, 6H). LC-MS [M + 1]: 430.4 |
| 24 | 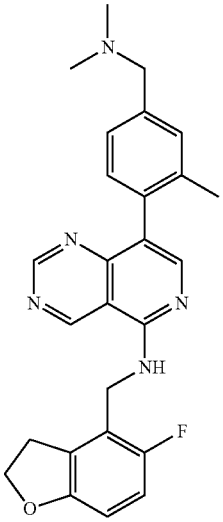<br>8-(4-((dimethylamino)methyl)-2-methylphenyl)-N-((5-fluoro-2,3-dihydrobenzofuran-4-yl)methyl)pyrido[4,3-d]pyrimidin-5-amine | $^1$H NMR (400 MHz, DMSO-$d_6$) δ = 9.87 (s, 1H), 9.21 (s, 1H), 8.57 (t, J = 5.2 Hz, 1H), 8.19 (s, 1H), 7.20 (s, 1H), 7.13 (s, 2H), 6.98-6.88 (m, 1H), 6.68 (dd, J = 3.6, 8.4 Hz, 1H), 4.73 (br d, J = 4.4 Hz, 2H), 4.54 (t, J = 8.8 Hz, 2H), 3.39 (s, 2H), 3.35-3.29 (m, 2H), 2.18 (s, 6H), 2.01 (s, 3H). LC-MS [M + 1]: 444.4. |

TABLE 2-continued

Characterization of EXAMPLES 23-25

| Ex. # | Structure | Analytical Data |
|---|---|---|
| 25 | 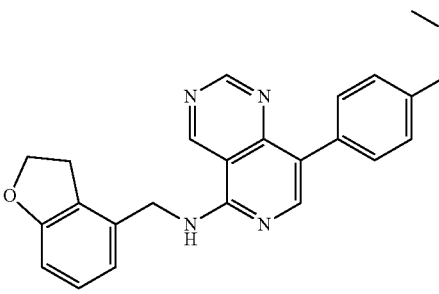<br>N-((2,3-dihydrobenzofuran-4-yl)methyl)-8-(4-((dimethylamino)methyl)phenyl)pyrido[4,3-d]pyrimidin-5-amine | $^1$H NMR (400 MHz, CD$_3$OD) δ = 9.73 (s, 1H), 9.22 (s, 1H), 8.33 (s, 1H), 7.61 (d, J = 8.4 Hz, 2H), 7.40 (d, J = 8.4 Hz, 2H), 7.05 (t, J = 7.6 Hz, 1H), 6.88 (d, J = 7.6 Hz, 1H), 6.64 (d, J = 7.6 Hz, 1H), 4.79 (s, 2H), 4.56 (t, J = 8.8 Hz, 2H), 3.55 (s, 2H), 3.29-3.25 (m, 2H), 2.30 (s, 6H). LC-MS [M + 1]: 412.3. |

Example 26

N-((5-fluoro-2,3-dihydrobenzofuran-4-yl)methyl)-8-(2-methyl-4-((methylamino)methyl)phenyl)pyrido[4,3-d]pyrimidin-5-amine

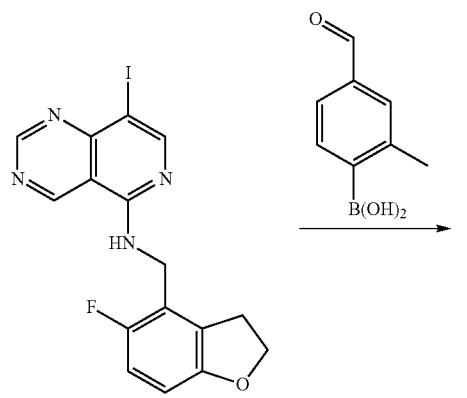

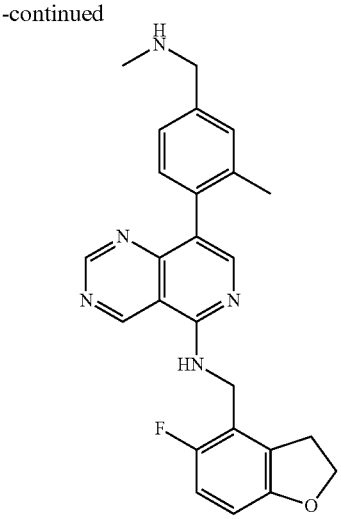

Step A: A mixture of N-((5-fluoro-2,3-dihydrobenzofuran-4-yl)methyl)-8-iodopyrido[4,3-d]pyrimidin-5-amine (100 mg, 237 μmol, 1.00 equiv.), (4-formyl-2-methylphenyl)boronic acid (77.7 mg, 474 μmol, 2.00 equiv.), sodium carbonate (75.3 mg, 711 μmol, 3.00 equiv.) and Pd(dppf)Cl$_2$ (17.3 mg, 23.7 μmol, 0.10 equiv.) in dioxane (2.00 mL) and water (0.40 mL) was degassed and purged with nitrogen 3 times, and then the mixture was stirred at 80° C. for 2 hours under a nitrogen atmosphere. The mixture was diluted with ethyl acetate (5.00 mL), washed with brine (5.00 mL), dried over sodium sulfate, filtered, and concentrated under reduced pressure to give a residue. The residue was purified by prep-TLC (SiO$_2$, dichloromethane/methanol=10/1) to give 4-(5-(((5-fluoro-2,3-dihydrobenzofuran-4-yl)methyl)amino)pyrido[4,3-d]pyrimidin-8-yl)-3-methylbenzaldehyde (80.0 mg, 167 μmol, 70.7% yield, 86.7% purity) as a yellow solid. LC-MS [M+1]: 415.0.

$^1$H NMR (400 MHz, DMSO-d$_6$) δ=9.97 (s, 1H), 9.23 (s, 1H), 8.71 (br t, J=5.2 Hz, 1H), 8.32 (s, 1H), 8.26 (s, 1H), 7.84 (s, 1H), 7.79 (d, J=7.6 Hz, 1H), 7.46 (d, J=7.6 Hz, 1H), 6.99-6.89 (m, 1H), 6.69 (dd, J=4.0, 8.8 Hz, 1H), 4.76 (br d, J=4.8 Hz, 2H), 4.55 (t, J=8.8 Hz, 2H), 3.31-3.30 (m, 2H), 2.13 (s, 3H).

Example 26: A mixture of 4-(5-(((5-fluoro-2,3-dihydrobenzofuran-4-yl)methyl)amino)pyrido[4,3-d]pyrimidin- 8-yl)-3-methylbenzaldehyde (40.0 mg, 96.5 µmol, 1.00 equiv.) and methylamine (2.00 M in THF, 483 µL, 10.0 equiv.) was adjusted to pH=5 with acetic acid (105 mg, 1.75 mmol, 0.10 mL, 18.1 equiv.). The mixture was stirred at 40° C. for 30 minutes, and then sodium triacetoxyborohydride (61.4 mg, 290 µmol, 3.00 equiv.) was added, and the mixture was stirred at 15° C. for 2.5 hours under a nitrogen atmosphere. The mixture was diluted with ethyl acetate (5.00 mL), washed with brine, dried over sodium sulfate, filtered, and concentrated under reduced pressure to give a residue. The residue was purified by prep-HPLC [column: Waters Xbridge 150*25 5 u; mobile phase: phase A—water (10 mM $NH_4HCO_3$), phase B—ACN; B %: 32%-59%] to give N-((5-fluoro-2,3-dihydrobenzofuran-4-yl)methyl)-8-(2-methyl-4-((methylamino)methyl)phenyl)pyrido[4,3-d]pyrimidin-5-amine (11.8 mg, 26.5 µmol, 27.4% yield, 96.2% purity) as a yellow solid. LC-MS [M+1]: 430.2.

$^1$H NMR (400 MHz, DMSO-$d_6$) δ=9.86 (s, 1H), 9.20 (s, 1H), 8.55 (t, J=5.2 Hz, 1H), 8.18 (s, 1H), 7.22 (s, 1H), 7.18-7.07 (m, 2H), 6.97-6.87 (m, 1H), 6.67 (dd, J=3.6, 8.4 Hz, 1H), 4.73 (br d, J=4.8 Hz, 2H), 4.53 (t, J=8.8 Hz, 2H), 3.65 (s, 2H), 3.34-3.33 (m, 2H), 2.30 (s, 3H), 2.00 (s, 3H).

Example 27

8-(1,3-dimethyl-1H-pyrazol-5-yl)-N-((5-fluoro-2,3-dihydrobenzofuran-4-yl)methyl)-2-(methylthio)pyrido[4,3-d]pyrimidin-5-amine

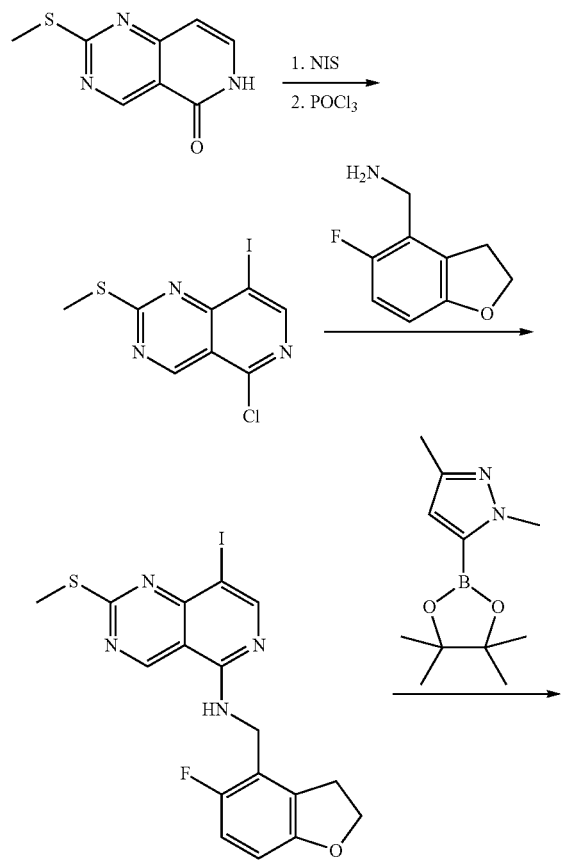

-continued

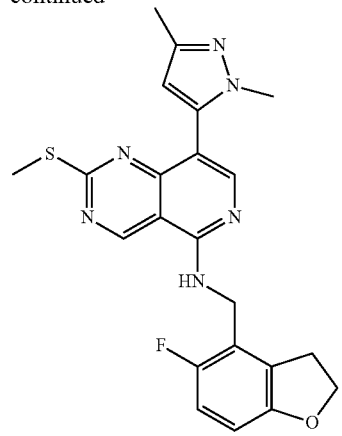

Step A: To a solution of 2 2-(methylthio)pyrido[4,3-d]pyrimidin-5(6H)-one (500 mg, 2.59 mmol, 1.00 equiv.) and potassium carbonate (716 mg, 5.18 mmol, 2.00 equiv.) in acetonitrile (100 mL) was added NIS (757 mg, 3.36 mmol, 1.30 equiv.) portionwise. The resulting suspension is heated to 75° C. for 3 hours. The reaction was cooled, filtered, washed with acetonitrile, and then the cake was collected. A minimal amount of water was added and the mixture was sonicated, then filtered and the resulting solid was dried in vacuo to give 8-iodo-2-(methylthio)pyrido[4,3-d]pyrimidin-5(6H)-one (900 mg, crude) as a yellow solid. LC-MS [M+1]: 319.9.

$^1$H NMR (400 MHz, DMSO-$d_6$) δ=8.95 (s, 1H), 8.88 (s, 1H), 8.42 (s, 1H), 8.16 (s, 1H), 2.63-2.51 (m, 6H).

To a solution of 8-iodo-2-(methylthio)pyrido[4,3-d]pyrimidin-5(6H)-one (200 mg, 627 µmol, 1.00 equiv.), benzyltriethylammonium chloride (286 mg, 1.25 mmol, 2.00 equiv.) and DIPEA (105 mg, 815 µmol, 142 µL, 1.30 equiv.) in acetonitrile (10.0 mL) was slowly added phosphorylchloride (288 mg, 1.88 mmol, 174 µL, 3.00 equiv.). Then the reaction mixture was heated to 80° C. and stirred for 14 hours. The suspension was cooled, diluted with ethyl acetate (5.00 mL) and slowly poured into ice water (10 mL). The resulting brown suspension was separated, the organic layer was concentrated to give 5-chloro-8-iodo-2-(methylthio)pyrido[4,3-d]pyrimidine (200 mg, 592 µmol, 94.5% yield) as a yellow solid. LC-MS [M+1]: 337.9.

Step B: To a solution of 5-chloro-8-iodo-2-(methylthio)pyrido[4,3-d]pyrimidine (200 mg, 592 µmol, 1.00 equiv.) and (5-fluoro-2,3-dihydrobenzofuran-4-yl) methanamine (119 mg, 712 µmol, 1.20 equiv.) in DMF (3.00 mL) was added DIEA (153 mg, 1.18 mmol, 206 µL, 2.00 equiv.). The mixture was stirred at 80° C. for 1 hour, cooled, triturated in water (20.0 mL), and collected by filtration. The solid was evaporated to remove solvent and water to give the N-((5-fluoro-2,3-dihydrobenzofuran-4-yl)methyl)-8-iodo-2-(methylthio)pyrido[4,3-d]pyrimidin-5-amine (250 mg, 534 µmol, 90.1% yield) as a yellow solid $^1$H NMR (400 MHz, DMSO-$d_6$) δ=9.46 (s, 1H), 8.66-8.52 (m, 2H), 6.91 (t, J=9.2 Hz, 1H), 6.66 (dd, J=4.0, 8.8 Hz, 1H), 4.66 (br d, J=4.8 Hz, 2H), 4.50 (br t, J=8.8 Hz, 2H), 3.24 (br t, J=8.8 Hz, 2H), 2.65 (s, 3H).

Example 27: To a solution of N-((5-fluoro-2,3-dihydrobenzofuran-4-yl)methyl)-8-iodo-2-(methylthio)pyrido[4,3-d]pyrimidin-5-amine (250 mg, 534 µmol, 1.00 equiv.), 1,3-dimethyl-5-(4,4,5,5-tetramethyl-1,3,2-dioxaborolan-2-yl)pyrazole (291 mg, 1.31 mmol, 2.45 equiv.) and sodium carbonate (170 mg, 1.60 mmol, 3.00 equiv.) in dioxane (4.00 mL) and water (0.80 mL) was added Pd(dppf)Cl$_2$ (39.1 mg, 53.4 µmol, 0.10 equiv.). The reaction solution was purged with nitrogen three times and heated to 80° C. and stirred for 1.5 hours. The reaction mixture was cooled and evaporated to give a residue. The residue was purified by column chromatography (SiO$_2$, petroleum ether/ethyl acetate=3/1 to 1/1) to give the crude product. The crude product was purified by prep-HPLC (Phenomenex Synergi C18 150*30 mm*4 µm; mobile phase: (A—water (0.05% HCl) and B—ACN); B %: 22%-42%) to give title compound 8-(1,3-dimethyl-1H-pyrazol-5-yl)-N-((5-fluoro-2,3-dihydrobenzofuran-4-yl)methyl)-2-(methylthio)pyrido[4,3-d]pyrimidin-5-amine (35.0 mg, 76.2 µmol, 83.1% yield, 95% purity) as a yellow solid. LC-MS [M+1]: 437.1.

$^1$H NMR (400 MHz, DMSO-d$_6$) δ=9.72 (s, 1H), 9.08 (s, 1H), 8.23 (s, 1H), 7.01-6.87 (m, 1H), 6.69 (dd, J=4.0, 8.8 Hz, 1H), 6.18 (s, 1H), 4.75 (br d, J=4.4 Hz, 2H), 4.53 (t, J=8.8 Hz, 2H), 3.58 (s, 3H), 3.30 (br t, J=8.8 Hz, 2H), 2.47 (s, 3H), 2.21 (s, 3H).

Example 28

8-(1,3-dimethyl-1H-pyrazol-5-yl)-N-((5-fluoro-2,3-dihydrobenzofuran-4-yl)methyl)-2-methoxypyrido[4,3-d]pyrimidin-5-amine

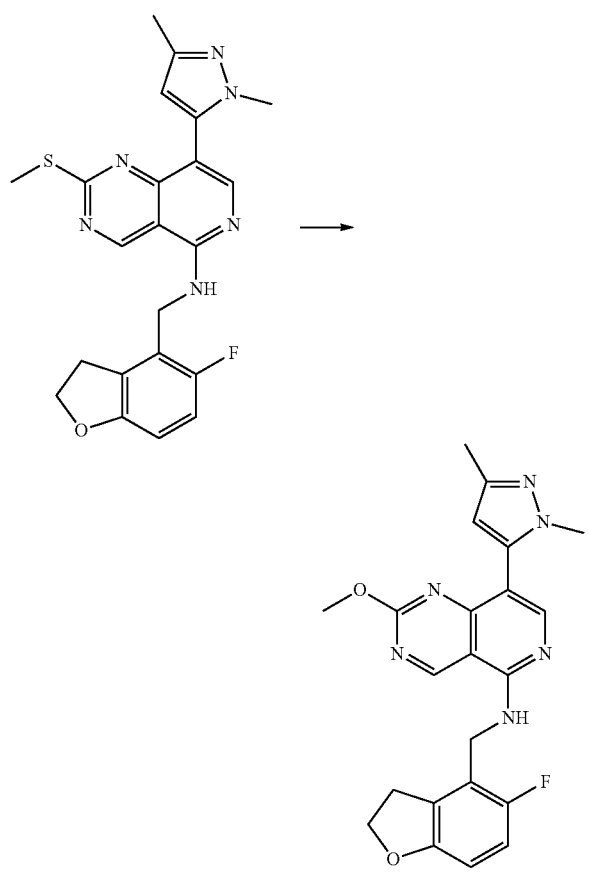

Example 28: Example 26 (25.0 mg, 54.4 µmol, 1.00 equiv.) was added to a solution of sodium methoxide (15.0 mg, 278 µmol, 5.10 equiv.) in methanol (1.50 mL), and the reaction was stirred at 70° C. for 12 hours. The reaction mixture was evaporated and the residue was purified by prep-HPLC (Phenomenex Synergi C18 150*30 mm*4 µm; mobile phase: (A—water (0.05% HCl) and B—ACN); B %: 22%-42%) to give title compound 8-(1,3-dimethyl-1H-pyrazol-5-yl)-N-((5-fluoro-2,3-dihydrobenzofuran-4-yl)methyl)-2-methoxypyrido[4,3-d]pyrimidin-5-amine (18.2 mg, 42.9 µmol, 78.9% yield, 99.2% purity) as a yellow solid. LC-MS [M+1]: 421.2.

$^1$H NMR (400 MHz, DMSO-d$_6$) δ=9.90 (s, 1H), 9.47 (s, 1H), 8.16 (s, 1H), 7.01-6.86 (m, 1H), 6.71 (dd, J=4.0, 8.8 Hz, 1H), 6.21 (s, 1H), 4.80 (br d, J=4.0 Hz, 2H), 4.54 (t, J=8.8 Hz, 2H), 3.93 (s, 3H), 3.62 (s, 3H), 3.31 (t, J=8.8 Hz, 2H), 2.22 (s, 3H).

Example 29

4-(1,3-dimethyl-1H-pyrazol-5-yl)-N-((5-fluoro-2,3-dihydrobenzofuran-4-yl)methyl)-2,7-naphthyridin-1-amine

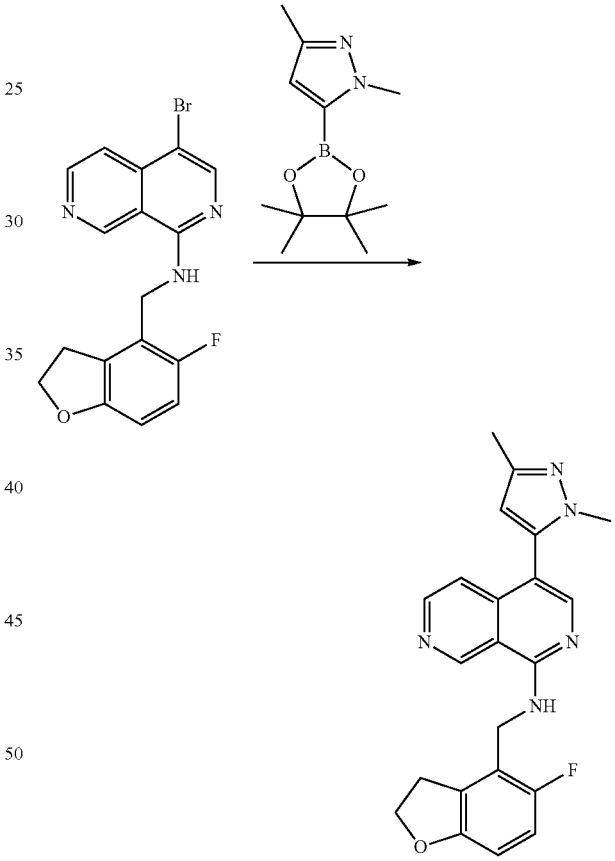

A mixture of 4-bromo-N-((5-fluoro-2,3-dihydrobenzofuran-4-yl)methyl)-2,7-naphthyridin-1-amine (Intermediate A-3, 110 mg, 294 µmol, 1.00 equiv.), 1,3-dimethyl-5-(4,4,5,5-tetramethyl-1,3,2-dioxaborolan-2-yl)-1H-pyrazole (165 mg, 743 µmol, 2.53 equiv.), sodium hydrogen carbonate (74.1 mg, 882 µmol, 34.3 µL, 3.00 equiv.) and Pd(dppf)Cl$_2$ (21.5 mg, 29.4 µmol, 0.10 equiv.) in dioxane (0.50 mL) and water (0.10 mL) was degassed and purged with nitrogen 3 times, and then the mixture was stirred at 95° C. for 2 hours under a nitrogen atmosphere. The reaction mixture was filtered and concentrated in vacuum to give a residue. The residue was purified by column chromatography (SiO$_2$, dichloromethane/methanol=1/0 to 10/1) to give the crude product. The crude product was further purified by prep-HPLC (Phenomenex Synergi C18 150*30 mm*4 μm; mobile phase: (A—water (0.05% HCl) and B—ACN); B %: 22%-42%) to give title compound 4-(1,3-dimethyl-1H-pyrazol-5-yl)-N-((5-fluoro-2,3-dihydrobenzofuran-4-yl)methyl)-2,7-naphthyridin-1-amine (55.5 mg, 143 μmol, 48.5% yield, 100% purity) as a yellow solid. LC-MS [M+1]: 390.3.

$^1$H NMR (400 MHz, DMSO-d$_6$) δ=10.17 (s, 1H), 9.66 (s, 1H), 8.67 (d, J=6.8 Hz, 1H), 8.40 (s, 1H), 7.63 (d, J=6.4 Hz, 1H), 6.94 (t, J=8.8 Hz, 1H), 6.70 (dd, J=4.0, 8.8 Hz, 1H), 6.25 (s, 1H), 4.80 (br d, J=4.4 Hz, 2H), 4.54 (br t, J=8.8 Hz, 2H), 3.57 (s, 3H), 3.34 (t, J=8.8 Hz, 2H), 2.24 (s, 3H).

Examples 30-31 were prepared following the procedure set forth in Example 29 and using the general reactions schemes and intermediates described herein.

TABLE 3

Characterization of EXAMPLES 30-31

| Ex. # | Structure | Analytical Data |
|---|---|---|
| 30 | 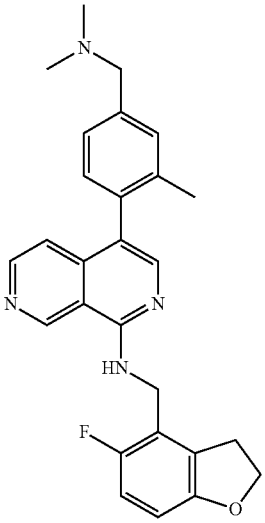<br>4-(4-((dimethylamino)methyl)-2-methylphenyl)-N-((5-fluoro-2,3-dihydrobenzofuran-4-yl)methyl)-2,7-naphthyridin-1-amine | $^1$H NMR (400 MHz, DMSO-d$_6$) δ = 9.69 (br s, 1H), 8.54 (br d, J = 6.0 Hz, 1H), 8.34 (br s, 1H), 7.96 (s, 1H), 7.29 (br s, 1H), 7.21 (br d, J = 7.2 Hz, 1H), 7.14 (br d, J = 7.2 Hz, 1H), 6.98 (br d, J = 5.6 Hz, 1H), 6.93 (br t, J = 8.4 Hz, 1H), 6.70-6.64 (m, 1H), 4.84-4.64 (m, 2H), 4.53 (br t, J = 8.4 Hz, 2H), 3.42 (br s, 2H), 3.30-3.25 (m, 2 H), 2.20 (br s, 6H), 2.00 (br s, 3H). LC-MS [M + 1]: 443.3. |
| 31 | 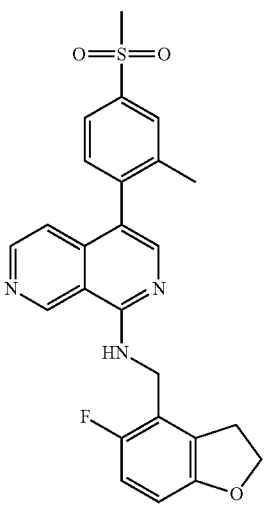<br>N-((5-fluoro-2,3-dihydrobenzofuran-4-yl)methyl)-4-(2-methyl-4-(methylsulfonyl)phenyl)-2,7-naphthyridin-1-amine | $^1$H NMR (400 MHz, DMSO-d$_6$) δ = 9.68 (s, 1H), 8.56 (d, J = 6.0 Hz, 1H), 7.99 (s, 1H), 7.92 (s, 1H), 7.84 (br d, J = 8.4 Hz, 1H), 7.49 (d, J = 8.0 Hz, 1H), 6.99 (d, J = 6.0 Hz, 1H), 6.91 (t, J = 9.6 Hz, 1H), 6.67 (dd, J = 3.6, 8.4 Hz, 1H), 4.80-4.67 (m, 2H), 4.54 (t, J = 8.4 Hz, 2H), 3.36-3.92 (m, 2H), 3.26 (s, 3H), 2.11 (s, 3H). LC-MS [M + 1]: 464.0. |

Example 32

5-(1-(((5-fluoro-2,3-dihydrobenzofuran-4-yl)methyl)amino)-2,7-naphthyridin-4-yl)-N,N,1-trimethyl-1H-pyrazole-3-carboxamide

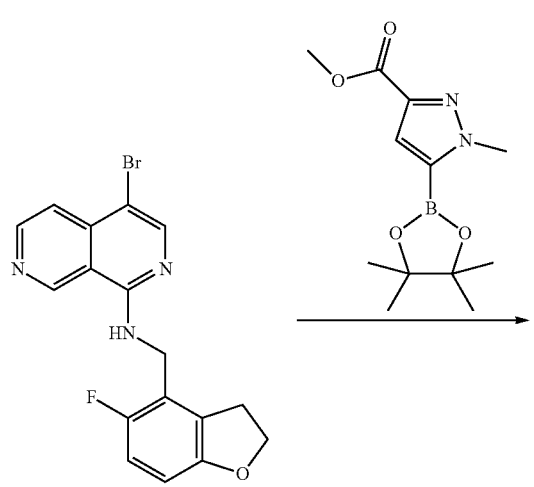

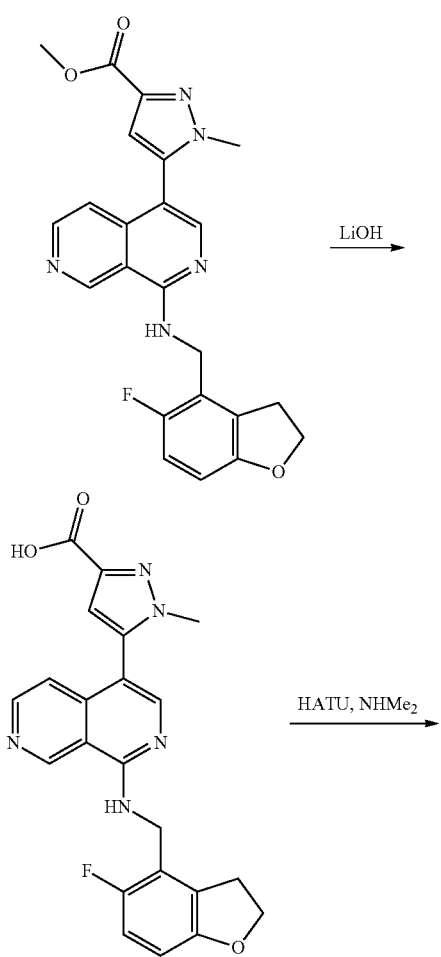

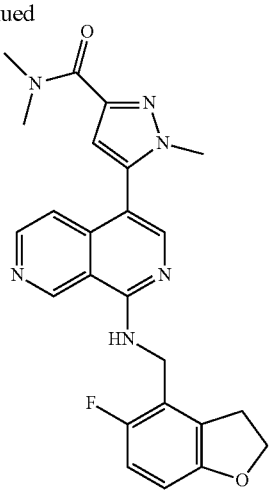

Step A: A mixture of 4-bromo-N-((5-fluoro-2,3-dihydrobenzofuran-4-yl)methyl)-2,7-naphthyridin-1-amine (Intermediate A-3, 200 mg, 534 μmol, 1.00 equiv.), methyl 1-methyl-5-(4,4,5,5-tetramethyl-1,3,2-dioxaborolan-2-yl)-1H-pyrazole-3-carboxylate (213 mg, 802 μmol, 1.50 equiv.), potassium carbonate (369 mg, 2.67 mmol, 5.00 equiv.) and Bis(tri-tert-butylphosphine)palladium(0) (27.3 mg, 53.5 μmol, 0.10 equiv.) in dioxane (5.00 mL) and water (1.00 mL) was degassed and purged with nitrogen three times, and then the mixture was stirred at 80° C. for 1 hour under a nitrogen atmosphere. The reaction mixture was filtered and concentrated under reduced pressure to give methyl 5-[1-[(5-fluoro-2,3-dihydrobenzofuran-4-yl)methylamino]-2,7-naphthyridin-4-yl]-1-methyl-pyrazole-3-carboxylate (300 mg, crude) as a brown solid. The crude product was used without further purification. LC-MS [M+1]: 434.2.

Step B: A mixture of methyl 54-[1-[(5-fluoro-2,3-dihydrobenzofuran-4-yl)methylamino]-2,7-naphthyridin-4-yl]-1-methyl-pyrazole-3-carboxylate (280 mg, 646 μmol, 1.00 equiv) and lithium hydroxide (46.4 mg, 1.94 mmol, 3.00 equiv.) in THF (10.0 mL) and water (3.00 mL) was degassed and purged with nitrogen 3 times, and then the mixture was stirred at 25° C. for 2 hours under a nitrogen atmosphere. The reaction mixture was filtered and concentrated under reduced pressure to give 5-(1-(((5-fluoro-2,3-dihydrobenzofuran-4-yl)methyl)amino)-2,7-naphthyridin-4-yl)-1-methyl-1H-pyrazole-3-carboxylic acid (250 mg, crude) as a brown solid which was used into the next step without further purification. LC-MS [M+1]: 420.2.

Example 32: A mixture of 5-(1-(((5-fluoro-2,3-dihydrobenzofuran-4-yl)methyl)amino)-2,7-naphthyridin-4-yl)-1-methyl-1H-pyrazole-3-carboxylic acid (100 mg, 238 μmol, 1.00 equiv), DIEA (108 mg, 835 μmol, 145 μL, 3.50 equiv) and HATU (181 mg, 477 μmol, 2.00 equiv) in DMF (1.00 mL) was degassed and purged with nitrogen for three times, and then the mixture was stirred at 25° C. for 0.5 hour under a nitrogen atmosphere. Then dimethylamine (2.00 M in THF, 596 μL, 5.00 equiv) was added, the mixture was stirred at 25° C. for 1.5 hours under a nitrogen atmosphere. The reaction mixture was diluted with water 10.0 mL and extracted with ethyl acetate (15.0 mL×3). The combined organic layers were washed with brine (15.0 mL×2), dried over anhydrous sodium sulfate, filtered and concentrated under reduced pressure to give a residue. The residue was purified by prep-HPLC [column: Phenomenex Gemini 150× 25 mm×10 μm; mobile phase: phase A—water (10 mM NH₄HCO₃), phase B—ACN]; B %: 25%-55%] to give title compound 5-[1(5-fluoro-2,3-dihydrobenzofuran-4-yl)methyl-amino]-2,7-naphthyridin-4-yl]-N,N,1-trimethyl-pyrazole-3-carboxamide (12.3 mg, 27.3 µmol, 11.4% yield, 98.9% purity) as a white solid. LC-MS [M+1]: 447.1.

¹H NMR (400 MHz, DMSO-d₆) δ=9.71 (s, 1H), 8.63 (d, J=5.6 Hz, 2H), 8.17 (s, 1H), 7.22 (d, J=6.0 Hz, 1H), 6.92 (t, J=9.2 Hz, 1H), 6.70-6.62 (m, 2H), 4.76 (br d, J=4.8 Hz, 2H), 4.53 (t, J=8.8 Hz, 2H), 3.66 (s, 3H), 3.34 (s, 3H), 3.30-3.27 (s, 2H), 3.00 (s, 3H).

Example 33

5-(1-(((5-fluoro-2,3-dihydrobenzofuran-4-yl)methyl)amino)-2,7-naphthyridin-4-yl)-N,N,1-trimethyl-1H-pyrazol-e-3-carboxamide

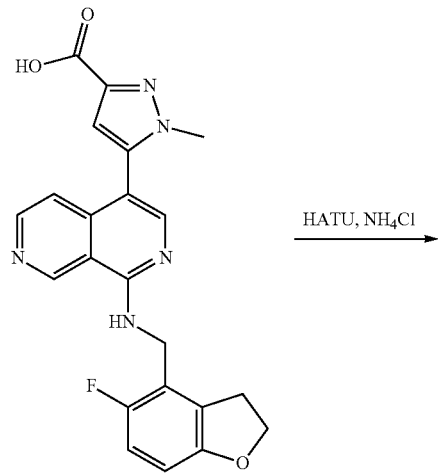

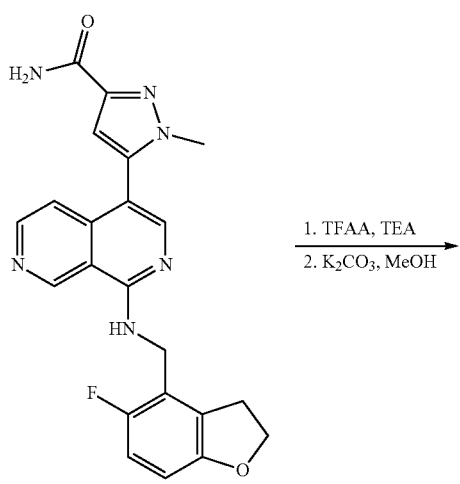

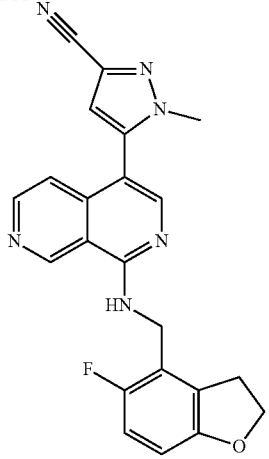

Step A: A mixture of 5-(1-(((5-fluoro-2,3-dihydrobenzofuran-4-yl)methyl)amino)-2,7-naphthyridin-4-yl)-1-methyl-1H-pyrazole-3-carboxylic acid (Example 32, Step B; 130 mg, 310 µmol, 1.00 equiv.), DIEA (140 mg, 1.08 mmol, 189 µL, 3.50 equiv.) and HATU (236 mg, 620 µmol, 2.00 equiv.) in DMF (1.00 mL) were degassed and purged with nitrogen three times, and then the mixture was stirred at 25° C. for 0.5 hour under a nitrogen atmosphere. Then ammonium chloride (82.9 mg, 1.55 mmol, 5.00 equiv) was added, and the mixture was stirred at 25° C. for 1.5 hour. The reaction mixture was diluted with water 10.0 mL and extracted with ethyl acetate (15.0 mL×3), the combined organic layers were washed with brine (15.0 mL×2), dried over anhydrous sodium sulfate, filtered and concentrated under reduced pressure to give 5-(1-(((5-fluoro-2,3-dihydrobenzofuran-4-yl)methyl)amino)-2,7-naphthyridin-4-yl)-1-methyl-1H-pyrazole-3-carboxamide (160 mg, crude) as a white solid, which was used into the next step without further purification. LC-MS [M+1]: 419.4.

Example 33: To a solution of 5-(1-(((5-fluoro-2,3-dihydrobenzofuran-4-yl)methyl)amino)-2,7-naphthyridin-4-yl)-1-methyl-1H-pyrazole-3-carboxamide (50.0 mg, 120 µmol, 1.00 equiv.), TEA (121 mg, 1.19 mmol, 166 µL, 10.0 equiv.) in THF (2.00 mL) at 0° C. was added TFAA (125 mg, 597 µmol, 83.1 µL, 5.00 equiv.), the reaction was stirred at 25° C. for 1.5 hours. The reaction mixture was diluted with water (10.0 mL) and extracted with ethyl acetate (15.0 mL×3), the combined organic layers were washed with brine (20.0 mL×2), dried over anhydrous sodium sulfate, filtered and concentrated under reduced pressure to give N-[4-(5-cyano-2-methyl-pyrazol-3-yl)-2,7-naphthyridin-1-yl]-2,2,2-trifluoro-N-[(5-fluoro-2,3-dihydrobenzofuran-4-yl)methyl]acetamide (60.0 mg, crude) as a yellow solid. To a solution of N-[4-(5-cyano-2-methyl-pyrazol-3-yl)-2,7-naphthyridin-1-yl]-2,2,2-trifluoro-N-[(5-fluoro-2,3-dihydrobenzofuran-4-yl)methyl]acetamide (60.0 mg, 121 µmol, 1.00 equiv.) in methanol (0.80 mL) was added a solution of potassium carbonate (33.4 mg, 242 µmol, 2.00 equiv.) in water (0.20 mL). The mixture was stirred at 30° C. for 2 hours. The reaction mixture was filtered and concentrated under reduced pressure to give a residue. The residue was purified by prep-HPLC (hydrochloric acid condition) to give title compound 5-[1-[(5-fluoro-2,3-dihydrobenzofuran-4-yl)methylamino]-2,7-naphthyridin-4-yl]-1-methyl-pyrazole-3-carbonitrile (13.6 mg, 31.1 µmol, 25.8% yield, 91.7% purity) as a white solid. LC-MS [M+1]: 401.1.

$^1$H NMR (400 MHz, DMSO-d$_6$) δ=10.2 (s, 1H), 9.68 (br s, 1H), 8.67 (d, J=6.4 Hz, 1H), 8.47 (s, 1H), 7.62 (d, J=6.4 Hz, 1H), 7.20 (s, 1H), 6.94 (t, J=9.6 Hz, 1H), 6.70 (dd, J=3.6, 8.4 Hz, 1H), 4.80 (br d, J=4.4 Hz, 2H), 4.54 (t, J=8.8 Hz, 2H), 3.75 (s, 3H), 3.34 (br t, J=8.4 Hz, 2H).

Example 34

4-(1,3-dimethyl-1H-pyrazol-5-yl)-N-((5-fluoro-2,3-dihydrobenzofuran-4-yl)methyl)-6-methoxy-2,7-naphthyridin-1-amine

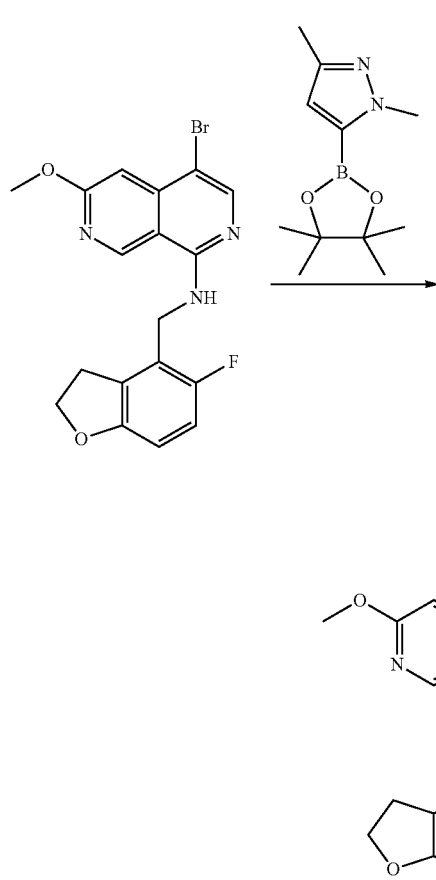

A mixture of Intermediate A-4 (150 mg, 371 μmol, 1.00 equiv.), 1,3-dimethyl-5-(4,4,5,5-tetramethyl-1,3,2-dioxaborolan-2-yl)pyrazole (206 mg, 928 μmol, 2.50 equiv.), Pd(dppf)Cl$_2$ (27.8 mg, 38.0 μmol, 0.01 equiv.) and sodium bicarbonate (93.8 mg, 1.12 mmol, 43.4 μL, 3.01 equiv.) in dioxane (3.50 mL) and water (0.50 mL) was degassed and purged with nitrogen 3 times, then the mixture was stirred at 100° C. for 1 hour under nitrogen atmosphere. The reaction mixture was cooled and filtered through a pad of celite. The filtrate was evaporated to give a residue. The residue was purified by column chromatography (SiO$_2$, petroleum ether/ethyl acetate=5/1 to 3/1) to give title compound 4-(1,3-dimethyl-1H-pyrazol-5-yl)-N-((5-fluoro-2,3-dihydrobenzofuran-4-yl)methyl)-6-methoxy-2,7-naphthyridin-1-amine (90.0 mg, 215 μmol, 57.8% yield) as an off-white solid.

$^1$H NMR (400 MHz, CDCl$_3$) δ=8.93 (s, 1H), 7.96 (s, 1H), 6.91-6.83 (m, 1H), 6.67 (dd, J=4.0, 8.8 Hz, 1H), 6.63 (s, 1H), 6.10 (s, 1H), 5.94 (s, 1H), 4.86 (d, J=5.6 Hz, 2H), 4.62 (t, J=8.8 Hz, 2H), 3.99 (s, 1H), 3.63 (s, 3H), 3.42 (t, J=8.8 Hz, 2H), 2.35 (s, 3H).

Example 35

5-(1,3-dimethyl-1H-pyrazol-5-yl)-8-(((5-fluoro-2,3-dihydrobenzofuran-4-yl)methyl)amino)-2,7-naphthyridin-3(2H)-one

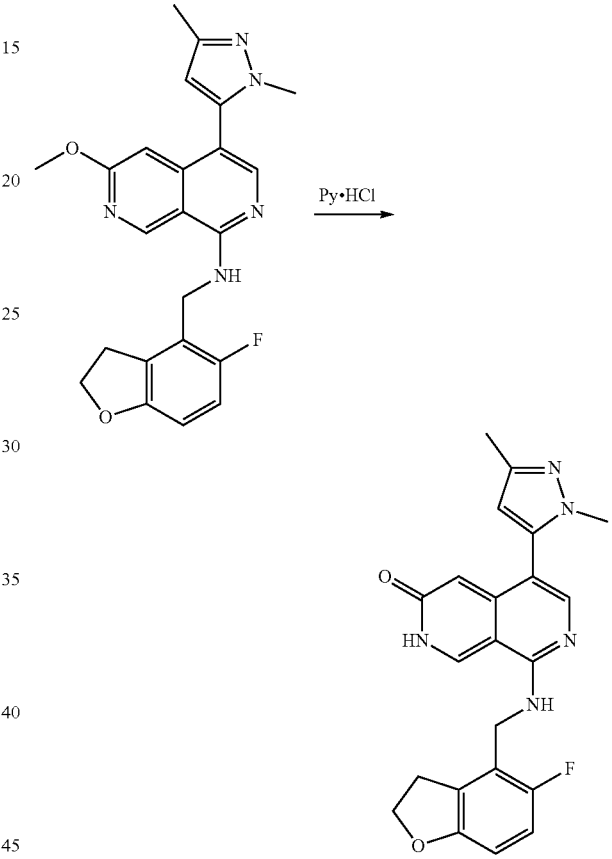

A mixture of 4-(1,3-dimethyl-1H-pyrazol-5-yl)-N-((5-fluoro-2,3-dihydrobenzofuran-4-yl)methyl)-6-methoxy-2,7-naphthyridin-1-amine (80.0 mg, 191 μmol, 1.00 equiv.) and pyridine; hydrochloride (110 mg, 954 μmol, 5.00 equiv.) was heated at 130° C. for 0.5 hour. The reaction was triturated with water (5.0 mL) and white precipitate was formed, the suspension was filtered, the filter cake was collected and dried under vacuum to give the crude product. The crude product was purified by prep-HPLC (Phenomenex Synergi C18 150*30 mm*4 μm; mobile phase: (A—water (0.05% HCl) and B—ACN); B %: 22%-42%) to give title compound 5 5-(1,3-dimethyl-1H-pyrazol-5-yl)-8-(((5-fluoro-2,3-dihydrobenzofuran-4-yl)methyl)amino)-2,7-naphthyridin-3(2H)-one (31.8 mg, 76.3 μmol, 40.0% yield, 97.3% purity) as a yellow solid. LC-MS [M+1]: 406.2.

$^1$H NMR (400 MHz, DMSO-d$_6$) δ=10.07 (s, 1H), 9.37 (br d, J=6.8 Hz, 1H), 7.53 (s, 1H), 7.02 (t, J=8.8 Hz, 1H), 6.80 (dd, J=4.0, 8.8 Hz, 1H), 6.21 (s, 1H), 5.92 (s, 1H), 4.79 (s, 2H), 4.59 (t, J=8.8 Hz, 2H), 3.60 (s, 3H), 3.34-3.24 (m, 2H), 2.23 (s, 3H).

Examples 36-41 were prepared following the procedures set forth in Example 34 and Example 35 and using the general reactions schemes and intermediates described herein.

TABLE 4

Characterization of EXAMPLES 36-41

| Ex. # | Structure | Analytical Data |
|---|---|---|
| 36 | 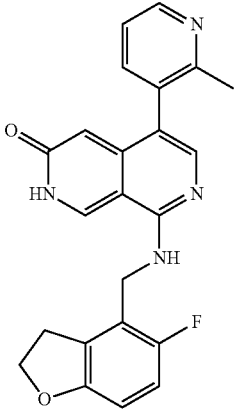<br>8-(((5-fluoro-2,3-dihydrobenzofuran-4-yl)methyl)amino)-5-(2-methylpyridin-3-yl)-2,7-naphthyridin-3(2H)-one | $^1$H NMR (400 MHz, DMSO-$d_6$) δ = 9.11 (br s, 1H), 8.51 (dd, J = 1.6, 5.2 Hz, 1H), 8.19-8.12 (m, 1H), 7.65-7.54 (m, 2H), 7.32 (dd, J = 4.8, 7.6 Hz, 1H), 6.96-6.88 (m, 1H), 6.67 (dd, J = 4.0, 8.8 Hz, 1H), 5.71 (br s, 1H), 4.75-4.68 (m, 1H), 4.66-4.59 (m, 1H), 4.54 (t, J = 8.8 Hz, 2H), 3.29 (br s, 2H), 2.25 (s, 3H). LC-MS [M + 1] = 403.3. |
| 37 | 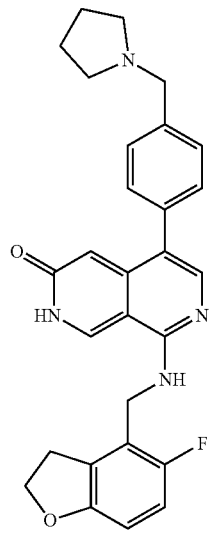<br>8-(((5-fluoro-2,3-dihydrobenzofuran-4-yl)methyl)amino)-5-(4-(pyrrolidin-1-ylmethyl)phenyl)-2,7-naphthyridin-3(2H)-one | $^1$H NMR (400 MHz, DMSO-$d_6$) δ = 9.04 (br s, 1H), 7.99-7.85 (m, 1H), 7.57 (br s, 1H), 7.38-7.32 (m, 2H), 7.32-7.27 (m, 2H), 6.90 (t, J = 9.6 Hz, 1H), 6.64 (dd, J = 4.0, 8.8 Hz, 1H), 6.26-6.15 (m, 1H), 4.66 (br d, J = 4.8 Hz, 2H), 4.51 (t, J = 8.8 Hz, 2H), 3.60 (s, 2H), 3.26 (t, J = 8.8 Hz, 2H), 2.45 (m, 4H), 1.75-1.67 (m, 4H). LC-MS [M + 1]: 471.2. |

TABLE 4-continued

Characterization of EXAMPLES 36-41

| Ex. # | Structure | Analytical Data |
|---|---|---|
| 38 | 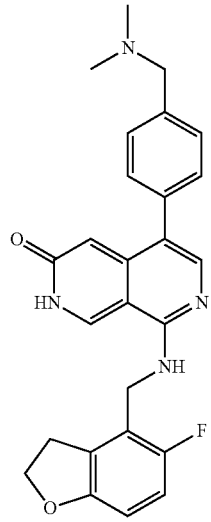<br>5-(4-((dimethylamino)methyl)phenyl)-8-(((5-fluoro-2,3-dihydrobenzofuran-4-yl)methyl)amino)-2,7-naphthyridin-3(2H)-one | $^1$H NMR (400 MHz, DMSO-$d_6$) δ ppm 2.18 (s, 6H) 3.28 (br s, 2H) 3.43 (s, 2H) 4.52 (t, J = 8.8 Hz, 2H) 4.66 (br d, J = 4.4 Hz, 2H) 6.36 (br d, J = 1.2 Hz, 1H) 6.65 (dd, J = 8.4, 3.6 Hz, 1H) 6.90 (t, J = 9.6 Hz, 1H) 7.29-7.41 (m, 4H) 7.67 (s, 1H) 8.09 (br s, 1H) 9.09 (br s, 1H). LC-MS [M + 1]: 445.3. |
| 39 | 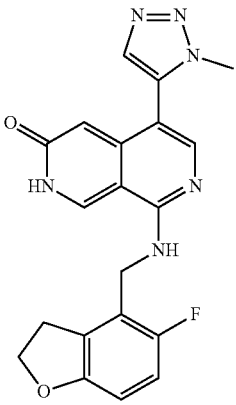<br>8-(((5-fluoro-2,3-dihydrobenzofuran-4-yl)methyl)amino)-5-(1-methyl-1H-1,2,3-triazol-5-yl)-2,7-naphthyridin-3(2H)-one | $^1$H NMR (400 MHz, DMSO-$d_6$) δ = 9.07 (s, 1H), 8.13-7.95 (m, 2H), 7.74-7.68 (m, 2H), 6.90-6.83 (m, 1H), 6.63 (dd, J = 4.0, 8.8 Hz, 1H), 5.78 (br s, 1H), 4.71 (d, J = 4.8 Hz, 2H), 4.52 (t, J = 8.8 Hz, 2H), 3.87 (s, 1H), 3.82 (s, 3H), 3.32-3.24 (m, 2H). LC-MS [M + 1]: 392.9. |

TABLE 4-continued

Characterization of EXAMPLES 36-41

| Ex. # | Structure | Analytical Data |
|---|---|---|
| 40 | 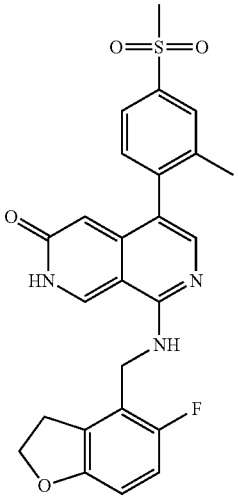<br>8-(((5-fluoro-2,3-dihydrobenzo-furan-4-yl)methyl)amino)-5-(2-methyl-4-(methylsulfonyl)phenyl)-2,7-naphthyridin-3(2H)-one | $^1$H NMR (400 MHz, DMSO-$d_6$) δ = 9.08 (s, 1H), 8.07 (br s, 1H), 7.90 (d, J = 1.2 Hz, 1H), 7.80 (dd, J = 2.0, 8.0 Hz, 1H), 7.55 (s, 1H), 7.42 (d, J = 8.0 Hz, 1H), 6.94-6.88 (m, 1H), 6.66 (dd, J = 4.0, 8.8 Hz, 1H), 5.60 (br s, 1H), 4.78-4.68 (m, 1H), 4.66-4.59 (m, 1H), 4.53 (t, J = 8.8 Hz, 2H), 3.32-3.30 (m, 2H), 3.30 (s, 3H), 2.17 (s, 3H). LC-MS [M + 1]: 480.0. |
| 41 | 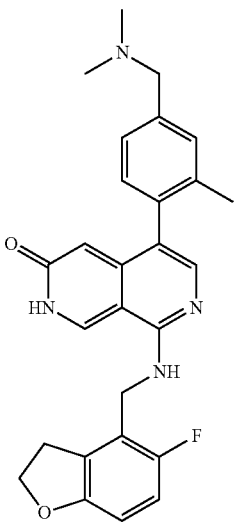<br>5-(4-((dimethylamino)methyl)-2-methylphenyl)-8-(((5-fluoro-2,3-dihydrobenzofuran-4-yl)methyl)amino)-2,7-naphthyridin-3(2H)-one | $^1$H NMR (400 MHz, CD$_3$OD) δ ppm = 8.86 (s, 1H) 7.52 (s, 1H) 7.29 (s, 1H) 7.20-7.25 (m, 1H) 7.15 (d, J = 7.6 Hz, 1H) 6.81-6.90 (m, 1H) 6.63 (dd, J = 8.8, 4.0 Hz, 1H) 5.94 (s, 1H) 4.74-4.71 (m, 2H) 4.55 (t, J = 8.8 Hz, 2H) 3.52 (s, 2H) 3.31-3.36 (m, 2H) 2.29 (s, 6H) 2.12 (s, 3H). LC-MS [M + 1]: 459.4. |

Example 42

4-(1,3-dimethyl-1H-pyrazol-5-yl)-6-ethoxy-N-((5-fluoro-2,3-dihydrobenzofuran-4-yl)methyl)-2,7-naphthyridin-1-amine

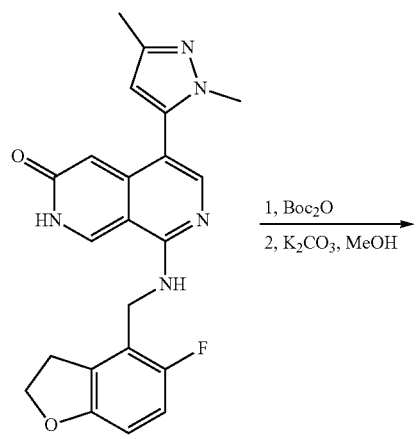

1, Boc₂O
2, K₂CO₃, MeOH

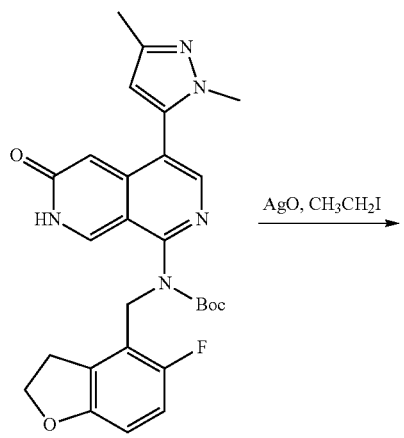

AgO, CH₃CH₂I

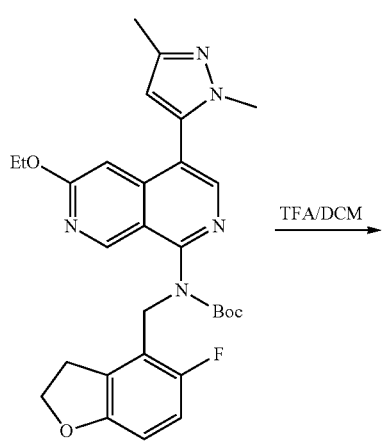

TFA/DCM

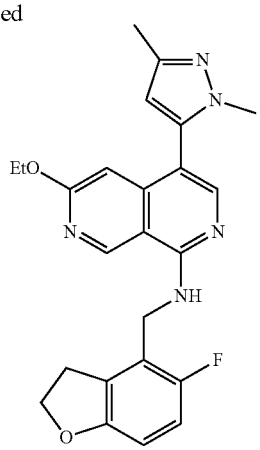

Step A: A mixture of 5-(1,3-dimethyl-1H-pyrazol-5-yl)-8-4(5-fluoro-2,3-dihydrobenzofuran-4-yl)methyl)amino)-2,7-naphthyridin-3(2H)-one (Example 35, 200 mg, 493 μmol, 1.00 equiv.), DMAP (6.03 mg, 49.3 μmol, 0.10 equiv.), DIEA (128 mg, 987 μmol, 172 μL, 2.00 equiv.) and di-tert-butyl dicarbonate (215 mg, 987 μmol, 227 μL, 2.00 equiv.) in THF (10.0 mL) was degassed and purged with nitrogen for three times, and then the mixture was stirred at 60° C. for 3 hours under a nitrogen atmosphere. The reaction mixture was filtered and concentrated under reduced pressure to give tert-butyl 8-((tert-butoxycarbonyl)((5-fluoro-2,3-dihydrobenzofuran-4-yl)methyl)amino)-5-(1,3-dimethyl-1H-pyrazol-5-yl)-3-oxo-2,7-naphthyridine-2(3H)-carboxylate (200 mg, 330 μmol, 66.9% yield) as a white solid.

A mixture of tert-butyl 8-((tert-butoxycarbonyl)((5-fluoro-2,3-dihydrobenzofuran-4-yl)methyl)amino)-5-(1,3-dimethyl-1H-pyrazol-5-yl)-3-oxo-2,7-naphthyridine-2(3H)-carboxylate (200 mg, 330 μmol, 1.00 equiv.) and potassium carbonate (91.3 mg, 660 μmol, 2.00 equiv.) in methanol (5.00 mL) was degassed and purged with nitrogen for three times, and then the mixture was stirred at 25° C. for 1 hour under nitrogen atmosphere. The reaction mixture was filtered and concentrated under reduced pressure to give a residue. The residue was purified by prep-TLC (silicon dioxide, petroleum ether/ethyl acetate=1/1) to tert-butyl (4-(1,3-dimethyl-1H-pyrazol-5-yl)-6-oxo-6,7-dihydro-2,7-naphthyridin-1-yl)((5-fluoro-2,3-dihydrobenzofuran-4-yl)methyl)carbamate (120 mg, 237 μL, 71.9% yield) as a yellow solid. LC-MS [M+1]: 506.3.

To a solution of tert-butyl (4-(1,3-dimethyl-1H-pyrazol-5-yl)-6-oxo-6,7-dihydro-2,7-naphthyridin-1-yl)((5-fluoro-2,3-dihydrobenzofuran-4-yl)methyl)carbamate (60.0 mg, 119 μmol, 1.00 equiv.) and iodoethane (185 mg, 1.19 mmol, 94.9 μL, 10.0 equiv.) in toluene (2.00 mL) was added silver oxide (82.5 mg, 666 μmol, 11.0 μL, 5.61 equiv.). The mixture was stirred at 110° C. for 12 hours. The reaction mixture was then filtered and concentrated under reduced pressure to give a residue. The residue was purified by prep-TLC (silicon dioxide, petroleum ether/ethyl acetate=2/1) to give tert-butyl (4-(1,3-dimethyl-1H-pyrazol-5-yl)-6-ethoxy-2,7-naphthyridin-1-yl)((5-fluoro-2,3-dihydrobenzofuran-4-yl)methyl)carbamate (20.0 mg, 37.5 μmol, 31.6% yield) as a yellow solid.

$^1$H NMR (400 MHz, CDCl$_3$) δ=8.96 (s, 1H), 8.29 (s, 1H), 6.68 (s, 1H), 6.60 (t, J=8.4 Hz, 1H), 6.51 (dd, J=3.6, 8.4 Hz, 1H), 6.21 (s, 1H), 5.22 (br s, 2H), 4.53 (br t, J=8.4 Hz, 2H), 4.43-4.37 (m, 2H), 3.62 (s, 3H), 3.34-3.26 (m, 2H), 2.37 (s, 3H), 1.42 (t, J=7.2 Hz, 3H), 1.37 (s, 9H). LC-MS [M+1]: 534.6.

Example 42: A mixture of tert-butyl (4-(1,3-dimethyl-1H-pyrazol-5-yl)-6-ethoxy-2,7-naphthyridin-1-yl)((5-fluoro-2,3-dihydrobenzofuran-4-yl)methyl)carbamate (10.0 mg, 18.7 μmol, 1.00 equiv.) and trifluoroacetic acid (154 mg, 1.35 mmol, 100 μL, 72.1 equiv.) in DCM (1.00 mL) was degassed and purged with nitrogen for 3 times, and then the mixture was stirred at 25° C. for 1 hour under nitrogen atmosphere. The reaction mixture was filtered and concentrated under reduced pressure to give a residue. The residue was purified by prep-HPLC [Phenomenex Synergi C18 150*30 mm*4 μm; mobile phase: (A—water (0.05% HCl) and B: ACN; B %: 24%-44%)] to give title compound 4-(1,3-dimethyl-1H-pyrazol-5-yl)-6-ethoxy-N-((5-fluoro-2,3-dihydrobenzofuran-4-yl)methyl)-2,7-naphthyridin-1-amine (2.43 mg, 4.51 μmol, 29.9% yield, 97.8% purity) as a yellow solid. LC-MS [M+1]: 434.2.

$^1$H NMR (400 MHz, DMSO-d$_6$) δ=10.17 (s, 1H), 9.73 (s, 1H), 7.82 (s, 1H), 7.0 (t, J=8.8 Hz, 1H), 6.76 (dd, J=4.0, 8.8 Hz, 1H), 6.47 (s, 1H), 6.25 (s, 1H), 4.88 (br d, J=4.8 Hz, 2H), 4.56 (t, J=8.8 Hz, 2H), 4.44-4.38 (m, 2H), 3.59 (s, 3H), 3.31 (t, J=8.8 Hz, 3H), 2.24 (s, 3H), 1.33 (t, J=7.2 Hz, 3H).

Examples 43-45 were prepared following the procedure set forth in Example 42 and using the general reactions schemes and intermediates described herein.

TABLE 5

Characterization of EXAMPLES 43-45

| | | |
|---|---|---|
| 43 | 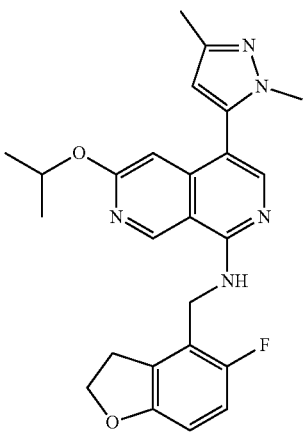<br>4-(1,3-dimethyl-1H-pyrazol-5-yl)-N-((5-fluoro-2,3-dihydrobenzofuran-4-yl)methyl)-6-isopropoxy-2,7-naphthyridin-1-amine | $^1$H NMR (400 MHz, DMSO-d$_6$) δ = 10.47 (s, 1H), 9.80 (s, 1H), 7.79 (s, 1H), 7.00 (t, J = 8.8 Hz, 1H), 6.77 (dd, J = 4.0, 8.8 Hz, 1H), 6.43 (s, 1H), 6.27 (s, 1H), 5.41-5.34 (m, 1H), 4.92 (d, J = 4.4 Hz, 2H), 4.56 (t, J = 8.8 Hz, 2H), 3.59 (s, 3H), 3.32 (t, J = 8.8 Hz, 2H), 2.24 (s, 3H), 1.32 (s, 3H), 1.30 (s, 3H). LC-MS [M + 1]: 448.4. |
| 44 | 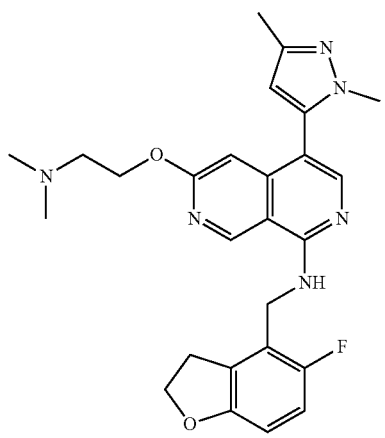<br>4-(1,3-dimethyl-1H-pyrazol-5-yl)-6-(2-(dimethylamino)ethoxy)-N-((5-fluoro-2,3-dihydrobenzofuran-4-yl)methyl)-2,7-naphthyridin-1-amine | $^1$H NMR (400 MHz, CD$_3$OD) δ = 9.64 (s, 1H), 7.85 (s, 1H), 6.97 (t, J = 8.8 Hz, 1H), 6.86 (s, 1H), 6.78 (dd, J = 4.0, 8.8 Hz, 1H), 6.52 (s, 1H), 4.90 (br s, 2H), 4.85-4.83 (m, 2H), 4.65 (t, J = 8.8 Hz, 2H), 3.78 (s, 3H), 3.66-3.62 (m, 2H), 3.37 (t, J = 8.4 Hz, 2H), 2.98 (s, 6H), 2.42 (s, 3H). LC-MS [M + 1]: 477.4. |

TABLE 5-continued

Characterization of EXAMPLES 43-45

| 45 | 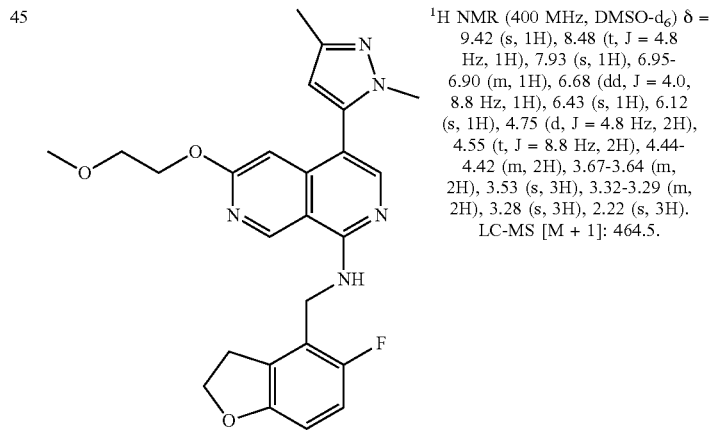 4-(1,3-dimethyl-1H-pyrazol-5-yl)-N-((5-fluoro-2,3-dihydrobenzofuran-4-yl)methyl)-6-(2-methoxyethoxy)-2,7-naphthyridin-1-amine | $^1$H NMR (400 MHz, DMSO-d$_6$) δ = 9.42 (s, 1H), 8.48 (t, J = 4.8 Hz, 1H), 7.93 (s, 1H), 6.95-6.90 (m, 1H), 6.68 (dd, J = 4.0, 8.8 Hz, 1H), 6.43 (s, 1H), 6.12 (s, 1H), 4.75 (d, J = 4.8 Hz, 2H), 4.55 (t, J = 8.8 Hz, 2H), 4.44-4.42 (m, 2H), 3.67-3.64 (m, 2H), 3.53 (s, 3H), 3.32-3.29 (m, 2H), 3.28 (s, 3H), 2.22 (s, 3H). LC-MS [M + 1]: 464.5. |
|---|---|---|

Example 46

5-(1-(2-(dimethylamino)ethyl)-1H-pyrazol-5-yl)-8-(((5-fluoro-2,3-dihydrobenzofuran-4-yl)methyl)amino)-2,7-naphthyridin-3(2H)-one

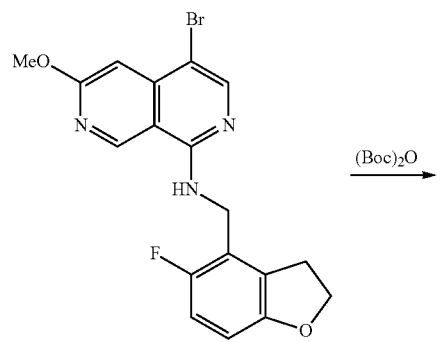

(Boc)$_2$O →

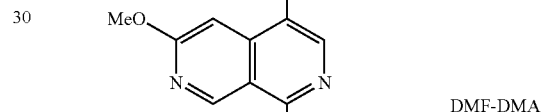

DMF-DMA →

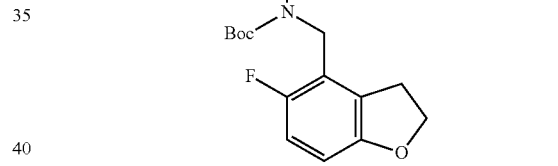

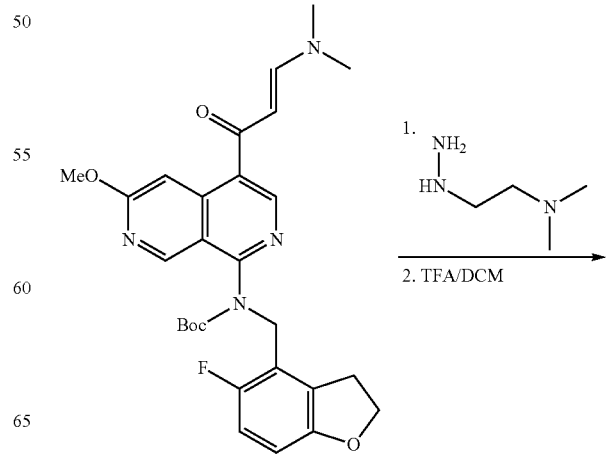

1. <chemical structure: H$_2$N-NH-CH$_2$CH$_2$-N(CH$_3$)$_2$>
2. TFA/DCM →

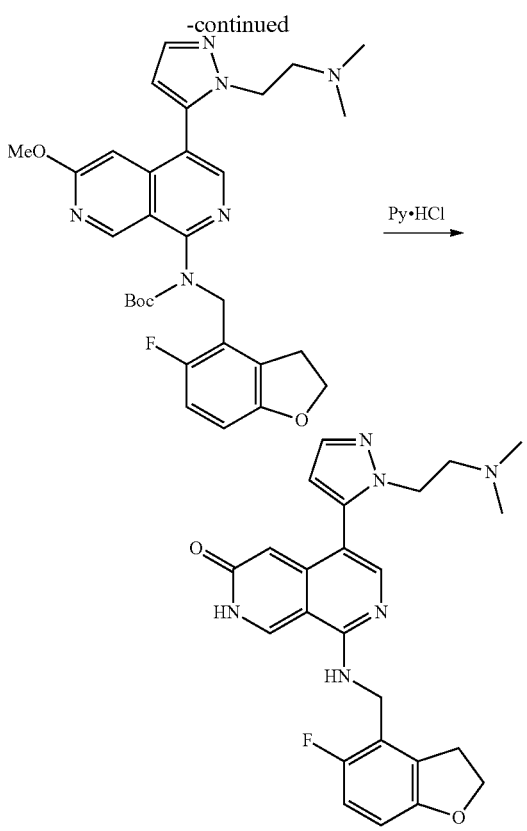

Step A: To a mixture of Intermediate A-4 (130 mg, 322 µmol, 1.00 equiv.) in di-tert-butyl dicarbonate (1.90 g, 8.71 mmol, 2 mL, 27.1 equiv.) was added DMAP (3.93 mg, 32.2 µmol, 0.1 equiv.). The mixture was stirred at 50° C. for 4 hours under nitrogen. The reaction mixture was purified by column chromatography (SiO$_2$, petroleum ether/ethyl acetate=1/0 to 10/1) to give tert-butyl (4-bromo-6-methoxy-2,7-naphthyridin-1-yl)((5-fluoro-2,3-dihydrobenzofuran-4-yl)methyl)carbamate (140 mg, crude) as colorless oil. LC-MS [M+1]: 506.1.

Step B: To a degassed solution of tert-butyl (4-bromo-6-methoxy-2,7-naphthyridin-1-yl)((5-fluoro-2,3-dihydrobenzofuran-4-yl)methyl)carbamate (140 mg, 278 µmol, 1.00 equiv.) and tributyl(1-ethoxyvinyl)stannane (130 mg, 361 µmol, 122 µL, 1.30 equiv.) in dioxane (5.00 mL) under N$_2$ atmosphere was added Pd(PPh$_3$)$_2$Cl$_2$ (39.0 mg, 55.5 µmol, 0.20 equiv.). The reaction was stirred at 100° C. for 2.5 hours. The reaction mixture was used directly for the next step without any purification. To the crude reaction mixtures was added H$_2$O (2.50 mL) and pyridinium para-toluenesulfonate (284 mg, 1.13 mmol, 4.00 equiv.). The mixture was stirred at 40° C. for 4 hours, then diluted with ethyl acetate (4.00 mL) and treated with aqueous potassium fluoride solution (140 mg of potassium fluoride in 4 mL water). The mixture was stirred vigorously for 1 hour before being filtered through Celite. The filtrate was diluted with ethyl acetate (5.00 mL) and the organic phase was washed with saturated sodium bicarbonate solution, then brine, dried over magnesium sulfate, filtered, and concentrated under reduced pressure to give a residue, the residue was purified by Prep-TLC (petroleum ether/ethyl acetate=1/1) to give tert-butyl (4-acetyl-6-methoxy-2,7-naphthyridin-1-yl)((5-fluoro-2,3-dihydrobenzofuran-4-yl)methyl)carbamate (100 mg, 214 µL, 75.7% yield) as a yellow solid.

$^1$H NMR (400 MHz, CDCl$_3$) δ=8.97 (s, 1H), 8.95 (s, 1H), 8.18 (d, J=0.8 Hz, 1H), 6.59 (t, J=8.8 Hz, 1H), 6.51 (dd, J=8.8, 4.0 Hz, 1H), 5.24 (s, 2H), 4.56 (t, J=8.8 Hz, 2H), 4.06 (s, 3H), 3.35 (br t, J=8.8 Hz, 2H), 2.75 (s, 3H), 1.30 (s, 9H).

Step C: tert-butyl (4-acetyl-6-methoxy-2,7-naphthyridin-1-yl)((5-fluoro-2,3-dihydrobenzofuran-4-yl)methyl)carbamate (100 mg, 213.91 µmol, 1 equiv.) was dissolved in DMF-DMA (2.24 g, 18.82 mmol, 2.50 mL, 87.98 equiv.) and stirred at 100° C. for 0.5 hour under a nitrogen atmosphere. After cooling to 15° C., DMF-DMA was removed in vacuum by distillation to give tert-butyl (E)-(4-(3-(dimethylamino)acryloyl)-6-methoxy-2,7-naphthyridin-1-yl)((5-fluoro-2,3-dihydrobenzofuran-4-yl)methyl)carbamate (100 mg, crude) as a brown solid which used for the next step without further purification. LC-MS [M+1]: 523.5.

Step D: 2-hydrazino-N,N-dimethyl-ethanamine hydrochloride (53.4 mg, 382 µmol, 4.00 equiv.) and tert-butyl (E)-(4-(3-(dimethylamino)acryloyl)-6-methoxy-2,7-naphthyridin-1-yl)((5-fluoro-2,3-dihydrobenzofuran-4-yl)methyl)carbamate (100 mg, crude) was dissolved in ethyl alcohol (5.00 mL). The reaction mixture was stirred at 80° C. for 0.5 hour under nitrogen. The solvent was removed under reduce pressure to give tert-butyl (4-(1-(2-(dimethylamino)ethyl)-1H-pyrazol-5-yl)-6-methoxy-2,7-naphthyridin-1-yl)((5-fluoro-2,3-dihydrobenzofuran-4-yl)methyl)carbamate (80.0 mg, crude) as a gray solid which used for the next step without further purification. LC-MS [M+1]: 563.4.

To a mixture of tert-butyl (4-(1-(2-(dimethylamino)ethyl)-1H-pyrazol-5-yl)-6-methoxy-2,7-naphthyridin-1-yl)((5-fluoro-2,3-dihydrobenzofuran-4-yl)methyl)carbamate (80.0 mg, 142 µmol, 1.00 equiv.) in DCM (3.00 mL) was added TFA (1.54 g, 13.5 mmol, 1.00 mL, 95.0 equiv.) in one portion at 20° C. under nitrogen and the reaction mixture was stirred for 2 hours. The solvent was removed under reduce pressure. Then the residue was purified by Prep-HPLC [Xtimate C18 150*25 mm*5 µm; (mobile phase: phase A—water (0.04% NH$_3$H$_2$O), phase B-ACN) B %: 33%-63%] to give 4-(1-(2-(dimethylamino)ethyl)-1H-pyrazol-5-yl)-N-((5-fluoro-2,3-dihydrobenzofuran-4-yl)methyl)-6-methoxy-2,7-naphthyridin-1-amine (29.0 mg, 61.5 µmol, 43.3% yield, 98.1% purity) as a white solid. LC-MS [M+1]: 463.4.

$^1$H NMR (400 MHz, CDCl$_3$) δ=8.93 (s, 1H), 7.99 (s, 1H), 7.64 (d, J=1.6 Hz, 1H), 6.86 (t, J=9.6 Hz, 1H), 6.67 (dd, J=4.0, 8.8 Hz, 1H), 6.57 (s, 1H), 6.29 (d, J=1.6 Hz, 1H), 5.97 (br t, J=5.2 Hz, 1H), 4.86 (d, J=5.2 Hz, 2H), 4.62 (t, J=8.8 Hz, 2H), 4.02 (br t, J=7.2 Hz, 2H), 3.97 (s, 3H), 3.41 (t, J=8.8 Hz, 2H), 2.65 (t, J=7.2 Hz, 2H), 2.12-2.03 (s, 6H).

Example 46: A mixture of 4-(1-(2-(dimethylamino)ethyl)-1H-pyrazol-5-yl)-N-((5-fluoro-2,3-dihydrobenzofuran-4-yl)methyl)-6-methoxy-2,7-naphthyridin-1-amine (16.0 mg, 34.6 µmol, 1.00 equiv.) in pyridine hydrochloride (12.0 mg, 104 µmol, 3.00 equiv.) was stirred at 130° C. for 0.5 hour. The mixture was adjusted to pH=8 with saturated sodium carbonate aqueous solution (3.00 mL), and the aqueous phase was extracted with ethyl acetate (2.00 mL×3). The combined organic phase was washed with brine (2.00 mL×2), dried with anhydrous sodium sulfate, filtered, and concentrated in vacuum to give a residue. The residue was triturated with methanol (1.00 mL) to give title compound 5-(1-(2-(dimethylamino)ethyl)-1H-pyrazol-5-yl)-8-(((5-fluoro-2,3-dihydrobenzofuran-4-yl)methyl)amino)-2,7-naphthyridin-3(2H)-one (11.0 mg, 23.6 µmol, 68.1% yield, 96.0% purity) as a yellow solid. LC-MS [M+1]: 449.3

$^1$H NMR (400 MHz, CD$_3$OD) δ=8.89 (br s, 1H), 7.73 (s, 1H), 7.63 (br s, 1H), 6.84 (br t, J=9.2 Hz, 1H), 6.62 (dd, J=3.2, 8.0 Hz, 1H), 6.34 (br s, 1H), 6.07 (s, 1H), 4.75 (br s,

2H), 4.55 (br t, J=8.8 Hz, 2H), 4.06 (t, J=5.2 Hz, 2H), 3.45-3.33 (m, 2H), 2.69 (t, J=5.2 Hz, 2H), 2.11 (s, 6H).

Example 47

5-(1-(((5-fluoro-2,3-dihydrobenzofuran-4-yl)methyl) amino)-6-oxo-6,7-dihydro-2,7-naphthyridin-4-yl)-N, N,1-trimethyl-1H-pyrazole-3-carboxamide

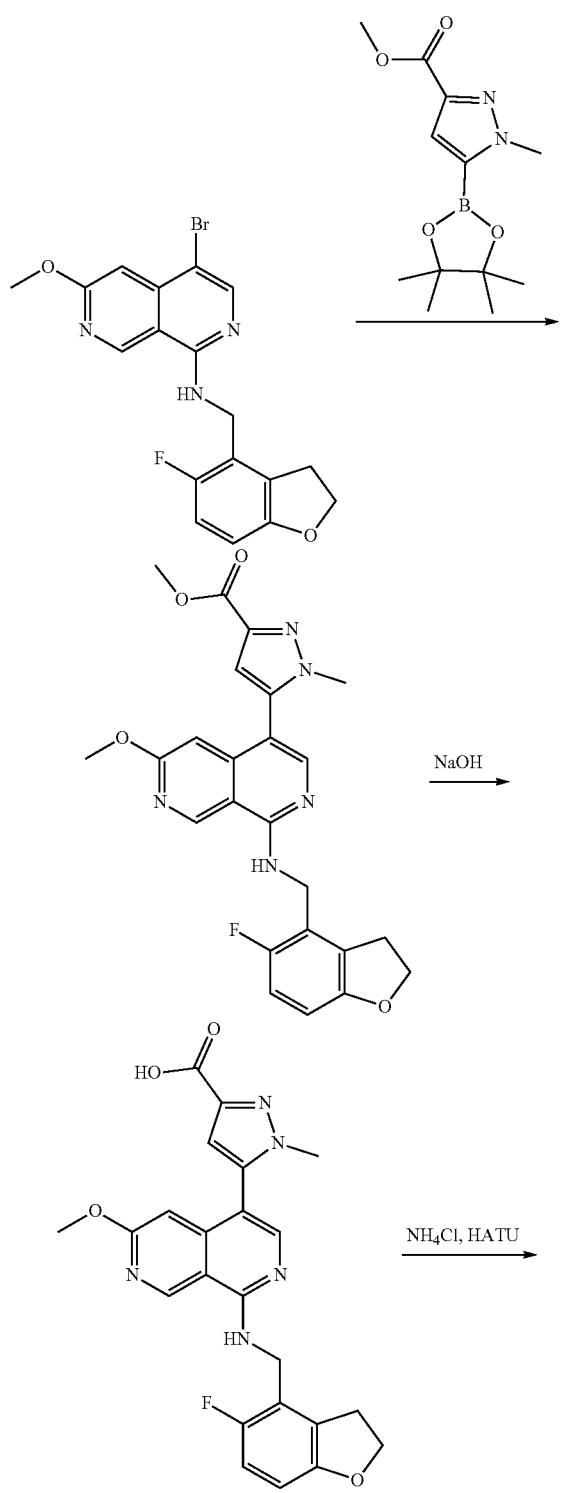

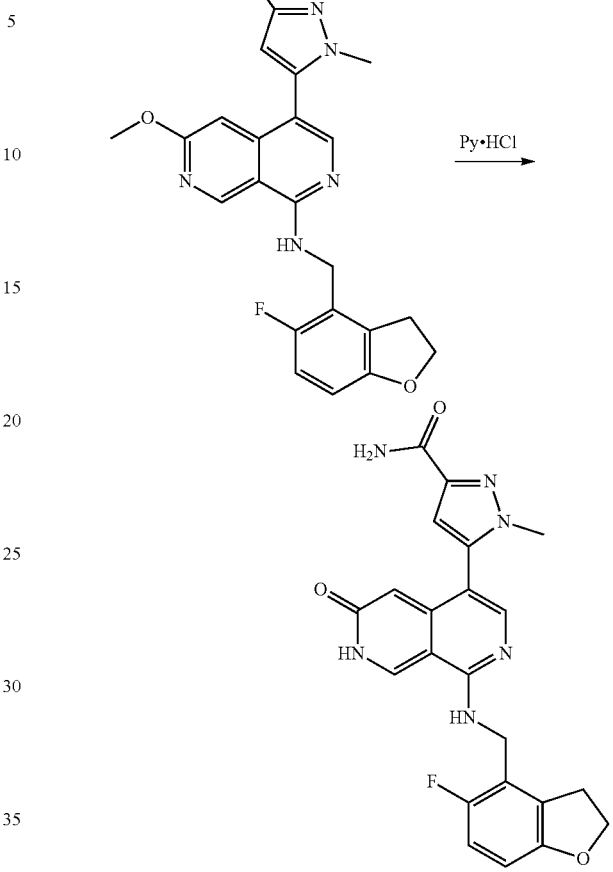

Step A: A mixture of 4-bromo-N-[(5-fluoro-2,3-dihydrobenzofuran-4-yl) methyl]-6-methoxy-2,7-naphthyridin-1-amine (Intermediate A-4, 620 mg, 1.38 mmol, 1.00 equiv.), methyl 1-methyl-5-(4,4,5,5-tetramethyl-1,3,2-dioxaborolan-2-yl)-1H-pyrazole-3-carboxylate (Intermediate C45, 844 mg, 3.17 mmol, 2.30 equiv.), potassium carbonate (954 mg, 6.90 mmol, 5.00 equiv.), Pd(t-Bu$_3$P)$_2$ (70.6 mg, 138 µmol, 0.10 equiv.) in dioxane (6.00 mL) and water (1.00 mL) was degassed and purged with nitrogen for 3 times, and then the mixture was stirred at 95° C. for 1 hour under nitrogen atmosphere. The reaction mixture was filtered and concentrated under reduced pressure to give a residue. The residue was purified by column chromatography (SiO$_2$, petroleum ether/ethyl acetate=5/1 to 0/1) to give 5-(1-(((5-fluoro-2,3-dihydrobenzofuran-4-yl)methyl)amino)-6-methoxy-2,7-naphthyridin-4-yl)-1-methyl-1H-pyrazole-3-carboxylic acid (520 mg, 81.3% yield) as a yellow solid. LC-MS [M+1]: 464.1.

Step B: To a solution of 5-(1-(((5-fluoro-2,3-dihydrobenzofuran-4-yl)methyl)amino)-6-methoxy-2,7-naphthyridin-4-yl)-1-methyl-1H-pyrazole-3-carboxylic acid (520 mg, 1.12 mmol, 1.00 equiv.) in THF (50.0 mL) and water (10.0 mL) was added sodium hydroxide (135 mg, 3.37 mmol, 3.00 equiv.). The mixture was stirred at 45° C. for 1 hour. The reaction mixture was concentrated in vacuo, and the aqueous solution was adjusted to pH=6 with hydrochloric acid aqueous solution (6.00 M, 3.00 mL). The suspension was filtered, and the filter cake was wash with water (2 mL×2) and dried in vacuo to give methyl 5-(1-(((5-fluoro-2,3-dihydrobenzofuran-4-yl)methyl)amino)-6-methoxy-2,7-naphthyridin-4-yl)-1-methyl-1H-pyrazole-3-carboxylate (450 mg, 89.2% yield) as a yellow solid. LC-MS [M+1]: 450.1.

$^1$H NMR (400 MHz, DMSO-$d_6$) δ=9.45 (s, 1H), 8.55 (br s, 1H), 7.94 (s, 1H), 6.91 (t, J=9.2 Hz, 1H), 6.65 (br dd, J=3.6, 8.8 Hz, 1H), 6.48 (br s, 1H), 6.39 (br s, 1H), 4.74 (br d, J=4.4 Hz, 2H), 4.51 (br t, J=8.4 Hz, 2H), 3.92 (s, 3H), 3.60 (br s, 3H), 3.27 (m, 2H).

Step C: To a solution of methyl 5-(1-(((5-fluoro-2,3-dihydrobenzofuran-4-yl)methyl)amino)-6-methoxy-2,7-naphthyridin-4-yl)-1-methyl-1H-pyrazole-3-carboxylate (100 mg, 222 μmol, 1.00 equiv.) in DMF (1.50 mL) were added HATU (211 mg, 556 μmol, 2.50 equiv.), N-methylmethanamine (2.00 M, 334 μL, 3.00 equiv.) and DIEA (86.3 mg, 668 μmol, 113 μL, 3.00 equiv.). The mixture was stirred at 25° C. for 1 hour. The reaction mixture was diluted with water (3.00 mL), then the suspension was filtered and washed with water (1.00 mL×3). The filter cake was collected and concentrated under reduced pressure to give 5-(1-(((5-fluoro-2,3-dihydrobenzofuran-4-yl)methyl)amino)-6-methoxy-2,7-naphthyridin-4-yl)-N,N,1-trimethyl-1H-pyrazole-3-carboxamide (60 mg, 56.6% yield) as a yellow solid. LC-MS [M+1]: 477.1.

Example 47: A mixture of 5-(1-(((5-fluoro-2,3-dihydrobenzofuran-4-yl)methyl)amino)-6-methoxy-2,7-naphthyridin-4-yl)-N, N,1-trimethyl-1H-pyrazole-3-carboxamide (50.0 mg, 105 μmol, 1.00 equiv.) in pyridine hydrochloride (121 mg, 1.05 mmol, 10.0 equiv.) was stirred at 130° C. for 1 hour. The reaction mixture was cooled to 25° C. and diluted with water (1.00 mL), the crude product was purified by prep-HPLC [column: Phenomenex Synergi C18 150× 25×10 μm; (mobile phase: phase A—water (0.05% HCl), phase B—ACN) B %:0%-30%] to give title compound 5-(1-(((5-fluoro-2,3-dihydrobenzofuran-4-yl)methyl)amino)-6-oxo-6,7-dihydro-2,7-naphthyridin-4-yl)-N,N,1-trimethyl-1H-pyrazole-3-carboxamide (12.2 mg, 24.5% yield, 97.2% purity) as a yellow solid. LC-MS [M+1]: 463.1.

$^1$H NMR (400 MHz, CD$_3$OD) δ=9.25 (s, 1H), 7.55 (s, 1H), 6.97 (t, J=9.6 Hz, 1H), 6.83-6.77 (m, 2H), 6.14 (s, 1H), 4.80 (s, 2H), 4.65 (t, J=8.8 Hz, 2H), 3.81 (s, 3H), 3.42 (br s, 3H), 3.38-3.33 (m, 2H), 3.14 (br s, 3H).

Example 48

5-(1-4(5-fluoro-2,3-dihydrobenzofuran-4-yl)methyl) amino)-6-oxo-6,7-dihydro-2,7-naphthyridin-4-yl)-1-methyl-1H-pyrazole-3-carbonitrile

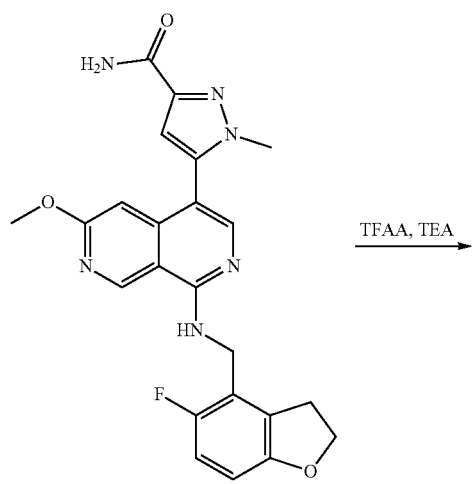

TFAA, TEA →

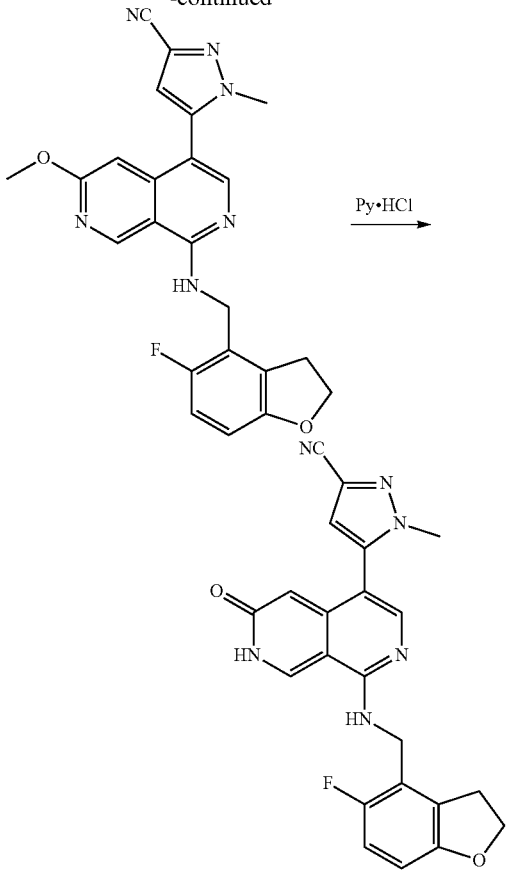

Py·HCl →

Step A: To a solution of 5-(1-4(5-fluoro-2,3-dihydrobenzofuran-4-yl)methyl)amino)-6-methoxy-2,7-naphthyridin-4-yl)-N,N,1-trimethyl-1H-pyrazole-3-carboxamide (Example 42, Step C; 140 mg, 312 μmol, 1.00 equiv.) and triethylamine (632 mg, 6.24 mmol, 869 μL, 20.0 equiv.) in tetrahydrofuran (2.00 mL) was added trifluoroacetic anhydride (656 mg, 3.12 mmol, 434 μL, 10.0 equiv.) drop-wise at 0° C. The mixture was stirred at 25° C. for 1 hour. The reaction mixture was filtered and concentrated under reduced pressure to give a residue. The residue was purified by prep-TLC (SiO$_2$, petroleum ether/ethyl acetate=1/1) to give 5-(1-(((5-fluoro-2,3-dihydrobenzofuran-4-yl)methyl) amino)-6-methoxy-2,7-naphthyridin-4-yl)-1-methyl-1H-pyrazole-3-carbonitrile (70 mg, crude) as a white solid. LC-MS [M+1]: 431.1.

Example 48: A mixture of 5-(1-4(5-fluoro-2,3-dihydrobenzofuran-4-yl)methyl)amino)-6-methoxy-2,7-naphthyridin-4-yl)-1-methyl-1H-pyrazole-3-carbonitrile (70.0 mg, 163 μmol, 1.00 equiv.) and pyridine hydrochloride (140 mg, 1.21 mmol, 7.45 equiv.) was stirred at 130° C. for 1 hour. The reaction mixture cooled to 25° C., then diluted with water (2.00 mL). Then the crude product was purified by prep-HPLC [column: Phenomenex Synergi C18 150*25*10 μm; mobile phase: phase A—water (0.05% HCl), phase B—ACN) B %: 15%-45%] to give title compound 5-(1-(((5-fluoro-2,3-dihydrobenzofuran-4-yl)methyl)amino)-6-oxo-6,7-dihydro-2,7-naphthyridin-4-yl)-1-methyl-1H-pyrazole-3-carbonitrile (24.1 mg, 35.5% yield, 99.8% purity) as a yellow solid. LC-MS [M+1]: 417.0.

$^1$H NMR (400 MHz, CD$_3$OD) δ=9.22 (s, 1H), 7.58 (s, 1H), 6.99 (s, 1H), 6.96 (d, J=10.0 Hz, 1H), 6.78 (dd, J=4.0, 8.8 Hz, 1H), 6.07 (s, 1H), 4.79 (s, 2H), 4.65 (t, J=8.8 Hz, 2H), 3.85 (s, 3H), 3.38-3.33 (m, 2H).

Example 49

4-(1,3-dimethyl-1H-pyrazol-5-yl)-N$^1$-((5-fluoro-2,3-dihydrobenzofuran-4-yl)methyl)-N$^6$,N$^6$-dimethyl-2,7-naphthyridine-1,6-diamine

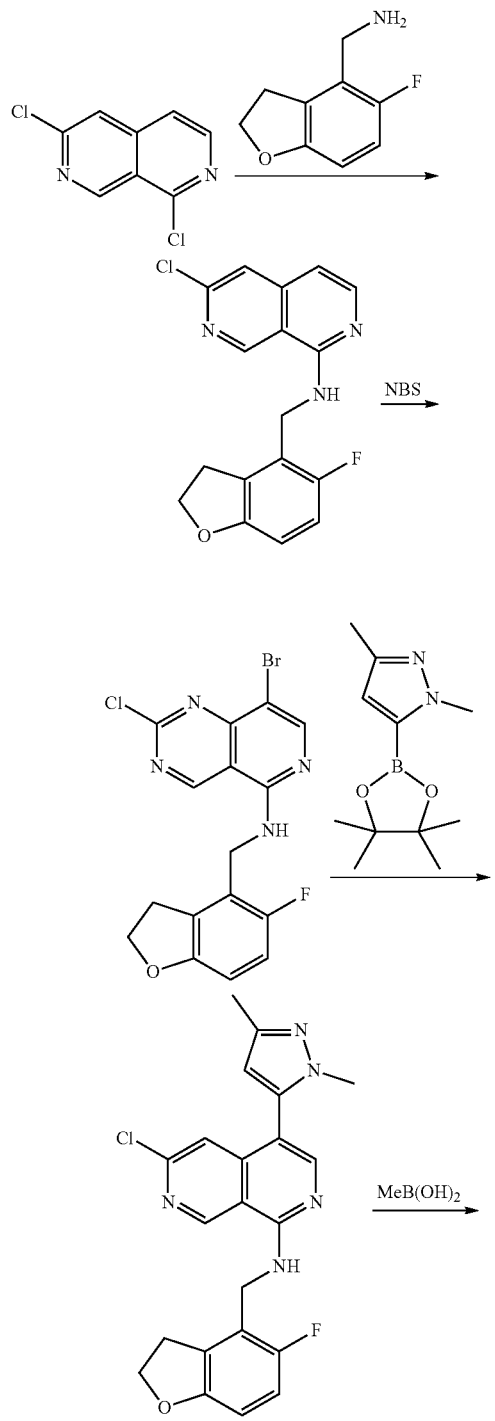

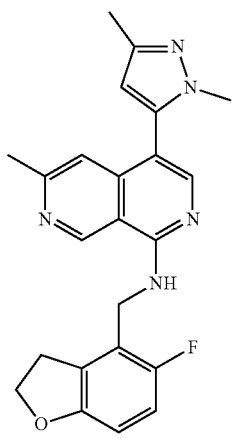

Step A: To a solution of 1,6-dichloro-2,7-naphthyridine (200 mg, 1.00 mmol, 1.00 equiv.) and (5-fluoro-2,3-dihydrobenzofuran-4-yl)methanamine (168 mg, 1.00 mmol, 1.00 equiv.) in DMF (4.00 mL) was added potassium fluoride (175 mg, 3.01 mmol, 70.6 μL, 3.00 equiv.), and the reaction mixture was stirred at 120° C. for 3 hours under a nitrogen atmosphere. To the reaction mixture was added water (15.0 mL), the precipitate was filtered and dried in vacuo to give 6-chloro-N-((5-fluoro-2,3-dihydrobenzofuran-4-yl)methyl)-2,7-naphthyridin-1-amine (230 mg, 697 μmol, 69.4% yield) as a white solid.

$^1$H NMR (400 MHz, DMSO-d$_6$) δ=9.46 (s, 1H), 8.38 (br t, J=4.8 Hz, 1H), 8.10 (d, J=5.6 Hz, 1H), 7.78 (s, 1H), 6.94-6.86 (m, 2H), 6.65 (dd, J=3.6, 8.4 Hz, 1H), 4.70 (d, J=5.2 Hz, 2H), 4.50 (t, J=8.8 Hz, 2H), 3.25 (br t, J=8.8 Hz, 3H).

Step B: To a solution of 6-chloro-N-[(5-fluoro-2,3-dihydrobenzofuran-4-yl) methyl]-2,7-naphthyridin-1-amine (230 mg, 697 μmol, 1.00 equiv.) in DCM (4.00 mL) was added NBS (124 mg, 697 μmol, 1.00 equiv.) at 0° C., and the reaction mixture was stirred at 0° C. for 0.5 hour. The reaction was diluted with DCM (50.0 mL), washed with brine (20.0 mL×2), dried with anhydrous sodium sulfate, filtered, and concentrated in vacuo to give 4-bromo-6-chloro-N-((5-fluoro-2,3-dihydrobenzofuran-4-yl)methyl)-2,7-naphthyridin-1-amine (280 mg, 685 μmol, 98.2% yield) as a yellow solid.

$^1$H NMR (400 MHz, DMSO-d$_6$) δ=9.52 (s, 1H), 8.70 (br s, 1H), 8.33 (s, 1H), 7.69 (s, 1H), 6.91 (t, J=9.2 Hz, 1H), 6.66 (dd, J=4.4, 8.4 Hz, 1H), 4.69 (br d, J=4.8 Hz, 2H), 4.52 (t, J=8.4 Hz, 2H), 3.25 (br t, J=8.8 Hz, 2H).

Step C: To a solution of 4-bromo-6-chloro-N-((5-fluoro-2,3-dihydrobenzofuran-4-yl)methyl)-2,7-naphthyridin-1-amine (280 mg, 685 μmol, 1.00 equiv.) and 1,3-dimethyl-5-(4,4,5,5-tetramethyl-1,3,2-dioxaborolan-2-yl)pyrazole (228 mg, 1.03 mmol, 1.50 equiv.) in dioxane (4.00 mL) and water (0.80 mL) was added sodium bicarbonate (173 mg, 2.06 mmol, 79.9 μL, 3.00 equiv.) and Pd(dppf)Cl$_2$ (50.1 mg, 68.5 μmol, 0.10 equiv.) under nitrogen, and the reaction mixture was stirred at 100° C. for 1 hour under a nitrogen atmosphere. The reaction was filtered and concentrated in vacuo to give a residue, and the residue was purified by prep-TLC (petroleum ether/ethyl acetate=1/1) to give 6-chloro-4-(1,3-dimethyl-1H-pyrazol-5-yl)-N-((5-fluoro-2,3-dihydrobenzofuran-4-yl)methyl)-2,7-naphthyridin-1-amine (260 mg, crude) as a brown solid.

$^1$H NMR (400 MHz, DMSO-d$_6$) δ=9.57 (s, 1H), 8.70 (t, J=5.2 Hz, 1H), 8.14 (s, 1H), 7.22 (s, 1H), 6.97-6.88 (m, 1H), 6.68 (dd, J=4.0, 8.8 Hz, 1H), 6.18 (s, 1H), 4.75 (d, J=4.8 Hz, 2H), 4.53 (t, J=8.8 Hz, 2H), 3.55 (s, 3H), 3.31-3.26 (m, 2H), 2.23 (s, 3H).

Example 49: In a sealed tube, a mixture of 6-chloro-4-(1,3-dimethyl-1H-pyrazol-5-yl)-N-((5-fluoro-2,3-dihydrobenzofuran-4-yl)methyl)-2,7-naphthyridin-1-amine (50.0 mg, 118 µmol, 1.00 equiv.) in dimethylamine (2.00 M in THF, 2.50 mL, 42.4 equiv.) was stirred at 140° C. for 12 hours. The reaction was concentrated in vacuo to give a residue, and the residue was purified by prep-TLC (petroleum ether/ethyl acetate=2/1) to give a crude product. The crude product was further triturated with petroleum ether/ethyl acetate=3/1 (2.00 mL), filtered, and the filter cake was collected and dried in vacuum to give title compound 4-(1,3-dimethyl-1H-pyrazol-5-yl)-$N^1$-((5-fluoro-2,3-dihydrobenzofuran-4-yl)methyl)-$N^6$,$N^6$-dimethyl-2,7-naphthyridine-1,6-diamine (11.4 mg, 26.1 µmol, 22.1% yield, 98.8% purity) as a yellow solid. LC-MS [M+1]: 433.2.

$^1$H NMR (400 MHz, CD$_3$OD) δ=9.17 (s, 1H), 7.73 (s, 1H), 6.86 (t, J=9.2 Hz, 1H), 6.64 (dd, J=4.0, 8.4 Hz, 1H), 6.18 (s, 1H), 6.09 (s, 1H), 4.79 (s, 2H), 4.55 (t, J=8.8 Hz, 2H), 3.61 (s, 3H), 3.32-3.27 (m, 2H), 3.10 (s, 6H), 2.32 (s, 3H).

Example 50

4-(1,3-dimethyl-1H-pyrazol-5-yl)-$N^1$-((5-fluoro-2,3-dihydrobenzofuran-4-yl)methyl)-2,7-naphthyridine-1,6-diamine

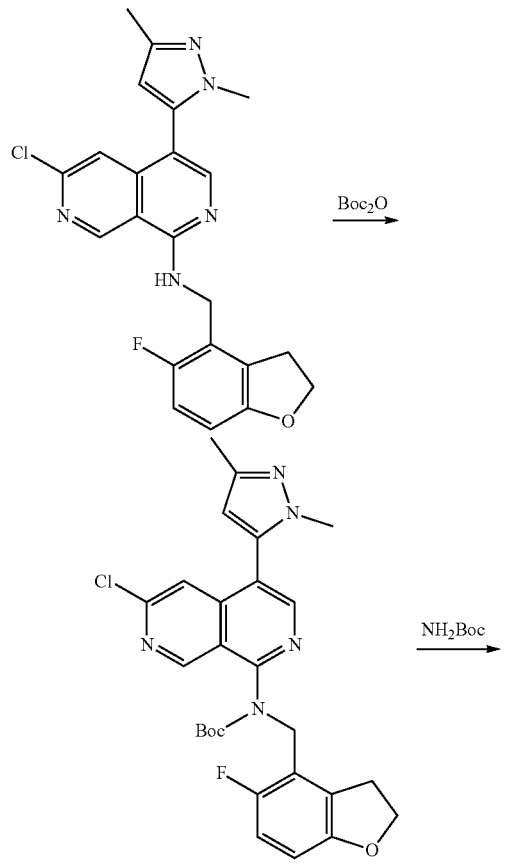

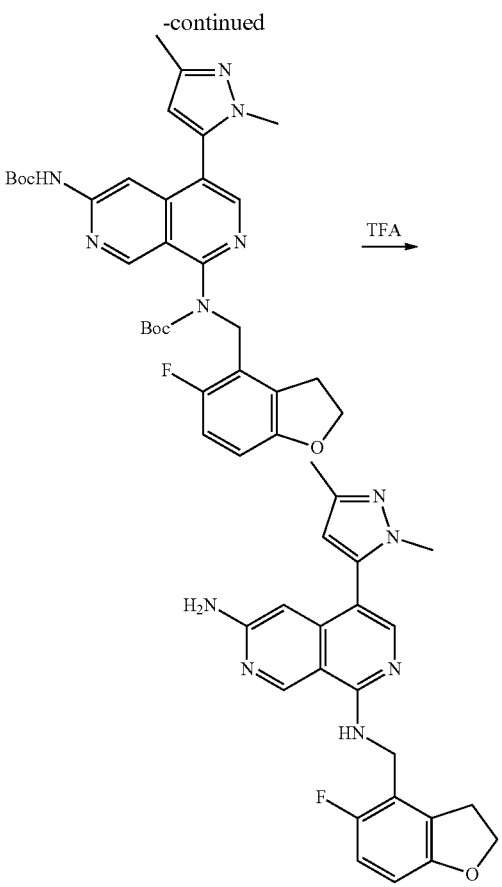

Step A: A mixture of 6-chloro-4-(1,3-dimethyl-1H-pyrazol-5-yl)-N-((5-fluoro-2,3-dihydrobenzofuran-4-yl)methyl)-2,7-naphthyridin-1-amine (Example 43, Step C; 50.0 mg, 118 µmol, 1.00 equiv.), di-tert-butyl dicarbonate (30.9 mg, 142 µmol, 32.5 µL, 1.20 equiv.), diisopropylethylamine (45.7 mg, 354 µmol, 61.6 µL, 3.00 equiv.) and dimethylaminopyridine (1.44 mg, 11.8 µmol, 0.10 equiv.) was degassed and purged with nitrogen for 3 times, and then the mixture was stirred at 25° C. for 2 hours under a nitrogen atmosphere. The reaction mixture was diluted with ethyl acetate (5.00 mL) and concentrated under reduced pressure to give a residue. The residue was triturated with petroleum ether (2.00 mL) to give tert-butyl (6-chloro-4-(1,3-dimethyl-1H-pyrazol-5-yl)-2,7-naphthyridin-1-yl)((5-fluoro-2,3-dihydrobenzofuran-4-yl)methyl)carbamate (50.0 mg, 80.7 µmol, 68.4% yield, 84.6% purity) as a yellow solid. LC-MS [M+1]: 524.5.

Step B: A mixture of tert-butyl (6-chloro-4-(1,3-dimethyl-1H-pyrazol-5-yl)-2,7-naphthyridin-1-yl)((5-fluoro-2,3-dihydrobenzofuran-4-yl)methyl)carbamate (50.0 mg, 95.4 µmol, 1.00 equiv.), tert-butyl carbamate (55.9 mg, 477 µmol, 5.00 equiv.), Pd$_2$(dba)$_3$ (1.75 mg, 1.91 µmol, 0.02 equiv.), cesium carbonate (125 mg, 382 µmol, 4.00 equiv.) and Xantphos (1.10 mg, 1.91 µmol, 0.02 equiv.) in dioxane (1.00 mL) was degassed and purged with nitrogen 3 times, and then the mixture was stirred at 100° C. for 12 hours under a nitrogen atmosphere. The mixture was filtered and concentrated under reduced pressure to give a residue. The residue was purified by prep-TLC (dichloromethane/methyl alcohol=10/1) to give tert-butyl (6-((tert-butoxycarbonyl)amino)-4-(1,3-dimethyl-1H-pyrazol-5-yl)-2,7-naphthyridin- 1-yl)((5-fluoro-2,3-dihydrobenzofuran-4-yl)methyl)carbamate (15.0 mg, 24.8 µmol, 26.0% yield) as yellow oil. LC-MS [M+1]: 606.0.

Example 50: A mixture of tert-butyl (6-((tert-butoxycarbonyl)amino)-4-(1,3-dimethyl-1H-pyrazol-5-yl)-2,7-naphthyridin-1-yl)((5-fluoro-2,3-dihydrobenzofuran-4-yl)methyl)carbamate (15.0 mg, 24.8 µL, 1.00 equiv.) and trifluoroacetic acid (1.54 g, 13.5 mmol, 1.00 mL, 544 equiv.) in dichloromethane (1.00 mL) was degassed and purged with nitrogen 3 times, and then the mixture was stirred at 25° C. for 1 hour under a nitrogen atmosphere. The mixture was concentrated under reduced pressure to give a residue. The residue was purified by prep-HPLC [column: Waters Xbridge 150*25 5µ; mobile phase: phase A—10 mM NH₄HCO₃ in water, phase B—ACN; B %: 25%-65%] to give title compound 4-(2,5-dimethylpyrazol-3-yl)-N1-[(5-fluoro-2,3-dihydrobenzofuran-4-yl)methyl]-2,7-naphthyridine-1,6-diamine (8.72 mg, 20.9 µmol, 84.3% yield, 97.0% purity) as a yellow solid. LC-MS [M+1]: 405.4.

¹H NMR (400 MHz, DMSO-d₆) δ=9.16 (s, 1H), 8.05 (br t, J=4.8 Hz, 1H), 7.69 (s, 1H), 6.89 (t, J=9.2 Hz, 1H), 6.64 (dd, J=4.0, 8.8 Hz, 1H), 6.31 (s, 2H), 6.06 (s, 1H), 6.04 (s, 1H), 4.67 (br d, J=4.8 Hz, 2H), 4.51 (t, J=8.8 Hz, 2H), 3.49 (s, 3H), 3.28-3.22 (m, 2H), 2.19 (s, 3H).

Example 51

8-(1,3-dimethyl-1H-pyrazol-5-yl)-N-((5-fluoro-2,3-dihydrobenzofuran-4-yl)methyl)-1,6-naphthyridin-5-amine

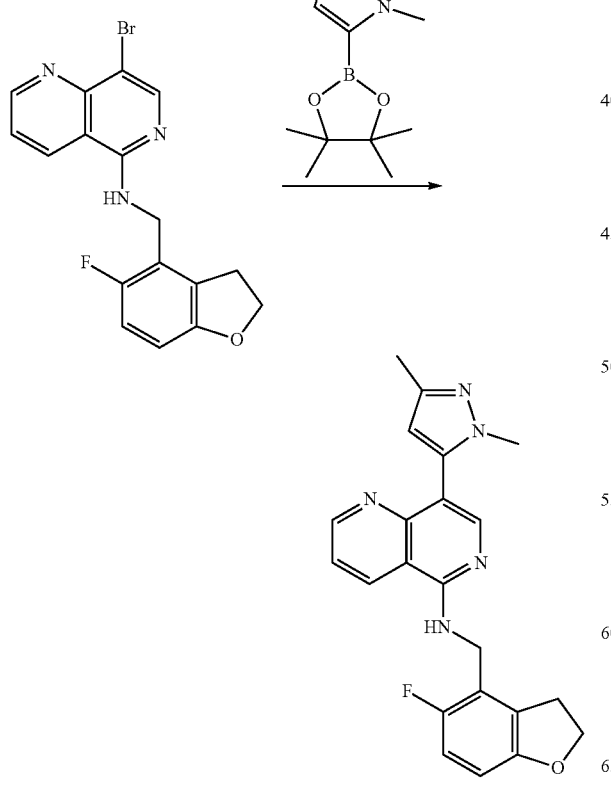

To a solution of Intermediate A-5 (40.0 mg, 107 µmol, 1.00 equiv.) and 1,3-dimethyl-5-(4,4,5,5-tetramethyl-1,3,2-dioxaborolan-2-yl)pyrazole (30.9 mg, 139 µmol, 1.30 equiv.) in dioxane (0.50 mL) and water (0.10 mL) was added Pd(dppf)Cl₂ (7.82 mg, 10.7 µmol, 0.10 equiv.) and sodium bicarbonate (18.0 mg, 214 µmol, 8.31 µL, 2.00 equiv.) under nitrogen atmosphere. The mixture was stirred at 100° C. for 1 hour. The mixture was concentrated in vacuum to give a residue. The residue was purified by prep-HPLC [Waters Xbridge 150*25 5µ; mobile phase: (A: water (10 mM NH₄HCO₃), B: ACN), B %: 20%-50%] to give title compound 8-(1,3-dimethyl-1H-pyrazol-5-yl)-N-((5-fluoro-2,3-dihydrobenzofuran-4-yl)methyl)-1,6-naphthyridin-5-amine (25.0 mg, 64.2 µmol, 60.1% yield, 100% purity) as a white solid. LC-MS [M+1]: 390.3.

¹H NMR (400 MHz, DMSO-d₆) δ=8.96-8.91 (m, 1H), 8.81 (br d, J=7.6 Hz, 1H), 8.25 (br t, J=4.8 Hz, 1H), 8.08 (s, 1H), 7.55 (dd, J=4.4, 8.4 Hz, 1H), 6.91 (t, J=9.6 Hz, 1H), 6.66 (dd, J=4.0, 8.8 Hz, 1H), 6.05 (s, 1H), 4.72 (br d, J=4.8 Hz, 2H), 4.52 (t, J=8.8 Hz, 2H), 3.47 (s, 3H), 3.30-3.25 (m, 2H), 2.18 (s, 3H).

Example 52

8-(1,3-dimethyl-1H-pyrazol-5-yl)-N-((5-fluoro-2,3-dihydrobenzofuran-4-yl)methyl)-2-methoxy-1,6-naphthyridin-5-amine

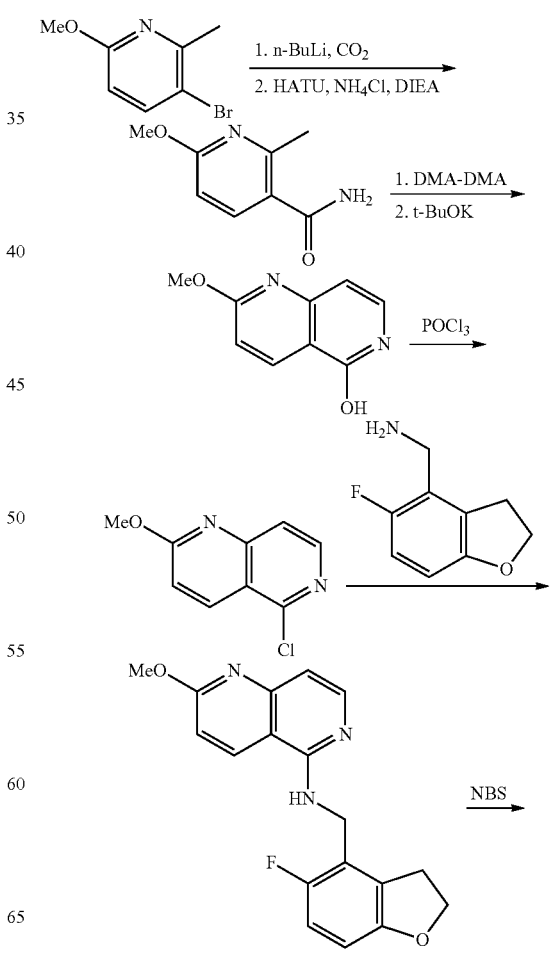

-continued

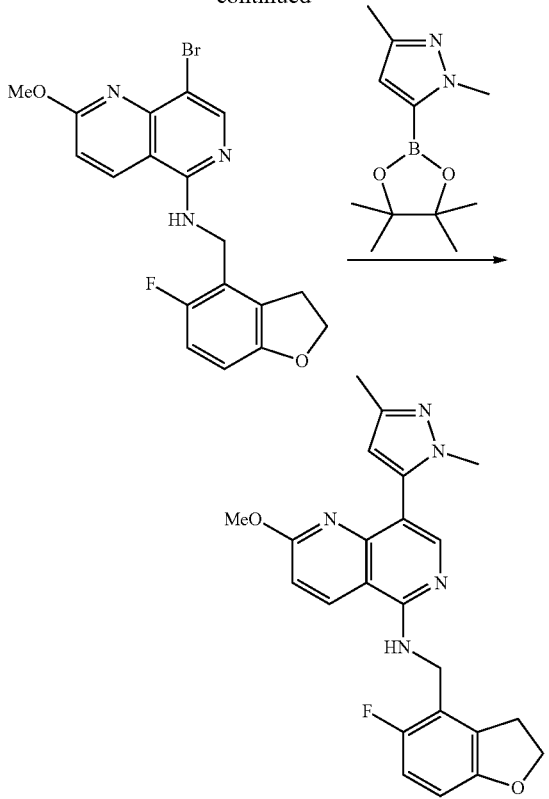

Step A: To a solution of 3-bromo-6-methoxy-2-methylpyridine (5.00 g, 24.8 mmol, 1.00 equiv.) in THF (50.0 mL) was added n-butyllithium (2.5 M, 9.90 mL, 1.00 equiv.) drop-wise at −78° C., then the reaction mixture was stirred at −78° C. for 0.5 hours. Carbon dioxide (15 psi) was bubbled into to reaction slowly for 30 mins. The mixture was warmed to 25° C. and stirred for 1 hour. The reaction mixture was quenched by addition water (50.0 mL), the aqueous solution was adjusted to pH=6 with hydrochloric acid aqueous solution (6.00 M in water, 20.0 mL), the suspension was filtered, and the filter cake was wash with water (50.0 mL×2) and then dried in vacuum to give 6-methoxy-2-methylnicotinic acid (3.30 g, 79.8% yield) as a white solid. LC-MS [M+1]: 168.2.

$^1$H NMR (400 MHz, DMSO-$d_6$) δ=12.9 (br s, 1H), 8.10 (d, J=8.4 Hz, 1H), 6.72 (d, J=8.4 Hz, 1H), 3.90 (s, 3H), 2.67 (s, 3H).

To a solution of 6-methoxy-2-methylnicotinic acid (3.30 g, 19.7 mmol, 1.00 equiv.) in DMF (40.0 mL) was added ammonium chloride (3.17 g, 59.2 mmol, 3.00 equiv.), DIEA (7.65 g, 59.2 mmol, 10.3 mL, 3.00 equiv.) and HATU (11.3 g, 29.6 mmol, 1.50 equiv.). The mixture was stirred at 25° C. for 1 hour. After this time water (40.0 mL) was added to the mixture, and the mixture was extracted with ethyl acetate (20.0 mL×5). The combined organic phases were washed with brine, dried over sodium sulfate, filtered, and concentrated to give a residue. The residue was triturated with petroleum ether (20.0 mL) to give a suspension, the precipitate was filtered, and the filter cake was collected and dried in vacuum to give 6-methoxy-2-methylnicotinamide (1.45 g, 44.2% yield) as a white solid.

$^1$H NMR (400 MHz, $CD_3OD$) δ=7.73 (d, J=8.4 Hz, 1H), 6.63 (d, J=8.4 Hz, 1H), 3.92 (s, 3H), 2.57 (s, 3H).

Step B: To a solution of 6-methoxy-2-methylnicotinamide (1.45 g, 8.73 mmol, 1.00 equiv.) was added DMF-DMA (23.4 g, 196 mmol, 26.1 mL, 22.5 equiv.). The mixture was stirred at 115° C. for 2 hours. The reaction mixture was filtered and concentrated under reduced pressure to give a residue. The residue was triturated with petroleum ether (10.0 mL) and filtered, the filter cake was collected and dried in vacuum to give (E)-N-((dimethylamino)methylene)-6-methoxy-2-methylnicotinamide (1.74 g, crude) as a white solid.

$^1$H NMR (400 MHz, $CDCl_3$) δ=8.58 (s, 1H), 8.41 (d, J=8.4 Hz, 1H), 6.57 (d, J=8.4 Hz, 1H), 3.97 (s, 3H), 3.19 (s, 3H), 3.18 (s, 3H), 2.82 (s, 3H).

To a solution of (E)-N-((dimethylamino)methylene)-6-methoxy-2-methylnicotinamide (1.60 g, 7.23 mmol, 1.00 equiv.) in THF (17.0 mL) was added potassium tert-butoxide (1.00 M in THF, 9.40 mL, 1.30 equiv.) dropwise. The mixture was stirred at 80° C. for 3 hours. After this time water (10.0 mL) was added to the mixture and the pH was adjusted to pH=5 with hydrochloric acid aqueous solution (2.00 M, 5.00 mL). The reaction was extracted with ethyl acetate (20.0 mL×4). The organic phases were collected, dried over sodium sulfate, and then concentrated in vacuo to give 2-methoxy-1,6-naphthyridin-5-ol (780 mg, crude) as a yellow solid.

$^1$H NMR (400 MHz, $CD_3OD$) δ=8.41 (d, J=8.8 Hz, 1H), 7.39 (d, J=7.6 Hz, 1H), 6.89 (d, J=8.8 Hz, 1H), 6.66 (d, J=7.2 Hz, 1H), 4.04 (s, 3H). LC-MS [M+1]: 177.2.

Step C: To a solution of 2-methoxy-1,6-naphthyridin-5-ol (580 mg, 3.29 mmol, 1.00 equiv.) in phosphorus oxychloride (6.00 mL) was added DIEA (851 mg, 6.58 mmol, 1.15 mL, 2.00 equiv.). The mixture was stirred at 120° C. for 5 hours. The reaction mixture was concentrated in vacuo, then the residue was diluted with dichloromethane (15.0 mL) and the mixture poured onto ice. After stirring for 15 minutes, the mixture was adjusted to pH=8 with saturated sodium bicarbonate aqueous solution (10.0 mL). The organic layer was separated, washed with water (10.0 mL×3), dried over sodium sulfate, filtered and concentrated under reduced pressure to give a residue. The residue was purified by column chromatography ($SiO_2$, petroleum ether/ethyl acetate=50/1 to 20/1) to give 5-chloro-2-methoxy-1,6-naphthyridine (410 mg, crude) as a yellow solid.

$^1$H NMR (400 MHz, $CD_3OD$) δ=8.50 (dd, J=0.8, 9.2 Hz, 1H), 8.36 (d, J=5.6 Hz, 1H), 7.69 (dd, J=0.4, 6.0 Hz, 1H), 7.17 (d, J=9.2 Hz, 1H), 4.11 (s, 3H).

Step D: A mixture of 5-chloro-2-methoxy-1,6-naphthyridine (200 mg, 832 μmol, 1.00 equiv.), (5-fluoro-2,3-dihydrobenzofuran-4-yl)methanamine (209 mg, 1.25 mmol, 1.50 equiv.), [2-(2-aminoethyl)phenyl]-chloro-palladium; dicyclohexyl-[3,6-dimethoxy-2-(2,4,6-triisopropylphenyl)phenyl]phosphane (66.5 mg, 83.2 μmol, 0.10 equiv.) and sodium tert-butoxide (160 mg, 1.66 mmol, 2.00 equiv.) in dioxane (2.00 mL) was degassed and purged with nitrogen for 3 times, and then the mixture was stirred at 100° C. for 2 hours under nitrogen atmosphere. The reaction mixture was filtered and concentrated under reduced pressure to give a residue. The residue was purified by column chromatography ($SiO_2$, petroleum ether/ethyl acetate=20/1 to 10/1) to give N-((5-fluoro-2,3-dihydrobenzofuran-4-yl)methyl)-2-methoxy-1,6-naphthyridin-5-amine (110 mg, 40.6% yield) as a yellow solid. LC-MS [M+1]: 326.1.

$^1$H NMR (400 MHz, $CDCl_3$) δ=8.16 (d, J=6.0 Hz, 1H), 7.89 (d, J=9.2 Hz, 1H), 7.00 (d, J=6.0 Hz, 1H), 6.87-6.80 (m, 2H), 6.64 (dd, J=3.6, 8.4 Hz, 1H), 5.36-5.22 (m, 1H), 4.79 (d, J=5.2 Hz, 2H), 4.60 (t, J=8.4 Hz, 2H), 4.06 (s, 3H), 3.37 (t, J=8.4 Hz, 2H).

Step E: To a solution of N-((5-fluoro-2,3-dihydrobenzofuran-4-yl)methyl)-2-methoxy-1,6-naphthyridin-5-amine (80.0 mg, 246 μmol, 1.00 equiv.) in dichloromethane (1.50 mL) was added NBS (39.4 mg, 221 μmol, 0.90 equiv.) at 0° C. The mixture was stirred at 0° C. for 5 min. The reaction mixture was quenched by water (2.00 mL) and extracted with ethyl acetate (3.00 mL×3). The combined organic layers were washed with brine (3.00 mL×2), dried over sodium sulfate, filtered and concentrated under reduced pressure to give a residue. The residue was purified by prep-TLC (SiO$_2$, petroleum ether/ethyl acetate=5/1) to give 8-bromo-N-((5-fluoro-2,3-dihydrobenzofuran-4-yl)methyl)-2-methoxy-1,6-naphthyridin-5-amine (60.0 mg, 60.4% yield) as a yellow solid.

$^1$H NMR (400 MHz, CDCl$_3$) δ=8.36 (s, 1H), 7.88 (d, J=8.8 Hz, 1H), 6.87 (d, J=9.2 Hz, 1H), 6.87-6.82 (m, 1H), 6.64 (dd, J=3.6, 8.4 Hz, 1H), 5.34 (br s, 1H), 4.76 (d, J=5.6 Hz, 2H), 4.60 (t, J=8.8 Hz, 2H), 4.14 (s, 3H), 3.37 (t, J=8.8 Hz, 2H).

Example 52: A mixture of 8-bromo-N-[(5-fluoro-2,3-dihydrobenzofuran-4-yl) methyl]-2-methoxy-1,6-naphthyridin-5-amine (60.0 mg, 148 μmol, 1.00 equiv.), 1,3-dimethyl-5-(4,4,5,5-tetramethyl-1,3,2-dioxaborolan-2-yl)pyrazole (49.5 mg, 222 μmol, 1.50 equiv.), sodium bicarbonate (37.4 mg, 445 μmol, 17.3 μL, 3.00 equiv.) and Pd(dppf)Cl$_2$ (10.9 mg, 14.8 μmol, 0.10 equiv.) in dioxane (1.00 mL) and water (0.20 mL) was degassed and purged with nitrogen for 3 times, and then the mixture was stirred at 100° C. for 1 hour under nitrogen atmosphere. The reaction mixture was filtered and concentrated under reduced pressure to give a residue. The residue was purified by prep-TLC (SiO$_2$, petroleum ether/ethyl acetate=1/1). The crude product was triturated with methanol (2.00 mL), the suspension was filtered, the filter cake was collected and dried in vacuum to give title compound 8-(1,3-dimethyl-1H-pyrazol-5-yl)-N-((5-fluoro-2,3-dihydrobenzofuran-4-yl)methyl)-2-methoxy-1,6-naphthyridin-5-amine (35.0 mg, 55.4% yield, 98.5% purity) as a white solid. LC-MS [M+1]: 420.3.

$^1$H NMR (400 MHz, CDCl$_3$) δ=8.18 (s, 1H), 7.95 (d, J=9.2 Hz, 1H), 6.88-6.82 (m, 2H), 6.66 (dd, J=4.0, 8.4 Hz, 1H), 6.11 (s, 1H), 5.48 (br t, J=4.8 Hz, 1H), 4.82 (d, J=5.6 Hz, 2H), 4.62 (t, J=8.8 Hz, 2H), 3.92 (s, 3H), 3.70 (s, 3H), 3.42 (t, J=8.8 Hz, 2H), 2.35 (s, 3H).

Example 53

8-(1,3-dimethyl-1H-pyrazol-5-yl)-N-((5-fluoro-2,3-dihydrobenzofuran-4-yl)methyl)-2-methoxy-1,6-naphthyridin-5-amine

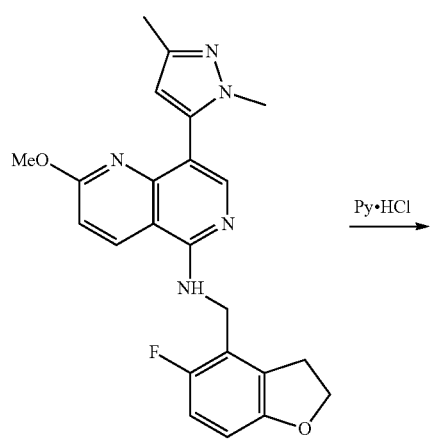

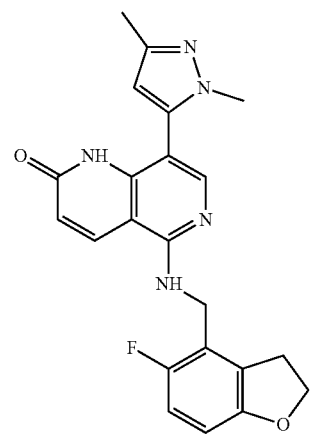

To a solution of 8-(1,3-dimethyl-1H-pyrazol-5-yl)-N-((5-fluoro-2,3-dihydrobenzofuran-4-yl)methyl)-2-methoxy-1,6-naphthyridin-5-amine (Example 46, 20.0 mg, 47.0 μmol, 1.00 equiv.) was added pyridine hydrochloride (78.8 mg, 682 μmol, 14.5 equiv.). The mixture was stirred at 130° C. for 0.5 hours. The reaction mixture cooled to room temperature, diluted with water (1.00 mL) and purified by prep-HPLC [Phenomenex Synergi C18 150*30 mm*4 μm; mobile phase: (phase A—water (0.05% HCl), phase B—ACN) B %: 20%-50%] and lyophilization to give title compound 8-(1,3-dimethyl-1H-pyrazol-5-yl)-N-((5-fluoro-2,3-dihydrobenzofuran-4-yl)methyl)-2-methoxy-1,6-naphthyridin-5-amine (8.67 mg, 44.9% yield, 98.6% purity) as a white solid. LC-MS [M+1]: 406.3.

$^1$H NMR (400 MHz, DMSO-d$_6$) δ=10.2 (br s, 1H), 8.29 (br d, J=10.0 Hz, 1H), 7.89 (s, 1H), 7.78 (br s, 1H), 6.89 (br t, J=8.8 Hz, 1H), 6.69-6.59 (m, 1H), 6.42 (br d, J=9.6 Hz, 1H), 6.11 (s, 1H), 4.64 (br d, J=4.4 Hz, 2H), 4.51 (br t, J=8.4 Hz, 2H), 3.53 (s, 3H), 3.26-3.24 (m, 2H), 2.19 (s, 3H).

Example 54

4-(1,3-dimethyl-1H-pyrazol-5-yl)-N-((5-fluoro-2,3-dihydrobenzofuran-4-yl)methyl)-5-methoxy-2,6-naphthyridin-1-amine

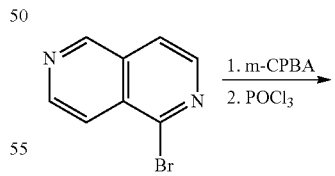

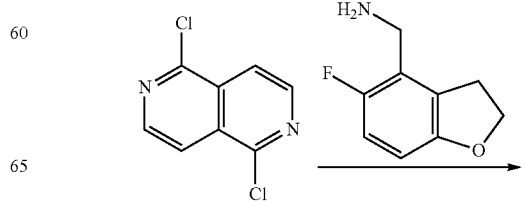

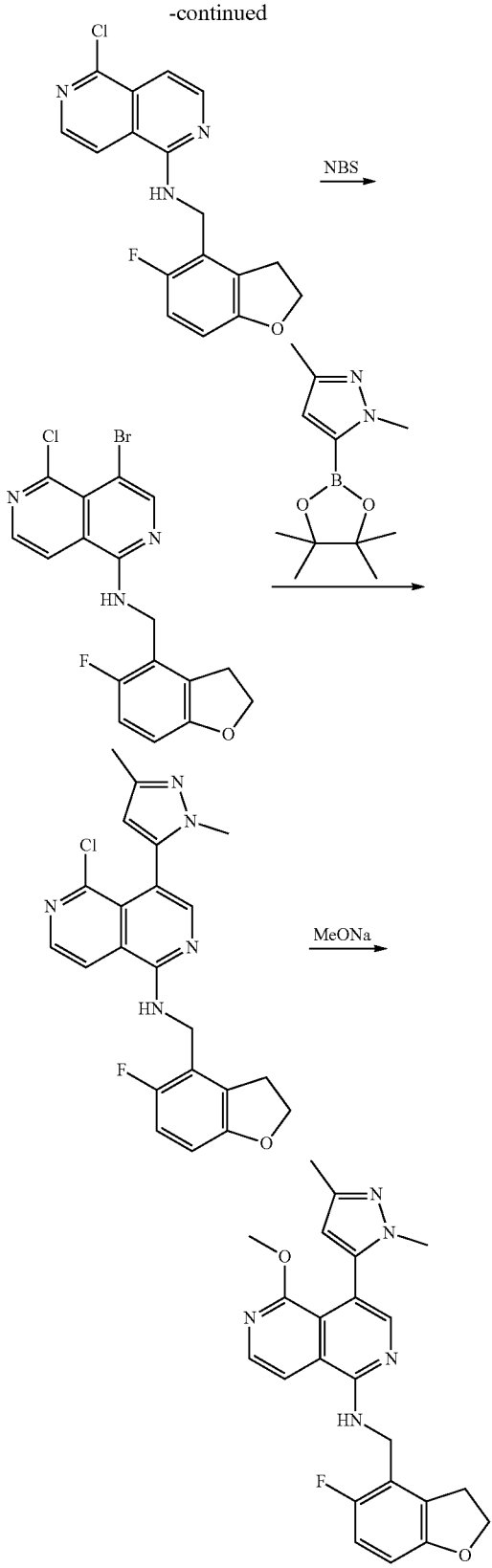

warmed to 25° C. and stirred for 16 hours. The reaction mixture was diluted with water (50.0 mL) and extracted with dichloromethane (100 mL×2). The combined organic layers were washed with saturated sodium bicarbonate in water (100 mL) then brine (100 mL), dried over anhydrous sodium sulfate, filtered, and concentrated under reduced pressure to 5-bromo-2,6-naphthyridine 2-oxide (1.40 g, 6.22 mmol, 81.3% yield) as a white solid which was used without further purification.

A solution of 5-bromo-2,6-naphthyridine 2-oxide (1.40 g, 6.22 mmol, 1.00 equiv.) and phosphorus oxychloride (20.0 mL) was stirred at 90° C. for 16 hours. Phosphorus oxychloride was removed under reduce pressure to give a residue, the residue was diluted with ethyl acetate (200 mL) and quenched with ice-water (300 mL), the organic phase was separated and washed with saturated sodium bicarbonate (100 mL) and brine (100 mL), dried and concentrated to give a yellow solid. The crude product was purified by column chromatography ($SiO_2$, petroleum ether/ethyl acetate=1/0 to 5/1) to give 1,5-dichloro-2,6-naphthyridine (540 mg, 2.71 mmol, 43.6% yield) as a white solid.

$^1$H NMR (400 MHz, $CDCl_3$) δ=8.56 (d, J=5.6 Hz, 2H), 8.07 (d, J=5.6 Hz, 2H).

Step B: A mixture of 1,5-dichloro-2,6-naphthyridine (500 mg, 2.51 mmol, 1.00 equiv.), (5-fluoro-2,3-dihydrobenzofuran-4-yl)methanamine (420 mg, 2.51 mmol, 1.00 equiv.) and potassium fluoride (437 mg, 7.52 mmol, 176 µL, 2.99 equiv) in DMSO (10.0 mL) was degassed and purged with nitrogen 3 times, and then the mixture was stirred at 120° C. for 2 hours under nitrogen atmosphere. The reaction mixture was diluted with water (50.0 mL) and extracted with ethyl acetate (60.0 mL×2). The combined organic layers were washed with brine (100 mL×3), dried over anhydrous sodium sulfate and concentrated under reduced pressure to give a residue. The residue was purified by column chromatography ($SiO_2$, petroleum ether/ethyl acetate=1/0 to 10/1) to give 5-chloro-N-((5-fluoro-2,3-dihydrobenzofuran-4-yl)methyl)-2,6-naphthyridin-1-amine (600 mg, 1.82 mmol, 72.4% yield) as a white solid.

$^1$H NMR (400 MHz, DMSO-$d_6$) δ=8.36 (d, J=5.6 Hz, 1H), 8.24 (dd, J=0.8, 5.6 Hz, 1H), 8.21 (t, J=5.2 Hz, 1H), 8.16 (d, J=6.0 Hz, 1H), 7.11 (d, J=6.0 Hz, 1H), 6.94-6.84 (m, 1H), 6.64 (dd, J=4.0, 8.8 Hz, 1H), 4.69 (d, J=5.2 Hz, 2H), 4.50 (t, J=8.8 Hz, 2H), 3.23 (t, J=8.8 Hz, 2H).

Step C: To a solution of 5-chloro-N-((5-fluoro-2,3-dihydrobenzofuran-4-yl)methyl)-2,6-naphthyridin-1-amine (500 mg, 1.52 mmol, 1.00 equiv) in dichloromethane (60.0 mL) was added NBS (243 mg, 1.36 mmol, 0.90 equiv), portionwise. The reaction was stirred at −40° C. for 4 hours then evaporated to give a residue. The residue was purified by column chromatography ($SiO_2$, petroleum ether/ethyl acetate=10/1 to 3/1) to give 4-bromo-5-chloro-N-((5-fluoro-2,3-dihydrobenzofuran-4-yl)methyl)-2,6-naphthyridin-1-amine (280 mg, 685 µmol, 45.2% yield) as a yellow solid.

$^1$H NMR (400 MHz, DMSO-$d_6$) δ=8.46 (d, J=5.6 Hz, 1H), 8.42-8.37 (m, 1H), 8.33 (s, 1H), 8.30 (d, J=5.6 Hz, 1H), 6.92-6.86 (m, 1H), 6.65 (dd, J=4.0, 8.8 Hz, 1H), 4.65 (d, J=5.2 Hz, 2H), 4.50 (t, J=8.8 Hz, 2H), 3.24-3.20 (m, 2H).

Step D: A mixture of 4-bromo-5-chloro-N-((5-fluoro-2,3-dihydrobenzofuran-4-yl)methyl)-2,6-naphthyridin-1-amine (200 mg, 489 µmol, 1.00 equiv), 1,3-dimethyl-5-(4,4,5,5-tetramethyl-1,3,2-dioxaborolan-2-yl)-1H-pyrazole (217 mg, 979 µmol, 2.00 equiv.), [1,1'-Bis(di-tert-butylphosphino)ferrocene]dichloropalladium(II) (31.9 mg, 48.9 µmol, 0.10 equiv.) and cesium carbonate (159 mg, 489 µmol, 1.00 equiv.) in tetrahydrofuran (4.00 mL) and water (0.80 mL) was degassed and purged with nitrogen 3 times. The mixture Step A: To a solution of 1-bromo-2,6-naphthyridine (1.60 g, 7.65 mmol, 1.00 equiv.) in dichloromethane (30.0 mL) was added metachloroperbenzoic acid (2.33 g, 11.5 mmol, 85.0% purity, 1.50 equiv.) at 0° C. The resulting mixture was was then stirred at 70° C. for 1 hours under a nitrogen atmosphere. After completion of the reaction, the reaction mixture was evaporated to give a residue. The residue was purified by column chromatography (SiO₂, petroleum ether/ ethyl acetate=3/1 to 1/1) to give 5-chloro-4-(1,3-dimethyl-1H-pyrazol-5-yl)-N-((5-fluoro-2,3-dihydrobenzofuran-4-yl) methyl)-2,6-naphthyridin-1-amine (170 mg, 401 μmol, 82.0% yield) as a yellow solid.

¹H NMR (400 MHz, DMSO-d₆) δ=8.50-8.45 (m, 1H), 8.44 (d, J=5.6 Hz, 1H), 8.33 (d, J=5.6 Hz, 1H), 7.98 (s, 1H), 6.96-6.86 (m, 1H), 6.66 (dd, J=4.0, 8.8 Hz, 1H), 6.05 (s, 1H), 4.77-4.64 (m, 2H), 4.52 (t, J=8.8 Hz, 2H), 3.39 (s, 3H), 3.29-3.26 (m, 2H), 2.18 (s, 3H).

Example 54: 5-chloro-4-(1,3-dimethyl-1H-pyrazol-5-yl)-N-((5-fluoro-2,3-dihydrobenzofuran-4-yl)methyl)-2,6-naphthyridin-1-amine (50.0 mg, 118 μmol, 1.00 equiv) was added to a solution of sodium methoxide (20.0 mg, 370 μmol, 3.14 equiv) in methanol (2.00 mL), and the solution was stirred at 70° C. for 6 hours. After completion of the reaction, the reaction mixture was diluted with water (20.0 mL) and extracted with dichloromethane (20.0 mL×2). The combined organic layers were washed with brine (20.0 mL), dried over anhydrous sodium sulfate and concentrated under reduced pressure to give a crude product. The crude product was purified by prep-HPLC [Phenomenex Synergi C18 150*30 mm*4 μm; mobile phase: (phase A—water (0.05% HCl), phase B—ACN) B %: 20%-50%] to give title compound 4-(1,3-dimethyl-1H-pyrazol-5-yl)-N-((5-fluoro-2,3-dihydrobenzofuran-4-yl)methyl)-5-methoxy-2,6-naphthyridin-1-amine (16.0 mg, 34.7 μmol, 29.4% yield, 90.9% purity) as a white solid. LC-MS [M+1]: 420.2.

¹H NMR (400 MHz, CD₃OD) δ=8.18 (d, J=5.6 Hz, 1H), 7.82 (s, 1H), 7.71 (d, J=5.6 Hz, 1H), 6.90-6.80 (m, 1H), 6.64 (dd, J=4.0, 8.8 Hz, 1H), 6.07 (s, 1H), 4.79 (s, 2H), 4.55 (t, J=8.8 Hz, 2H), 3.80 (s, 3H), 3.47 (s, 3H), 3.30-3.28 (m, 2H), 2.30 (s, 3H).

Example 55

8-(1,3-dimethyl-1H-pyrazol-5-yl)-5-(((5-fluoro-2,3-dihydrobenzofuran-4-yl)methyl)amino)-2,6-naphthyridin-1(2H)-one

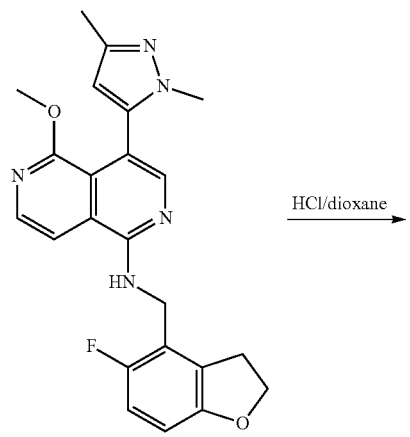

HCl/dioxane →

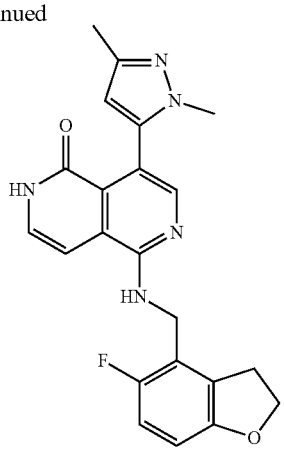

A mixture of 4-(1,3-dimethyl-1H-pyrazol-5-yl)-N-((5-fluoro-2,3-dihydrobenzofuran-4-yl)methyl)-5-methoxy-2,6-naphthyridin-1-amine (25.0 mg, 59.6 μmol, 1.00 equiv.) in HCl in dioxane (8.00 mL) was heated at 90° C. for 0.5 hour. The reaction mixture was concentrated under reduced pressure to give a residue. The residue was purified by prep-HPLC [column: Xtimate C18 150*25 mm*5 μm; mobile phase: phase A—water (0.05% ammonia hydroxide v/v), phase B—ACN; B %: 20%-60%] to give title compound 8-(1,3-dimethyl-1H-pyrazol-5-yl)-5-4(5-fluoro-2,3-dihydrobenzofuran-4-yl)methyl)amino)-2,6-naphthyridin-1(2H)-one (9.30 mg, 21.9 μmol, 36.8% yield, 95.5% purity) as an off-white solid. LC-MS [M+1]: 406.1.

¹H NMR (400 MHz, DMSO-d₆) δ=7.71 (s, 1H), 7.67 (s, 1H), 7.31 (d, J=7.2 Hz, 1H), 6.93-6.81 (m, 2H), 6.63 (dd, J=4.0, 8.8 Hz, 1H), 5.82 (s, 1H), 4.62 (s, 2H), 4.51 (t, J=8.8 Hz, 2H), 3.29-3.25 (m, 2H), 3.17 (s, 3H), 2.14 (s, 3H).

Example 56

4-(1,3-dimethyl-1H-pyrazol-5-yl)-N-((5-fluoro-2,3-dihydrobenzofuran-4-yl)methyl)-2,6-naphthyridin-1-amine

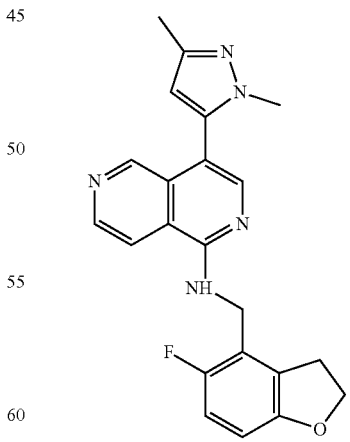

Step A: A mixture of 1-chloro-2,6-naphthyridine (50.0 mg, 304 μmol, 1.00 equiv), (5-fluoro-2,3-dihydrobenzofuran-4-yl)methanamine (50.8 mg, 303 μmol, 1.00 equiv.), [2-(dicyclohexylphosphino)-3,6-dimethoxy-2',4', 6'-triisopropyl-1,1'-biphenyl][2-(2-aminoethyl)phenyl]palladium (II) (24.3 mg, 30.4 µmol, 0.10 equiv) and sodium tert-butoxide (58.4 mg, 608 µmol, 2.00 equiv) in dioxane (1.00 mL) was degassed and purged with nitrogen 3 times, and then the mixture was stirred at 95° C. for 2 hours under a nitrogen atmosphere. The reaction mixture was filtered and concentrated under reduced pressure to give a residue. The residue was purified by prep-TLC (SiO$_2$, petroleum ether/ethyl acetate=1/1) to give N-((5-fluoro-2,3-dihydrobenzofuran-4-yl)methyl)-2,6-naphthyridin-1-amine (30.0 mg, 33.4% yield) as a yellow solid.

$^1$H NMR (400 MHz, CDCl$_3$) δ=9.13 (s, 1H), 8.59 (d, J=5.6 Hz, 1H), 8.17 (d, J=5.6 Hz, 1H), 7.50 (d, J=6.0 Hz, 1H), 7.05 (d, J=5.6 Hz, 1H), 6.85 (t, J=9.2 Hz, 1H), 6.66 (dd, J=3.6, 8.4 Hz, 1H), 5.56 (br s, 1H), 4.82 (d, J=5.2 Hz, 2H), 4.61 (t, J=8.8 Hz, 2H), 3.39 (t, J=8.8 Hz, 2H).

Step B: To a solution of N-((5-fluoro-2,3-dihydrobenzofuran-4-yl)methyl)-2,6-naphthyridin-1-amine (50.0 mg, 169 µmol, 1.00 equiv) in dichloromethane (2.00 mL) was added NBS (25.6 mg, 144 µmol, 0.85 equiv.). The mixture was stirred at 0° C. for 10 mins. The reaction mixture was quenched by water (2.00 mL), then extracted with ethyl acetate (3.00 mL×3). The combined organic layers were washed with brine (3.00 mL×2), dried over sodium sulfate, filtered and concentrated under reduced pressure to give a residue. The residue was purified by prep-TLC (SiO$_2$, petroleum ether/ethyl acetate=2/1) to give 4-bromo-N-((5-fluoro-2,3-dihydrobenzofuran-4-yl)methyl)-2,6-naphthyridin-1-amine (50.0 mg, 78.9% yield) as a yellow solid.

$^1$H NMR (400 MHz, CDCl$_3$) δ=9.44 (s, 1H), 8.72-8.66 (m, 1H), 8.26 (d, J=2.0 Hz, 1H), 7.47 (br d, J=4.4 Hz, 1H), 6.84 (br t, J=8.8 Hz, 1H), 6.69-6.61 (m, 1H), 5.67 (br s, 1H), 4.79 (br d, J=4.4 Hz, 2H), 4.66-4.58 (m, 2H), 3.38 (br t, J=8.8 Hz, 2H).

Example 56: A mixture of 4-bromo-N-((5-fluoro-2,3-dihydrobenzofuran-4-yl)methyl)-2,6-naphthyridin-1-amine (50.0 mg, 134 µmol, 1.00 equiv), 1,3-dimethyl-5-(4,4,5,5-tetramethyl-1,3,2-dioxaborolan-2-yl)pyrazole (29.7 mg, 134 µmol, 1.00 equiv), sodium bicarbonate (33.7 mg, 401 µmol, 15.6 µL, 3.00 equiv) and Pd(dppf)Cl$_2$ (9.78 mg, 13.4 µmol, 0.10 equiv) in dioxane (1.00 mL) and water (0.20 mL) was degassed and purged with nitrogen 3 times, and then the mixture was stirred at 100° C. for 1 hour under a nitrogen atmosphere. The reaction mixture was filtered and concentrated under reduced pressure to give a residue. The residue was purified by prep-TLC (SiO$_2$, petroleum ether/ethyl acetate=0/100) to give a crude product. The crude product was triturated with methanol (2.00 mL), the suspension was filtered, and the filter cake was collected and dried in vacuo to give title compound 4-(1,3-dimethyl-1H-pyrazol-5-yl)-N-((5-fluoro-2,3-dihydrobenzofuran-4-yl)methyl)-2,6-naphthyridin-1-amine (11.7 mg, 22.3% yield, 99.2% purity) as a white solid. LC-MS[M+1]: 390.1.

$^1$H NMR (400 MHz, CDCl$_3$) δ=8.99 (s, 1H), 8.66 (d, J=5.6 Hz, 1H), 8.08 (s, 1H), 7.56 (d, J=5.6 Hz, 1H), 6.87 (t, J=9.2 Hz, 1H), 6.68 (dd, J=4.0, 8.8 Hz, 1H), 6.18 (s, 1H), 5.80 (br t, J=5.2 Hz, 1H), 4.85 (d, J=5.2 Hz, 2H), 4.63 (t, J=8.8 Hz, 2H), 3.67 (s, 3H), 3.42 (t, J=8.4 Hz, 2H), 2.37 (s, 3H).

Example 57

5-(1,3-dimethyl-1H-pyrazol-5-yl)-N-((5-fluoro-2,3-dihydrobenzofuran-4-yl)methyl)-4-methoxypyrido[3,4-d]pyrimidin-8-amine

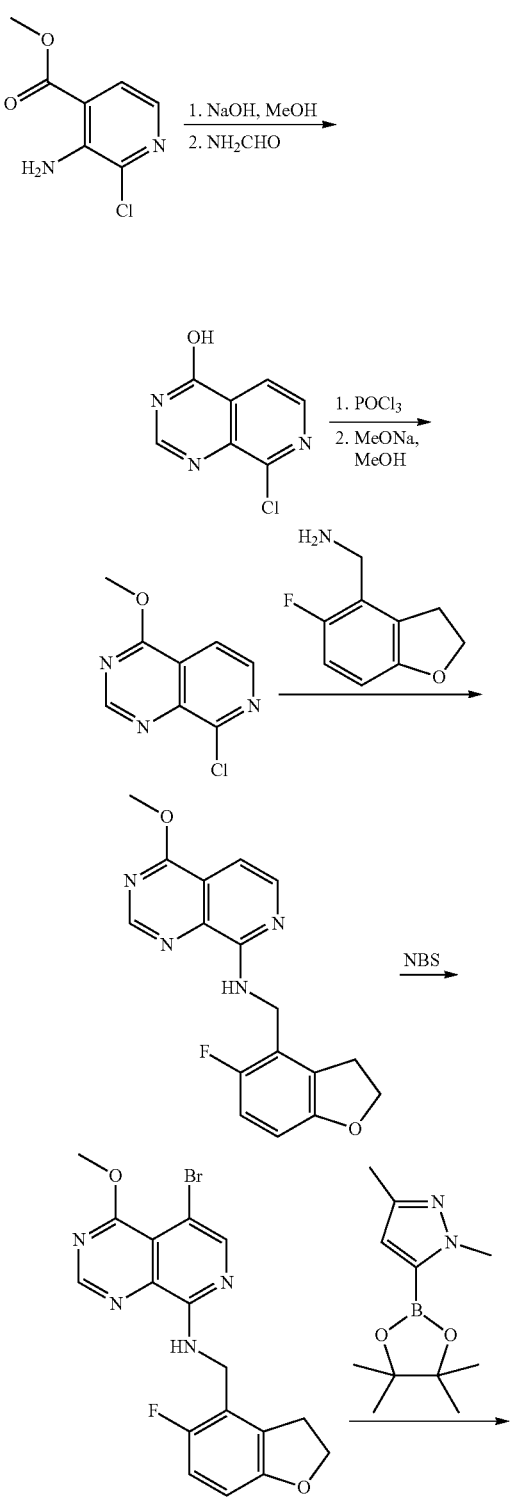

-continued

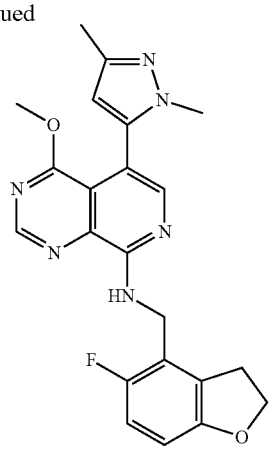

Step A: To a solution of methyl 3-amino-2-chloroisonicotinate (5.00 g, 26.8 mmol, 1.00 equiv) in methanol (25.0 mL) and water (25.0 mL) was added sodium hydroxide (3.22 g, 80.4 mmol, 3.00 equiv), the reaction mixture was stirred at 25° C. for 1 hour. The reaction was concentrated in vacuo to remove the methanol, the aqueous solution was then adjusted to pH=6 with acetic acid. The precipitate was filtered, and the solid was collected and dried in vacuum to give 3-amino-2-chloroisonicotinic acid (4.20 g, 24.3 mmol, 90.8% yield) as a white solid.

$^1$H NMR (400 MHz, DMSO-$d_6$) δ=7.61 (d, J=4.8 Hz, 1H), 7.59 (d, J=4.8 Hz, 1H), 6.82 (br. s, 2H).

A solution of 3-amino-2-chloroisonicotinic acid (2.20 g, 12.8 mmol, 1.00 equiv.) in formamide (20.0 mL) was stirred at 140° C. for 12 hours. The reaction mixture was added water (100 mL). The resulting precipitate was filtered, and the solid was collected and dried in vacuo to give 8-chloropyrido[3,4-d]pyrimidin-4-ol (1.6 g, crude) as a yellow solid.

$^1$H NMR (400 MHz, DMSO-$d_6$) δ=12.7 (br s, 1H), 11.9 (br s, 1H), 8.10 (s, 1H), 7.31 (d, J=6.8 Hz, 1H), 6.58 (d, J=6.8 Hz, 1H).

Step B: To a solution of 8-chloropyrido[3,4-d]pyrimidin-4-ol (400 mg, 2.20 mmol, 1.00 equiv.) in POCl$_3$ (5.00 mL) was added DIEA (569 mg, 4.41 mmol, 767 μL, 2.00 equiv.), the reaction was stirred at 120° C. for 12 hours. The reaction was concentrated in vacuum under reduced pressure to remove the POCl$_3$ to give 4,8-dichloropyrido[3,4-d]pyrimidine (400 mg, crude) as brown oil which was used in the next step directly. LC-MS [M+1]: 199.8.

To a solution of 4,8-dichloropyrido[3,4-d]pyrimidine (150 mg, 750 mL, 1.00 equiv.) in DCM (4.00 mL) was added DIEA (485 mg, 3.75 mmol, 653 μL, 5.00 equiv.) at −40° C. The reaction was stirred at −40° C. for 30 min, then a solution of sodium methoxide (40.5 mg, 750 μmol, 1.00 equiv.) in methanol (1 mL) was added dropwise, and the reaction was warmed slowly to 25° C. and stirred for 1 hour. The reaction was diluted with DCM (20.0 mL), washed with brine (10.0 mL×2), dried with anhydrous sodium sulfate, filtered, and concentrated in vacuum to give 8-chloro-4-methoxypyrido[3,4-d]pyrimidine (120 mg, 613 μmol, 81.8% yield) as a brown solid.

$^1$H NMR (400 MHz, CDCl$_3$) δ=9.02 (s, 1H), 8.49 (d, J=5.6 Hz, 1H), 7.90 (d, J=5.2 Hz, 1H), 4.25 (s, 3H).

Step C: To a solution of (5-fluoro-2,3-dihydrobenzofuran-4-yl)methanamine (92.3 mg, 552 μmol, 1.20 equiv.) and 8-chloro-4-methoxypyrido[3,4-d]pyrimidine (90.0 mg, 460 μmol, 1.00 equiv.) in dioxane (3.00 mL) was added potassium fluoride (80.2 mg, 1.38 mmol, 32.3 μL, 3.00 equiv.), and the reaction was stirred at 120° C. for 12 hours under a nitrogen atmosphere. The reaction was filtered, and the filtrate was concentrated in vacuo to give a residue. The residue was purified by prep-TLC (petroleum ether/ethyl acetate=1/1) to give N-((5-fluoro-2,3-dihydrobenzofuran-4-yl)methyl)-4-methoxypyrido[3,4-d]pyrimidin-8-amine (76.0 mg, 233 μmol, 50.6% yield) as a brown solid.

$^1$H NMR (400 MHz, CD$_3$OD) δ=8.73 (s, 1H), 8.04 (d, J=6.0 Hz, 1H), 7.06 (d, J=5.6 Hz, 1H), 6.85 (t, J=9.2 Hz, 1H), 6.62 (dd, J=4.0, 8.8 Hz, 1H), 4.78 (s, 2H), 4.54 (br t, J=8.8 Hz, 2H), 4.19 (s, 3H), 3.31-3.25 (m, 2H).

Step D: To a solution of N-((5-fluoro-2,3-dihydrobenzofuran-4-yl)methyl)-4-methoxypyrido[3,4-d]pyrimidin-8-amine (76.0 mg, 233 μmol, 1.00 equiv.) in DCM (1.00 mL) was added NBS (41.5 mg, 233 μmol, 1.00 equiv.) at 0° C., the reaction was stirred at 0° C. for 0.5 hour. After this time, the reaction was concentrated in vacuo at 25° C. to give 5-bromo-N-((5-fluoro-2,3-dihydrobenzofuran-4-yl)methyl)-4-methoxypyrido[3,4-d]pyrimidin-8-amine (80.0 mg, crude) as a brown solid which was used in the next step directly.

$^1$H NMR (400 MHz, DMSO-$d_6$) δ=8.84 (s, 1H), 8.17 (s, 1H), 8.06-8.01 (m, 1H), 6.92-6.83 (m, 1H), 6.61 (dd, J=4.0, 8.8 Hz, 1H), 4.68 (d, J=6.0 Hz, 2H), 4.48 (t, J=8.4 Hz, 2H), 4.11 (s, 3H), 3.24 (t, J=8.8 Hz, 2H).

Example 57: To a solution of 5-bromo-N-((5-fluoro-2,3-dihydrobenzofuran-4-yl)methyl)-4-methoxypyrido[3,4-d]pyrimidin-8-amine (70.0 mg, 173 μmol, 1.00 equiv.) and 1,3-dimethyl-5-(4,4,5,5-tetramethyl-1,3,2-dioxaborolan-2-yl)pyrazole (57.6 mg, 259 μmol, 1.50 equiv.) in dioxane (2.00 mL) and water (0.40 mL) was added sodium bicarbonate (43.5 mg, 518 μmol, 20.2 μL, 3.00 equiv.) and Pd(dppf)Cl$_2$ (12.6 mg, 17.3 μmol, 0.10 equiv.). The mixture was stirred at 110° C. for 1 hour under a nitrogen atmosphere. The reaction was filtered and concentrated in vacuo to give a residue, and the residue was purified by prep-TLC (petroleum ether/ethyl acetate=1/1) to give a crude product. The crude product was triturated with methanol (1.00 mL), filtered, and the filter cake was collected and dried in vacuo to give title compound 5-(1,3-dimethyl-1H-pyrazol-5-yl)-N-((5-fluoro-2,3-dihydrobenzofuran-4-yl)methyl)-4-methoxypyrido[3,4-d]pyrimidin-8-amine (27.5 mg, 64.8 μmol, 37.5% yield, 99.1% purity) as a yellow solid. LC-MS [M+1]: 421.4.

$^1$H NMR (400 MHz, CD$_3$OD) δ=8.77 (s, 1H), 7.92 (s, 1H), 6.89-6.80 (m, 1H), 6.62 (dd, J=3.6, 8.4 Hz, 1H), 6.05 (s, 1H), 4.82 (s, 2H), 4.55 (t, J=8.8 Hz, 2H), 3.92 (s, 3H), 3.48 (s, 3H), 3.39-3.34 (m, 2H), 2.29 (s, 3H).

Example 58

5-(1,3-dimethyl-1H-pyrazol-5-yl)-8-(((5-fluoro-2,3-dihydrobenzofuran-4-yl)methyl)amino)pyrido[3,4-d]pyrimidin-4(3H)-one

Example 59

5-(1,3-dimethyl-1H-pyrazol-5-yl)-N-((5-fluoro-2,3-dihydrobenzofuran-4-yl)methyl)pyrido[3,4-d]pyrimidin-8-amine

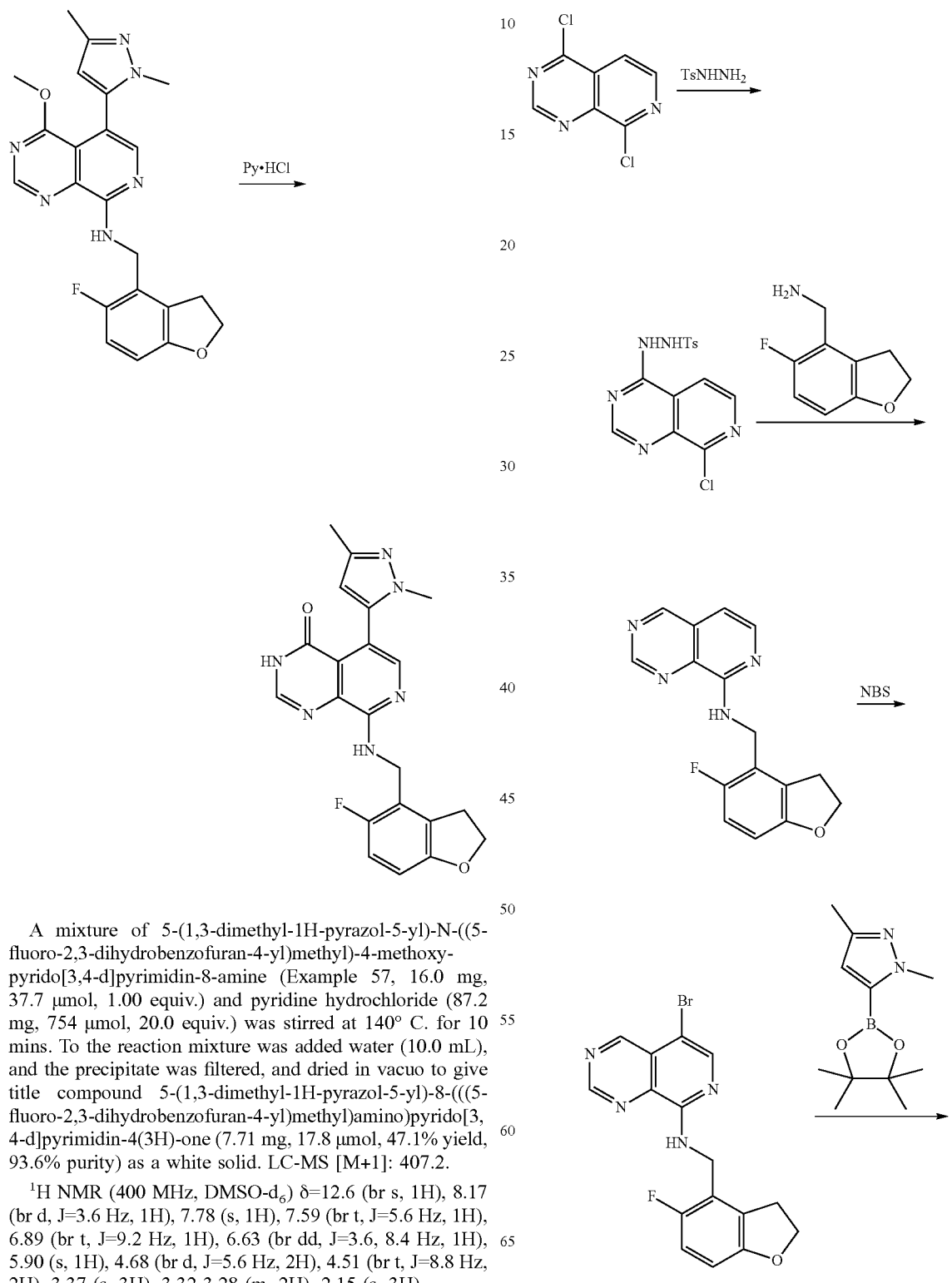

A mixture of 5-(1,3-dimethyl-1H-pyrazol-5-yl)-N-((5-fluoro-2,3-dihydrobenzofuran-4-yl)methyl)-4-methoxy-pyrido[3,4-d]pyrimidin-8-amine (Example 57, 16.0 mg, 37.7 µmol, 1.00 equiv.) and pyridine hydrochloride (87.2 mg, 754 µmol, 20.0 equiv.) was stirred at 140° C. for 10 mins. To the reaction mixture was added water (10.0 mL), and the precipitate was filtered, and dried in vacuo to give title compound 5-(1,3-dimethyl-1H-pyrazol-5-yl)-8-(((5-fluoro-2,3-dihydrobenzofuran-4-yl)methyl)amino)pyrido[3,4-d]pyrimidin-4(3H)-one (7.71 mg, 17.8 µmol, 47.1% yield, 93.6% purity) as a white solid. LC-MS [M+1]: 407.2.

$^1$H NMR (400 MHz, DMSO-$d_6$) δ=12.6 (br s, 1H), 8.17 (br d, J=3.6 Hz, 1H), 7.78 (s, 1H), 7.59 (br t, J=5.6 Hz, 1H), 6.89 (br t, J=9.2 Hz, 1H), 6.63 (br dd, J=3.6, 8.4 Hz, 1H), 5.90 (s, 1H), 4.68 (br d, J=5.6 Hz, 2H), 4.51 (br t, J=8.8 Hz, 2H), 3.37 (s, 3H), 3.32-3.28 (m, 2H), 2.15 (s, 3H).

-continued

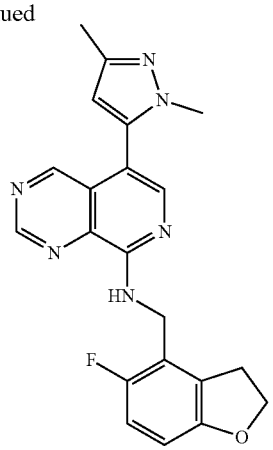

Step A: To a solution of 4,8-dichloropyrido[3,4-d]pyrimidine (400 mg, 2.00 mmol, 1.00 equiv), DIEA (258 mg, 2.00 mmol, 348 μL, 1.00 equiv) in DCM (10.0 mL) was added p-toluenesulfonyl hydrazide (745 mg, 4.00 mmol, 2.00 equiv), and the reaction was stirred at 25° C. for 1 hour. The mixture was then diluted with DCM (20.0 mL), washed with hydrochloric acid aqueous solution (1.00 M, 20.0 mL×3) and brine (10.0 mL×2), dried with anhydrous sodium sulfate, filtered and concentrated in vacuo to give a residue. The residue was purified by silica gel chromatography (petroleum ether/ethyl acetate=10/1 to 1/1) to give N-(8-chloropyrido[3,4-d]pyrimidin-4-yl)-4-methylbenzenesulfonohydrazide (360 mg, 1.03 mmol, 51.5% yield) as a brown solid.

$^1$H NMR (400 MHz, DMSO-$d_6$) δ=11.77-11.32 (m, 1H), 10.20-9.49 (m, 1H), 8.21 (br s, 1H), 7.81 (br d, J=6.4 Hz, 2H), 7.69 (br d, J=8.0 Hz, 1H), 7.46-7.34 (m, 3H), 2.40 (br s, 3H).

Step B: To a solution of (5-fluoro-2,3-dihydrobenzofuran-4-yl)methanamine (91.8 mg, 549 μmol, 1.20 equiv) and N-(8-chloropyrido[3,4-d]pyrimidin-4-yl)-4-methylbenzenesulfonohydrazide (160 mg, 457 μmol, 1.00 equiv) in DMSO (3.00 mL) was added potassium fluoride (79.7 mg, 1.37 mmol, 32.2 μL, 3.00 equiv), the reaction was stirred at 120° C. for 12 hours under nitrogen atmosphere. The reaction was diluted with ethyl acetate (15.0 mL) washed with brine (10.0 mL×2), dried with anhydrous sodium sulfate, filtered and concentrated in vacuum to give a residue, the residue was purified by prep-TLC (petroleum ether/ethyl acetate=1/1) to give N-((5-fluoro-2,3-dihydrobenzofuran-4-yl)methyl)pyrido[3,4-d]pyrimidin-8-amine (40.0 mg, 135 μmol, 29.5% yield) as a brown solid.

$^1$H NMR (400 MHz, CDCl$_3$) δ=9.24 (s, 1H), 9.22 (s, 1H), 8.17 (d, J=6.0 Hz, 1H), 6.99 (br s, 1H), 6.89 (d, J=6.0 Hz, 1H), 6.88-6.82 (m, 1H), 6.65 (dd, J=4.0, 8.8 Hz, 1H), 4.83 (d, J=5.6 Hz, 2H), 4.60 (t, J=8.8 Hz, 2H), 3.37 (t, J=8.8 Hz, 2H).

Step C: To a solution N-((5-fluoro-2,3-dihydrobenzofuran-4-yl)methyl)pyrido[3,4-d]pyrimidin-8-amine (35.0 mg, 118 μmol, 1.00 equiv) in DCM (2.00 mL) was added NBS (21.0 mg, 118 μmol, 1.00 equiv) at 0° C., the reaction was stirred at 0° C. for 30 minutes. The reaction was concentrated in vacuo at 25° C. to give 5-bromo-N-((5-fluoro-2,3-dihydrobenzofuran-4-yl)methyl)pyrido[3,4-d]pyrimidin-8-amine (40.0 mg, crude) as a brown solid which was used in the next step directly.

$^1$H NMR (400 MHz, CDCl$_3$) δ=9.48 (s, 1H), 9.28 (s, 1H), 8.25 (s, 1H), 7.08 (br s, 1H), 6.89-6.80 (m, 1H), 6.65 (dd, J=4.0, 8.8 Hz, 1H), 4.80 (d, J=5.6 Hz, 2H), 4.60 (t, J=8.8 Hz, 2H), 3.36 (t, J=8.8 Hz, 2H).

Example 59: To a solution of 5-bromo-N-((5-fluoro-2,3-dihydrobenzofuran-4-yl)methyl)pyrido[3,4-d]pyrimidin-8-amine (40.0 mg, 107 μmol, 1.00 equiv) and 1,3-dimethyl-5-(4,4,5,5-tetramethyl-1,3,2-dioxaborolan-2-yl)pyrazole (35.5 mg, 160 μmol, 1.50 equiv.) in dioxane (1.50 mL) and water (0.30 mL) was added sodium bicarbonate (26.9 mg, 320 μmol, 12.4 μL, 3.00 equiv.) and Pd(dppf)Cl$_2$ (7.80 mg, 10.7 μmol, 0.10 equiv.) under a nitrogen atmosphere. The reaction mixture was stirred at 105° C. for 1 hour under a nitrogen atmosphere. The reaction was filtered and the filtrate was concentrated in vacuo to give residue, the residue was purified by prep-TLC (dichloromethane/methanol=10/1), then triturated with methanol (1.00 mL), the precipitate was filtered and the filter cake was collected and dried in vacuo to give 5-(1,3-dimethyl-1H-pyrazol-5-yl)-N-((5-fluoro-2,3-dihydrobenzofuran-4-yl)methyl)pyrido[3,4-d]pyrimidin-8-amine (18.9 mg, 45.6 μmol, 42.7% yield, 94.2% purity) as a yellow solid. LC-MS [M+1]: 391.0.

$^1$H NMR (400 MHz, CD$_3$OD) δ=9.29 (s, 1H), 9.10 (s, 1H), 8.09 (s, 1H), 6.88-6.81 (m, 1H), 6.62 (dd, J=4.0, 8.8 Hz, 1H), 6.28 (s, 1H), 4.87 (s, 2H), 4.55 (t, J=8.8 Hz, 2H), 3.68 (s, 3H), 3.38 (t, J=8.8 Hz, 2H), 2.34 (s, 3H).

The compounds of the present invention may have one or more chiral center and, if so, are synthesized as stereoisomeric mixtures, isomers of identical constitution that differ in the arrangement of their atoms in space. The compounds may be used as mixtures or the individual components/isomers may be separated using commercially available reagents and conventional methods for isolation of stereoisomers and enantiomers well-known to those skilled in the art, e.g., using CHIRALPAK® (Sigma-Aldrich) or CHIRALCEL® (Diacel Corp) chiral chromatographic HPLC columns according to the manufacturer's instructions. Alternatively, compounds of the present invention may be synthesized using optically pure, chiral reagents and intermediates to prepare individual isomers or enantiomers. Unless otherwise indicated, all chiral (enantiomeric and diastereomeric) and racemic forms are within the scope of the invention.

Also contemplated within the scope of the invention are variants of compounds of the present invention in which one or more hydrogen atoms have been replaced with deuterium. As exemplified herein, Intermediate C-31 have one or more hydrogen atom replaced with deuterium. Intermediates B-7 and B-8 also contain deuteriums substituted as specifies location(s). By substituting one or more hydrogen for deuterium on the Intermediates A-C exemplified herein, deuterated versions of the compounds of the present invention can be readily generated using methods well known in the art.

Example A

This Example illustrates that compounds of the present invention inhibit PRC2 enzymatic activity.

Ten-point dose-response curves for compounds of the present invention were determined using a Hot Spot HMT assay (Reaction Biology Corp; see Horiuchi et al., Assay Drug Dev Technol. (2013) 4: 227-236 doi: 10.1089/adt.2012.480). The assay uses purified human, His-tagged PRC2 complex, including N-terminal His-tagged EZH2 enzyme, N-terminal Flag-tagged embryonic ectoderm development protein (EED), N-terminal His-tagged suppressor of zeste 12 (SUZ12), N-terminal His-tagged AEBP2, and N-terminal His-tagged RbAp48. In this assay, the transfer of the tritiated methyl group from radiolabeled S-adenosyl methionine (SAM) to purified core histone protein by EZH2 is quantitated after filtration to determine the activity of the core PRC2 complex in the presence and absence of compound.

Briefly, compounds of the present invention were solubilized in DMSO and a series of 10, three-fold serial dilutions were made for each compound in 15% DMSO. The initial starting concentration for the serial dilutions of each compound was 1.0 µM. Control samples lacking compound, EZH2 enzyme or various reaction components also were prepared and processed in parallel with compound test samples. SAH (S-(5-adenosyl)-L-homocysteine) was used as a positive control for assay validation.

An aliquot of each serial dilution of test compound was added to deep 384 well plate using Acoustic Technology instrument (Echo 550, LabCyte) containing reaction buffer (50 mM Tris-HCl (pH 8)), 0.01% Brij35, 1 mM EDTA, 1 mM DTT, 1 mM PMSF and 1% DMSO), 10 nM purified PRC2 complex and 0.05 mg/ml core histone H3 in a 5 µl volume. The reaction was mixed gently and then pre-incubated for 20 min at 30° C. The enzymatic reaction was initiated by adding 1 µM S-Adenosyl-L-[methyl-$^3$H]methionine and incubated for 1 hr at 30° C. After 1 hr, the reaction product was detected using a filter binding method and the amount of tritiated H3 core histone was quantitated using a scintillation counter. The $IC_{50}$ value for each compound was determined from each 10-point dose-response curve using GraphPad Prism software and the results for compounds of present invention, including compounds of Formula (I) and Formula (II) are shown in Table 6. Key: A=<100 nM; B=>100 nM–<250 nM; and C=>250 nM.

TABLE 6

Inhibition of PRC2-mediated Enzymatic Activity by Compounds of the Present Invention

| Example No. | $IC_{50}$ |
|---|---|
| 1 | A |
| 2 | A |
| 3 | A |
| 4 | B |
| 5 | C |
| 6 | A |
| 7 | A |
| 8 | A |
| 9 | B |
| 10 | A |
| 11 | A |
| 12 | A |
| 13 | A |
| 14 | A |
| 15 | A |
| 16 | A |
| 17 | A |
| 18 | C |
| 19 | A |
| 20 | A |
| 21 | B |
| 22 | A |
| 23 | A |
| 24 | A |
| 25 | C |
| 26 | A |
| 27 | A |
| 28 | A |
| 29 | A |
| 30 | C |
| 31 | B |
| 32 | A |
| 33 | B |
| 34 | B |
| 35 | A |
| 36 | C |

TABLE 6-continued

Inhibition of PRC2-mediated Enzymatic Activity by Compounds of the Present Invention

| Example No. | $IC_{50}$ |
|---|---|
| 37 | B |
| 38 | B |
| 39 | C |
| 40 | B |
| 41 | B |
| 42 | B |
| 43 | C |
| 44 | C |
| 45 | B |
| 46 | C |
| 47 | A |
| 48 | A |
| 49 | B |
| 50 | C |
| 51 | C |
| 52 | C |
| 53 | C |
| 54 | C |
| 55 | C |
| 56 | C |
| 57 | C |
| 58 | C |
| 59 | C |

Example B

This Example illustrates that compounds of the present invention inhibit the growth of tumor cells harboring PRC2 complexes containing EZH2 activating mutations.

The Pfeiffer cell line was established from a pleural infusion from a patient having metastatic diffuse large B-cell lymphoma (DLBCL). This cell line expresses a mutant form of the EZH2 enzyme (A677G) that results in enhanced EZH2 activity leading to increased methylation of histone H3 Lys27. Increased trimethylation of histone H3 Lys27 is believed to be implicated in tumorgenesis and poor clinical prognosis in lymphomas (McCabe et al., (2012) Nature 492:108-112).

Inhibition of PRC2-mediated histone H3 methylation by compounds of Formula (I) was measured by ELISA using a Tri-Methyl Histone H3 (Lys 27) Sandwich ELISA Kit (Cell Signaling Tech #7866C) in accordance with the manufacturer's instructions. Briefly, Pfeiffer cells were cultured in RPMI medium supplemented with 10% fetal bovine serum and 1% penicillin and 1% streptomycin in 96 well culture plates at 37° C. to a density of 8000 cells/90 µl/well and the cells were harvested. A series of 3-fold serial dilutions of each test compound of Formula (I) were prepared in RPMI medium and added to the cells at final concentrations ranging from 1 M to 0.15 nM. The plates were incubated at 37° C. for 96 hours.

After incubation, the cells were pelleted by centrifugation in a pre-cooled 4° C. rotor at 1,100 rpm for 10 min and the supernatant was removed by aspiration. The cell pellet was resuspended in 55 µl of Lysis Buffer (0.4M HCl) and incubated on ice with periodic shaking for 30 minutes. The lysed cells were subjected to centrifugation at 4,200 rpm for 10 min at 4° C. and the supernatant containing acid-soluble proteins was collected and the remainder discarded. The acid-soluble proteins were brought to a neutral pH by the addition of 20 µl of Neutralization Buffer (1 M Sodium phosphate, dibasic (pH 12.5), 2.5 mM DTT and 1 mM PMSF) and the neutralized lysates were analyzed by ELISA.

A 65 µl aliquot of each cell lysate was added to a well of a microwell strip, the microwells were sealed using tape and incubated either at 37° C. for two hours or at 4° C. overnight. After incubation, the tape was removed at the microwells were washed four times using 200 µl of 1× Wash Buffer. To each washed microwell, a 100 µl aliquot of an anti-trimethyl histone H3 Lys27 Detection Antibody solution was added and the microwells were incubated at 37° C. for one hour. The Detection Antibody solution was removed by aspiration and the wells were washed four times each using 200 µl of 1× Wash Buffer.

A 100 µl aliquot of an HRP-linked secondary antibody was added to each well, the wells were sealed with tape and incubated at 37° C. for 30 min. The HRP-linked secondary antibody solution was removed by aspiration and the wells were washed four times using 200 µl of 1× Wash Buffer. A 100 µl aliquot of a TMB substrate was added to each well, the wells were sealed with tape and incubated at 37° C. for 10 min or 25° C. for 30 min. The reaction was stopped by the addition of 100 µl aliquot of a STOP solution and the plate was shaken briefly. The degree of histone H3 trimethylation was determined using a spectrophotometric readout by measuring the absorbance at 450 nm and then calculating the amount of trimethylated histone H3. The results are shown in Table 7. A=≤100 nM; B=>100 nM–≤500 nM; C=>500 nM and N.D.=not determined.

TABLE 7

Inhibition of EZH2-mediated Histone H3 Trimethylation by Compounds of the Present Invention

| Example No. | IC$_{50}$ (nM) |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | B |
| 19 | A |
| 20 | A |
| 21 | B |
| 22 | A |
| 23 | B |
| 24 | A |
| 25 | B |
| 26 | A |
| 27 | B |
| 28 | B |
| 29 | B |
| 30 | C |
| 31 | C |
| 32 | A |
| 33 | C |
| 34 | C |
| 35 | A |
| 36 | B |
| 37 | B |
| 38 | B |
| 39 | C |
| 40 | B |
| 41 | B |

TABLE 7-continued

Inhibition of EZH2-mediated Histone H3 Trimethylation by Compounds of the Present Invention

| Example No. | IC$_{50}$ (nM) |
|---|---|
| 42 | N.D. |
| 43 | C |
| 44 | B |
| 45 | B |
| 46 | B |
| 47 | B |
| 48 | B |
| 49 | C |
| 50 | C |
| 51 | B |
| 52 | C |
| 53 | B |
| 54 | C |
| 55 | C |
| 56 | B |
| 57 | C |
| 58 | C |
| 59 | C |

Example C

This Example illustrates that compounds of the present invention exhibit a greater potency against DLBCL cell lines expressing an activating mutant form of EZH2 enzyme than wild type EZH2.

Karpas 422 cell line is a human B cell non-Hodgkin's lymphoma cell line established from a female patient having DLBCL. This EZH2 heterozygotic cell line expresses a mutant form of EZH2 enzyme (Y641N) that increases histone H3 methylation and this mutation has been implicated in the tumorgenesis of lymphomas, such as DLBCL.

Karpas 422 cells (PHE cat no., 06101702) were cultured in RPMI medium supplemented with 20% fetal bovine serum and 1% penicillin/1% streptomycin and plated at a density of 1000 cells/90 µl/well in 96 well white assay plates. A dose response curve for compounds of the present invention was determined by adding a 10 µl aliquot of stock solutions of varying concentrations of compounds to the same medium in each well, over a concentration range of 10 µM using 3-fold dilutions to a final concentration of 1.5 nM. The plates were incubated at 37° C. for predetermined time periods, Day 4, Day 7, or Day 11, and the viability of the cells was measured using a CTG assay kit (Cell Titre Glo; Promega cat. no G7573) on Day 4 and Day 7 in accordance with the manufacturer's instructions.

For the viability assay for the Day 11 plates, the plates were subjected to centrifugation at 1100 rpm for five minutes on Day 7 and the supernatant was removed by aspiration. The cells were resuspended in 90 µl aliquot of the appropriate growth medium lacking the compound followed by addition of 10 µl of a 10× stock of the same compound at the same concentration. The viability of the Day 11 cells was measured using the CTG assay kit described above in accordance with the manufacturer's instructions. The IC$_{50}$ values for each compound at each predetermined time point were calculated using Graph pad PRISM software and the results are shown in Table 8. A=≤250 nM; B=<250 nM–≤500 nM; C=>500 nM and N.D.=not determined.

TABLE 8

Enhanced Potency of Compounds Inhibiting Proliferation of Cells Expressing an Activating Mutant Form of EZH2

| Example No. | IC$_{50}$ (nM) |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | B |
| 30 | C |
| 31 | C |
| 32 | A |
| 33 | C |
| 34 | C |
| 35 | A |
| 36 | A |
| 37 | A |
| 38 | A |
| 39 | C |
| 40 | A |
| 41 | B |
| 42 | N.D. |
| 43 | C |
| 44 | A |
| 45 | A |
| 46 | A |
| 47 | A |
| 48 | A |
| 49 | C |
| 50 | C |
| 51 | A |
| 52 | C |
| 53 | A |
| 54 | B |
| 55 | A |
| 56 | C |
| 57 | C |
| 58 | C |
| 59 | C |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:
1. A compound of Formula (II):

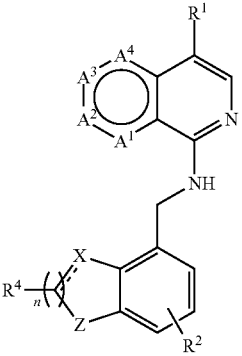

Formula (II)

or a pharmaceutically acceptable salt thereof, wherein:

======= represents a single or a double bond;

$A^1$, $A^2$, $A^3$ and $A^4$ are each independently N or $CR^4$, wherein no more than two of $A^1$, $A^2$, $A^3$, and $A^4$ are N, and wherein at least one of $A^2$, $A^3$ and $A^4$ is N;

Z is O or S;

X is O, $CR^5$, $CR^5OH$, or $C(R^5)_2$, wherein:
  when X is O, ======= is a single bond;
  when X is $C(R^5)_2$, ======= is a single bond;
  when X is $CR^5OH$, ======= is a single bond; or
  when X is $CR^5$, ======= is a double bond;

$R^1$ is aryl, heteroaryl, -L-cycloalkyl, —N($R^5$)heterocyclyl, or -L-heterocyclyl, wherein the aryl, the heteroaryl and the cyclyl portion of the -L-cycloalkyl, —N($R^5$)heterocyclyl, and -L-heterocyclyl are optionally substituted with one or more independently selected $R^3$;

$R^2$ is independently C1-C3 alkyl or halogen;

each $R^3$ is independently oxo, cyano, halogen, hydroxyl, —PO$_3$(C1-C3 alkyl)$_2$, alkoxy, hydroxyalkyl, heteroalkyl, aralkyl, haloalkyl, —COOR$^5$, —Y$^2$-haloalkyl, —Y$^1$—C1-C6 alkyl, —Y$^2$-C1-C6 alkyl, -L-cycloalkyl, -L-heteroaryl, -L-heterocyclyl, —Y$^1$-heterocyclyl, —Y$^2$-heterocyclyl, -L-N(R$^5$)$_2$, —O-L-N(R$^5$)$_2$, —C(CF$_3$)N(R$^5$)$_2$, —Y$^1$—N(R$^5$)$_2$, or —Y$^2$—N(R$^5$)$_2$ wherein the ring portion of the aralkyl, -L-cycloalkyl, -L-heteroaryl, -L-heterocyclyl, and —Y$^1$-heterocyclyl is optionally substituted with one or more independently selected R$^6$;

$R^4$ is hydrogen, C1-C3 alkyl, halogen, haloalkyl, hydroxyalkyl, or heteroalkyl;

L is a bond or C1-C4 alkylene;

$Y^1$ is a bond, —C(O)—, or —NHC(O)—;

$Y^2$ is a bond, —S—, —SO—, —SO$_2$—, or —NR$^5$SO$_2$—, each $R^5$ is independently hydrogen or C1-C3 alkyl;

each $R^6$ is oxo, cyano, hydroxyl, alkoxy, halogen, haloalkyl, hydroxyalkyl, heteroalkyl, cycloalkyl, -L-N(R$^5$)$_2$, C1-C6 alkyl, or —Y$^1$-heterocyclyl, wherein —Y$^1$-heterocyclyl is optionally substituted with one or more R$^7$;

each $R^7$ is independently hydrogen, C1-C3 alkyl, halogen, haloalkyl, hydroxyalkyl, or heteroalkyl;

each $R^4$ is independently hydrogen, alkoxy, heteroalkyl, —N(R$^5$)$_2$, heteroalkylN(R$^5$)$_2$, C1-C3 alkyl, S—C1-C3 alkyl, or aryl; and n is 1 or 2.

2. The compound of claim 1, or a pharmaceutically acceptable salt thereof, wherein $A^3$ is N.

3. The compound of claim 1, or a pharmaceutically acceptable salt thereof, wherein $A^1$ and $A^3$ are each N.

4. The compound according to claim 1, or a pharmaceutically acceptable salt thereof, wherein $A^2$ is $CR^4$ and $R^4$ is alkoxy.

5. The compound according to claim 1, or a pharmaceutically acceptable salt thereof, wherein $A^4$ is $CR^4$ and $R^4$ is alkoxy.

6. The compound of claim 1, or a pharmaceutically acceptable salt thereof, wherein $A^2$ is N.

7. The compound of claim 1, or a pharmaceutically acceptable salt thereof, wherein $A^2$ and $A^4$ are each N.

8. The compound according to claim 1, or a pharmaceutically acceptable salt thereof, wherein $A^3$ is $CR^4$ and $R^4$ is alkoxy, heteroalkyl, —$N(R^5)_2$, heteroalkylN$(R^5)_2$, C1-C3 alkyl, S—C1-C3 alkyl, or aryl.

9. The compound of claim 1, or a pharmaceutically acceptable salt thereof, wherein $A^2$ and $A^3$ are each N.

10. The compound of claim 1, or a pharmaceutically acceptable salt thereof, wherein $A^4$ is N.

11. The compound of claim 1, or a pharmaceutically acceptable salt thereof, wherein $A^3$ is N, $A^4$ is $CR^4$ and $R^4$ is alkoxy, —$N(R^5)_2$, or aryl.

12. The compound according to claim 1, or a pharmaceutically acceptable salt thereof, wherein Z is O.

13. The compound according to claim 1, or a pharmaceutically acceptable salt thereof, wherein n is 1.

14. The compound according to claim 1, or a pharmaceutically acceptable salt thereof, wherein $R^2$ is halogen.

15. The compound of claim 14, or a pharmaceutically acceptable salt thereof, wherein $R^2$ is fluorine.

16. The compound according to claim 1, or a pharmaceutically acceptable salt thereof, wherein X is $C(R^5)_2$ and ------ is a single bond.

17. The compound according to claim 1, or a pharmaceutically acceptable salt thereof, wherein $R^1$ is aryl optionally substituted with one or more independently selected $R^3$.

18. The compound of claim 17, or a pharmaceutically acceptable salt thereof, wherein $R^1$ is phenyl optionally substituted with one or more independently selected $R^3$.

19. The compound of claim 18, or a pharmaceutically acceptable salt thereof, wherein $R^1$ is phenyl substituted with one, two or three $R^3$.

20. The compound of claim 19, or a pharmaceutically acceptable salt thereof, wherein the one, two or three $R^3$ are each independently halogen, hydroxyl, haloalkyl, —$COOR^5$, —$Y^1$—C1-C6 alkyl, —$Y^2$—C1-C6 alkyl, -L-N$(R^5)_2$, —O-L-N$(R^5)_2$, —$C(CF_3)N(R^5)_2$, —$Y^1$—N$(R^5)_2$, —$Y^2$—N$(R^5)_2$, —$Y^2$-haloalkyl, -L-heterocyclyl, or —$Y^1$-heterocyclyl, wherein the heterocyclyl portion of the -L-heterocyclyl and —$Y^1$-heterocyclyl is optionally substituted with one or more independently selected $R^6$.

21. The compound according claim 1, or a pharmaceutically acceptable salt thereof, wherein $R^1$ is heteroaryl optionally substituted with one or more independently selected $R^3$.

22. The compound of claim 21, or a pharmaceutically acceptable salt thereof, wherein $R^1$ is heteroaryl selected from pyrazolyl, imidazolyl, oxazolyl, isoxazolyl, thiazolyl, triazinyl, pyridyl, pyridinyl-2-one, pyrazinyl, pyridazinyl, pyrimidinyl, isoxazolyl, isoindolinyl, naphthridinyl, 1,2,3,4-tetrahydroisoquinolinyl, and 5,6-dihydro-4H-pyrrolo[1,2-b]pyrazolyl, each optionally substituted with one or more independently selected $R^3$.

23. The compound of claim 22, or a pharmaceutically acceptable salt thereof, wherein $R^1$ is substituted with one or more $R^3$; wherein each $R^3$ is independently cyano, halogen, —$Y^1$-C1-C6 alkyl, —$Y^2$-C1-C6 alkyl, alkoxy, hydroxyalkyl, heteroalkyl, haloalkyl, -L-cycloalkyl, -L-N$(R^5)_2$, —$Y^1$—N$(R^5)_2$, -L-heteroaryl, -L-heterocyclyl, or —$Y^1$-heterocyclyl, wherein the heteroaryl of the-L-heteroaryl and the heterocyclyl portion of the -L-heterocyclyl and —$Y^1$-heterocyclyl are optionally substituted with one or more independently selected $R^6$.

24. A compound selected from the group consisting of:

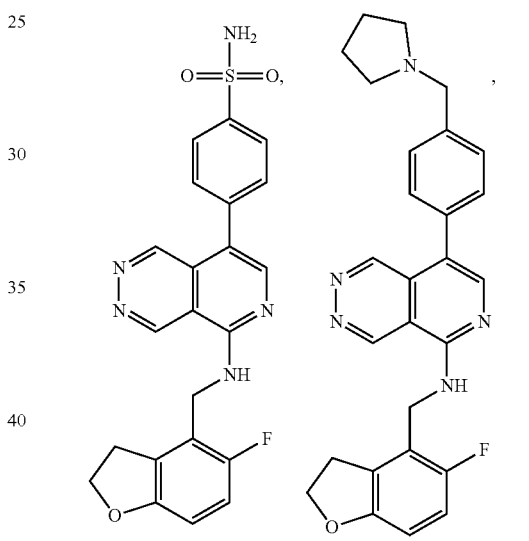

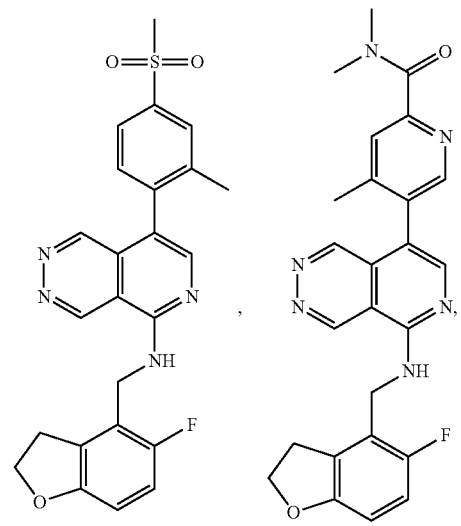

-continued
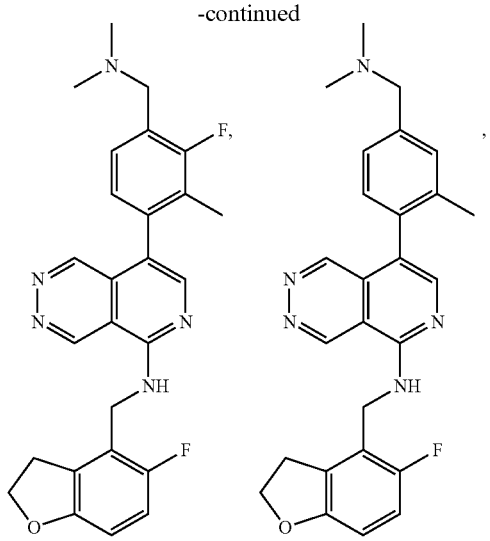
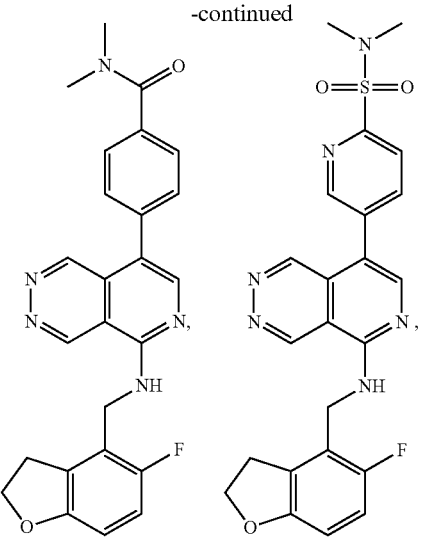
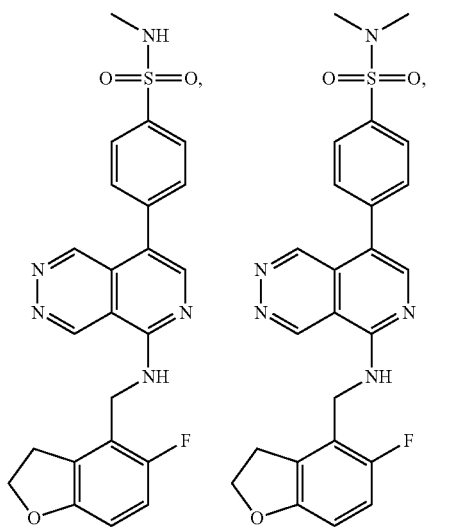
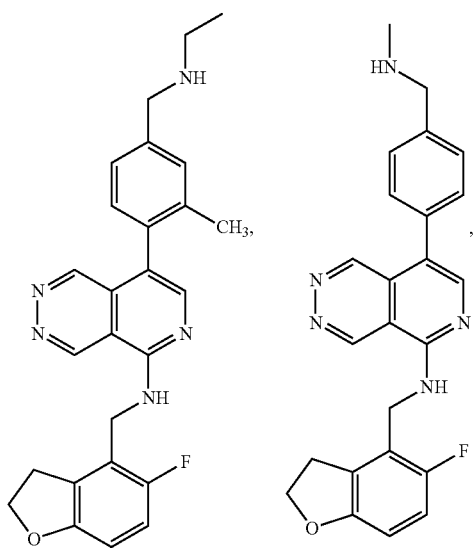
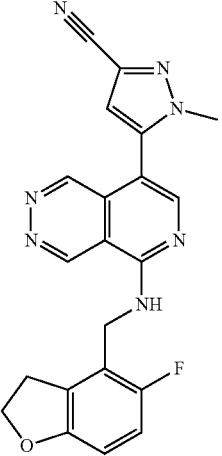

187
-continued
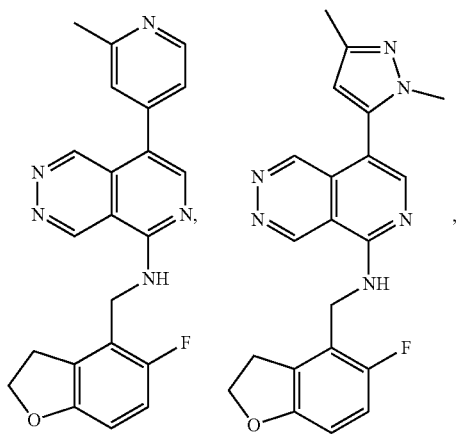
188
-continued
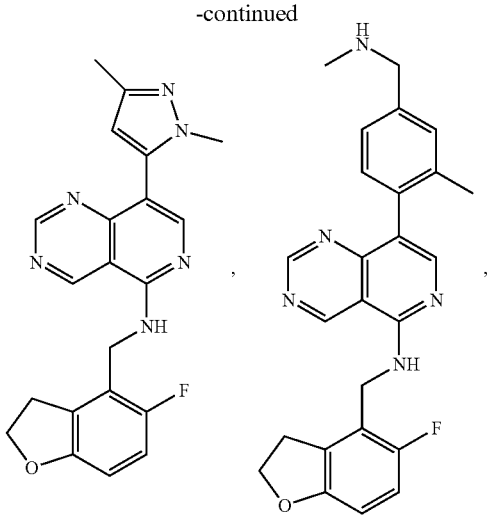

189
-continued
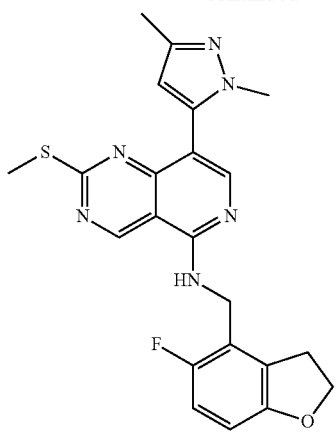
,
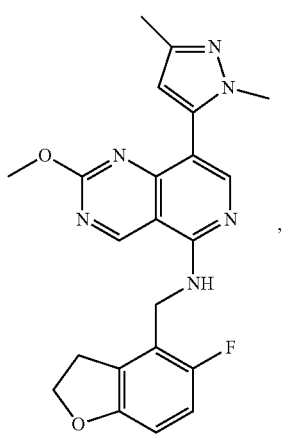
,
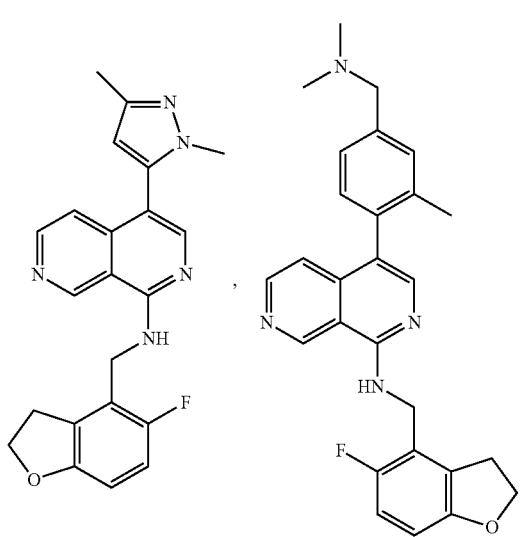
190
-continued
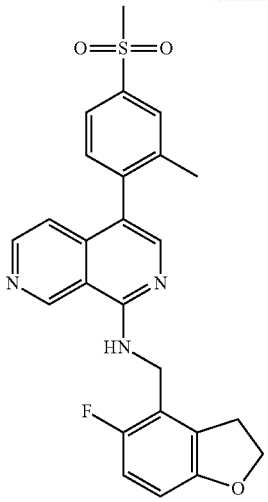
,
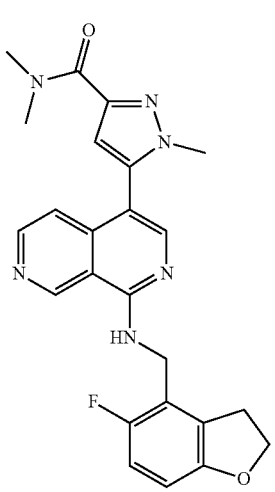 [SMILES: CN(C)C(=O)c1cc(-c2cnc(NCc3c(F)ccc4c3CCO4)c3cnccc23)n(C)n1]
,
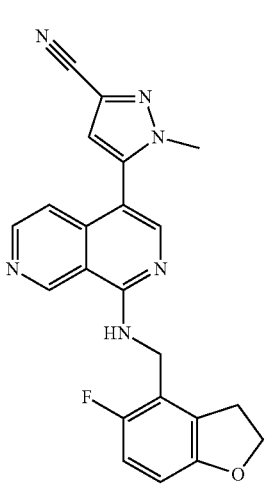
, 191
-continued
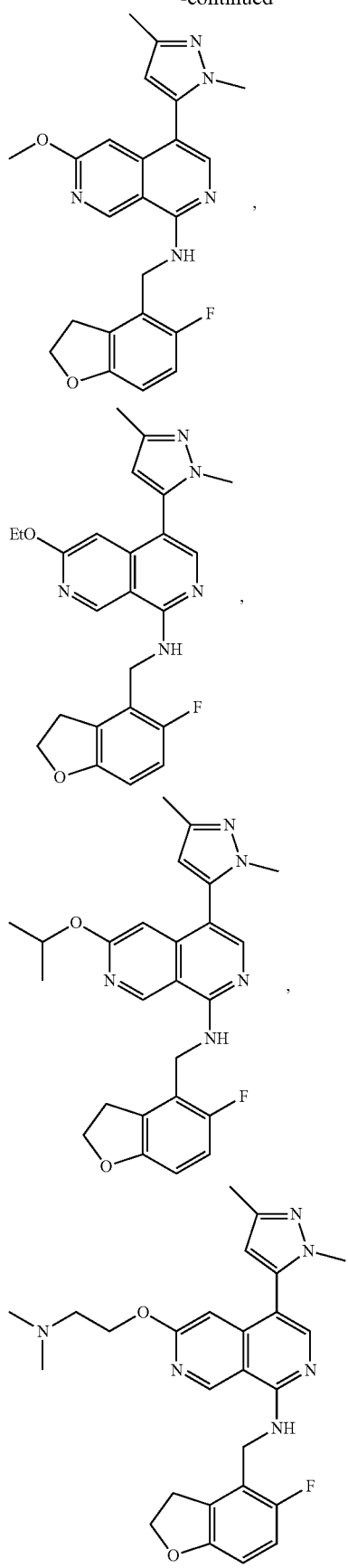
192
-continued
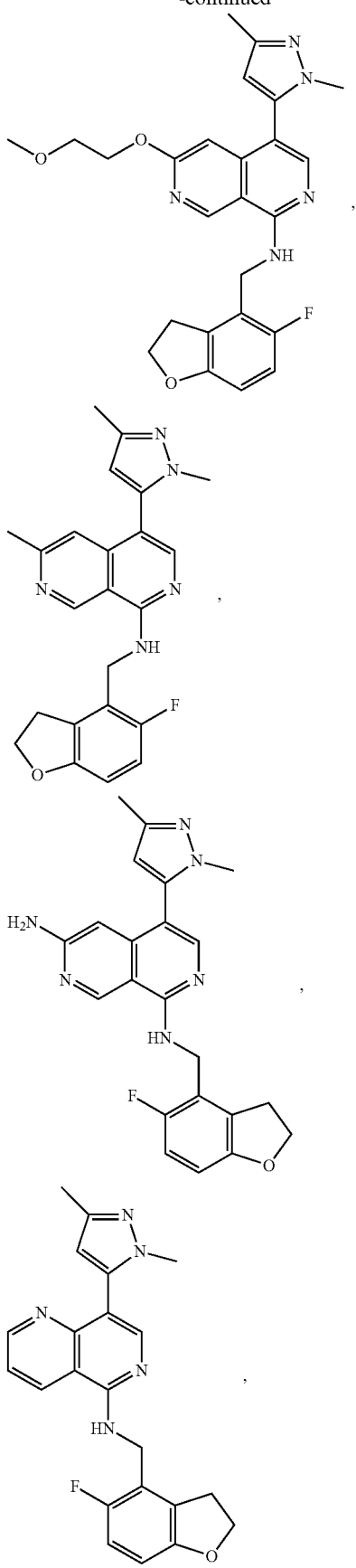

-continued

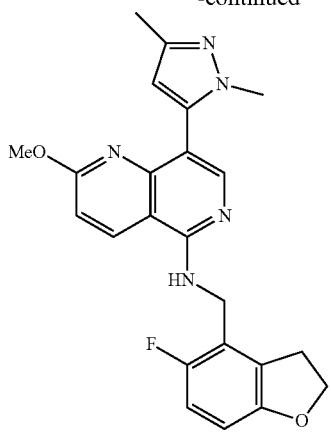

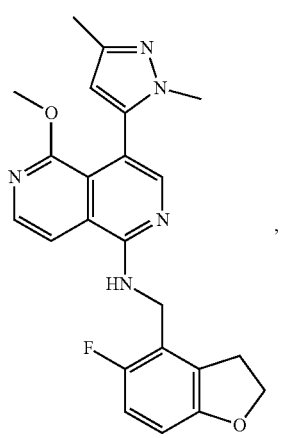

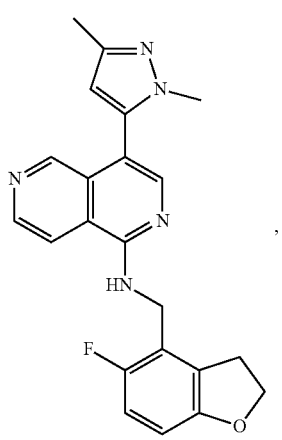

-continued

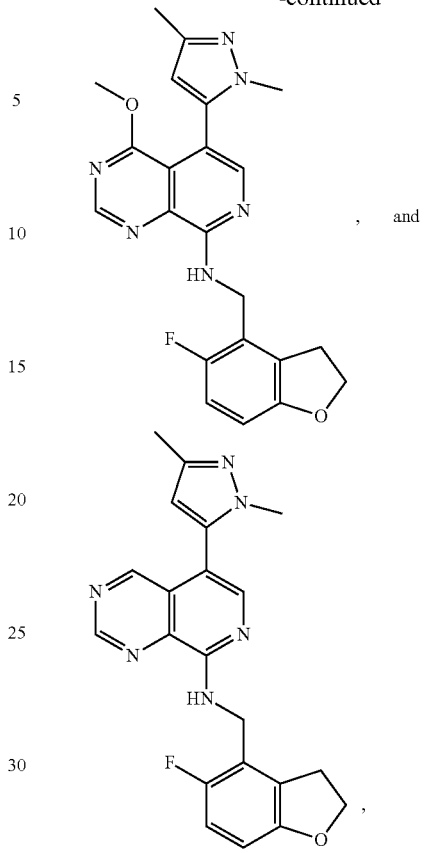

or a pharmaceutically acceptable salt thereof.

25. A pharmaceutical composition comprising a therapeutically effective amount of a compound according to claim 1, or a pharmaceutically acceptable salt, and a pharmaceutically acceptable excipient.

26. The compound of claim 1, or a pharmaceutically acceptable salt thereof, wherein:
Z is O;
n is 1;
$R^2$ is fluorine;
X is $C(R^5)_2$ and ------ is a single bond; and
$R^5$ is hydrogen.

27. The compound of claim 26, or a pharmaceutically acceptable salt thereof, wherein $R^1$ is phenyl substituted with one or more independently selected $R^3$.

28. The compound of claim 26, or a pharmaceutically acceptable salt thereof, wherein $R^1$ is heteroaryl substituted with one or more independently selected $R^3$.

29. The compound of claim 28, or a pharmaceutically acceptable salt thereof, wherein $R^1$ is pyrazolyl or pyridyl, substituted with one or more independently selected $R^3$.

* * * * *